(12) United States Patent
Otterlei et al.

(10) Patent No.: US 10,570,180 B2
(45) Date of Patent: Feb. 25, 2020

(54) ANTI-BACTERIAL AGENTS AND THEIR USE IN THERAPY

(71) Applicant: Norwegian University of Science and Technology (NTNU), Trondheim (NO)

(72) Inventors: Marit Otterlei, Trondheim (NO); Siri Bachke, Trondheim (NO)

(73) Assignee: NORWEGIAN UNIVERSITY OF SCIENCE AND TECHNOLOGY (NTNU), Trondheim (NO)

( * ) Notice: Subject to any disclaimer, the term of this patent is extended or adjusted under 35 U.S.C. 154(b) by 0 days.

(21) Appl. No.: 15/570,837

(22) PCT Filed: May 6, 2016

(86) PCT No.: PCT/EP2016/060232
§ 371 (c)(1),
(2) Date: Oct. 31, 2017

(87) PCT Pub. No.: WO2016/177899
PCT Pub. Date: Nov. 10, 2016

(65) Prior Publication Data
US 2018/0141977 A1 May 24, 2018

(30) Foreign Application Priority Data
May 6, 2015 (GB) .................................. 1507722.5

(51) Int. Cl.
| | | |
|---|---|---|
| *A01N 37/18* | (2006.01) |
| *A61K 38/00* | (2006.01) |
| *A61P 31/04* | (2006.01) |
| *A61K 38/08* | (2019.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 14/00* | (2006.01) |
| *A61K 38/17* | (2006.01) |
| *C07K 14/47* | (2006.01) |
| *A61K 47/50* | (2017.01) |

(Continued)

(52) U.S. Cl.
CPC ........ *C07K 14/003* (2013.01); *A61K 38/1709* (2013.01); *A61K 47/50* (2017.08); *A61L 9/20* (2013.01); *A61L 27/227* (2013.01); *C07K 14/4738* (2013.01); *C12N 5/0634* (2013.01); *Y02A 50/402* (2018.01); *Y02A 50/475* (2018.01); *Y02A 50/478* (2018.01); *Y02A 50/479* (2018.01); *Y02A 50/481* (2018.01)

(58) Field of Classification Search
None
See application file for complete search history.

(56) References Cited

U.S. PATENT DOCUMENTS

| 5,656,122 A | 8/1997 | Lenz et al. |
|---|---|---|
| 6,080,724 A | 6/2000 | Chassaing et al. |

(Continued)

FOREIGN PATENT DOCUMENTS

| WO | 91/18981 | 12/1991 |
|---|---|---|
| WO | 94/20532 | 9/1994 |

(Continued)

OTHER PUBLICATIONS

International Search Report and Written Opinion of the International Searching Authority, dated Sep. 5, 2016 in corresponding International Patent Application No. PCT/EP2016/060232.
Cokol et al., "Finding nuclear localization signals", EMBO Reports, 1(5): 411-415 (2000).
Elmquist et al., "In vitro Uptake and Stability Study of pVEC and its All-D Analog", Biol. Chem, 384: 387-393 (2003).
Eriksson et al., "Identification of Cell-Penetrating Peptides That are Bactericidal to *Neisseria meningitidis* and Prevent Inflammatory Responses upon Infection", Antimicrobial Agents and Chemotherapy, 57(8): 3704-3712 (2013).

(Continued)

*Primary Examiner* — Christina Bradley
*Assistant Examiner* — Zachary J Miknis
(74) *Attorney, Agent, or Firm* — Wenderoth, Lind & Ponack, L.L.P.

(57) ABSTRACT

The present invention provides an agent, or a composition containing an agent, for use in treating or preventing a bacterial infection in a subject, wherein said agent comprises: (i) an oligopeptidic compound comprising a PCNA interacting motif and a domain that facilitates the cellular uptake of said compound, wherein the PCNA interacting motif is $X_1X_2X_3X_4X_5X_6$ (SEQ ID NO: 1) and wherein: $X_1$ is a basic amino acid; $X_2$ is an aromatic amino acid; $X_3$ is an aromatic amino acid or a hydrophobic amino acid that has an R group comprising at least three carbon atoms; $X_4$ is an uncharged amino acid other than an aromatic amino acid, Glycine (G) and Proline (P); $X_5$ is any amino acid other than an acidic amino acid or an aromatic amino acid; and $X_6$ is any amino acid other than an acidic amino acid or an aromatic amino acid, preferably a basic amino acid or Proline (P), wherein when $X_3$ is not an aromatic amino acid, $X_5$ is not lysine (K) and $X_6$ is a basic amino acid or Proline (P); or (ii) a nucleic acid molecule comprising a sequence encoding the oligopeptidic compound of (i). In certain aspects the agent and composition of the invention may be used as single agents. In other aspects of the invention the agents and composition may be used in conjunction with one or more addition active agents, such as antibiotics, or in combination with UV radiation.

26 Claims, 39 Drawing Sheets
Specification includes a Sequence Listing.

(51) Int. Cl.
*A61L 9/20* (2006.01)
*A61L 27/22* (2006.01)
*C12N 5/078* (2010.01)

(56) References Cited

U.S. PATENT DOCUMENTS

| | | | |
|---|---|---|---|
| 6,645,501 B2 | 11/2003 | Dowdy | |
| 6,902,893 B1 | 6/2005 | Choi | |
| 2009/0075875 A1* | 3/2009 | Hoffman | A61K 38/177 514/8.9 |
| 2013/0065267 A1* | 3/2013 | Mao | G01N 33/5076 435/29 |
| 2013/0065832 A1* | 3/2013 | Chen | A61K 38/177 514/12.3 |

FOREIGN PATENT DOCUMENTS

| | | | |
|---|---|---|---|
| WO | 95/19372 | 7/1995 | |
| WO | 00/01417 | 1/2000 | |
| WO | 00/29427 | 5/2000 | |
| WO | 2004/069279 | 8/2004 | |
| WO | 2009/104001 | 8/2009 | |
| WO | 2011/104309 | 9/2011 | |
| WO | WO-2012112869 A2 * | 8/2012 | A61K 38/1709 |
| WO | WO-2012177892 A2 * | 12/2012 | A61K 38/16 |
| WO | 2015/067712 | 5/2015 | |
| WO | 2015/067713 | 5/2015 | |
| WO | WO-2015067713 A1 * | 5/2015 | |

OTHER PUBLICATIONS

Gautam et al., "CPPsite: a curated database of cell penetrating peptides", Database, vol. 2012 Article ID bas015: 1-7 (2012).
Gilljam et al., "Identification of a novel, widespread, and functionally important PCNA-binding motif", The Journal of Cell Biology, 186(5): 645-654 (2009).
Gilljam et al., "Nucleotide Excision Repair is Associated with the Replisome and its Efficiency Depends on a Direct Interaction between XPA and PCNA", PLOS One, 7(11): 1-11, e49199 (2012).
Hällbrink et al., "Prediction of Cell-Penetrating Peptides", International Journal of Peptide Research and Therapeutics, 11(4): 249-259 (2005).
Hansen et al., "Predicting cell-penetrating peptides", Advanced Drug Delivery Reviews, 60: 572-579 (2008).
Holm et al., "Uptake of cell-penetrating peptides in yeasts", FEBS Letters, 579: 5217-5222 (2005).
Jarver et al., "Cell-penetrating peptides—A brief introduction", Biochimica et Biophysica Acta, 1758: 260-263 (2006).
Krauss et al., "In vitro gene delivery by a novel human calcitonin (hCT)-derived carrier peptide", Bioorganic & Medicinal Chemistry Letters, 14: 51-54 (2004).
Lange et al., "Classical Nuclear Localization Signals: Definition, Function, and Interaction with Importin α", Minireview, The Journal of Biological Chemistry, 282 (8): 5101-5105 (2007).
Leslie et al., "Studying nuclear protein import in yeast", Methods, 39: 291-308 (2006).
Lusk et al., "Highway to the inner nuclear membrane: rules for the road", Nature Reviews MCB, 8: 414-420 (2007).
Makkerh et al., "Comparative mutagenesis of nuclear localization signals reveals the importance of neutral and acidic amino acids", Current Biology, 6(8): 1025-1027 (1996).
Müller et al., "Targeting Proliferating Cell Nuclear Antigen and its Protein Interactions Induces Apoptosis in Multiple Myeloma Cells", PLOS One, 8(7): 1-12, e70430 (2013).
Oh et al., "Antibacterial Activities of Amphiphilic Cyclic Cell-Penetrating Peptides against Multidrug-Resistant Pathogens", Molecular Pharmaceutics, 11: 3528-3536 (2014).
Olaisen et al., "PCNA-interacting peptides reduce Akt phosphorylation and TLR-mediated cytokine secretion suggesting a role of PCNA in cellular signaling", Cellular Signalling, 27: 1478-1487 (2015).
Pujals et al., "Proline-rich, amphipathic cell-penetrating peptides", Advanced Drug Delivery Reviews, 60: 473-484 (2008).
Sanders et al., "Prediction of Cell Penetrating Peptides by Support Vector Machines", PLOS Computational Biology, 7(7): 1-12, e1002102 (2011).

* cited by examiner

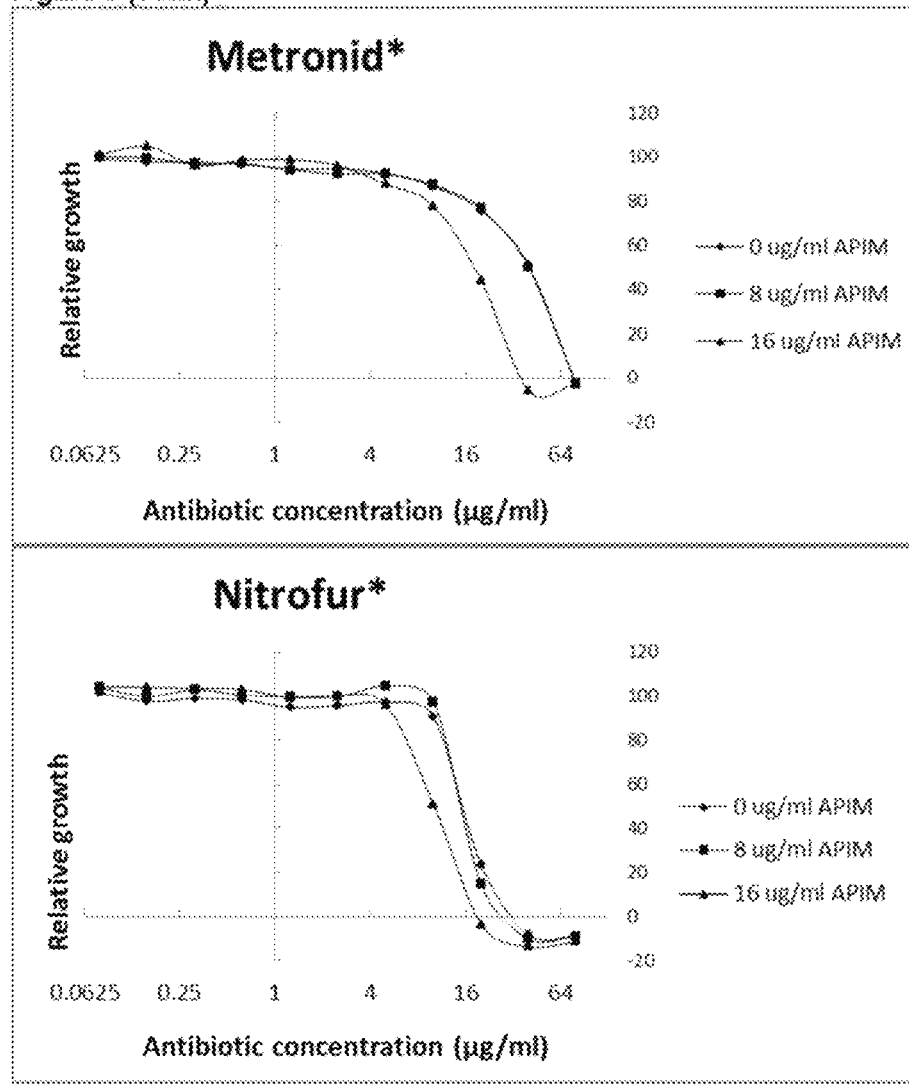

1525
...AGCCAGCTGTCTCTCAGTTTATGGACCAGAACAACCCGCTGTCTGAGATTACGCACAA
       C C                                  T
101-F1
       C C T T
                       C C T T 1596 1690                 1722
               T T T
ACGTCGGTATCTCCGCA...CCTGAAGGTCCGAACATCGGTCTGATCAACTCT

AGCCAGCTGTCTCAGTTTATGGACCAGAACAACCCGCTGTCTGAGATTACGCACAA

ACGTCGTATCTCCGCA...CCTGAAGGTCCGAACATCGGTCTGATCAACTCT

SEQUENCE LISTING

```
<160> NUMBER OF SEQ ID NOS: 1320

<210> SEQ ID NO 1
<211> LENGTH: 6
<212> TYPE: PRT
<213> ORGANISM: Artificial sequence
<220> FEATURE:
<223> OTHER INFORMATION: Consensus APIM
<220> FEATURE:
<221> NAME/KEY: VARIANT
<222> LOCATION: (1)..(1)
```

```
<223> OTHER INFORMATION: X is a basic amino acid
<220> FEATURE:
<221> NAME/KEY: VARIANT
<222> LOCATION: (2)..(2)
<223> OTHER INFORMATION: X is an aromatic amino acid
<220> FEATURE:
<221> NAME/KEY: VARIANT
<222> LOCATION: (3)..(3)
<223> OTHER INFORMATION: X is is an aromatic amino acid or a hydrophobic
      amino acid that has an R group comprising at least three carbon
      atoms
<220> FEATURE:
<221> NAME/KEY: VARIANT
<222> LOCATION: (4)..(4)
<223> OTHER INFORMATION: X is an uncharged amino acid other than an
      aromatic amino acid, glycine and proline
<220> FEATURE:
<221> NAME/KEY: VARIANT
<222> LOCATION: (5)..(5)
<223> OTHER INFORMATION: X is any amino acid other than an aromatic
      amino acid or an acidic amino acid
<220> FEATURE:
<221> NAME/KEY: VARIANT
<222> LOCATION: (6)..(6)
<223> OTHER INFORMATION: X is any amino acid other than an acidic amino
      acid or an aromatic amino acid

<400> SEQUENCE: 1

Xaa Xaa Xaa Xaa Xaa Xaa
1               5

<210> SEQ ID NO 2
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M, S, T, N, Q or C
<220> FEATURE:
<221> NAME/KEY: variant
<222> LOCATION: (5)..(5)
<223> OTHER INFORMATION: X is L, I, V, A, M, G, S, T, N, Q, R, H, K, C
      or P
<220> FEATURE:
<221> NAME/KEY: variant
<222> LOCATION: (6)..(6)
<223> OTHER INFORMATION: X is L, I, V, A, M, G, S, T, N, Q, R, H, K, C
      or P

<400> SEQUENCE: 2

Xaa Xaa Xaa Xaa Xaa Xaa
1               5

<210> SEQ ID NO 3
<211> LENGTH: 6
<212> TYPE: PRT
<213> ORGANISM: Artificial sequence
<220> FEATURE:
<223> OTHER INFORMATION: APIM variant
<220> FEATURE:
```

```
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S, T, N, Q or C
<220> FEATURE:
<221> NAME/KEY: variant
<222> LOCATION: (5)..(5)
<223> OTHER INFORMATION: X is L, I, V, A, M, G, S, T, N, Q, R, H, C or P
<220> FEATURE:
<221> NAME/KEY: variant
<222> LOCATION: (6)..(6)
<223> OTHER INFORMATION: X is R, H, K, or P

<400> SEQUENCE: 3

Xaa Xaa Xaa Xaa Xaa Xaa
1               5

<210> SEQ ID NO 4
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S, T, N, Q, R or H
<220> FEATURE:
<221> NAME/KEY: variant
<222> LOCATION: (6)..(6)
<223> OTHER INFORMATION: X is R, H, K or P

<400> SEQUENCE: 4

Xaa Xaa Xaa Xaa Xaa Xaa
1               5

<210> SEQ ID NO 5
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
```

-continued

```
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S, T or R
<220> FEATURE:
<221> NAME/KEY: variant
<222> LOCATION: (6)..(6)
<223> OTHER INFORMATION: X is R, H or K

<400> SEQUENCE: 5

Xaa Xaa Xaa Xaa Xaa Xaa
1               5

<210> SEQ ID NO 6
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S, T or R
<220> FEATURE:
<221> NAME/KEY: variant
<222> LOCATION: (6)..(6)
<223> OTHER INFORMATION: X is R, H or K

<400> SEQUENCE: 6

Xaa Xaa Xaa Xaa Xaa Xaa
1               5

<210> SEQ ID NO 7
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
```

```
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S or T
<220> FEATURE:
<221> NAME/KEY: variant
<222> LOCATION: (6)..(6)
<223> OTHER INFORMATION: X is  R, H or K

<400> SEQUENCE: 7

Xaa Xaa Xaa Xaa Xaa Xaa
1               5

<210> SEQ ID NO 8
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S or T
<220> FEATURE:
<221> NAME/KEY: variant
<222> LOCATION: (6)..(6)
<223> OTHER INFORMATION: X is R or K

<400> SEQUENCE: 8

Xaa Xaa Xaa Xaa Xaa Xaa
1               5

<210> SEQ ID NO 9
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S or T
```

-continued

```
<220> FEATURE:
<221> NAME/KEY: variant
<222> LOCATION: (5)..(5)
<223> OTHER INFORMATION: X is L, I, V, A, M, G, S or T
<220> FEATURE:
<221> NAME/KEY: variant
<222> LOCATION: (6)..(6)
<223> OTHER INFORMATION: X is R or K

<400> SEQUENCE: 9

Xaa Xaa Xaa Xaa Xaa Xaa
1               5

<210> SEQ ID NO 10
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M or T
<220> FEATURE:
<221> NAME/KEY: variant
<222> LOCATION: (5)..(5)
<223> OTHER INFORMATION: X is L, I, V, A, M, G, S or T
<220> FEATURE:
<221> NAME/KEY: variant
<222> LOCATION: (6)..(6)
<223> OTHER INFORMATION: X is R or K

<400> SEQUENCE: 10

Xaa Xaa Xaa Xaa Xaa Xaa
1               5

<210> SEQ ID NO 11
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M or T
<220> FEATURE:
<221> NAME/KEY: variant
<222> LOCATION: (5)..(5)
<223> OTHER INFORMATION: X is L, I, V, A, M, S or T
<220> FEATURE:
```

```
<221> NAME/KEY: variant
<222> LOCATION: (6)..(6)
<223> OTHER INFORMATION: X is R or K

<400> SEQUENCE: 11

Xaa Xaa Xaa Xaa Xaa Xaa
1               5

<210> SEQ ID NO 12
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M or G
<220> FEATURE:
<221> NAME/KEY: variant
<222> LOCATION: (6)..(6)
<223> OTHER INFORMATION: X is R or K

<400> SEQUENCE: 12

Xaa Xaa Xaa Xaa Xaa Xaa
1               5

<210> SEQ ID NO 13
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M or T
<220> FEATURE:
<221> NAME/KEY: variant
<222> LOCATION: (5)..(5)
<223> OTHER INFORMATION: X is L, I, V, A, M, S or T
<220> FEATURE:
<221> NAME/KEY: variant
<222> LOCATION: (6)..(6)
<223> OTHER INFORMATION: X is R or K

<400> SEQUENCE: 13
```

Xaa Xaa Xaa Xaa Xaa Xaa
1               5

<210> SEQ ID NO 14
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, S or T
<220> FEATURE:
<221> NAME/KEY: variant
<222> LOCATION: (6)..(6)
<223> OTHER INFORMATION: X is R or K

<400> SEQUENCE: 14

Xaa Xaa Xaa Xaa Xaa Xaa
1               5

<210> SEQ ID NO 15
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, I, V, A, S or T
<220> FEATURE:
<221> NAME/KEY: variant
<222> LOCATION: (6)..(6)
<223> OTHER INFORMATION: X is R or K

<400> SEQUENCE: 15

Xaa Xaa Xaa Xaa Xaa Xaa
1               5

```
<210> SEQ ID NO 16
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L,  V, A, M, S or T
<220> FEATURE:
<221> NAME/KEY: variant
<222> LOCATION: (6)..(6)
<223> OTHER INFORMATION: X is R or K

<400> SEQUENCE: 16

Arg Xaa Xaa Xaa Xaa Xaa
1               5

<210> SEQ ID NO 17
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, or M
<220> FEATURE:
<221> NAME/KEY: variant
<222> LOCATION: (5)..(5)
<223> OTHER INFORMATION: X is L, V, A, S, T or M

<400> SEQUENCE: 17

Arg Xaa Xaa Xaa Xaa Lys
1               5

<210> SEQ ID NO 18
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is Y or F
<220> FEATURE:
<221> NAME/KEY: variant
<222> LOCATION: (3)..(3)
```

```
<223> OTHER INFORMATION: X is L, I, V or M
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, I, V, A or M
<220> FEATURE:
<221> NAME/KEY: variant
<222> LOCATION: (6)..(6)
<223> OTHER INFORMATION: X is R or K

<400> SEQUENCE: 18

Xaa Xaa Xaa Xaa Xaa Xaa
1               5

<210> SEQ ID NO 19
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, I, V or A
<220> FEATURE:
<221> NAME/KEY: variant
<222> LOCATION: (6)..(6)
<223> OTHER INFORMATION: X is R or K

<400> SEQUENCE: 19

Xaa Xaa Xaa Xaa Xaa Xaa
1               5

<210> SEQ ID NO 20
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or Y
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A, S or T
```

```
<220> FEATURE:
<221> NAME/KEY: variant
<222> LOCATION: (5)..(5)
<223> OTHER INFORMATION: X is L, V, A, M, S or T
<220> FEATURE:
<221> NAME/KEY: variant
<222> LOCATION: (6)..(6)
<223> OTHER INFORMATION: X is R or K

<400> SEQUENCE: 20

Xaa Xaa Xaa Xaa Xaa Xaa
1               5

<210> SEQ ID NO 21
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I, V or M
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, I, V, A, S, T or M

<400> SEQUENCE: 21

Lys Xaa Xaa Xaa Xaa Lys
1               5

<210> SEQ ID NO 22
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (3)..(3)
<223> OTHER INFORMATION: X is W, F, Y, L, I, V or M

<400> SEQUENCE: 22

Arg Trp Xaa Leu Leu Lys
1               5

<210> SEQ ID NO 23
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (3)..(3)
<223> OTHER INFORMATION: X is W, F, Y, L, I, V or M

<400> SEQUENCE: 23

Arg Phe Xaa Leu Leu Lys
1               5

<210> SEQ ID NO 24
```

```
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 24

Arg Tyr Xaa Leu Leu Lys
1               5

<210> SEQ ID NO 25
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 25

Arg Trp Xaa Leu Leu Arg
1               5

<210> SEQ ID NO 26
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 26

Arg Phe Xaa Leu Leu Arg
1               5

<210> SEQ ID NO 27
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 27

Arg Tyr Xaa Leu Leu Arg
1               5

<210> SEQ ID NO 28
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 28
```

```
Arg Trp Xaa Leu Val Lys
1               5

<210> SEQ ID NO 29
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 29

Arg Phe Xaa Leu Val Lys
1               5

<210> SEQ ID NO 30
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 30

Arg Tyr Xaa Leu Val Lys
1               5

<210> SEQ ID NO 31
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 31

Arg Trp Xaa Leu Val Arg
1               5

<210> SEQ ID NO 32
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 32

Arg Phe Xaa Leu Val Arg
1               5

<210> SEQ ID NO 33
<211> LENGTH: 6
<212> TYPE: PRT
<213> ORGANISM: Artificial sequence
<220> FEATURE:
<223> OTHER INFORMATION: APIM variant
```

```
<220> FEATURE:
<221> NAME/KEY: VARIANT
<222> LOCATION: (3)..(3)
<223> OTHER INFORMATION: X is W, F, Y, L, I, V or M

<400> SEQUENCE: 33

Arg Tyr Xaa Leu Val Arg
1               5

<210> SEQ ID NO 34
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 34

Arg Trp Xaa Ile Val Lys
1               5

<210> SEQ ID NO 35
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 35

Arg Phe Xaa Ile Val Lys
1               5

<210> SEQ ID NO 36
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 36

Arg Tyr Xaa Ile Val Lys
1               5

<210> SEQ ID NO 37
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 37

Arg Trp Xaa Ile Val Arg
1               5
```

```
<210> SEQ ID NO 38
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 38

Arg Phe Xaa Ile Val Arg
1               5

<210> SEQ ID NO 39
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 39

Arg Tyr Xaa Ile Val Arg
1               5

<210> SEQ ID NO 40
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 40

Arg Trp Xaa Leu Ser Lys
1               5

<210> SEQ ID NO 41
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 41

Arg Phe Xaa Leu Ser Lys
1               5

<210> SEQ ID NO 42
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M
```

-continued

```
<400> SEQUENCE: 42

Arg Tyr Xaa Leu Ser Lys
1               5

<210> SEQ ID NO 43
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 43

Arg Trp Xaa Leu Ser Arg
1               5

<210> SEQ ID NO 44
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 44

Arg Phe Xaa Leu Ser Arg
1               5

<210> SEQ ID NO 45
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 45

Arg Tyr Xaa Leu Ser Arg
1               5

<210> SEQ ID NO 46
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 46

Arg Trp Xaa Ile Ser Lys
1               5

<210> SEQ ID NO 47
<211> LENGTH: 6
<212> TYPE: PRT
<213> ORGANISM: Artificial sequence
<220> FEATURE:
```

```
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 47

Arg Phe Xaa Ile Ser Lys
1               5

<210> SEQ ID NO 48
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 48

Arg Tyr Xaa Ile Ser Lys
1               5

<210> SEQ ID NO 49
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 49

Arg Trp Xaa Ile Ser Arg
1               5

<210> SEQ ID NO 50
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 50

Arg Phe Xaa Ile Ser Arg
1               5

<210> SEQ ID NO 51
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 51

Arg Tyr Xaa Ile Ser Arg
1               5
```

```
<210> SEQ ID NO 52
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 52

Arg Trp Xaa Ser Val Lys
1               5

<210> SEQ ID NO 53
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 53

Arg Phe Xaa Ser Val Lys
1               5

<210> SEQ ID NO 54
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 54

Arg Tyr Xaa Ser Val Lys
1               5

<210> SEQ ID NO 55
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 55

Arg Trp Xaa Ser Val Arg
1               5

<210> SEQ ID NO 56
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M
```

-continued

```
<400> SEQUENCE: 56

Arg Phe Xaa Ser Val Arg
1               5

<210> SEQ ID NO 57
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 57

Arg Tyr Xaa Ser Val Arg
1               5

<210> SEQ ID NO 58
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 58

Arg Trp Xaa Ala Val Lys
1               5

<210> SEQ ID NO 59
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 59

Arg Phe Xaa Ala Val Lys
1               5

<210> SEQ ID NO 60
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 60

Arg Tyr Xaa Ala Val Lys
1               5

<210> SEQ ID NO 61
<211> LENGTH: 6
<212> TYPE: PRT
<213> ORGANISM: Artificial sequence
```

```
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 61

Arg Trp Xaa Ala Val Arg
1               5

<210> SEQ ID NO 62
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 62

Arg Phe Xaa Ala Val Arg
1               5

<210> SEQ ID NO 63
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 63

Arg Tyr Xaa Ala Val Arg
1               5

<210> SEQ ID NO 64
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 64

Arg Trp Xaa Leu Gly Arg
1               5

<210> SEQ ID NO 65
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 65

Arg Phe Xaa Leu Gly Arg
1               5
```

<210> SEQ ID NO 66
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 66

Arg Tyr Xaa Leu Gly Arg
1               5

<210> SEQ ID NO 67
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 67

Arg Trp Xaa Leu Gly Lys
1               5

<210> SEQ ID NO 68
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 68

Arg Phe Xaa Leu Gly Lys
1               5

<210> SEQ ID NO 69
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 69

Arg Tyr Xaa Leu Gly Lys
1               5

<210> SEQ ID NO 70
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)

<223> OTHER INFORMATION: X is W, F, Y, L, I, V or M

<400> SEQUENCE: 70

Arg Trp Xaa Leu Ala Arg
1               5

<210> SEQ ID NO 71
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 71

Arg Phe Xaa Leu Ala Arg
1               5

<210> SEQ ID NO 72
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 72

Arg Tyr Xaa Leu Ala Arg
1               5

<210> SEQ ID NO 73
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 73

Arg Trp Xaa Leu Ala Lys
1               5

<210> SEQ ID NO 74
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 74

Arg Phe Xaa Leu Ala Lys
1               5

<210> SEQ ID NO 75
<211> LENGTH: 6
<212> TYPE: PRT

```
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 75

Arg Tyr Xaa Leu Ala Lys
1               5

<210> SEQ ID NO 76
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 76

Arg Trp Xaa Leu Thr Lys
1               5

<210> SEQ ID NO 77
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 77

Arg Phe Xaa Leu Thr Lys
1               5

<210> SEQ ID NO 78
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 78

Arg Tyr Xaa Leu Thr Lys
1               5

<210> SEQ ID NO 79
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 79

Arg Trp Xaa Leu Thr Arg
```

```
<210> SEQ ID NO 80
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 80

Arg Phe Xaa Leu Thr Arg
1               5

<210> SEQ ID NO 81
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 81

Arg Tyr Xaa Leu Thr Arg
1               5

<210> SEQ ID NO 82
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 82

Arg Trp Xaa Ile Thr Lys
1               5

<210> SEQ ID NO 83
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 83

Arg Phe Xaa Ile Thr Lys
1               5

<210> SEQ ID NO 84
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
```

```
<222> LOCATION: (3)..(3)
<223> OTHER INFORMATION: X is W, F, Y, L, I, V or M

<400> SEQUENCE: 84

Arg Tyr Xaa Ile Thr Lys
1               5

<210> SEQ ID NO 85
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 85

Arg Trp Xaa Ile Thr Arg
1               5

<210> SEQ ID NO 86
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 86

Arg Phe Xaa Ile Thr Arg
1               5

<210> SEQ ID NO 87
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 87

Arg Tyr Xaa Ile Thr Arg
1               5

<210> SEQ ID NO 88
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 88

Arg Trp Xaa Thr Val Lys
1               5

<210> SEQ ID NO 89
<211> LENGTH: 6
```

```
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 89

Arg Phe Xaa Thr Val Lys
1               5

<210> SEQ ID NO 90
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 90

Arg Tyr Xaa Thr Val Lys
1               5

<210> SEQ ID NO 91
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 91

Arg Trp Xaa Thr Val Arg
1               5

<210> SEQ ID NO 92
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 92

Arg Phe Xaa Thr Val Arg
1               5

<210> SEQ ID NO 93
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 93
```

Arg Tyr Xaa Thr Val Arg
1               5

<210> SEQ ID NO 94
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 94

Arg Trp Xaa Ile Arg Lys
1               5

<210> SEQ ID NO 95
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 95

Arg Phe Xaa Ile Arg Lys
1               5

<210> SEQ ID NO 96
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 96

Arg Tyr Xaa Ile Arg Lys
1               5

<210> SEQ ID NO 97
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 97

Arg Trp Xaa Ile Arg Arg
1               5

<210> SEQ ID NO 98
<211> LENGTH: 6
<212> TYPE: PRT
<213> ORGANISM: Artificial sequence
<220> FEATURE:
<223> OTHER INFORMATION: APIM variant
<220> FEATURE:

-continued

<221> NAME/KEY: VARIANT
<222> LOCATION: (3)..(3)
<223> OTHER INFORMATION: X is W, F, Y, L, I, V or M

<400> SEQUENCE: 98

Arg Phe Xaa Ile Arg Arg
1               5

<210> SEQ ID NO 99
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 99

Arg Tyr Xaa Ile Arg Arg
1               5

<210> SEQ ID NO 100
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 100

Arg Trp Xaa Leu Arg Lys
1               5

<210> SEQ ID NO 101
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 101

Arg Phe Xaa Leu Arg Lys
1               5

<210> SEQ ID NO 102
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 102

Arg Tyr Xaa Leu Arg Lys
1               5

<210> SEQ ID NO 103

```
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 103

Arg Trp Xaa Leu Arg Arg
1               5

<210> SEQ ID NO 104
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 104

Arg Phe Xaa Leu Arg Arg
1               5

<210> SEQ ID NO 105
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 105

Arg Tyr Xaa Leu Arg Arg
1               5

<210> SEQ ID NO 106
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 106

Lys Trp Xaa Leu Leu Lys
1               5

<210> SEQ ID NO 107
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 107
```

Lys Phe Xaa Leu Leu Lys
1               5

<210> SEQ ID NO 108
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 108

Lys Tyr Xaa Leu Leu Lys
1               5

<210> SEQ ID NO 109
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 109

Lys Trp Xaa Leu Leu Arg
1               5

<210> SEQ ID NO 110
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 110

Lys Phe Xaa Leu Leu Arg
1               5

<210> SEQ ID NO 111
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 111

Lys Tyr Xaa Leu Leu Arg
1               5

<210> SEQ ID NO 112
<211> LENGTH: 6
<212> TYPE: PRT
<213> ORGANISM: Artificial sequence
<220> FEATURE:
<223> OTHER INFORMATION: APIM variant

```
<220> FEATURE:
<221> NAME/KEY: VARIANT
<222> LOCATION: (3)..(3)
<223> OTHER INFORMATION: X is W, F, Y, L, I, V or M

<400> SEQUENCE: 112

Lys Trp Xaa Leu Val Lys
1               5

<210> SEQ ID NO 113
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 113

Lys Phe Xaa Leu Val Lys
1               5

<210> SEQ ID NO 114
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 114

Lys Tyr Xaa Leu Val Lys
1               5

<210> SEQ ID NO 115
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 115

Lys Trp Xaa Leu Val Arg
1               5

<210> SEQ ID NO 116
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 116

Lys Phe Xaa Leu Val Arg
1               5
```

```
<210> SEQ ID NO 117
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 117

Lys Tyr Xaa Leu Val Arg
1               5

<210> SEQ ID NO 118
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 118

Lys Trp Xaa Ile Val Lys
1               5

<210> SEQ ID NO 119
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 119

Lys Phe Xaa Ile Val Lys
1               5

<210> SEQ ID NO 120
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 120

Lys Tyr Xaa Ile Val Lys
1               5

<210> SEQ ID NO 121
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M
```

```
<400> SEQUENCE: 121

Lys Trp Xaa Ile Val Arg
1               5

<210> SEQ ID NO 122
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 122

Lys Phe Xaa Ile Val Arg
1               5

<210> SEQ ID NO 123
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 123

Lys Tyr Xaa Ile Val Arg
1               5

<210> SEQ ID NO 124
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 124

Lys Trp Xaa Leu Ser Lys
1               5

<210> SEQ ID NO 125
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 125

Lys Phe Xaa Leu Ser Lys
1               5

<210> SEQ ID NO 126
<211> LENGTH: 6
<212> TYPE: PRT
<213> ORGANISM: Artificial sequence
<220> FEATURE:
```

```
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 126

Lys Tyr Xaa Leu Ser Lys
1               5

<210> SEQ ID NO 127
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 127

Lys Trp Xaa Leu Ser Arg
1               5

<210> SEQ ID NO 128
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 128

Lys Phe Xaa Leu Ser Arg
1               5

<210> SEQ ID NO 129
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 129

Lys Tyr Xaa Leu Ser Arg
1               5

<210> SEQ ID NO 130
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 130

Lys Trp Xaa Ile Ser Lys
1               5
```

```
<210> SEQ ID NO 131
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 131

Lys Phe Xaa Ile Ser Lys
1               5

<210> SEQ ID NO 132
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 132

Lys Tyr Xaa Ile Ser Lys
1               5

<210> SEQ ID NO 133
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 133

Lys Trp Xaa Ile Ser Arg
1               5

<210> SEQ ID NO 134
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 134

Lys Phe Xaa Ile Ser Arg
1               5

<210> SEQ ID NO 135
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M
```

```
<400> SEQUENCE: 135

Lys Tyr Xaa Ile Ser Arg
1               5

<210> SEQ ID NO 136
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 136

Lys Trp Xaa Ser Val Lys
1               5

<210> SEQ ID NO 137
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 137

Lys Phe Xaa Ser Val Lys
1               5

<210> SEQ ID NO 138
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 138

Lys Tyr Xaa Ser Val Lys
1               5

<210> SEQ ID NO 139
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 139

Lys Trp Xaa Ser Val Arg
1               5

<210> SEQ ID NO 140
<211> LENGTH: 6
<212> TYPE: PRT
<213> ORGANISM: Artificial sequence
```

-continued

```
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 140

Lys Phe Xaa Ser Val Arg
1               5

<210> SEQ ID NO 141
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 141

Lys Tyr Xaa Ser Val Arg
1               5

<210> SEQ ID NO 142
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 142

Lys Trp Xaa Ala Val Lys
1               5

<210> SEQ ID NO 143
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 143

Lys Phe Xaa Ala Val Lys
1               5

<210> SEQ ID NO 144
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 144

Lys Tyr Xaa Ala Val Lys
1               5
```

```
<210> SEQ ID NO 145
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 145

Lys Trp Xaa Ala Val Arg
1               5

<210> SEQ ID NO 146
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 146

Lys Phe Xaa Ala Val Arg
1               5

<210> SEQ ID NO 147
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 147

Lys Tyr Xaa Ala Val Arg
1               5

<210> SEQ ID NO 148
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 148

Lys Trp Xaa Leu Gly Arg
1               5

<210> SEQ ID NO 149
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
```

```
<223> OTHER INFORMATION: X is W, F, Y, L, I, V or M

<400> SEQUENCE: 149

Lys Phe Xaa Leu Gly Arg
1               5

<210> SEQ ID NO 150
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 150

Lys Tyr Xaa Leu Gly Arg
1               5

<210> SEQ ID NO 151
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 151

Lys Trp Xaa Leu Gly Lys
1               5

<210> SEQ ID NO 152
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 152

Lys Phe Xaa Leu Gly Lys
1               5

<210> SEQ ID NO 153
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 153

Lys Tyr Xaa Leu Gly Lys
1               5

<210> SEQ ID NO 154
<211> LENGTH: 6
<212> TYPE: PRT
```

```
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 154

Lys Trp Xaa Leu Ala Arg
1               5

<210> SEQ ID NO 155
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 155

Lys Phe Xaa Leu Ala Arg
1               5

<210> SEQ ID NO 156
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 156

Lys Tyr Xaa Leu Ala Arg
1               5

<210> SEQ ID NO 157
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 157

Lys Trp Xaa Leu Ala Lys
1               5

<210> SEQ ID NO 158
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 158

Lys Phe Xaa Leu Ala Lys
```

-continued

```
1               5

<210> SEQ ID NO 159
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 159

Lys Tyr Xaa Leu Ala Lys
1               5

<210> SEQ ID NO 160
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 160

Lys Trp Xaa Leu Thr Lys
1               5

<210> SEQ ID NO 161
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 161

Lys Phe Xaa Leu Thr Lys
1               5

<210> SEQ ID NO 162
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 162

Lys Tyr Xaa Leu Thr Lys
1               5

<210> SEQ ID NO 163
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
```

<222> LOCATION: (3)..(3)
<223> OTHER INFORMATION: X is W, F, Y, L, I, V or M

<400> SEQUENCE: 163

Lys Trp Xaa Leu Thr Arg
1               5

<210> SEQ ID NO 164
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 164

Lys Phe Xaa Leu Thr Arg
1               5

<210> SEQ ID NO 165
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 165

Lys Tyr Xaa Leu Thr Arg
1               5

<210> SEQ ID NO 166
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 166

Lys Trp Xaa Ile Thr Lys
1               5

<210> SEQ ID NO 167
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 167

Lys Phe Xaa Ile Thr Lys
1               5

<210> SEQ ID NO 168
<211> LENGTH: 6

```
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 168

Lys Tyr Xaa Ile Thr Lys
1               5

<210> SEQ ID NO 169
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 169

Lys Trp Xaa Ile Thr Arg
1               5

<210> SEQ ID NO 170
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 170

Lys Phe Xaa Ile Thr Arg
1               5

<210> SEQ ID NO 171
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 171

Lys Tyr Xaa Ile Thr Arg
1               5

<210> SEQ ID NO 172
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 172
```

```
Lys Trp Xaa Thr Val Lys
1               5

<210> SEQ ID NO 173
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 173

Lys Phe Xaa Thr Val Lys
1               5

<210> SEQ ID NO 174
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 174

Lys Tyr Xaa Thr Val Lys
1               5

<210> SEQ ID NO 175
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 175

Lys Trp Xaa Thr Val Arg
1               5

<210> SEQ ID NO 176
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 176

Lys Phe Xaa Thr Val Arg
1               5

<210> SEQ ID NO 177
<211> LENGTH: 6
<212> TYPE: PRT
<213> ORGANISM: Artificial sequence
<220> FEATURE:
<223> OTHER INFORMATION: APIM variant
<220> FEATURE:
```

-continued

```
<221> NAME/KEY: VARIANT
<222> LOCATION: (3)..(3)
<223> OTHER INFORMATION: X is W, F, Y, L, I, V or M

<400> SEQUENCE: 177

Lys Tyr Xaa Thr Val Arg
1               5

<210> SEQ ID NO 178
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 178

Lys Trp Xaa Leu Arg Lys
1               5

<210> SEQ ID NO 179
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 179

Lys Phe Xaa Leu Arg Lys
1               5

<210> SEQ ID NO 180
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 180

Lys Tyr Xaa Leu Arg Lys
1               5

<210> SEQ ID NO 181
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 181

Lys Trp Xaa Leu Arg Arg
1               5

<210> SEQ ID NO 182
```

```
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 182

Lys Phe Xaa Leu Arg Arg
1               5

<210> SEQ ID NO 183
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 183

Lys Tyr Xaa Leu Arg Arg
1               5

<210> SEQ ID NO 184
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 184

Lys Trp Xaa Ile Arg Lys
1               5

<210> SEQ ID NO 185
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 185

Lys Phe Xaa Ile Arg Lys
1               5

<210> SEQ ID NO 186
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 186
```

```
Lys Tyr Xaa Ile Arg Lys
1               5

<210> SEQ ID NO 187
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 187

Lys Trp Xaa Ile Arg Arg
1               5

<210> SEQ ID NO 188
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 188

Lys Phe Xaa Ile Arg Arg
1               5

<210> SEQ ID NO 189
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 189

Lys Tyr Xaa Ile Arg Arg
1               5

<210> SEQ ID NO 190
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 190

Arg Trp Xaa Val Val Lys
1               5

<210> SEQ ID NO 191
<211> LENGTH: 6
<212> TYPE: PRT
<213> ORGANISM: Artificial sequence
<220> FEATURE:
<223> OTHER INFORMATION: APIM variant
```

```
<220> FEATURE:
<221> NAME/KEY: VARIANT
<222> LOCATION: (3)..(3)
<223> OTHER INFORMATION: X is W, F, Y, L, I, V or M

<400> SEQUENCE: 191

Arg Phe Xaa Val Val Lys
1               5

<210> SEQ ID NO 192
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 192

Arg Tyr Xaa Val Val Lys
1               5

<210> SEQ ID NO 193
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 193

Arg Trp Xaa Val Val Arg
1               5

<210> SEQ ID NO 194
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 194

Arg Phe Xaa Val Val Arg
1               5

<210> SEQ ID NO 195
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 195

Arg Tyr Xaa Val Val Arg
1               5
```

```
<210> SEQ ID NO 196
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 196

Lys Trp Xaa Val Val Lys
1               5

<210> SEQ ID NO 197
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 197

Lys Phe Xaa Val Val Lys
1               5

<210> SEQ ID NO 198
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 198

Lys Tyr Xaa Val Val Lys
1               5

<210> SEQ ID NO 199
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 199

Lys Trp Xaa Val Val Arg
1               5

<210> SEQ ID NO 200
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M
```

```
<400> SEQUENCE: 200

Lys Phe Xaa Val Val Arg
1               5

<210> SEQ ID NO 201
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 201

Lys Tyr Xaa Val Val Arg
1               5

<210> SEQ ID NO 202
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 202

Arg Trp Xaa Ala Leu Lys
1               5

<210> SEQ ID NO 203
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 203

Arg Phe Xaa Ala Leu Lys
1               5

<210> SEQ ID NO 204
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 204

Arg Tyr Xaa Ala Leu Lys
1               5

<210> SEQ ID NO 205
<211> LENGTH: 6
<212> TYPE: PRT
<213> ORGANISM: Artificial sequence
<220> FEATURE:
```

```
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 205

Arg Trp Xaa Ala Leu Arg
1               5

<210> SEQ ID NO 206
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 206

Arg Phe Xaa Ala Leu Arg
1               5

<210> SEQ ID NO 207
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 207

Arg Tyr Xaa Ala Leu Arg
1               5

<210> SEQ ID NO 208
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 208

Lys Trp Xaa Ala Leu Lys
1               5

<210> SEQ ID NO 209
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 209

Lys Phe Xaa Ala Leu Lys
1               5
```

```
<210> SEQ ID NO 210
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 210

Lys Tyr Xaa Ala Leu Lys
1               5

<210> SEQ ID NO 211
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 211

Lys Trp Xaa Ala Leu Arg
1               5

<210> SEQ ID NO 212
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 212

Lys Phe Xaa Ala Leu Arg
1               5

<210> SEQ ID NO 213
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 213

Lys Tyr Xaa Ala Leu Arg
1               5

<210> SEQ ID NO 214
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M
```

<400> SEQUENCE: 214

Arg Trp Xaa Val Leu Lys
1               5

<210> SEQ ID NO 215
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 215

Arg Phe Xaa Val Leu Lys
1               5

<210> SEQ ID NO 216
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 216

Arg Tyr Xaa Val Leu Lys
1               5

<210> SEQ ID NO 217
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 217

Arg Trp Xaa Val Leu Arg
1               5

<210> SEQ ID NO 218
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 218

Arg Phe Xaa Val Leu Arg
1               5

<210> SEQ ID NO 219
<211> LENGTH: 6
<212> TYPE: PRT
<213> ORGANISM: Artificial sequence -continued

```
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 219

Arg Tyr Xaa Val Leu Arg
1               5

<210> SEQ ID NO 220
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 220

Lys Trp Xaa Val Leu Lys
1               5

<210> SEQ ID NO 221
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 221

Lys Phe Xaa Val Leu Lys
1               5

<210> SEQ ID NO 222
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 222

Lys Tyr Xaa Val Leu Lys
1               5

<210> SEQ ID NO 223
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 223

Lys Trp Xaa Val Leu Arg
1               5
```

```
<210> SEQ ID NO 224
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 224

Lys Phe Xaa Val Leu Arg
1               5

<210> SEQ ID NO 225
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 225

Lys Tyr Xaa Val Leu Arg
1               5

<210> SEQ ID NO 226
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 226

Arg Trp Xaa Ile Leu Lys
1               5

<210> SEQ ID NO 227
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 227

Arg Phe Xaa Ile Leu Lys
1               5

<210> SEQ ID NO 228
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
```

```
<223> OTHER INFORMATION: X is W, F, Y, L, I, V or M

<400> SEQUENCE: 228

Arg Tyr Xaa Ile Leu Lys
1               5

<210> SEQ ID NO 229
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 229

Arg Trp Xaa Ile Leu Arg
1               5

<210> SEQ ID NO 230
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 230

Arg Phe Xaa Ile Leu Arg
1               5

<210> SEQ ID NO 231
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 231

Arg Tyr Xaa Ile Leu Arg
1               5

<210> SEQ ID NO 232
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 232

Lys Trp Xaa Ile Leu Lys
1               5

<210> SEQ ID NO 233
<211> LENGTH: 6
<212> TYPE: PRT
```

<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 233

Lys Phe Xaa Ile Leu Lys
1               5

<210> SEQ ID NO 234
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 234

Lys Tyr Xaa Ile Leu Lys
1               5

<210> SEQ ID NO 235
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 235

Lys Trp Xaa Ile Leu Arg
1               5

<210> SEQ ID NO 236
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 236

Lys Phe Xaa Ile Leu Arg
1               5

<210> SEQ ID NO 237
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 237

Lys Tyr Xaa Ile Leu Arg

```
<210> SEQ ID NO 238
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 238

Arg Trp Xaa Val Ile Lys
1               5

<210> SEQ ID NO 239
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 239

Arg Phe Xaa Val Ile Lys
1               5

<210> SEQ ID NO 240
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 240

Arg Tyr Xaa Val Ile Lys
1               5

<210> SEQ ID NO 241
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 241

Arg Trp Xaa Val Ile Arg
1               5

<210> SEQ ID NO 242
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
```

-continued

```
<222> LOCATION: (3)..(3)
<223> OTHER INFORMATION: X is W, F, Y, L, I, V or M

<400> SEQUENCE: 242

Arg Phe Xaa Val Ile Arg
1               5

<210> SEQ ID NO 243
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 243

Arg Tyr Xaa Val Ile Arg
1               5

<210> SEQ ID NO 244
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 244

Lys Trp Xaa Val Ile Lys
1               5

<210> SEQ ID NO 245
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 245

Lys Phe Xaa Val Ile Lys
1               5

<210> SEQ ID NO 246
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 246

Lys Tyr Xaa Val Ile Lys
1               5

<210> SEQ ID NO 247
<211> LENGTH: 6
```

```
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 247

Lys Trp Xaa Val Ile Arg
1               5

<210> SEQ ID NO 248
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 248

Lys Phe Xaa Val Ile Arg
1               5

<210> SEQ ID NO 249
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 249

Lys Tyr Xaa Val Ile Arg
1               5

<210> SEQ ID NO 250
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 250

Arg Trp Xaa Ile Ile Lys
1               5

<210> SEQ ID NO 251
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 251
```

```
Arg Phe Xaa Ile Ile Lys
1               5

<210> SEQ ID NO 252
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 252

Arg Tyr Xaa Ile Ile Lys
1               5

<210> SEQ ID NO 253
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 253

Arg Trp Xaa Ile Ile Arg
1               5

<210> SEQ ID NO 254
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 254

Arg Phe Xaa Ile Ile Arg
1               5

<210> SEQ ID NO 255
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 255

Arg Tyr Xaa Ile Ile Arg
1               5

<210> SEQ ID NO 256
<211> LENGTH: 6
<212> TYPE: PRT
<213> ORGANISM: Artificial sequence
<220> FEATURE:
<223> OTHER INFORMATION: APIM variant
<220> FEATURE:
```

-continued

```
<221> NAME/KEY: VARIANT
<222> LOCATION: (3)..(3)
<223> OTHER INFORMATION: X is W, F, Y, L, I, V or M

<400> SEQUENCE: 256

Lys Trp Xaa Ile Ile Lys
1               5

<210> SEQ ID NO 257
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 257

Lys Phe Xaa Ile Ile Lys
1               5

<210> SEQ ID NO 258
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 258

Lys Tyr Xaa Ile Ile Lys
1               5

<210> SEQ ID NO 259
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 259

Lys Trp Xaa Ile Ile Arg
1               5

<210> SEQ ID NO 260
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 260

Lys Phe Xaa Ile Ile Arg
1               5

<210> SEQ ID NO 261
```

-continued

```
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 261

Lys Tyr Xaa Ile Ile Arg
1               5

<210> SEQ ID NO 262
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 262

Arg Trp Xaa Leu Ile Lys
1               5

<210> SEQ ID NO 263
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 263

Arg Phe Xaa Leu Ile Lys
1               5

<210> SEQ ID NO 264
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 264

Arg Tyr Xaa Leu Ile Lys
1               5

<210> SEQ ID NO 265
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 265
```

Arg Trp Xaa Leu Ile Arg
1               5

<210> SEQ ID NO 266
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 266

Arg Phe Xaa Leu Ile Arg
1               5

<210> SEQ ID NO 267
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 267

Arg Tyr Xaa Leu Ile Arg
1               5

<210> SEQ ID NO 268
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 268

Lys Trp Xaa Leu Ile Lys
1               5

<210> SEQ ID NO 269
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 269

Lys Phe Xaa Leu Ile Lys
1               5

<210> SEQ ID NO 270
<211> LENGTH: 6
<212> TYPE: PRT
<213> ORGANISM: Artificial sequence
<220> FEATURE:
<223> OTHER INFORMATION: APIM variant -continued
<220> FEATURE:
<221> NAME/KEY: VARIANT
<222> LOCATION: (3)..(3)
<223> OTHER INFORMATION: X is W, F, Y, L, I, V or M

<400> SEQUENCE: 270

Lys Tyr Xaa Leu Ile Lys
1               5

<210> SEQ ID NO 271
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 271

Lys Trp Xaa Leu Ile Arg
1               5

<210> SEQ ID NO 272
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 272

Lys Phe Xaa Leu Ile Arg
1               5

<210> SEQ ID NO 273
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 273

Lys Tyr Xaa Leu Ile Arg
1               5

<210> SEQ ID NO 274
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 274

Arg Trp Xaa Ile Ala Lys
1               5

-continued

```
<210> SEQ ID NO 275
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 275

Arg Phe Xaa Ile Ala Lys
1               5

<210> SEQ ID NO 276
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 276

Arg Tyr Xaa Ile Ala Lys
1               5

<210> SEQ ID NO 277
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 277

Arg Trp Xaa Ile Ala Arg
1               5

<210> SEQ ID NO 278
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 278

Arg Phe Xaa Ile Ala Arg
1               5

<210> SEQ ID NO 279
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M
```

-continued

<400> SEQUENCE: 279

Arg Tyr Xaa Ile Ala Arg
1               5

<210> SEQ ID NO 280
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 280

Lys Trp Xaa Ile Ala Lys
1               5

<210> SEQ ID NO 281
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 281

Lys Phe Xaa Ile Ala Lys
1               5

<210> SEQ ID NO 282
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 282

Lys Tyr Xaa Ile Ala Lys
1               5

<210> SEQ ID NO 283
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 283

Lys Trp Xaa Ile Ala Arg
1               5

<210> SEQ ID NO 284
<211> LENGTH: 6
<212> TYPE: PRT
<213> ORGANISM: Artificial sequence
<220> FEATURE:

```
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 284

Lys Phe Xaa Ile Ala Arg
1               5

<210> SEQ ID NO 285
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 285

Lys Tyr Xaa Ile Ala Arg
1               5

<210> SEQ ID NO 286
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 286

Arg Trp Xaa Val Ala Lys
1               5

<210> SEQ ID NO 287
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 287

Arg Phe Xaa Val Ala Lys
1               5

<210> SEQ ID NO 288
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 288

Arg Tyr Xaa Val Ala Lys
1               5
```

```
<210> SEQ ID NO 289
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 289

Arg Trp Xaa Val Ala Arg
1               5

<210> SEQ ID NO 290
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 290

Arg Phe Xaa Val Ala Arg
1               5

<210> SEQ ID NO 291
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 291

Arg Tyr Xaa Val Ala Arg
1               5

<210> SEQ ID NO 292
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 292

Lys Trp Xaa Val Ala Lys
1               5

<210> SEQ ID NO 293
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M
```

<400> SEQUENCE: 293

Lys Phe Xaa Val Ala Lys
1               5

<210> SEQ ID NO 294
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 294

Lys Tyr Xaa Val Ala Lys
1               5

<210> SEQ ID NO 295
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 295

Lys Trp Xaa Val Ala Arg
1               5

<210> SEQ ID NO 296
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 296

Lys Phe Xaa Val Ala Arg
1               5

<210> SEQ ID NO 297
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 297

Lys Tyr Xaa Val Ala Arg
1               5

<210> SEQ ID NO 298
<211> LENGTH: 6
<212> TYPE: PRT
<213> ORGANISM: Artificial sequence

```
<220> FEATURE:
<223> OTHER INFORMATION: APIM variant

<400> SEQUENCE: 298

Arg Trp Leu Val Lys Arg
1               5

<210> SEQ ID NO 299
<211> LENGTH: 6
<212> TYPE: PRT
<213> ORGANISM: Artificial sequence
<220> FEATURE:
<223> OTHER INFORMATION: APIM variant

<400> SEQUENCE: 299

Arg Trp Leu Val Lys Lys
1               5

<210> SEQ ID NO 300
<211> LENGTH: 6
<212> TYPE: PRT
<213> ORGANISM: Artificial sequence
<220> FEATURE:
<223> OTHER INFORMATION: APIM variant

<400> SEQUENCE: 300

Arg Phe Val Val Ile Lys
1               5

<210> SEQ ID NO 301
<211> LENGTH: 6
<212> TYPE: PRT
<213> ORGANISM: Artificial sequence
<220> FEATURE:
<223> OTHER INFORMATION: APIM variant

<400> SEQUENCE: 301

Arg Phe Met Val Ile Lys
1               5

<210> SEQ ID NO 302
<211> LENGTH: 16
<212> TYPE: PRT
<213> ORGANISM: Artificial sequence
<220> FEATURE:
<223> OTHER INFORMATION: Penetratin

<400> SEQUENCE: 302

Arg Gln Ile Lys Ile Trp Phe Gln Asn Arg Arg Met Lys Trp Lys Lys
1               5                   10                  15

<210> SEQ ID NO 303
<211> LENGTH: 7
<212> TYPE: PRT
<213> ORGANISM: Artificial sequence
<220> FEATURE:
<223> OTHER INFORMATION: Penetratin derivative

<400> SEQUENCE: 303

Arg Arg Met Lys Trp Lys Lys
1               5

<210> SEQ ID NO 304
<211> LENGTH: 8
<212> TYPE: PRT
<213> ORGANISM: Artificial sequence
<220> FEATURE:
```

```
<223> OTHER INFORMATION: Penetratin derivative
<220> FEATURE:
<221> NAME/KEY: MOD_RES
<222> LOCATION: (1)..(1)
<223> OTHER INFORMATION: Nle

<400> SEQUENCE: 304

Xaa Arg Arg Met Lys Trp Lys Lys
1               5

<210> SEQ ID NO 305
<211> LENGTH: 9
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (2)..(2)
<223> OTHER INFORMATION: Nle

<400> SEQUENCE: 305

Gln Xaa Arg Arg Met Lys Trp Lys Lys
1               5

<210> SEQ ID NO 306
<211> LENGTH: 10
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (3)..(3)
<223> OTHER INFORMATION: Nle

<400> SEQUENCE: 306

Phe Gln Xaa Arg Arg Met Lys Trp Lys Lys
1               5                  10

<210> SEQ ID NO 307
<211> LENGTH: 7
<212> TYPE: PRT
<213> ORGANISM: Artificial sequence
<220> FEATURE:
<223> OTHER INFORMATION: Penetratin derivative

<400> SEQUENCE: 307

Arg Arg Glu Lys Trp Lys Lys
1               5

<210> SEQ ID NO 308
<211> LENGTH: 7
<212> TYPE: PRT
<213> ORGANISM: Artificial sequence
<220> FEATURE:
<223> OTHER INFORMATION: Penetratin derivative

<400> SEQUENCE: 308

Arg Arg Gln Lys Trp Lys Lys
1               5

<210> SEQ ID NO 309
<211> LENGTH: 7
<212> TYPE: PRT
<213> ORGANISM: Artificial sequence
<220> FEATURE:
<223> OTHER INFORMATION: Penetratin derivative
```

```
<400> SEQUENCE: 309

Lys Arg Met Lys Trp Lys Lys
1               5

<210> SEQ ID NO 310
<211> LENGTH: 7
<212> TYPE: PRT
<213> ORGANISM: Artificial sequence
<220> FEATURE:
<223> OTHER INFORMATION: Penetratin derivative

<400> SEQUENCE: 310

Arg Lys Met Lys Trp Lys Lys
1               5

<210> SEQ ID NO 311
<211> LENGTH: 7
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (3)..(3)
<223> OTHER INFORMATION: Orn

<400> SEQUENCE: 311

Arg Arg Xaa Lys Trp Lys Lys
1               5

<210> SEQ ID NO 312
<211> LENGTH: 7
<212> TYPE: PRT
<213> ORGANISM: Artificial sequence
<220> FEATURE:
<223> OTHER INFORMATION: Penetratin derivative

<400> SEQUENCE: 312

Arg Arg Met Lys Gln Lys Lys
1               5

<210> SEQ ID NO 313
<211> LENGTH: 7
<212> TYPE: PRT
<213> ORGANISM: Artificial sequence
<220> FEATURE:
<223> OTHER INFORMATION: Penetratin derivative

<400> SEQUENCE: 313

Arg Arg Met Lys Trp Phe Lys
1               5

<210> SEQ ID NO 314
<211> LENGTH: 7
<212> TYPE: PRT
<213> ORGANISM: Artificial sequence
<220> FEATURE:
<223> OTHER INFORMATION: Penetratin derivative
<220> FEATURE:
<221> NAME/KEY: MOD_RES
<222> LOCATION: (2)..(2)
<223> OTHER INFORMATION: Orn

<400> SEQUENCE: 314

Arg Xaa Arg Lys Trp Lys Lys
1               5
```

```
<210> SEQ ID NO 315
<211> LENGTH: 7
<212> TYPE: PRT
<213> ORGANISM: Artificial sequence
<220> FEATURE:
<223> OTHER INFORMATION: Penetratin derivative

<400> SEQUENCE: 315

Arg Arg Met Trp Lys Lys Lys
1               5

<210> SEQ ID NO 316
<211> LENGTH: 7
<212> TYPE: PRT
<213> ORGANISM: Artificial sequence
<220> FEATURE:
<223> OTHER INFORMATION: Penetratin derivative

<400> SEQUENCE: 316

Arg Arg Met Lys Lys Trp Lys
1               5

<210> SEQ ID NO 317
<211> LENGTH: 16
<212> TYPE: PRT
<213> ORGANISM: Artificial sequence
<220> FEATURE:
<223> OTHER INFORMATION: D-penetratin

<400> SEQUENCE: 317

Arg Gln Ile Lys Ile Trp Phe Gln Asn Arg Arg Met Lys Trp Lys Lys
1               5                   10                  15

<210> SEQ ID NO 318
<211> LENGTH: 18
<212> TYPE: PRT
<213> ORGANISM: Artificial sequence
<220> FEATURE:
<223> OTHER INFORMATION: Pegelin (SynB)

<400> SEQUENCE: 318

Arg Gly Gly Arg Leu Ser Tyr Ser Arg Arg Phe Ser Thr Ser Thr
1               5                   10                  15

Gly Arg

<210> SEQ ID NO 319
<211> LENGTH: 13
<212> TYPE: PRT
<213> ORGANISM: Artificial sequence
<220> FEATURE:
<223> OTHER INFORMATION: HIV-TAT

<400> SEQUENCE: 319

Gly Arg Lys Lys Arg Arg Gln Arg Arg Arg Pro Pro Gln
1               5                   10

<210> SEQ ID NO 320
<211> LENGTH: 11
<212> TYPE: PRT
<213> ORGANISM: Artificial sequence
<220> FEATURE:
<223> OTHER INFORMATION: Residues 47-57 of HIV-TAT

<400> SEQUENCE: 320

Tyr Gly Arg Lys Lys Arg Arg Gln Arg Arg Arg
1               5                   10
```

```
<210> SEQ ID NO 321
<211> LENGTH: 33
<212> TYPE: PRT
<213> ORGANISM: Artificial sequence
<220> FEATURE:
<223> OTHER INFORMATION: VP22

<400> SEQUENCE: 321

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Val
            20                  25                  30

Asp

<210> SEQ ID NO 322
<211> LENGTH: 18
<212> TYPE: PRT
<213> ORGANISM: Artificial sequence
<220> FEATURE:
<223> OTHER INFORMATION: MAP

<400> SEQUENCE: 322

Lys Leu Ala Leu Lys Leu Ala Leu Lys Ala Leu Lys Ala Ala Leu Lys
1               5                   10                  15

Leu Ala

<210> SEQ ID NO 323
<211> LENGTH: 27
<212> TYPE: PRT
<213> ORGANISM: Artificial sequence
<220> FEATURE:
<223> OTHER INFORMATION: Transportan

<400> SEQUENCE: 323

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 324
<211> LENGTH: 21
<212> TYPE: PRT
<213> ORGANISM: Artificial sequence
<220> FEATURE:
<223> OTHER INFORMATION: Transportan-10

<400> SEQUENCE: 324

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 325
<211> LENGTH: 30
<212> TYPE: PRT
<213> ORGANISM: Artificial sequence
<220> FEATURE:
<223> OTHER INFORMATION: KALA

<400> SEQUENCE: 325

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
```

-continued

```
                    20                  25                  30

<210> SEQ ID NO 326
<211> LENGTH: 21
<212> TYPE: PRT
<213> ORGANISM: Artificial sequence
<220> FEATURE:
<223> OTHER INFORMATION: Pep-1

<400> SEQUENCE: 326

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 327
<211> LENGTH: 21
<212> TYPE: PRT
<213> ORGANISM: Artificial sequence
<220> FEATURE:
<223> OTHER INFORMATION: Pep-2

<400> SEQUENCE: 327

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 328
<211> LENGTH: 27
<212> TYPE: PRT
<213> ORGANISM: Artificial sequence
<220> FEATURE:
<223> OTHER INFORMATION: MPG

<400> SEQUENCE: 328

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 329
<211> LENGTH: 19
<212> TYPE: PRT
<213> ORGANISM: Artificial sequence
<220> FEATURE:
<223> OTHER INFORMATION: Vectocell peptide

<400> SEQUENCE: 329

Val Lys Arg Gly Leu Lys Leu Arg His Val Arg Pro Arg Val Thr Arg
1               5                   10                  15

Met Asp Val

<210> SEQ ID NO 330
<211> LENGTH: 14
<212> TYPE: PRT
<213> ORGANISM: Artificial sequence
<220> FEATURE:
<223> OTHER INFORMATION: Vectocell peptide

<400> SEQUENCE: 330

Ser Arg Arg Ala Arg Arg Ser Pro Arg His Leu Gly Ser Gly
1               5                   10
```

```
<210> SEQ ID NO 331
<211> LENGTH: 16
<212> TYPE: PRT
<213> ORGANISM: Artificial sequence
<220> FEATURE:
<223> OTHER INFORMATION: Vectocell peptide

<400> SEQUENCE: 331

Leu Arg Arg Glu Arg Gln Ser Arg Leu Arg Arg Glu Arg Gln Ser Arg
1               5                   10                  15

<210> SEQ ID NO 332
<211> LENGTH: 22
<212> TYPE: PRT
<213> ORGANISM: Artificial sequence
<220> FEATURE:
<223> OTHER INFORMATION: Vectocell peptide

<400> SEQUENCE: 332

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 333
<211> LENGTH: 29
<212> TYPE: PRT
<213> ORGANISM: Artificial sequence
<220> FEATURE:
<223> OTHER INFORMATION: Wr-T transporter
<220> FEATURE:
<221> NAME/KEY: variant
<222> LOCATION: (22)..(29)
<223> OTHER INFORMATION: /REPLACE= D enantiomer arginine

<400> SEQUENCE: 333

Lys Glu Thr Trp Trp Glu Thr Trp Trp Thr Glu Trp Trp Thr Glu Trp
1               5                   10                  15

Ser Gln Gly Pro Gly Xaa Xaa Xaa Xaa Xaa Xaa Xaa
            20                  25

<210> SEQ ID NO 334
<211> LENGTH: 7
<212> TYPE: PRT
<213> ORGANISM: Artificial sequence
<220> FEATURE:
<223> OTHER INFORMATION: R7

<400> SEQUENCE: 334

Arg Arg Arg Arg Arg Arg Arg
1               5

<210> SEQ ID NO 335
<211> LENGTH: 9
<212> TYPE: PRT
<213> ORGANISM: Artificial sequence
<220> FEATURE:
<223> OTHER INFORMATION: HIV-TAT peptide

<400> SEQUENCE: 335

Arg Lys Lys Arg Arg Gln Arg Arg Arg
1               5

<210> SEQ ID NO 336
<211> LENGTH: 8
<212> TYPE: PRT
<213> ORGANISM: Artificial sequence
```

<220> FEATURE:
<223> OTHER INFORMATION: R8

<400> SEQUENCE: 336

Arg Arg Arg Arg Arg Arg Arg Arg
1               5

<210> SEQ ID NO 337
<211> LENGTH: 11
<212> TYPE: PRT
<213> ORGANISM: Artificial sequence
<220> FEATURE:
<223> OTHER INFORMATION: R11

<400> SEQUENCE: 337

Arg Arg Arg Arg Arg Arg Arg Arg Arg Arg Arg
1               5                   10

<210> SEQ ID NO 338
<211> LENGTH: 10
<212> TYPE: PRT
<213> ORGANISM: Artificial sequence
<220> FEATURE:
<223> OTHER INFORMATION: QSR8

<400> SEQUENCE: 338

Gln Ser Arg Arg Arg Arg Arg Arg Arg Arg
1               5                   10

<210> SEQ ID NO 339
<211> LENGTH: 14
<212> TYPE: PRT
<213> ORGANISM: Artificial sequence
<220> FEATURE:
<223> OTHER INFORMATION: HIV-Tat derivative

<400> SEQUENCE: 339

Gly Arg Lys Lys Arg Arg Gln Arg Arg Arg Pro Pro Gln Gln
1               5                   10

<210> SEQ ID NO 340
<211> LENGTH: 13
<212> TYPE: PRT
<213> ORGANISM: Human immunodeficiency virus type 1

<400> SEQUENCE: 340

Gly Arg Lys Lys Arg Arg Gln Arg Arg Arg Pro Pro Gln
1               5                   10

<210> SEQ ID NO 341
<211> LENGTH: 18
<212> TYPE: PRT
<213> ORGANISM: Human immunodeficiency virus type 1

<400> SEQUENCE: 341

Leu Gly Ile Ser Tyr Gly Arg Lys Lys Arg Arg Gln Arg Arg Arg Pro
1               5                   10                  15

Pro Gln

<210> SEQ ID NO 342
<211> LENGTH: 23
<212> TYPE: PRT
<213> ORGANISM: Human immunodeficiency virus type 1

<400> SEQUENCE: 342

```
Phe Ile Thr Lys Ala Leu Gly Ile Ser Tyr Gly Arg Lys Lys Arg Arg
1               5                   10                  15

Gln Arg Arg Arg Pro Pro Gln
            20

<210> SEQ ID NO 343
<211> LENGTH: 16
<212> TYPE: PRT
<213> ORGANISM: Human immunodeficiency virus type 1

<400> SEQUENCE: 343

Phe Ile Thr Lys Ala Leu Gly Ile Ser Tyr Gly Arg Lys Lys Arg Arg
1               5                   10                  15

<210> SEQ ID NO 344
<211> LENGTH: 10
<212> TYPE: PRT
<213> ORGANISM: Human immunodeficiency virus type 1

<400> SEQUENCE: 344

Gly Arg Lys Lys Arg Arg Gln Arg Arg Arg
1               5                   10

<210> SEQ ID NO 345
<211> LENGTH: 9
<212> TYPE: PRT
<213> ORGANISM: Human immunodeficiency virus type 1

<400> SEQUENCE: 345

Arg Lys Lys Arg Arg Gln Arg Arg Arg
1               5

<210> SEQ ID NO 346
<211> LENGTH: 8
<212> TYPE: PRT
<213> ORGANISM: Human immunodeficiency virus type 1

<400> SEQUENCE: 346

Arg Lys Lys Arg Arg Gln Arg Arg
1               5

<210> SEQ ID NO 347
<211> LENGTH: 7
<212> TYPE: PRT
<213> ORGANISM: Human immunodeficiency virus type 1

<400> SEQUENCE: 347

Arg Lys Lys Arg Arg Gln Arg
1               5

<210> SEQ ID NO 348
<211> LENGTH: 8
<212> TYPE: PRT
<213> ORGANISM: Human immunodeficiency virus type 1

<400> SEQUENCE: 348

Lys Lys Arg Arg Gln Arg Arg Arg
1               5

<210> SEQ ID NO 349
<211> LENGTH: 7
<212> TYPE: PRT
<213> ORGANISM: Human immunodeficiency virus type 1

<400> SEQUENCE: 349
```

Lys Arg Arg Gln Arg Arg Arg
1               5

<210> SEQ ID NO 350
<211> LENGTH: 9
<212> TYPE: PRT
<213> ORGANISM: Human immunodeficiency virus type 1

<400> SEQUENCE: 350

Arg Lys Lys Arg Arg Gln Arg Arg Arg
1               5

<210> SEQ ID NO 351
<211> LENGTH: 9
<212> TYPE: PRT
<213> ORGANISM: Human immunodeficiency virus type 1

<400> SEQUENCE: 351

Arg Arg Arg Gln Arg Arg Lys Lys Arg
1               5

<210> SEQ ID NO 352
<211> LENGTH: 9
<212> TYPE: PRT
<213> ORGANISM: Human immunodeficiency virus type 1

<400> SEQUENCE: 352

Arg Arg Arg Gln Arg Arg Lys Lys Arg
1               5

<210> SEQ ID NO 353
<211> LENGTH: 9
<212> TYPE: PRT
<213> ORGANISM: Human immunodeficiency virus type 1

<400> SEQUENCE: 353

Ala Lys Lys Arg Arg Gln Arg Arg Arg
1               5

<210> SEQ ID NO 354
<211> LENGTH: 9
<212> TYPE: PRT
<213> ORGANISM: Human immunodeficiency virus type 1

<400> SEQUENCE: 354

Arg Ala Lys Arg Arg Gln Arg Arg Arg
1               5

<210> SEQ ID NO 355
<211> LENGTH: 9
<212> TYPE: PRT
<213> ORGANISM: Human immunodeficiency virus type 1

<400> SEQUENCE: 355

Arg Lys Ala Arg Arg Gln Arg Arg Arg
1               5

<210> SEQ ID NO 356
<211> LENGTH: 9
<212> TYPE: PRT
<213> ORGANISM: Human immunodeficiency virus type 1

<400> SEQUENCE: 356

Arg Lys Lys Ala Arg Gln Arg Arg Arg

```
1               5
```

<210> SEQ ID NO 357
<211> LENGTH: 9
<212> TYPE: PRT
<213> ORGANISM: Human immunodeficiency virus type 1

<400> SEQUENCE: 357

```
Arg Lys Lys Arg Ala Gln Arg Arg
1               5
```

<210> SEQ ID NO 358
<211> LENGTH: 9
<212> TYPE: PRT
<213> ORGANISM: Human immunodeficiency virus type 1

<400> SEQUENCE: 358

```
Arg Lys Lys Arg Arg Ala Arg Arg
1               5
```

<210> SEQ ID NO 359
<211> LENGTH: 9
<212> TYPE: PRT
<213> ORGANISM: Human immunodeficiency virus type 1

<400> SEQUENCE: 359

```
Arg Lys Lys Arg Arg Gln Ala Arg Arg
1               5
```

<210> SEQ ID NO 360
<211> LENGTH: 9
<212> TYPE: PRT
<213> ORGANISM: Human immunodeficiency virus type 1

<400> SEQUENCE: 360

```
Arg Lys Lys Arg Arg Gln Arg Ala Arg
1               5
```

<210> SEQ ID NO 361
<211> LENGTH: 9
<212> TYPE: PRT
<213> ORGANISM: Human immunodeficiency virus type 1

<400> SEQUENCE: 361

```
Arg Lys Lys Arg Arg Gln Arg Arg Ala
1               5
```

<210> SEQ ID NO 362
<211> LENGTH: 13
<212> TYPE: PRT
<213> ORGANISM: Human immunodeficiency virus type 1

<400> SEQUENCE: 362

```
Gly Arg Lys Lys Arg Arg Gln Arg Arg Pro Pro Gln Cys
1               5                   10
```

<210> SEQ ID NO 363
<211> LENGTH: 12
<212> TYPE: PRT
<213> ORGANISM: Human immunodeficiency virus type 1

<400> SEQUENCE: 363

```
Gly Arg Lys Lys Arg Arg Gln Arg Pro Pro Gln Cys
1               5                   10
```

<210> SEQ ID NO 364
<211> LENGTH: 11
<212> TYPE: PRT
<213> ORGANISM: Human immunodeficiency virus type 1

<400> SEQUENCE: 364

Gly Arg Lys Lys Arg Arg Gln Pro Pro Gln Cys
1               5                   10

<210> SEQ ID NO 365
<211> LENGTH: 11
<212> TYPE: PRT
<213> ORGANISM: Human immunodeficiency virus type 1

<400> SEQUENCE: 365

Gly Arg Lys Lys Arg Arg Gln Arg Arg Arg Cys
1               5                   10

<210> SEQ ID NO 366
<211> LENGTH: 14
<212> TYPE: PRT
<213> ORGANISM: Human immunodeficiency virus type 1

<400> SEQUENCE: 366

Gly Arg Lys Lys Arg Arg Gln Arg Ala Arg Pro Pro Gln Cys
1               5                   10

<210> SEQ ID NO 367
<211> LENGTH: 14
<212> TYPE: PRT
<213> ORGANISM: Human immunodeficiency virus type 1

<400> SEQUENCE: 367

Gly Arg Lys Lys Arg Arg Gln Ala Arg Ala Pro Pro Gln Cys
1               5                   10

<210> SEQ ID NO 368
<211> LENGTH: 17
<212> TYPE: PRT
<213> ORGANISM: Human immunodeficiency virus type 1

<400> SEQUENCE: 368

Thr Arg Gln Ala Arg Arg Asn Arg Arg Arg Arg Trp Arg Glu Arg Gln
1               5                   10                  15

Arg

<210> SEQ ID NO 369
<211> LENGTH: 30
<212> TYPE: PRT
<213> ORGANISM: Homo sapiens

<400> SEQUENCE: 369

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
                20                  25                  30

<210> SEQ ID NO 370
<211> LENGTH: 14
<212> TYPE: PRT
<213> ORGANISM: Vespula vulgaris

<400> SEQUENCE: 370

```
Ile Asn Leu Lys Ala Leu Ala Ala Leu Ala Lys Lys Ile Leu
1               5                   10
```

<210> SEQ ID NO 371
<211> LENGTH: 16
<212> TYPE: PRT
<213> ORGANISM: Drosophila melanogaster

<400> SEQUENCE: 371

```
Arg Gln Ile Lys Ile Trp Phe Gln Asn Arg Arg Met Lys Trp Lys Lys
1               5                   10                  15
```

<210> SEQ ID NO 372
<211> LENGTH: 16
<212> TYPE: PRT
<213> ORGANISM: Drosophila melanogaster

<400> SEQUENCE: 372

```
Arg Gln Ile Lys Ile Trp Phe Gln Asn Arg Arg Met Lys Trp Lys Lys
1               5                   10                  15
```

<210> SEQ ID NO 373
<211> LENGTH: 16
<212> TYPE: PRT
<213> ORGANISM: Drosophila melanogaster

<400> SEQUENCE: 373

```
Lys Lys Trp Lys Met Arg Arg Asn Gln Phe Trp Ile Lys Ile Gln Arg
1               5                   10                  15
```

<210> SEQ ID NO 374
<211> LENGTH: 16
<212> TYPE: PRT
<213> ORGANISM: Drosophila melanogaster

<400> SEQUENCE: 374

```
Arg Gln Ile Lys Ile Trp Phe Gln Asn Arg Arg Met Lys Trp Lys Lys
1               5                   10                  15
```

<210> SEQ ID NO 375
<211> LENGTH: 16
<212> TYPE: PRT
<213> ORGANISM: Drosophila melanogaster

<400> SEQUENCE: 375

```
Arg Gln Ile Lys Ile Trp Phe Pro Asn Arg Arg Met Lys Trp Lys Lys
1               5                   10                  15
```

<210> SEQ ID NO 376
<211> LENGTH: 16
<212> TYPE: PRT
<213> ORGANISM: Drosophila melanogaster

<400> SEQUENCE: 376

```
Arg Gln Pro Lys Ile Trp Phe Pro Asn Arg Arg Lys Pro Trp Lys Lys
1               5                   10                  15
```

<210> SEQ ID NO 377
<211> LENGTH: 16
<212> TYPE: PRT
<213> ORGANISM: Drosophila melanogaster

<400> SEQUENCE: 377

```
Arg Gln Ile Lys Ile Trp Phe Gln Asn Arg Arg Met Lys Trp Lys Lys
1               5                   10                  15
```

<210> SEQ ID NO 378
<211> LENGTH: 15
<212> TYPE: PRT
<213> ORGANISM: Drosophila melanogaster

<400> SEQUENCE: 378

Arg Gln Ile Lys Ile Trp Phe Gln Asn Arg Arg Met Lys Trp Lys
1               5                   10                  15

<210> SEQ ID NO 379
<211> LENGTH: 14
<212> TYPE: PRT
<213> ORGANISM: Drosophila melanogaster

<400> SEQUENCE: 379

Arg Gln Ile Lys Ile Trp Phe Gln Asn Arg Arg Met Lys Trp
1               5                   10

<210> SEQ ID NO 380
<211> LENGTH: 13
<212> TYPE: PRT
<213> ORGANISM: Drosophila melanogaster

<400> SEQUENCE: 380

Arg Gln Ile Lys Ile Trp Phe Gln Asn Arg Arg Met Lys
1               5                   10

<210> SEQ ID NO 381
<211> LENGTH: 12
<212> TYPE: PRT
<213> ORGANISM: Drosophila melanogaster

<400> SEQUENCE: 381

Arg Gln Ile Lys Ile Trp Phe Gln Asn Arg Arg Met
1               5                   10

<210> SEQ ID NO 382
<211> LENGTH: 11
<212> TYPE: PRT
<213> ORGANISM: Drosophila melanogaster

<400> SEQUENCE: 382

Arg Gln Ile Lys Ile Trp Phe Gln Asn Arg Arg
1               5                   10

<210> SEQ ID NO 383
<211> LENGTH: 10
<212> TYPE: PRT
<213> ORGANISM: Drosophila melanogaster

<400> SEQUENCE: 383

Arg Gln Ile Lys Ile Trp Phe Gln Asn Arg
1               5                   10

<210> SEQ ID NO 384
<211> LENGTH: 9
<212> TYPE: PRT
<213> ORGANISM: Drosophila melanogaster

<400> SEQUENCE: 384

Arg Gln Ile Lys Ile Trp Phe Gln Asn
1               5

<210> SEQ ID NO 385
<211> LENGTH: 8
<212> TYPE: PRT
<213> ORGANISM: Drosophila melanogaster

<400> SEQUENCE: 385

Arg Gln Ile Lys Ile Trp Phe Gln
1               5

<210> SEQ ID NO 386
<211> LENGTH: 6
<212> TYPE: PRT
<213> ORGANISM: Drosophila melanogaster

<400> SEQUENCE: 386

Arg Gln Ile Lys Ile Trp
1               5

<210> SEQ ID NO 387
<211> LENGTH: 15
<212> TYPE: PRT
<213> ORGANISM: Drosophila melanogaster

<400> SEQUENCE: 387

Gln Ile Lys Ile Trp Phe Gln Asn Arg Arg Met Lys Trp Lys Lys
1               5                   10                  15

<210> SEQ ID NO 388
<211> LENGTH: 14
<212> TYPE: PRT
<213> ORGANISM: Drosophila melanogaster

<400> SEQUENCE: 388

Ile Lys Ile Trp Phe Gln Asn Arg Arg Met Lys Trp Lys Lys
1               5                   10

<210> SEQ ID NO 389
<211> LENGTH: 13
<212> TYPE: PRT
<213> ORGANISM: Drosophila melanogaster

<400> SEQUENCE: 389

Lys Ile Trp Phe Gln Asn Arg Arg Met Lys Trp Lys Lys
1               5                   10

<210> SEQ ID NO 390
<211> LENGTH: 12
<212> TYPE: PRT
<213> ORGANISM: Drosophila melanogaster

<400> SEQUENCE: 390

Ile Trp Phe Gln Asn Arg Arg Met Lys Trp Lys Lys
1               5                   10

<210> SEQ ID NO 391
<211> LENGTH: 11
<212> TYPE: PRT
<213> ORGANISM: Drosophila melanogaster

<400> SEQUENCE: 391

Trp Phe Gln Asn Arg Arg Met Lys Trp Lys Lys
1               5                   10

<210> SEQ ID NO 392
<211> LENGTH: 10

```
<212> TYPE: PRT
<213> ORGANISM: Drosophila melanogaster

<400> SEQUENCE: 392

Phe Gln Asn Arg Arg Met Lys Trp Lys Lys
1               5                   10

<210> SEQ ID NO 393
<211> LENGTH: 9
<212> TYPE: PRT
<213> ORGANISM: Drosophila melanogaster

<400> SEQUENCE: 393

Gln Asn Arg Arg Met Lys Trp Lys Lys
1               5

<210> SEQ ID NO 394
<211> LENGTH: 8
<212> TYPE: PRT
<213> ORGANISM: Drosophila melanogaster

<400> SEQUENCE: 394

Asn Arg Arg Met Lys Trp Lys Lys
1               5

<210> SEQ ID NO 395
<211> LENGTH: 7
<212> TYPE: PRT
<213> ORGANISM: Drosophila melanogaster

<400> SEQUENCE: 395

Arg Arg Met Lys Trp Lys Lys
1               5

<210> SEQ ID NO 396
<211> LENGTH: 6
<212> TYPE: PRT
<213> ORGANISM: Drosophila melanogaster

<400> SEQUENCE: 396

Arg Met Lys Trp Lys Lys
1               5

<210> SEQ ID NO 397
<211> LENGTH: 16
<212> TYPE: PRT
<213> ORGANISM: Drosophila melanogaster

<400> SEQUENCE: 397

Ala Gln Ile Lys Ile Trp Phe Gln Asn Arg Arg Met Lys Trp Lys Lys
1               5                   10                  15

<210> SEQ ID NO 398
<211> LENGTH: 16
<212> TYPE: PRT
<213> ORGANISM: Drosophila melanogaster

<400> SEQUENCE: 398

Arg Ala Ile Lys Ile Trp Phe Gln Asn Arg Arg Met Lys Trp Lys Lys
1               5                   10                  15

<210> SEQ ID NO 399
<211> LENGTH: 16
<212> TYPE: PRT
<213> ORGANISM: Drosophila melanogaster
```

<400> SEQUENCE: 399

Arg Gln Ala Lys Ile Trp Phe Gln Asn Arg Arg Met Lys Trp Lys Lys
1               5                   10                  15

<210> SEQ ID NO 400
<211> LENGTH: 16
<212> TYPE: PRT
<213> ORGANISM: Drosophila melanogaster

<400> SEQUENCE: 400

Arg Gln Ile Ala Ile Trp Phe Gln Asn Arg Arg Met Lys Trp Lys Lys
1               5                   10                  15

<210> SEQ ID NO 401
<211> LENGTH: 16
<212> TYPE: PRT
<213> ORGANISM: Drosophila melanogaster

<400> SEQUENCE: 401

Arg Gln Ile Lys Ala Trp Phe Gln Asn Arg Arg Met Lys Trp Lys Lys
1               5                   10                  15

<210> SEQ ID NO 402
<211> LENGTH: 16
<212> TYPE: PRT
<213> ORGANISM: Drosophila melanogaster

<400> SEQUENCE: 402

Arg Gln Ile Lys Ile Ala Phe Gln Asn Arg Arg Met Lys Trp Lys Lys
1               5                   10                  15

<210> SEQ ID NO 403
<211> LENGTH: 16
<212> TYPE: PRT
<213> ORGANISM: Drosophila melanogaster

<400> SEQUENCE: 403

Arg Gln Ile Lys Ile Trp Ala Gln Asn Arg Arg Met Lys Trp Lys Lys
1               5                   10                  15

<210> SEQ ID NO 404
<211> LENGTH: 16
<212> TYPE: PRT
<213> ORGANISM: Drosophila melanogaster

<400> SEQUENCE: 404

Arg Gln Ile Lys Ile Trp Phe Ala Asn Arg Arg Met Lys Trp Lys Lys
1               5                   10                  15

<210> SEQ ID NO 405
<211> LENGTH: 16
<212> TYPE: PRT
<213> ORGANISM: Drosophila melanogaster

<400> SEQUENCE: 405

Arg Gln Ile Lys Ile Trp Phe Gln Ala Arg Arg Met Lys Trp Lys Lys
1               5                   10                  15

<210> SEQ ID NO 406
<211> LENGTH: 16
<212> TYPE: PRT
<213> ORGANISM: Drosophila melanogaster

<400> SEQUENCE: 406

Arg Gln Ile Lys Ile Trp Phe Gln Asn Ala Arg Met Lys Trp Lys Lys
1               5                   10                  15

<210> SEQ ID NO 407
<211> LENGTH: 16
<212> TYPE: PRT
<213> ORGANISM: Drosophila melanogaster

<400> SEQUENCE: 407

Arg Gln Ile Lys Ile Trp Phe Gln Asn Arg Ala Met Lys Trp Lys Lys
1               5                   10                  15

<210> SEQ ID NO 408
<211> LENGTH: 16
<212> TYPE: PRT
<213> ORGANISM: Drosophila melanogaster

<400> SEQUENCE: 408

Arg Gln Ile Lys Ile Trp Phe Gln Asn Arg Arg Ala Lys Trp Lys Lys
1               5                   10                  15

<210> SEQ ID NO 409
<211> LENGTH: 16
<212> TYPE: PRT
<213> ORGANISM: Drosophila melanogaster

<400> SEQUENCE: 409

Arg Gln Ile Lys Ile Trp Phe Gln Asn Arg Arg Met Ala Trp Lys Lys
1               5                   10                  15

<210> SEQ ID NO 410
<211> LENGTH: 16
<212> TYPE: PRT
<213> ORGANISM: Drosophila melanogaster

<400> SEQUENCE: 410

Arg Gln Ile Lys Ile Trp Phe Gln Asn Arg Arg Met Lys Ala Lys Lys
1               5                   10                  15

<210> SEQ ID NO 411
<211> LENGTH: 16
<212> TYPE: PRT
<213> ORGANISM: Drosophila melanogaster

<400> SEQUENCE: 411

Arg Gln Ile Lys Ile Trp Phe Gln Asn Arg Arg Met Lys Trp Ala Lys
1               5                   10                  15

<210> SEQ ID NO 412
<211> LENGTH: 16
<212> TYPE: PRT
<213> ORGANISM: Drosophila melanogaster

<400> SEQUENCE: 412

Arg Gln Ile Lys Ile Trp Phe Gln Asn Arg Arg Met Lys Trp Lys Ala
1               5                   10                  15

<210> SEQ ID NO 413
<211> LENGTH: 18
<212> TYPE: PRT
<213> ORGANISM: Drosophila melanogaster

<400> SEQUENCE: 413

Cys Arg Gln Ile Lys Ile Trp Phe Pro Asn Arg Arg Met Lys Trp Lys

```
1               5                  10                  15
Lys Cys

<210> SEQ ID NO 414
<211> LENGTH: 16
<212> TYPE: PRT
<213> ORGANISM: Drosophila melanogaster

<400> SEQUENCE: 414

Arg Gln Ile Lys Ile Trp Phe Pro Asn Arg Arg Met Lys Trp Lys Lys
1               5                  10                  15

<210> SEQ ID NO 415
<211> LENGTH: 16
<212> TYPE: PRT
<213> ORGANISM: Drosophila melanogaster

<400> SEQUENCE: 415

Arg Gln Ile Lys Ile Trp Phe Gln Asn Arg Arg Met Lys Trp Lys Lys
1               5                  10                  15

<210> SEQ ID NO 416
<211> LENGTH: 16
<212> TYPE: PRT
<213> ORGANISM: Drosophila melanogaster

<400> SEQUENCE: 416

Arg Gln Ile Lys Ile Phe Phe Gln Asn Arg Arg Met Lys Phe Lys Lys
1               5                  10                  15

<210> SEQ ID NO 417
<211> LENGTH: 16
<212> TYPE: PRT
<213> ORGANISM: Drosophila melanogaster

<400> SEQUENCE: 417

Arg Gln Ile Arg Ile Trp Phe Gln Asn Arg Arg Met Arg Trp Arg Arg
1               5                  10                  15

<210> SEQ ID NO 418
<211> LENGTH: 13
<212> TYPE: PRT
<213> ORGANISM: Human immunodeficiency virus type 1

<400> SEQUENCE: 418

Gly Arg Lys Lys Arg Arg Gln Arg Arg Arg Pro Trp Gln
1               5                  10

<210> SEQ ID NO 419
<211> LENGTH: 13
<212> TYPE: PRT
<213> ORGANISM: Human immunodeficiency virus type 1

<400> SEQUENCE: 419

Gly Arg Lys Lys Arg Arg Gln Arg Arg Arg Pro Trp Gln
1               5                  10

<210> SEQ ID NO 420
<211> LENGTH: 16
<212> TYPE: PRT
<213> ORGANISM: Drosophila melanogaster

<400> SEQUENCE: 420

Arg Gln Ile Arg Ile Trp Phe Gln Asn Arg Arg Met Arg Trp Arg Arg
```

<210> SEQ ID NO 421
<211> LENGTH: 16
<212> TYPE: PRT
<213> ORGANISM: Drosophila melanogaster

<400> SEQUENCE: 421

Arg Arg Trp Arg Arg Trp Trp Arg Arg Trp Trp Arg Arg Trp Arg Arg
1               5                   10                  15

<210> SEQ ID NO 422
<211> LENGTH: 16
<212> TYPE: PRT
<213> ORGANISM: Drosophila melanogaster

<400> SEQUENCE: 422

Arg Gln Ile Lys Ile Trp Phe Gln Asn Met Arg Arg Lys Trp Lys Lys
1               5                   10                  15

<210> SEQ ID NO 423
<211> LENGTH: 13
<212> TYPE: PRT
<213> ORGANISM: Crotalus durissus

<400> SEQUENCE: 423

Lys Met Asp Cys Arg Trp Arg Trp Lys Cys Cys Lys Lys
1               5                   10

<210> SEQ ID NO 424
<211> LENGTH: 12
<212> TYPE: PRT
<213> ORGANISM: Crotalus durissus

<400> SEQUENCE: 424

Met Asp Cys Arg Trp Arg Trp Lys Cys Cys Lys Lys
1               5                   10

<210> SEQ ID NO 425
<211> LENGTH: 11
<212> TYPE: PRT
<213> ORGANISM: Crotalus durissus

<400> SEQUENCE: 425

Asp Cys Arg Trp Arg Trp Lys Cys Cys Lys Lys
1               5                   10

<210> SEQ ID NO 426
<211> LENGTH: 10
<212> TYPE: PRT
<213> ORGANISM: Crotalus durissus

<400> SEQUENCE: 426

Cys Arg Trp Arg Trp Lys Cys Cys Lys Lys
1 5 10

<210> SEQ ID NO 427
<211> LENGTH: 9
<212> TYPE: PRT
<213> ORGANISM: Crotalus durissus

<400> SEQUENCE: 427

Arg Trp Arg Trp Lys Cys Cys Lys Lys
1 5

<210> SEQ ID NO 428
<211> LENGTH: 12
<212> TYPE: PRT
<213> ORGANISM: Crotalus durissus

<400> SEQUENCE: 428

Lys Met Asp Cys Arg Trp Arg Trp Lys Cys Lys Lys
1               5                   10

<210> SEQ ID NO 429
<211> LENGTH: 11
<212> TYPE: PRT
<213> ORGANISM: Crotalus durissus

<400> SEQUENCE: 429

Lys Met Asp Cys Arg Trp Arg Trp Lys Lys Lys
1               5                   10

<210> SEQ ID NO 430
<211> LENGTH: 10
<212> TYPE: PRT
<213> ORGANISM: Crotalus durissus

<400> SEQUENCE: 430

Lys Met Asp Arg Trp Arg Trp Lys Lys Lys
1               5                   10

<210> SEQ ID NO 431
<211> LENGTH: 12
<212> TYPE: PRT
<213> ORGANISM: Crotalus durissus

<400> SEQUENCE: 431

Lys Asp Cys Arg Trp Arg Trp Lys Cys Cys Lys Lys
1               5                   10

<210> SEQ ID NO 432
<211> LENGTH: 11
<212> TYPE: PRT
<213> ORGANISM: Crotalus durissus

<400> SEQUENCE: 432

Lys Cys Arg Trp Arg Trp Lys Cys Cys Lys Lys
1               5                   10

<210> SEQ ID NO 433
<211> LENGTH: 10
<212> TYPE: PRT
<213> ORGANISM: Crotalus durissus

<400> SEQUENCE: 433

Lys Arg Trp Arg Trp Lys Cys Cys Lys Lys
1               5                   10

<210> SEQ ID NO 434
<211> LENGTH: 12
<212> TYPE: PRT
<213> ORGANISM: Crotalus durissus
<220> FEATURE:
<221> NAME/KEY: misc_feature
<222> LOCATION: (9)..(9)
<223> OTHER INFORMATION: Xaa can be any naturally occurring amino acid

<400> SEQUENCE: 434

Met Asp Cys Arg Trp Arg Trp Lys Xaa Cys Lys Lys

-continued

```
<210> SEQ ID NO 435
<211> LENGTH: 11
<212> TYPE: PRT
<213> ORGANISM: Crotalus durissus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 435

Asp Cys Arg Trp Arg Trp Lys Xaa Cys Lys Lys
1               5                   10

<210> SEQ ID NO 436
<211> LENGTH: 11
<212> TYPE: PRT
<213> ORGANISM: Crotalus durissus
<220> FEATURE:
<221> NAME/KEY: misc_feature
<222> LOCATION: (9)..(9)
<223> OTHER INFORMATION: Xaa can be any naturally occurring amino acid

<400> SEQUENCE: 436

Asp Cys Arg Trp Arg Trp Lys Cys Xaa Lys Lys
1               5                   10

<210> SEQ ID NO 437
<211> LENGTH: 10
<212> TYPE: PRT
<213> ORGANISM: Crotalus durissus
<220> FEATURE:
<221> NAME/KEY: misc_feature
<222> LOCATION: (7)..(7)
<223> OTHER INFORMATION: Xaa can be any naturally occurring amino acid

<400> SEQUENCE: 437

Cys Arg Trp Arg Trp Lys Xaa Cys Lys Lys
1               5                   10

<210> SEQ ID NO 438
<211> LENGTH: 10
<212> TYPE: PRT
<213> ORGANISM: Crotalus durissus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 438

Cys Arg Trp Arg Trp Lys Cys Xaa Lys Lys
1               5                   10

<210> SEQ ID NO 439
<211> LENGTH: 9
<212> TYPE: PRT
<213> ORGANISM: Crotalus durissus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 439

Arg Trp Arg Trp Lys Xaa Cys Lys Lys
1               5

<210> SEQ ID NO 440
```

```
<211> LENGTH: 12
<212> TYPE: PRT
<213> ORGANISM: Crotalus durissus
<220> FEATURE:
<221> NAME/KEY: misc_feature
<222> LOCATION: (9)..(10)
<223> OTHER INFORMATION: Xaa can be any naturally occurring amino acid

<400> SEQUENCE: 440

Met Asp Cys Arg Trp Arg Trp Lys Xaa Xaa Lys Lys
1               5                   10

<210> SEQ ID NO 441
<211> LENGTH: 11
<212> TYPE: PRT
<213> ORGANISM: Crotalus durissus
<220> FEATURE:
<221> NAME/KEY: misc_feature
<222> LOCATION: (8)..(9)
<223> OTHER INFORMATION: Xaa can be any naturally occurring amino acid

<400> SEQUENCE: 441

Asp Cys Arg Trp Arg Trp Lys Xaa Xaa Lys Lys
1               5                   10

<210> SEQ ID NO 442
<211> LENGTH: 10
<212> TYPE: PRT
<213> ORGANISM: Crotalus durissus
<220> FEATURE:
<221> NAME/KEY: misc_feature
<222> LOCATION: (7)..(8)
<223> OTHER INFORMATION: Xaa can be any naturally occurring amino acid

<400> SEQUENCE: 442

Cys Arg Trp Arg Trp Lys Xaa Xaa Lys Lys
1               5                   10

<210> SEQ ID NO 443
<211> LENGTH: 9
<212> TYPE: PRT
<213> ORGANISM: Crotalus durissus
<220> FEATURE:
<221> NAME/KEY: misc_feature
<222> LOCATION: (6)..(7)
<223> OTHER INFORMATION: Xaa can be any naturally occurring amino acid

<400> SEQUENCE: 443

Arg Trp Arg Trp Lys Xaa Xaa Lys Lys
1               5

<210> SEQ ID NO 444
<211> LENGTH: 10
<212> TYPE: PRT
<213> ORGANISM: Crotalus durissus

<400> SEQUENCE: 444

Cys Arg Trp Arg Trp Lys Cys Ser Lys Lys
1               5                   10

<210> SEQ ID NO 445
<211> LENGTH: 10
<212> TYPE: PRT
<213> ORGANISM: Crotalus durissus

<400> SEQUENCE: 445

Ser Arg Trp Arg Trp Lys Cys Cys Lys Lys
1               5                   10
```

<210> SEQ ID NO 446
<211> LENGTH: 10
<212> TYPE: PRT
<213> ORGANISM: Crotalus durissus

<400> SEQUENCE: 446

Ser Arg Trp Arg Trp Lys Cys Ser Lys Lys
1               5                   10

<210> SEQ ID NO 447
<211> LENGTH: 10
<212> TYPE: PRT
<213> ORGANISM: Crotalus durissus

<400> SEQUENCE: 447

Ser Arg Trp Arg Trp Lys Ser Cys Lys Lys
1               5                   10

<210> SEQ ID NO 448
<211> LENGTH: 10
<212> TYPE: PRT
<213> ORGANISM: Crotalus durissus

<400> SEQUENCE: 448

Cys Arg Trp Arg Trp Lys Ser Ser Lys Lys
1               5                   10

<210> SEQ ID NO 449
<211> LENGTH: 10
<212> TYPE: PRT
<213> ORGANISM: Crotalus durissus

<400> SEQUENCE: 449

Ser Arg Trp Arg Trp Lys Ser Ser Lys Lys
1               5                   10

<210> SEQ ID NO 450
<211> LENGTH: 10
<212> TYPE: PRT
<213> ORGANISM: Crotalus durissus

<400> SEQUENCE: 450

Cys Arg Phe Arg Trp Lys Cys Cys Lys Lys
1               5                   10

<210> SEQ ID NO 451
<211> LENGTH: 10
<212> TYPE: PRT
<213> ORGANISM: Crotalus durissus

<400> SEQUENCE: 451

Cys Arg Trp Arg Phe Lys Cys Cys Lys Lys
1               5                   10

<210> SEQ ID NO 452
<211> LENGTH: 10
<212> TYPE: PRT
<213> ORGANISM: Crotalus durissus

<400> SEQUENCE: 452

Cys Arg Phe Arg Phe Lys Cys Cys Lys Lys
1               5                   10

```
<210> SEQ ID NO 453
<211> LENGTH: 10
<212> TYPE: PRT
<213> ORGANISM: Crotalus durissus

<400> SEQUENCE: 453

Cys Arg Trp Arg Trp Lys Cys Cys Lys Lys
1               5                   10

<210> SEQ ID NO 454
<211> LENGTH: 10
<212> TYPE: PRT
<213> ORGANISM: Crotalus durissus

<400> SEQUENCE: 454

Lys Cys Cys Lys Trp Arg Trp Arg Cys Lys
1               5                   10

<210> SEQ ID NO 455
<211> LENGTH: 10
<212> TYPE: PRT
<213> ORGANISM: Crotalus durissus

<400> SEQUENCE: 455

Lys Cys Cys Lys Trp Arg Trp Arg Cys Lys
1               5                   10

<210> SEQ ID NO 456
<211> LENGTH: 10
<212> TYPE: PRT
<213> ORGANISM: Crotalus durissus

<400> SEQUENCE: 456

Cys Arg Trp Arg Trp Lys Cys Cys Lys Lys
1               5                   10

<210> SEQ ID NO 457
<211> LENGTH: 10
<212> TYPE: PRT
<213> ORGANISM: Crotalus durissus

<400> SEQUENCE: 457

Cys Arg Trp Arg Trp Lys Cys Cys Lys Lys
1               5                   10

<210> SEQ ID NO 458
<211> LENGTH: 10
<212> TYPE: PRT
<213> ORGANISM: Crotalus durissus

<400> SEQUENCE: 458

Cys Arg Trp Arg Trp Lys Cys Cys Lys Lys
1               5                   10

<210> SEQ ID NO 459
<211> LENGTH: 10
<212> TYPE: PRT
<213> ORGANISM: Crotalus durissus

<400> SEQUENCE: 459

Cys Arg Trp Arg Trp Lys Cys Cys Lys Lys
1               5                   10

<210> SEQ ID NO 460
<211> LENGTH: 10
```

```
<212> TYPE: PRT
<213> ORGANISM: Crotalus durissus

<400> SEQUENCE: 460

Cys Arg Trp Arg Trp Lys Cys Cys Lys Lys
1               5                   10

<210> SEQ ID NO 461
<211> LENGTH: 11
<212> TYPE: PRT
<213> ORGANISM: Crotalus durissus

<400> SEQUENCE: 461

Cys Arg Trp Arg Trp Lys Cys Gly Cys Lys Lys
1               5                   10

<210> SEQ ID NO 462
<211> LENGTH: 14
<212> TYPE: PRT
<213> ORGANISM: Crotalus durissus

<400> SEQUENCE: 462

Lys Cys Gly Cys Arg Trp Arg Trp Lys Cys Gly Cys Lys Lys
1               5                   10

<210> SEQ ID NO 463
<211> LENGTH: 8
<212> TYPE: PRT
<213> ORGANISM: Crotalus durissus

<400> SEQUENCE: 463

Cys Arg Trp Arg Trp Lys Cys Gly
1               5

<210> SEQ ID NO 464
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 464

Lys Met Asp Xaa Arg Trp Arg Trp Lys Cys Cys Lys Lys
1               5                   10

<210> SEQ ID NO 465
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 465

Lys Met Asp Xaa Arg Trp Arg Trp Lys Xaa Cys Lys Lys
1               5                   10

<210> SEQ ID NO 466
<211> LENGTH: 13
<212> TYPE: PRT
```

```
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 466

Lys Met Asp Xaa Arg Trp Arg Trp Lys Xaa Xaa Lys Lys
1               5                   10

<210> SEQ ID NO 467
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 467

Lys Met Asp Xaa Arg Trp Arg Trp Lys Cys Xaa Lys Lys
1               5                   10

<210> SEQ ID NO 468
<211> LENGTH: 12
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 468

Met Asp Cys Arg Trp Arg Trp Lys Cys Xaa Lys Lys
1               5                   10

<210> SEQ ID NO 469
<211> LENGTH: 13
<212> TYPE: PRT
<213> ORGANISM: Crotalus durissus

<400> SEQUENCE: 469

Lys Met Asp Cys Arg Trp Arg Trp Lys Cys Ser Lys Lys
1               5                   10

<210> SEQ ID NO 470
<211> LENGTH: 13
<212> TYPE: PRT
<213> ORGANISM: Crotalus durissus

<400> SEQUENCE: 470

Lys Met Asp Cys Arg Trp Arg Trp Lys Ser Cys Lys Lys
1               5                   10

<210> SEQ ID NO 471
<211> LENGTH: 13
<212> TYPE: PRT
<213> ORGANISM: Crotalus durissus

<400> SEQUENCE: 471
```

-continued

Lys Met Asp Ser Arg Trp Arg Trp Lys Cys Cys Lys Lys
1               5                   10

<210> SEQ ID NO 472
<211> LENGTH: 13
<212> TYPE: PRT
<213> ORGANISM: Crotalus durissus

<400> SEQUENCE: 472

Lys Met Asp Cys Arg Trp Arg Trp Lys Ser Ser Lys Lys
1               5                   10

<210> SEQ ID NO 473
<211> LENGTH: 13
<212> TYPE: PRT
<213> ORGANISM: Crotalus durissus

<400> SEQUENCE: 473

Lys Met Asp Ser Arg Trp Arg Trp Lys Ser Ser Lys Lys
1               5                   10

<210> SEQ ID NO 474
<211> LENGTH: 13
<212> TYPE: PRT
<213> ORGANISM: Crotalus durissus

<400> SEQUENCE: 474

Lys Met Asp Ser Arg Trp Arg Trp Lys Ser Cys Lys Lys
1               5                   10

<210> SEQ ID NO 475
<211> LENGTH: 13
<212> TYPE: PRT
<213> ORGANISM: Crotalus durissus

<400> SEQUENCE: 475

Lys Met Asp Ser Arg Trp Arg Trp Lys Cys Ser Lys Lys
1               5                   10

<210> SEQ ID NO 476
<211> LENGTH: 13
<212> TYPE: PRT
<213> ORGANISM: Crotalus durissus

<400> SEQUENCE: 476

Lys Met Asp Cys Arg Trp Arg Pro Lys Cys Cys Lys Lys
1               5                   10

<210> SEQ ID NO 477
<211> LENGTH: 13
<212> TYPE: PRT
<213> ORGANISM: Crotalus durissus

<400> SEQUENCE: 477

Lys Met Asp Cys Arg Pro Arg Pro Lys Cys Cys Lys Lys
1               5                   10

<210> SEQ ID NO 478
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 478

Lys Met Asp Xaa Arg Pro Arg Pro Lys Cys Cys Lys Lys
1               5                   10

<210> SEQ ID NO 479
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 479

Lys Met Asp Xaa Arg Pro Arg Pro Lys Xaa Cys Lys Lys
1               5                   10

<210> SEQ ID NO 480
<211> LENGTH: 13
<212> TYPE: PRT
<213> ORGANISM: Crotalus durissus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 480

Lys Met Asp Xaa Arg Pro Arg Pro Lys Cys Xaa Lys Lys
1               5                   10

<210> SEQ ID NO 481
<211> LENGTH: 13
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 481

Lys Met Asp Cys Arg Pro Arg Pro Lys Xaa Cys Lys Lys
1               5                   10

<210> SEQ ID NO 482
<211> LENGTH: 13
<212> TYPE: PRT
<213> ORGANISM: Crotalus durissus
<220> FEATURE:
<221> NAME/KEY: misc_feature
<222> LOCATION: (11)..(11)
<223> OTHER INFORMATION: Xaa can be any naturally occurring amino acid

<400> SEQUENCE: 482

Lys Met Asp Cys Arg Pro Arg Pro Lys Cys Xaa Lys Lys
1               5                   10

<210> SEQ ID NO 483
<211> LENGTH: 16
<212> TYPE: PRT
<213> ORGANISM: Drosophila melanogaster

<400> SEQUENCE: 483

Arg Gln Ile Lys Ile Trp Phe Gln Asn Arg Arg Met Lys Trp Lys Lys
1               5                   10                  15

<210> SEQ ID NO 484
<211> LENGTH: 9
<212> TYPE: PRT
<213> ORGANISM: Human immunodeficiency virus type 1

<400> SEQUENCE: 484

Arg Lys Lys Arg Arg Gln Arg Arg Arg
1               5

<210> SEQ ID NO 485
<211> LENGTH: 9
<212> TYPE: PRT
<213> ORGANISM: Human immunodeficiency virus type 1

<400> SEQUENCE: 485

Arg Arg Arg Gln Arg Arg Lys Lys Arg
1               5

<210> SEQ ID NO 486
<211> LENGTH: 16
<212> TYPE: PRT
<213> ORGANISM: Homo sapiens

<400> SEQUENCE: 486

Arg Lys Lys Arg Arg Arg Glu Ser Arg Lys Lys Arg Arg Arg Glu Ser
1               5                   10                  15

<210> SEQ ID NO 487
<211> LENGTH: 17
<212> TYPE: PRT
<213> ORGANISM: Homo sapiens

<400> SEQUENCE: 487

Gly Arg Pro Arg Glu Ser Gly Lys Lys Arg Lys Arg Lys Arg Leu Lys
1               5                   10                  15

Pro

<210> SEQ ID NO 488
<211> LENGTH: 15
<212> TYPE: PRT
<213> ORGANISM: Homo sapiens

<400> SEQUENCE: 488

Gly Lys Arg Lys Lys Lys Gly Lys Leu Gly Lys Lys Arg Asp Pro
1               5                   10                  15

<210> SEQ ID NO 489
<211> LENGTH: 17
<212> TYPE: PRT
<213> ORGANISM: Homo sapiens

<400> SEQUENCE: 489

Gly Lys Arg Lys Lys Lys Gly Lys Leu Gly Lys Lys Arg Pro Arg Ser
1               5                   10                  15

Arg

<210> SEQ ID NO 490
<211> LENGTH: 18
<212> TYPE: PRT

<213> ORGANISM: Homo sapiens

<400> SEQUENCE: 490

Arg Lys Lys Arg Arg Glu Ser Arg Arg Ala Arg Arg Ser Pro Arg
1               5                   10                  15
His Leu

<210> SEQ ID NO 491
<211> LENGTH: 19
<212> TYPE: PRT
<213> ORGANISM: Homo sapiens

<400> SEQUENCE: 491

Ser Arg Arg Ala Arg Arg Ser Pro Arg Glu Ser Gly Lys Lys Arg Lys
1               5                   10                  15
Arg Lys Arg

<210> SEQ ID NO 492
<211> LENGTH: 19
<212> TYPE: PRT
<213> ORGANISM: Homo sapiens

<400> SEQUENCE: 492

Val Lys Arg Gly Leu Lys Leu Arg His Val Arg Pro Arg Val Thr Arg
1               5                   10                  15
Met Asp Val

<210> SEQ ID NO 493
<211> LENGTH: 14
<212> TYPE: PRT
<213> ORGANISM: Homo sapiens

<400> SEQUENCE: 493

Ser Arg Arg Ala Arg Arg Ser Pro Arg His Leu Gly Ser Gly
1               5                   10

<210> SEQ ID NO 494
<211> LENGTH: 16
<212> TYPE: PRT
<213> ORGANISM: Homo sapiens

<400> SEQUENCE: 494

Leu Arg Arg Glu Arg Gln Ser Arg Leu Arg Arg Glu Arg Gln Ser Arg
1               5                   10                  15

<210> SEQ ID NO 495
<211> LENGTH: 22
<212> TYPE: PRT
<213> ORGANISM: Homo sapiens

<400> SEQUENCE: 495

Gly Ala Tyr Asp Leu Arg Arg Arg Glu Arg Gln Ser Arg Leu Arg Arg
1               5                   10                  15
Arg Glu Arg Gln Ser Arg
            20

<210> SEQ ID NO 496
<211> LENGTH: 13
<212> TYPE: PRT
<213> ORGANISM: Human immunodeficiency virus type 1

<400> SEQUENCE: 496

-continued

Gly Arg Lys Lys Arg Gln Arg Arg Pro Pro Gln
1               5                   10

<210> SEQ ID NO 497
<211> LENGTH: 5
<212> TYPE: PRT
<213> ORGANISM: Homo sapiens

<400> SEQUENCE: 497

Val Pro Met Leu Lys
1               5

<210> SEQ ID NO 498
<211> LENGTH: 5
<212> TYPE: PRT
<213> ORGANISM: Homo sapiens

<400> SEQUENCE: 498

Val Pro Thr Leu Lys
1               5

<210> SEQ ID NO 499
<211> LENGTH: 5
<212> TYPE: PRT
<213> ORGANISM: Homo sapiens

<400> SEQUENCE: 499

Val Pro Ala Leu Arg
1               5

<210> SEQ ID NO 500
<211> LENGTH: 5
<212> TYPE: PRT
<213> ORGANISM: Homo sapiens

<400> SEQUENCE: 500

Val Ser Ala Leu Lys
1               5

<210> SEQ ID NO 501
<211> LENGTH: 5
<212> TYPE: PRT
<213> ORGANISM: Homo sapiens

<400> SEQUENCE: 501

Pro Met Leu Lys Glu
1               5

<210> SEQ ID NO 502
<211> LENGTH: 5
<212> TYPE: PRT
<213> ORGANISM: Homo sapiens

<400> SEQUENCE: 502

Val Pro Ala Leu Lys
1               5

<210> SEQ ID NO 503
<211> LENGTH: 5
<212> TYPE: PRT
<213> ORGANISM: Homo sapiens

<400> SEQUENCE: 503

Val Ser Leu Lys Lys
1               5

<210> SEQ ID NO 504
<211> LENGTH: 5
<212> TYPE: PRT
<213> ORGANISM: Homo sapiens

<400> SEQUENCE: 504

Val Ser Gly Lys Lys
1               5

<210> SEQ ID NO 505
<211> LENGTH: 5
<212> TYPE: PRT
<213> ORGANISM: Homo sapiens

<400> SEQUENCE: 505

Lys Leu Pro Val Met
1               5

<210> SEQ ID NO 506
<211> LENGTH: 5
<212> TYPE: PRT
<213> ORGANISM: Homo sapiens

<400> SEQUENCE: 506

Ile Pro Met Ile Lys
1               5

<210> SEQ ID NO 507
<211> LENGTH: 5
<212> TYPE: PRT
<213> ORGANISM: Homo sapiens

<400> SEQUENCE: 507

Lys Leu Gly Val Met
1               5

<210> SEQ ID NO 508
<211> LENGTH: 5
<212> TYPE: PRT
<213> ORGANISM: Homo sapiens

<400> SEQUENCE: 508

Lys Leu Pro Val Thr
1               5

<210> SEQ ID NO 509
<211> LENGTH: 5
<212> TYPE: PRT
<213> ORGANISM: Homo sapiens

<400> SEQUENCE: 509

Val Pro Met Ile Lys
1               5

<210> SEQ ID NO 510
<211> LENGTH: 5
<212> TYPE: PRT
<213> ORGANISM: Homo sapiens

<400> SEQUENCE: 510

Ile Pro Ala Leu Lys
1               5

```
<210> SEQ ID NO 511
<211> LENGTH: 5
<212> TYPE: PRT
<213> ORGANISM: Homo sapiens

<400> SEQUENCE: 511

Ile Pro Met Leu Lys
1               5

<210> SEQ ID NO 512
<211> LENGTH: 5
<212> TYPE: PRT
<213> ORGANISM: Homo sapiens

<400> SEQUENCE: 512

Val Pro Thr Leu Gln
1               5

<210> SEQ ID NO 513
<211> LENGTH: 5
<212> TYPE: PRT
<213> ORGANISM: Homo sapiens

<400> SEQUENCE: 513

Gln Leu Pro Val Met
1               5

<210> SEQ ID NO 514
<211> LENGTH: 5
<212> TYPE: PRT
<213> ORGANISM: Homo sapiens

<400> SEQUENCE: 514

Glu Leu Pro Val Met
1               5

<210> SEQ ID NO 515
<211> LENGTH: 5
<212> TYPE: PRT
<213> ORGANISM: Homo sapiens

<400> SEQUENCE: 515

Val Pro Thr Leu Glu
1               5

<210> SEQ ID NO 516
<211> LENGTH: 5
<212> TYPE: PRT
<213> ORGANISM: Homo sapiens

<400> SEQUENCE: 516

Val Pro Thr Leu Lys
1               5

<210> SEQ ID NO 517
<211> LENGTH: 20
<212> TYPE: PRT
<213> ORGANISM: Limulus polyphemus

<400> SEQUENCE: 517

Ala Tyr Arg Ile Lys Pro Thr Phe Arg Arg Leu Lys Trp Lys Tyr Lys
1               5                   10                  15

Gly Lys Phe Trp
            20
```

```
<210> SEQ ID NO 518
<211> LENGTH: 20
<212> TYPE: PRT
<213> ORGANISM: Limulus polyphemus

<400> SEQUENCE: 518

His Ala Arg Ile Lys Pro Thr Phe Arg Arg Leu Lys Trp Lys Tyr Lys
1               5                   10                  15

Gly Lys Phe Trp
            20

<210> SEQ ID NO 519
<211> LENGTH: 20
<212> TYPE: PRT
<213> ORGANISM: Limulus polyphemus

<400> SEQUENCE: 519

His Tyr Arg Ile Lys Pro Thr Ala Arg Arg Leu Lys Trp Lys Tyr Lys
1               5                   10                  15

Gly Lys Phe Trp
            20

<210> SEQ ID NO 520
<211> LENGTH: 20
<212> TYPE: PRT
<213> ORGANISM: Limulus polyphemus

<400> SEQUENCE: 520

His Tyr Arg Ile Lys Pro Thr Phe Arg Arg Leu Ala Trp Lys Tyr Lys
1               5                   10                  15

Gly Lys Phe Trp
            20

<210> SEQ ID NO 521
<211> LENGTH: 20
<212> TYPE: PRT
<213> ORGANISM: Limulus polyphemus

<400> SEQUENCE: 521

His Tyr Arg Ile Lys Pro Thr Phe Arg Arg Leu Lys Trp Lys Tyr Lys
1               5                   10                  15

Gly Lys Phe Ala
            20

<210> SEQ ID NO 522
<211> LENGTH: 21
<212> TYPE: PRT
<213> ORGANISM: Mycobacterium tuberculosis

<400> SEQUENCE: 522

Val Asn Ala Asp Ile Lys Ala Thr Thr Val Phe Gly Gly Lys Tyr Val
1               5                   10                  15

Ser Leu Thr Thr Pro
            20

<210> SEQ ID NO 523
<211> LENGTH: 22
<212> TYPE: PRT
<213> ORGANISM: Mycobacterium tuberculosis

<400> SEQUENCE: 523

Gly Lys Tyr Val Ser Leu Thr Thr Pro Lys Asn Pro Thr Lys Arg Arg
```

```
                1               5                  10                  15
Ile Thr Pro Lys Asp Val
            20

<210> SEQ ID NO 524
<211> LENGTH: 22
<212> TYPE: PRT
<213> ORGANISM: Mycobacterium tuberculosis

<400> SEQUENCE: 524

Thr Lys Arg Arg Ile Thr Pro Lys Asp Val Ile Asp Val Arg Ser Val
1               5                  10                  15

Thr Thr Glu Ile Asn Thr
            20

<210> SEQ ID NO 525
<211> LENGTH: 23
<212> TYPE: PRT
<213> ORGANISM: Mycobacterium tuberculosis

<400> SEQUENCE: 525

Arg Ser Val Thr Thr Glu Ile Asn Thr Leu Phe Gln Thr Leu Thr Ser
1               5                  10                  15

Ile Ala Glu Lys Val Asp Pro
            20

<210> SEQ ID NO 526
<211> LENGTH: 26
<212> TYPE: PRT
<213> ORGANISM: Mycobacterium tuberculosis

<400> SEQUENCE: 526

Ala Glu Lys Val Asp Pro Val Lys Leu Asn Leu Thr Leu Ser Ala Ala
1               5                  10                  15

Ala Glu Ala Leu Thr Gly Leu Gly Asp Lys
            20                  25

<210> SEQ ID NO 527
<211> LENGTH: 34
<212> TYPE: PRT
<213> ORGANISM: Mycobacterium tuberculosis

<400> SEQUENCE: 527

Gly Leu Gly Asp Lys Phe Gly Glu Ser Ile Val Asn Ala Asn Thr Val
1               5                  10                  15

Leu Asp Asp Leu Asn Ser Arg Met Pro Gln Ser Arg His Asp Ile Gln
            20                  25                  30

Gln Leu

<210> SEQ ID NO 528
<211> LENGTH: 27
<212> TYPE: PRT
<213> ORGANISM: Mycobacterium tuberculosis

<400> SEQUENCE: 528

Gly Asp Val Tyr Ala Asp Ala Pro Asp Leu Phe Asp Phe Leu Asp
1               5                  10                  15

Ser Ser Val Thr Thr Ala Arg Thr Ile Asn Ala
            20                  25

<210> SEQ ID NO 529
```

```
<211> LENGTH: 32
<212> TYPE: PRT
<213> ORGANISM: Mycobacterium tuberculosis

<400> SEQUENCE: 529

Ala Arg Thr Ile Asn Ala Gln Gln Ala Glu Leu Asp Ser Ala Leu Leu
1               5                   10                  15

Ala Ala Ala Gly Phe Gly Asn Thr Thr Ala Asp Val Phe Asp Arg Gly
            20                  25                  30

<210> SEQ ID NO 530
<211> LENGTH: 30
<212> TYPE: PRT
<213> ORGANISM: Mycobacterium tuberculosis

<400> SEQUENCE: 530

Ala Asp Val Phe Asp Arg Gly Gly Pro Tyr Leu Gln Arg Gly Val Ala
1               5                   10                  15

Asp Leu Val Pro Thr Ala Thr Leu Leu Asp Thr Tyr Ser Pro
            20                  25                  30

<210> SEQ ID NO 531
<211> LENGTH: 27
<212> TYPE: PRT
<213> ORGANISM: Mycobacterium tuberculosis

<400> SEQUENCE: 531

Leu Asp Thr Tyr Ser Pro Glu Leu Phe Cys Thr Ile Arg Asn Phe Tyr
1               5                   10                  15

Asp Ala Asp Arg Pro Asp Arg Gly Ala Ala Ala
            20                  25

<210> SEQ ID NO 532
<211> LENGTH: 22
<212> TYPE: PRT
<213> ORGANISM: Mycobacterium tuberculosis

<400> SEQUENCE: 532

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 533
<211> LENGTH: 22
<212> TYPE: PRT
<213> ORGANISM: Mycobacterium tuberculosis

<400> SEQUENCE: 533

Thr Lys Arg Arg Ile Thr Pro Asp Asp Val Ile Asp Val Arg Ser Val
1               5                   10                  15

Thr Thr Glu Ile Asn Thr
            20

<210> SEQ ID NO 534
<211> LENGTH: 22
<212> TYPE: PRT
<213> ORGANISM: Mycobacterium tuberculosis

<400> SEQUENCE: 534

Thr Lys Arg Arg Ile Thr Pro Lys Lys Val Ile Asp Val Arg Ser Val
1               5                   10                  15
```

-continued

Thr Thr Glu Ile Asn Thr
            20

<210> SEQ ID NO 535
<211> LENGTH: 22
<212> TYPE: PRT
<213> ORGANISM: Mycobacterium tuberculosis

<400> SEQUENCE: 535

Thr Lys Arg Arg Ile Thr Pro Lys Asp Val Ile Asp Val Arg Ser Val
1               5                   10                  15

Thr Thr Lys Ile Asn Thr
            20

<210> SEQ ID NO 536
<211> LENGTH: 13
<212> TYPE: PRT
<213> ORGANISM: Mycobacterium tuberculosis

<400> SEQUENCE: 536

Thr Lys Arg Arg Ile Thr Pro Lys Asp Val Ile Asp Val
1               5                   10

<210> SEQ ID NO 537
<211> LENGTH: 22
<212> TYPE: PRT
<213> ORGANISM: Mycobacterium tuberculosis

<400> SEQUENCE: 537

Thr Lys Arg Arg Ile Thr Pro Lys Asp Val Ile Asp Val Glu Ser Val
1               5                   10                  15

Thr Thr Glu Ile Asn Thr
            20

<210> SEQ ID NO 538
<211> LENGTH: 22
<212> TYPE: PRT
<213> ORGANISM: Mycobacterium tuberculosis

<400> SEQUENCE: 538

Thr Ala Arg Arg Ile Thr Pro Lys Asp Val Ile Asp Val Arg Ser Val
1               5                   10                  15

Thr Thr Glu Ile Asn Thr
            20

<210> SEQ ID NO 539
<211> LENGTH: 23
<212> TYPE: PRT
<213> ORGANISM: Mycobacterium tuberculosis

<400> SEQUENCE: 539

Thr Lys Ala Ala Arg Ile Thr Pro Lys Asp Val Ile Asp Val Arg Ser
1               5                   10                  15

Val Thr Thr Glu Ile Asn Thr
            20

<210> SEQ ID NO 540
<211> LENGTH: 28
<212> TYPE: PRT
<213> ORGANISM: Mycobacterium tuberculosis

<400> SEQUENCE: 540

His His His His His His Thr Lys Arg Arg Ile Thr Pro Lys Asp Val

```
            1               5                  10                  15
Ile Asp Val Arg Ser Val Thr Thr Glu Ile Asn Thr
            20                  25
```

<210> SEQ ID NO 541
<211> LENGTH: 12
<212> TYPE: PRT
<213> ORGANISM: Human immunodeficiency virus type 1

<400> SEQUENCE: 541

```
Tyr Gly Arg Lys Lys Arg Arg Gln Arg Arg
1               5                  10
```

<210> SEQ ID NO 542
<211> LENGTH: 18
<212> TYPE: PRT
<213> ORGANISM: Mus musculus

<400> SEQUENCE: 542

```
Leu Leu Ile Ile Leu Arg Arg Arg Ile Arg Lys Gln Ala His Ala His
1               5                  10                  15
Ser Lys
```

<210> SEQ ID NO 543
<211> LENGTH: 18
<212> TYPE: PRT
<213> ORGANISM: Mus musculus

<400> SEQUENCE: 543

```
Ala Leu Ile Ile Leu Arg Arg Arg Ile Arg Lys Gln Ala His Ala His
1               5                  10                  15
Ser Lys
```

<210> SEQ ID NO 544
<211> LENGTH: 18
<212> TYPE: PRT
<213> ORGANISM: Mus musculus

<400> SEQUENCE: 544

```
Leu Ala Ile Ile Leu Arg Arg Arg Ile Arg Lys Gln Ala His Ala His
1               5                  10                  15
Ser Lys
```

<210> SEQ ID NO 545
<211> LENGTH: 18
<212> TYPE: PRT
<213> ORGANISM: Mus musculus

<400> SEQUENCE: 545

```
Leu Leu Ala Ile Leu Arg Arg Arg Ile Arg Lys Gln Ala His Ala His
1               5                  10                  15
Ser Lys
```

<210> SEQ ID NO 546
<211> LENGTH: 18
<212> TYPE: PRT
<213> ORGANISM: Mus musculus

<400> SEQUENCE: 546

```
Leu Leu Ile Ala Leu Arg Arg Arg Ile Arg Lys Gln Ala His Ala His
1               5                  10                  15
```

Ser Lys

<210> SEQ ID NO 547
<211> LENGTH: 18
<212> TYPE: PRT
<213> ORGANISM: Mus musculus

<400> SEQUENCE: 547

Leu Leu Ile Ile Ala Arg Arg Arg Ile Arg Lys Gln Ala His Ala His
1               5                   10                  15

Ser Lys

<210> SEQ ID NO 548
<211> LENGTH: 18
<212> TYPE: PRT
<213> ORGANISM: Mus musculus

<400> SEQUENCE: 548

Leu Leu Ile Ile Leu Ala Arg Arg Ile Arg Lys Gln Ala His Ala His
1               5                   10                  15

Ser Lys

<210> SEQ ID NO 549
<211> LENGTH: 18
<212> TYPE: PRT
<213> ORGANISM: Mus musculus

<400> SEQUENCE: 549

Leu Leu Ile Ile Leu Arg Ala Arg Ile Arg Lys Gln Ala His Ala His
1               5                   10                  15

Ser Lys

<210> SEQ ID NO 550
<211> LENGTH: 18
<212> TYPE: PRT
<213> ORGANISM: Mus musculus

<400> SEQUENCE: 550

Leu Leu Ile Ile Leu Arg Arg Ala Ile Arg Lys Gln Ala His Ala His
1               5                   10                  15

Ser Lys

<210> SEQ ID NO 551
<211> LENGTH: 18
<212> TYPE: PRT
<213> ORGANISM: Mus musculus

<400> SEQUENCE: 551

Leu Leu Ile Ile Leu Arg Arg Arg Ala Arg Lys Gln Ala His Ala His
1               5                   10                  15

Ser Lys

<210> SEQ ID NO 552
<211> LENGTH: 19
<212> TYPE: PRT
<213> ORGANISM: Mus musculus

<400> SEQUENCE: 552

Leu Leu Ile Ile Leu Arg Arg Arg Ile Ala Arg Lys Gln Ala His Ala
1               5                   10                  15

His Ser Lys

<210> SEQ ID NO 553
<211> LENGTH: 18
<212> TYPE: PRT
<213> ORGANISM: Mus musculus

<400> SEQUENCE: 553

Leu Leu Ile Ile Leu Arg Arg Arg Ile Arg Ala Gln Ala His Ala His
1               5                   10                  15

Ser Lys

<210> SEQ ID NO 554
<211> LENGTH: 18
<212> TYPE: PRT
<213> ORGANISM: Mus musculus

<400> SEQUENCE: 554

Leu Leu Ile Ile Leu Arg Arg Arg Ile Arg Lys Ala Ala His Ala His
1               5                   10                  15

Ser Lys

<210> SEQ ID NO 555
<211> LENGTH: 18
<212> TYPE: PRT
<213> ORGANISM: Mus musculus

<400> SEQUENCE: 555

Leu Leu Ile Ile Leu Arg Arg Arg Ile Arg Lys Gln Ala His Ala His
1               5                   10                  15

Ser Lys

<210> SEQ ID NO 556
<211> LENGTH: 18
<212> TYPE: PRT
<213> ORGANISM: Mus musculus

<400> SEQUENCE: 556

Leu Leu Ile Ile Leu Arg Arg Arg Ile Arg Lys Gln Ala Ala Ala His
1               5                   10                  15

Ser Lys

<210> SEQ ID NO 557
<211> LENGTH: 18
<212> TYPE: PRT
<213> ORGANISM: Mus musculus

<400> SEQUENCE: 557

Leu Leu Ile Ile Leu Arg Arg Arg Ile Arg Lys Gln Ala His Ala His
1               5                   10                  15

Ser Lys

<210> SEQ ID NO 558
<211> LENGTH: 18
<212> TYPE: PRT
<213> ORGANISM: Mus musculus

<400> SEQUENCE: 558

Leu Leu Ile Ile Leu Arg Arg Arg Ile Arg Lys Gln Ala His Ala Ala
1               5                   10                  15

Ser Lys

<210> SEQ ID NO 559
<211> LENGTH: 18
<212> TYPE: PRT
<213> ORGANISM: Mus musculus

<400> SEQUENCE: 559

Leu Leu Ile Ile Leu Arg Arg Arg Ile Arg Lys Gln Ala His Ala His
1               5                   10                  15

Ala Lys

<210> SEQ ID NO 560
<211> LENGTH: 18
<212> TYPE: PRT
<213> ORGANISM: Mus musculus

<400> SEQUENCE: 560

Leu Leu Ile Ile Leu Arg Arg Arg Ile Arg Lys Gln Ala His Ala His
1               5                   10                  15

Ser Ala

<210> SEQ ID NO 561
<211> LENGTH: 18
<212> TYPE: PRT
<213> ORGANISM: Mus musculus

<400> SEQUENCE: 561

Lys Ser His Ala His Ala Gln Lys Arg Ile Arg Arg Arg Leu Ile Ile
1               5                   10                  15

Leu Leu

<210> SEQ ID NO 562
<211> LENGTH: 18
<212> TYPE: PRT
<213> ORGANISM: Mus musculus

<400> SEQUENCE: 562

Leu Leu Ile Ile Leu Arg Arg Arg Ile Arg Lys Gln Ala His Ala His
1               5                   10                  15

Ser Lys

<210> SEQ ID NO 563
<211> LENGTH: 7
<212> TYPE: PRT
<213> ORGANISM: Bos primigenius

<400> SEQUENCE: 563

Arg Arg Ile Arg Pro Arg Pro
1               5

<210> SEQ ID NO 564
<211> LENGTH: 15
<212> TYPE: PRT
<213> ORGANISM: Bos primigenius

<400> SEQUENCE: 564

Arg Arg Ile Arg Pro Arg Pro Pro Arg Leu Pro Arg Pro Arg Pro
1               5                   10                  15

<210> SEQ ID NO 565
<211> LENGTH: 24
<212> TYPE: PRT
<213> ORGANISM: Bos primigenius

<400> SEQUENCE: 565

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 566
<211> LENGTH: 17
<212> TYPE: PRT
<213> ORGANISM: Bos primigenius

<400> SEQUENCE: 566

Arg Arg Ile Arg Pro Arg Pro Pro Arg Leu Pro Arg Pro Arg Pro Arg
1               5                   10                  15

Pro

<210> SEQ ID NO 567
<211> LENGTH: 20
<212> TYPE: PRT
<213> ORGANISM: Bos primigenius

<400> SEQUENCE: 567

Pro Arg Pro Pro Arg Leu Pro Arg Pro Arg Pro Arg Pro Leu Pro Phe
1               5                   10                  15

Pro Arg Pro Gly
            20

<210> SEQ ID NO 568
<211> LENGTH: 18
<212> TYPE: PRT
<213> ORGANISM: Bos primigenius

<400> SEQUENCE: 568

Pro Pro Arg Leu Pro Arg Pro Arg Pro Arg Pro Leu Pro Phe Pro Arg
1               5                   10                  15

Pro Gly

<210> SEQ ID NO 569
<211> LENGTH: 16
<212> TYPE: PRT
<213> ORGANISM: Bos primigenius

<400> SEQUENCE: 569

Arg Leu Pro Arg Pro Arg Pro Arg Pro Leu Pro Phe Pro Arg Pro Gly
1               5                   10                  15

<210> SEQ ID NO 570
<211> LENGTH: 14
<212> TYPE: PRT
<213> ORGANISM: Bos primigenius

<400> SEQUENCE: 570

Pro Arg Pro Arg Pro Arg Pro Leu Pro Phe Pro Arg Pro Gly
1               5                   10

<210> SEQ ID NO 571
<211> LENGTH: 12
<212> TYPE: PRT
<213> ORGANISM: Bos primigenius

<400> SEQUENCE: 571

```
Pro Arg Pro Arg Pro Leu Pro Phe Pro Arg Pro Gly
1               5                   10
```

<210> SEQ ID NO 572
<211> LENGTH: 10
<212> TYPE: PRT
<213> ORGANISM: Bos primigenius

<400> SEQUENCE: 572

```
Pro Arg Pro Leu Pro Phe Pro Arg Pro Gly
1               5                   10
```

<210> SEQ ID NO 573
<211> LENGTH: 9
<212> TYPE: PRT
<213> ORGANISM: Human immunodeficiency virus type 1

<400> SEQUENCE: 573

```
Arg Lys Lys Arg Arg Gln Arg Arg Arg
1               5
```

<210> SEQ ID NO 574
<211> LENGTH: 27
<212> TYPE: PRT
<213> ORGANISM: African swine fever virus

<400> SEQUENCE: 574

```
Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25
```

<210> SEQ ID NO 575
<211> LENGTH: 22
<212> TYPE: PRT
<213> ORGANISM: African swine fever virus

<400> SEQUENCE: 575

```
Arg Val Thr Ser Trp Leu Gly Arg Gln Leu Arg Ile Ala Gly Lys Arg
1               5                   10                  15

Leu Glu Gly Arg Ser Lys
            20
```

<210> SEQ ID NO 576
<211> LENGTH: 16
<212> TYPE: PRT
<213> ORGANISM: African swine fever virus

<400> SEQUENCE: 576

```
Gly Arg Gln Leu Arg Ile Ala Gly Lys Arg Leu Glu Gly Arg Ser Lys
1               5                   10                  15
```

<210> SEQ ID NO 577
<211> LENGTH: 23
<212> TYPE: PRT
<213> ORGANISM: African swine fever virus

<400> SEQUENCE: 577

```
Arg Arg Val Thr Ser Trp Leu Gly Arg Gln Leu Arg Ile Ala Gly Lys
1               5                   10                  15

Arg Leu Glu Gly Arg Ser Lys
            20
```

-continued

```
<210> SEQ ID NO 578
<211> LENGTH: 22
<212> TYPE: PRT
<213> ORGANISM: African swine fever virus

<400> SEQUENCE: 578

Arg Val Arg Ser Trp Leu Gly Arg Gln Leu Arg Ile Ala Gly Lys Arg
1               5                   10                  15

Leu Glu Gly Arg Ser Lys
            20

<210> SEQ ID NO 579
<211> LENGTH: 16
<212> TYPE: PRT
<213> ORGANISM: African swine fever virus

<400> SEQUENCE: 579

Gly Arg Gln Leu Arg Ile Ala Gly Lys Arg Leu Arg Gly Arg Ser Lys
1               5                   10                  15

<210> SEQ ID NO 580
<211> LENGTH: 16
<212> TYPE: PRT
<213> ORGANISM: African swine fever virus

<400> SEQUENCE: 580

Gly Arg Gln Leu Arg Ile Ala Gly Arg Arg Leu Arg Gly Arg Ser Arg
1               5                   10                  15

<210> SEQ ID NO 581
<211> LENGTH: 16
<212> TYPE: PRT
<213> ORGANISM: African swine fever virus

<400> SEQUENCE: 581

Gly Arg Gln Leu Arg Arg Ala Gly Arg Arg Leu Arg Gly Arg Ser Arg
1               5                   10                  15

<210> SEQ ID NO 582
<211> LENGTH: 16
<212> TYPE: PRT
<213> ORGANISM: African swine fever virus

<400> SEQUENCE: 582

Gly Arg Gln Leu Arg Ile Ala Gly Arg Arg Leu Arg Arg Arg Ser Arg
1               5                   10                  15

<210> SEQ ID NO 583
<211> LENGTH: 16
<212> TYPE: PRT
<213> ORGANISM: African swine fever virus

<400> SEQUENCE: 583

Gly Arg Gln Leu Arg Arg Ala Gly Arg Arg Leu Arg Arg Arg Ser Arg
1               5                   10                  15

<210> SEQ ID NO 584
<211> LENGTH: 15
<212> TYPE: PRT
<213> ORGANISM: African swine fever virus

<400> SEQUENCE: 584

Arg Gln Leu Arg Ile Ala Gly Arg Arg Leu Arg Gly Arg Ser Arg
1               5                   10                  15
```

<210> SEQ ID NO 585
<211> LENGTH: 16
<212> TYPE: PRT
<213> ORGANISM: African swine fever virus

<400> SEQUENCE: 585

Arg Ser Arg G

```
                20                  25

<210> SEQ ID NO 591
<211> LENGTH: 25
<212> TYPE: PRT
<213> ORGANISM: Aspergillus restrictus

<400> SEQUENCE: 591

Lys Leu Ile Lys Gly Arg Thr Pro Ile Lys Phe Gly Lys Ala Arg Cys
1               5                   10                  15

Arg Arg Pro Pro Lys His Ser Gly Lys
            20                  25

<210> SEQ ID NO 592
<211> LENGTH: 13
<212> TYPE: PRT
<213> ORGANISM: Aspergillus restrictus

<400> SEQUENCE: 592

Lys Leu Ile Lys Gly Arg Thr Pro Ile Lys Phe Gly Lys
1               5                   10

<210> SEQ ID NO 593
<211> LENGTH: 37
<212> TYPE: PRT
<213> ORGANISM: Homo sapiens

<400> SEQUENCE: 593

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys Pro Gln
            20                  25                  30

Thr Thr Lys Pro Lys
        35

<210> SEQ ID NO 594
<211> LENGTH: 30
<212> TYPE: PRT
<213> ORGANISM: Homo sapiens

<400> SEQUENCE: 594

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys Asp Leu Lys
            20                  25                  30

<210> SEQ ID NO 595
<211> LENGTH: 27
<212> TYPE: PRT
<213> ORGANISM: Homo sapiens

<400> SEQUENCE: 595

Lys Arg Ile Pro Asn Lys Lys Pro Gly Lys Lys Thr Thr Thr Lys Pro
1               5                   10                  15

Thr Lys Lys Pro Thr Ile Lys Thr Thr Lys Lys
            20                  25

<210> SEQ ID NO 596
<211> LENGTH: 23
<212> TYPE: PRT
<213> ORGANISM: Homo sapiens

<400> SEQUENCE: 596
```

Lys Arg Ile Pro Asn Lys Lys Pro Gly Lys Lys Thr Thr Thr Lys Pro
1               5                   10                  15

Thr Lys Lys Pro Thr Ile Lys
            20

<210> SEQ ID NO 597
<211> LENGTH: 19
<212> TYPE: PRT
<213> ORGANISM: Homo sapiens

<400> SEQUENCE: 597

Lys Arg Ile Pro Asn Lys Lys Pro Gly Lys Lys Thr Thr Thr Lys Pro
1               5                   10                  15

Thr Lys Lys

<210> SEQ ID NO 598
<211> LENGTH: 12
<212> TYPE: PRT
<213> ORGANISM: Homo sapiens

<400> SEQUENCE: 598

Lys Arg Ile Pro Asn Lys Lys Pro Gly Lys Lys Thr
1               5                   10

<210> SEQ ID NO 599
<211> LENGTH: 11
<212> TYPE: PRT
<213> ORGANISM: Homo sapiens

<400> SEQUENCE: 599

Lys Arg Ile Pro Asn Lys Lys Pro Gly Lys Lys
1               5                   10

<210> SEQ ID NO 600
<211> LENGTH: 10
<212> TYPE: PRT
<213> ORGANISM: Homo sapiens

<400> SEQUENCE: 600

Lys Arg Ile Pro Asn Lys Lys Pro Lys Lys
1               5                   10

<210> SEQ ID NO 601
<211> LENGTH: 10
<212> TYPE: PRT
<213> ORGANISM: Homo sapiens

<400> SEQUENCE: 601

Arg Arg Ile Pro Asn Arg Arg Pro Arg Arg
1               5                   10

<210> SEQ ID NO 602
<211> LENGTH: 22
<212> TYPE: PRT
<213> ORGANISM: Homo sapiens

<400> SEQUENCE: 602

Lys Lys Pro Gly Lys Lys Thr Thr Thr Lys Pro Thr Lys Lys Pro Thr
1               5                   10                  15

Ile Lys Thr Thr Lys Lys
            20

```
<210> SEQ ID NO 603
<211> LENGTH: 14
<212> TYPE: PRT
<213> ORGANISM: Homo sapiens

<400> SEQUENCE: 603

Lys Lys Pro Gly Lys Lys Thr Thr Thr Lys Pro Thr Lys Lys
1               5                   10

<210> SEQ ID NO 604
<211> LENGTH: 10
<212> TYPE: PRT
<213> ORGANISM: Homo sapiens

<400> SEQUENCE: 604

Lys Lys Pro Thr Ile Lys Thr Thr Lys Lys
1               5                   10

<210> SEQ ID NO 605
<211> LENGTH: 10
<212> TYPE: PRT
<213> ORGANISM: Homo sapiens

<400> SEQUENCE: 605

Lys Lys Thr Thr Thr Lys Pro Thr Lys Lys
1               5                   10

<210> SEQ ID NO 606
<211> LENGTH: 15
<212> TYPE: PRT
<213> ORGANISM: Homo sapiens

<400> SEQUENCE: 606

Lys Ser Ile Cys Lys Thr Ile Pro Ser Asn Lys Pro Lys Lys Lys
1               5                   10                  15

<210> SEQ ID NO 607
<211> LENGTH: 11
<212> TYPE: PRT
<213> ORGANISM: Homo sapiens

<400> SEQUENCE: 607

Lys Thr Ile Pro Ser Asn Lys Pro Lys Lys Lys
1               5                   10

<210> SEQ ID NO 608
<211> LENGTH: 12
<212> TYPE: PRT
<213> ORGANISM: Homo sapiens

<400> SEQUENCE: 608

Lys Pro Arg Ser Lys Asn Pro Lys Lys Pro Lys
1               5                   10

<210> SEQ ID NO 609
<211> LENGTH: 22
<212> TYPE: PRT
<213> ORGANISM: Human immunodeficiency virus type 1

<400> SEQUENCE: 609

Asp Arg Arg Arg Arg Gly Ser Arg Pro Ser Gly Ala Glu Arg Arg
1               5                   10                  15

Arg Arg Ala Ala Ala Ala
            20
```

<210> SEQ ID NO 610
<211> LENGTH: 17
<212> TYPE: PRT
<213> ORGANISM: Human immunodeficiency virus type 1

<400> SEQUENCE: 610

Asp Arg Arg Arg Arg Gly Ser Arg Pro Ser Gly Ala Glu Arg Arg Arg
1               5                   10                  15

Arg

<210> SEQ ID NO 611
<211> LENGTH: 15
<212> TYPE: PRT
<213> ORGANISM: Bacteriophage lambda

<400> SEQUENCE: 611

Gln Thr Arg Arg Arg Glu Arg Arg Ala Glu Lys Gln Ala Gln Trp
1               5                   10                  15

<210> SEQ ID NO 612
<211> LENGTH: 9
<212> TYPE: PRT
<213> ORGANISM: Bacteriophage lambda

<400> SEQUENCE: 612

Arg Arg Arg Glu Arg Arg Ala Glu Lys
1               5

<210> SEQ ID NO 613
<211> LENGTH: 11
<212> TYPE: PRT
<213> ORGANISM: Flock house virus

<400> SEQUENCE: 613

Asn Arg Ala Arg Arg Asn Arg Arg Arg Val Arg
1               5                   10

<210> SEQ ID NO 614
<211> LENGTH: 10
<212> TYPE: PRT
<213> ORGANISM: Flock house virus

<400> SEQUENCE: 614

Arg Thr Arg Arg Asn Arg Arg Arg Val Arg
1               5                   10

<210> SEQ ID NO 615
<211> LENGTH: 8
<212> TYPE: PRT
<213> ORGANISM: Alphavirus

<400> SEQUENCE: 615

Arg Asn Arg Ser Arg His Arg Arg
1               5

<210> SEQ ID NO 616
<211> LENGTH: 9
<212> TYPE: PRT
<213> ORGANISM: Alphavirus

<400> SEQUENCE: 616

Lys Cys Pro Ser Arg Arg Pro Lys Arg
1               5

```
<210> SEQ ID NO 617
<211> LENGTH: 16
<212> TYPE: PRT
<213> ORGANISM: Drosophila melanogaster

<400> SEQUENCE: 617

Lys Arg Pro Ala Ala Ile Lys Lys Ala Gly Gln Ala Lys Lys Lys Lys
1               5                   10                  15

<210> SEQ ID NO 618
<211> LENGTH: 12
<212> TYPE: PRT
<213> ORGANISM: Kaposi's sarcoma-associated herpesvirus

<400> SEQUENCE: 618

Thr Arg Arg Ser Lys Arg Arg Ser His Arg Lys Phe
1               5                   10

<210> SEQ ID NO 619
<211> LENGTH: 17
<212> TYPE: PRT
<213> ORGANISM: Bufo bufo

<400> SEQUENCE: 619

Arg Ala Gly Leu Gln Phe Pro Val Gly Arg Val His Arg Leu Leu Arg
1               5                   10                  15

Lys

<210> SEQ ID NO 620
<211> LENGTH: 22
<212> TYPE: PRT
<213> ORGANISM: Homo sapiens

<400> SEQUENCE: 620

Met Val Arg Arg Phe Leu Val Thr Leu Arg Ile Arg Arg Ala Cys Gly
1               5                   10                  15

Pro Pro Arg Val Arg Val
            20

<210> SEQ ID NO 621
<211> LENGTH: 22
<212> TYPE: PRT
<213> ORGANISM: Homo sapiens

<400> SEQUENCE: 621

Phe Val Thr Arg Gly Cys Pro Arg Arg Leu Val Ala Arg Leu Ile Arg
1               5                   10                  15

Val Met Val Pro Arg Arg
            20

<210> SEQ ID NO 622
<211> LENGTH: 13
<212> TYPE: PRT
<213> ORGANISM: Homo sapiens

<400> SEQUENCE: 622

Val Arg Arg Phe Leu Val Thr Leu Arg Ile Arg Arg Ala
1               5                   10

<210> SEQ ID NO 623
<211> LENGTH: 13
<212> TYPE: PRT
<213> ORGANISM: Homo sapiens
```

-continued

<400> SEQUENCE: 623

Arg Val Arg Ile Leu Ala Arg Phe Leu Arg Thr Arg Val
1               5                   10

<210> SEQ ID NO 624
<211> LENGTH: 13
<212> TYPE: PRT
<213> ORGANISM: Homo sapiens

<400> SEQUENCE: 624

Arg Val Arg Val Phe Val Val His Ile Pro Arg Leu Thr
1               5                   10

<210> SEQ ID NO 625
<211> LENGTH: 13
<212> TYPE: PRT
<213> ORGANISM: Homo sapiens

<400> SEQUENCE: 625

Val Ile Arg Val His Phe Arg Leu Pro Val Arg Thr Val
1               5                   10

<210> SEQ ID NO 626
<211> LENGTH: 37
<212> TYPE: PRT
<213> ORGANISM: Homo sapiens

<400> SEQUENCE: 626

Met Val Arg Arg Phe Leu Val Thr Leu Arg Ile Arg Arg Ala Cys Gly
1               5                   10                  15

Pro Pro Arg Val Arg Val Phe Val Val His Ile Pro Arg Leu Thr Gly
            20                  25                  30

Glu Trp Ala Ala Pro
        35

<210> SEQ ID NO 627
<211> LENGTH: 37
<212> TYPE: PRT
<213> ORGANISM: Homo sapiens

<400> SEQUENCE: 627

Phe Arg Val Pro Leu Arg Ile Arg Pro Cys Val Val Ala Pro Arg Leu
1               5                   10                  15

Val Met Val Arg His Thr Phe Gly Arg Ile Ala Arg Trp Val Ala Gly
            20                  25                  30

Pro Leu Glu Thr Arg
        35

<210> SEQ ID NO 628
<211> LENGTH: 25
<212> TYPE: PRT
<213> ORGANISM: Homo sapiens

<400> SEQUENCE: 628

Gly Thr Lys Met Ile Phe Val Gly Ile Lys Lys Lys Glu Glu Arg Ala
1               5                   10                  15

Asp Leu Ile Ala Tyr Leu Lys Lys Ala
            20                  25

<210> SEQ ID NO 629
<211> LENGTH: 16

```
<212> TYPE: PRT
<213> ORGANISM: Homo sapiens

<400> SEQUENCE: 629

Lys Lys Lys Glu Glu Arg Ala Asp Leu Ile Ala Tyr Leu Lys Lys Ala
1               5                   10                  15

<210> SEQ ID NO 630
<211> LENGTH: 14
<212> TYPE: PRT
<213> ORGANISM: Homo sapiens

<400> SEQUENCE: 630

Lys Met Ile Phe Val Gly Ile Lys Lys Lys Glu Glu Arg Ala
1               5                   10

<210> SEQ ID NO 631
<211> LENGTH: 10
<212> TYPE: PRT
<213> ORGANISM: Homo sapiens

<400> SEQUENCE: 631

Lys Met Ile Phe Val Gly Ile Lys Lys Lys
1               5                   10

<210> SEQ ID NO 632
<211> LENGTH: 10
<212> TYPE: PRT
<213> ORGANISM: Homo sapiens

<400> SEQUENCE: 632

Glu Lys Gly Lys Lys Ile Phe Ile Met Lys
1               5                   10

<210> SEQ ID NO 633
<211> LENGTH: 9
<212> TYPE: PRT
<213> ORGANISM: Homo sapiens

<400> SEQUENCE: 633

Lys Gly Lys Lys Ile Phe Ile Met Lys
1               5

<210> SEQ ID NO 634
<211> LENGTH: 17
<212> TYPE: PRT
<213> ORGANISM: Flock house virus

<400> SEQUENCE: 634

Arg Arg Arg Arg Asn Arg Thr Arg Arg Asn Arg Arg Arg Val Arg Gly
1               5                   10                  15

Cys

<210> SEQ ID NO 635
<211> LENGTH: 15
<212> TYPE: PRT
<213> ORGANISM: Human T-cell lymphotropic virus type 2

<400> SEQUENCE: 635

Thr Arg Arg Gln Arg Thr Arg Arg Ala Arg Arg Asn Arg Gly Cys
1               5                   10                  15

<210> SEQ ID NO 636
<211> LENGTH: 21
```

```
<212> TYPE: PRT
<213> ORGANISM: Brome mosaic virus

<400> SEQUENCE: 636

Lys Met Thr Arg Ala Gln Arg Arg Ala Ala Ala Arg Arg Asn Arg Trp
1               5                   10                  15

Thr Ala Arg Gly Cys
            20

<210> SEQ ID NO 637
<211> LENGTH: 21
<212> TYPE: PRT
<213> ORGANISM: Cowpea Chlorotic Mottle Virus

<400> SEQUENCE: 637

Lys Leu Thr Arg Ala Gln Arg Arg Ala Ala Ala Arg Lys Asn Lys Arg
1               5                   10                  15

Asn Thr Arg Gly Cys
            20

<210> SEQ ID NO 638
<211> LENGTH: 19
<212> TYPE: PRT
<213> ORGANISM: Bacteriophage P22

<400> SEQUENCE: 638

Asn Ala Lys Thr Arg Arg His Glu Arg Arg Arg Lys Leu Ala Ile Glu
1               5                   10                  15

Arg Gly Cys

<210> SEQ ID NO 639
<211> LENGTH: 24
<212> TYPE: PRT
<213> ORGANISM: Bacteriophage lambda

<400> SEQUENCE: 639

Met Asp Ala Gln Thr Arg Arg Arg Glu Arg Arg Ala Glu Lys Gln Ala
1               5                   10                  15

Gln Trp Lys Ala Ala Asn Gly Cys
            20

<210> SEQ ID NO 640
<211> LENGTH: 20
<212> TYPE: PRT
<213> ORGANISM: Bacteriophage phi-21

<400> SEQUENCE: 640

Thr Ala Lys Thr Arg Tyr Lys Ala Arg Arg Ala Glu Leu Ile Ala Glu
1               5                   10                  15

Arg Arg Gly Cys
            20

<210> SEQ ID NO 641
<211> LENGTH: 14
<212> TYPE: PRT
<213> ORGANISM: Homo sapiens

<400> SEQUENCE: 641

Ser Gln Met Thr Arg Gln Ala Arg Arg Leu Tyr Asx Gly Cys
1               5                   10

<210> SEQ ID NO 642
```

```
<211> LENGTH: 28
<212> TYPE: PRT
<213> ORGANISM: Homo sapiens

<400> SEQUENCE: 642

Lys Arg Arg Ile Arg Arg Glu Arg Asn Lys Met Ala Ala Ala Lys Ser
1               5                   10                  15

Arg Asn Arg Arg Arg Glu Leu Thr Asp Thr Gly Cys
            20                  25

<210> SEQ ID NO 643
<211> LENGTH: 30
<212> TYPE: PRT
<213> ORGANISM: Homo sapiens

<400> SEQUENCE: 643

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg Gly Cys
            20                  25                  30

<210> SEQ ID NO 644
<211> LENGTH: 24
<212> TYPE: PRT
<213> ORGANISM: Saccharomyces cerevisiae

<400> SEQUENCE: 644

Lys Arg Ala Arg Asn Thr Glu Ala Ala Arg Arg Ser Arg Ala Arg Lys
1               5                   10                  15

Leu Gln Arg Met Lys Gln Gly Cys
            20

<210> SEQ ID NO 645
<211> LENGTH: 22
<212> TYPE: PRT
<213> ORGANISM: Homo sapiens

<400> SEQUENCE: 645

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 646
<211> LENGTH: 19
<212> TYPE: PRT
<213> ORGANISM: Homo sapiens

<400> SEQUENCE: 646

Lys Cys Phe Gln Trp Gln Arg Asn Met Arg Lys Val Arg Gly Pro Pro
1               5                   10                  15

Val Ser Cys

<210> SEQ ID NO 647
<211> LENGTH: 22
<212> TYPE: PRT
<213> ORGANISM: Homo sapiens

<400> SEQUENCE: 647

Lys Cys Phe Gln Trp Gln Arg Asn Met Arg Lys Val Arg Gly Pro Pro
1               5                   10                  15

Val Ser Ser Ile Lys Arg
```

-continued

```
<210> SEQ ID NO 648
<211> LENGTH: 13
<212> TYPE: PRT
<213> ORGANISM: Homo sapiens

<400> SEQUENCE: 648

Lys Cys Phe Gln Trp Gln Arg Asn Met Arg Lys Val Arg
1               5                   10

<210> SEQ ID NO 649
<211> LENGTH: 16
<212> TYPE: PRT
<213> ORGANISM: Homo sapiens

<400> SEQUENCE: 649

Phe Gln Trp Gln Arg Asn Met Arg Lys Val Arg Gly Pro Pro Val Ser
1               5                   10                  15

<210> SEQ ID NO 650
<211> LENGTH: 19
<212> TYPE: PRT
<213> ORGANISM: Homo sapiens

<400> SEQUENCE: 650

Gln Trp Gln Arg Asn Met Arg Lys Val Arg Gly Pro Pro Val Ser Cys
1               5                   10                  15

Ile Lys Arg

<210> SEQ ID NO 651
<211> LENGTH: 10
<212> TYPE: PRT
<213> ORGANISM: Homo sapiens

<400> SEQUENCE: 651

Gln Trp Gln Arg Asn Met Arg Lys Val Arg
1               5                   10

<210> SEQ ID NO 652
<211> LENGTH: 16
<212> TYPE: PRT
<213> ORGANISM: Drosophila melanogaster

<400> SEQUENCE: 652

Arg Gln Ile Lys Ile Trp Phe Gln Asn Arg Arg Met Lys Trp Lys Lys
1               5                   10                  15

<210> SEQ ID NO 653
<211> LENGTH: 22
<212> TYPE: PRT
<213> ORGANISM: Rattus rattus

<400> SEQUENCE: 653

Lys Cys Phe Met Trp Gln Glu Met Leu Asn Lys Ala Gly Val Pro Lys
1               5                   10                  15

Leu Arg Cys Ala Arg Lys
                20

<210> SEQ ID NO 654
<211> LENGTH: 20
<212> TYPE: PRT
<213> ORGANISM: Homo sapiens
```

-continued

```
<400> SEQUENCE: 654

Gly Leu Trp Arg Ala Leu Trp Arg Leu Leu Arg Ser Leu Trp Arg Leu
1               5                   10                  15

Leu Trp Arg Ala
            20

<210> SEQ ID NO 655
<211> LENGTH: 20
<212> TYPE: PRT
<213> ORGANISM: Homo sapiens

<400> SEQUENCE: 655

Gly Leu Trp Trp Arg Leu Trp Trp Arg Leu Arg Ser Trp Phe Arg Leu
1               5                   10                  15

Trp Phe Arg Ala
            20

<210> SEQ ID NO 656
<211> LENGTH: 34
<212> TYPE: PRT
<213> ORGANISM: Human herpesvirus 1

<400> SEQUENCE: 656

Asp Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Glu

<210> SEQ ID NO 657
<211> LENGTH: 34
<212> TYPE: PRT
<213> ORGANISM: Homo sapiens

<400> SEQUENCE: 657

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 658
<211> LENGTH: 34
<212> TYPE: PRT
<213> ORGANISM: Homo sapiens

<400> SEQUENCE: 658

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 659
<211> LENGTH: 12
<212> TYPE: PRT
<213> ORGANISM: Hepatitis B virus

<400> SEQUENCE: 659

Pro Leu Ser Ser Ile Phe Ser Arg Ile Gly Asp Pro
```

```
1               5                   10

<210> SEQ ID NO 660
<211> LENGTH: 12
<212> TYPE: PRT
<213> ORGANISM: Hepatitis B virus

<400> SEQUENCE: 660

Pro Ser Ser Ser Ser Ser Ser Arg Ile Gly Asp Pro
1               5                   10

<210> SEQ ID NO 661
<211> LENGTH: 18
<212> TYPE: PRT
<213> ORGANISM: Zea mays

<400> SEQUENCE: 661

Val Arg Leu Pro Pro Pro Val Arg Leu Pro Pro Pro Val Arg Leu Pro
1               5                   10                  15

Pro Pro

<210> SEQ ID NO 662
<211> LENGTH: 18
<212> TYPE: PRT
<213> ORGANISM: Zea mays

<400> SEQUENCE: 662

Val Glu Leu Pro Pro Pro Val Glu Leu Pro Pro Pro Val Glu Leu Pro
1               5                   10                  15

Pro Pro

<210> SEQ ID NO 663
<211> LENGTH: 28
<212> TYPE: PRT
<213> ORGANISM: Homo sapiens

<400> SEQUENCE: 663

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 664
<211> LENGTH: 13
<212> TYPE: PRT
<213> ORGANISM: Homo sapiens

<400> SEQUENCE: 664

Ala Leu Trp Lys Thr Leu Leu Lys Lys Val Leu Lys Ala
1               5                   10

<210> SEQ ID NO 665
<211> LENGTH: 10
<212> TYPE: PRT
<213> ORGANISM: Human immunodeficiency virus type 1

<400> SEQUENCE: 665

Arg Gln Ala Arg Arg Asn Arg Arg Arg Cys
1               5                   10

<210> SEQ ID NO 666
<211> LENGTH: 14
<212> TYPE: PRT
```

<213> ORGANISM: Human immunodeficiency virus type 1

<400> SEQUENCE: 666

Gly Arg Lys Lys Arg Arg Gln Arg Arg Arg Pro Pro Gln Cys
1               5                   10

<210> SEQ ID NO 667
<211> LENGTH: 8
<212> TYPE: PRT
<213> ORGANISM: Homo sapiens

<400> SEQUENCE: 667

Gly Arg Lys Arg Lys Lys Arg Thr
1               5

<210> SEQ ID NO 668
<211> LENGTH: 22
<212> TYPE: PRT
<213> ORGANISM: Homo sapiens

<400> SEQUENCE: 668

Met Val Thr Val Leu Phe Arg Arg Leu Arg Ile Arg Arg Ala Cys Gly
1               5                   10                  15

Pro Pro Arg Val Arg Val
            20

<210> SEQ ID NO 669
<211> LENGTH: 16
<212> TYPE: PRT
<213> ORGANISM: Drosophila melanogaster

<400> SEQUENCE: 669

Arg Gln Ile Lys Ile Trp Phe Gln Asn Arg Arg Met Lys Trp Lys Lys
1               5                   10                  15

<210> SEQ ID NO 670
<211> LENGTH: 10
<212> TYPE: PRT
<213> ORGANISM: Homo sapiens

<400> SEQUENCE: 670

Val Gln Arg Lys Arg Gln Lys Leu Met Pro
1               5                   10

<210> SEQ ID NO 671
<211> LENGTH: 8
<212> TYPE: PRT
<213> ORGANISM: Homo sapiens

<400> SEQUENCE: 671

Ser Lys Lys Lys Lys Thr Lys Val
1               5

<210> SEQ ID NO 672
<211> LENGTH: 8
<212> TYPE: PRT
<213> ORGANISM: Homo sapiens

<400> SEQUENCE: 672

Gly Arg Lys Arg Lys Lys Arg Thr
1               5

<210> SEQ ID NO 673
<211> LENGTH: 11

<212> TYPE: PRT
<213> ORGANISM: Homo sapiens

<400> SEQUENCE: 673

Gly Lys Lys Lys Arg Lys Arg Glu Lys Leu
1               5                   10

<210> SEQ ID NO 674
<211> LENGTH: 7
<212> TYPE: PRT
<213> ORGANISM: Homo sapiens

<400> SEQUENCE: 674

Pro Lys Lys Lys Arg Lys Val
1               5

<210> SEQ ID NO 675
<211> LENGTH: 8
<212> TYPE: PRT
<213> ORGANISM: Caenorhabditis elegans

<400> SEQUENCE: 675

Glu Arg Lys Lys Arg Arg Arg Glu
1               5

<210> SEQ ID NO 676
<211> LENGTH: 7
<212> TYPE: PRT
<213> ORGANISM: Homo sapiens

<400> SEQUENCE: 676

Phe Lys Lys Phe Arg Lys Phe
1               5

<210> SEQ ID NO 677
<211> LENGTH: 24
<212> TYPE: PRT
<213> ORGANISM: Homo sapiens

<400> SEQUENCE: 677

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 678
<211> LENGTH: 24
<212> TYPE: PRT
<213> ORGANISM: Homo sapiens

<400> SEQUENCE: 678

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 679
<211> LENGTH: 21
<212> TYPE: PRT
<213> ORGANISM: Homo sapiens

<400> SEQUENCE: 679

Tyr Thr Gln Asp Phe Asn Lys Phe His Thr Phe Pro Gln Thr Ala Ile
1               5                   10                  15

```
Gly Val Gly Ala Pro
            20

<210> SEQ ID NO 680
<211> LENGTH: 18
<212> TYPE: PRT
<213> ORGANISM: Homo sapiens

<400> SEQUENCE: 680

Asp Phe Asn Lys Phe His Thr Phe Pro Gln Thr Ala Ile Gly Val Gly
1               5                   10                  15

Ala Pro

<210> SEQ ID NO 681
<211> LENGTH: 15
<212> TYPE: PRT
<213> ORGANISM: Homo sapiens

<400> SEQUENCE: 681

Lys Phe His Thr Phe Pro Gln Thr Ala Ile Gly Val Gly Ala Pro
1               5                   10                  15

<210> SEQ ID NO 682
<211> LENGTH: 12
<212> TYPE: PRT
<213> ORGANISM: Homo sapiens

<400> SEQUENCE: 682

Thr Phe Pro Gln Thr Ala Ile Gly Val Gly Ala Pro
1               5                   10

<210> SEQ ID NO 683
<211> LENGTH: 13
<212> TYPE: PRT
<213> ORGANISM: Human immunodeficiency virus type 1

<400> SEQUENCE: 683

Gly Tyr Gly Arg Lys Lys Arg Arg Gln Arg Arg Arg Gly
1               5                   10

<210> SEQ ID NO 684
<211> LENGTH: 13
<212> TYPE: PRT
<213> ORGANISM: Human immunodeficiency virus type 1

<400> SEQUENCE: 684

Gly Tyr Gly Arg Lys Lys Arg Arg Gln Arg Arg Arg Gly
1               5                   10

<210> SEQ ID NO 685
<211> LENGTH: 13
<212> TYPE: PRT
<213> ORGANISM: Human immunodeficiency virus type 1

<400> SEQUENCE: 685

Gly Tyr Gly Arg Lys Lys Arg Arg Gln Arg Arg Arg Gly
1               5                   10

<210> SEQ ID NO 686
<211> LENGTH: 16
<212> TYPE: PRT
<213> ORGANISM: Drosophila melanogaster

<400> SEQUENCE: 686
```

```
Arg Gln Ile Lys Ile Trp Phe Gln Asn Arg Arg Met Lys Trp Lys Lys
1               5                   10                  15

<210> SEQ ID NO 687
<211> LENGTH: 16
<212> TYPE: PRT
<213> ORGANISM: Drosophila melanogaster

<400> SEQUENCE: 687

Arg Gln Ile Lys Ile Trp Phe Gln Asn Arg Arg Met Lys Trp Lys Lys
1               5                   10                  15

<210> SEQ ID NO 688
<211> LENGTH: 16
<212> TYPE: PRT
<213> ORGANISM: Drosophila melanogaster

<400> SEQUENCE: 688

Arg Gln Ile Lys Ile Trp Phe Gln Asn Arg Arg Met Lys Trp Lys Lys
1               5                   10                  15

<210> SEQ ID NO 689
<211> LENGTH: 15
<212> TYPE: PRT
<213> ORGANISM: Homo sapiens

<400> SEQUENCE: 689

Phe Leu Gly Lys Lys Phe Lys Lys Tyr Phe Leu Gln Leu Leu Lys
1               5                   10                  15

<210> SEQ ID NO 690
<211> LENGTH: 23
<212> TYPE: PRT
<213> ORGANISM: Homo sapiens

<400> SEQUENCE: 690

Phe Leu Ile Phe Ile Arg Val Ile Cys Ile Val Ile Ala Lys Leu Lys
1               5                   10                  15

Ala Asn Leu Met Cys Lys Thr
            20

<210> SEQ ID NO 691
<211> LENGTH: 17
<212> TYPE: PRT
<213> ORGANISM: Homo sapiens

<400> SEQUENCE: 691

Lys Lys Ala Ala Gln Ile Arg Ser Gln Val Met Thr His Leu Arg Val
1               5                   10                  15

Ile

<210> SEQ ID NO 692
<211> LENGTH: 16
<212> TYPE: PRT
<213> ORGANISM: Homo sapiens

<400> SEQUENCE: 692

Tyr Ile Val Leu Arg Arg Arg Arg Lys Arg Val Asn Thr Lys Arg Ser
1               5                   10                  15

<210> SEQ ID NO 693
<211> LENGTH: 11
<212> TYPE: PRT
```

<213> ORGANISM: Homo sapiens

<400> SEQUENCE: 693

Arg Arg Lys Leu Ser Gln Gln Lys Glu Lys Lys
1               5                   10

<210> SEQ ID NO 694
<211> LENGTH: 15
<212> TYPE: PRT
<213> ORGANISM: Homo sapiens

<400> SEQUENCE: 694

Val Gln Ala Ile Leu Arg Arg Asn Trp Asn Gln Tyr Lys Ile Gln
1               5                   10                  15

<210> SEQ ID NO 695
<211> LENGTH: 19
<212> TYPE: PRT
<213> ORGANISM: Homo sapiens

<400> SEQUENCE: 695

Lys Leu Pro Cys Arg Ser Asn Thr Phe Leu Asn Ile Phe Arg Arg Lys
1               5                   10                  15

Lys Pro Gly

<210> SEQ ID NO 696
<211> LENGTH: 16
<212> TYPE: PRT
<213> ORGANISM: Homo sapiens

<400> SEQUENCE: 696

Lys Lys Ile Cys Thr Arg Lys Pro Arg Phe Met Ser Ala Trp Ala Gln
1               5                   10                  15

<210> SEQ ID NO 697
<211> LENGTH: 16
<212> TYPE: PRT
<213> ORGANISM: Drosophila melanogaster

<400> SEQUENCE: 697

Arg Gln Ile Lys Ile Trp Phe Gln Asn Arg Arg Met Lys Trp Lys Lys
1               5                   10                  15

<210> SEQ ID NO 698
<211> LENGTH: 18
<212> TYPE: PRT
<213> ORGANISM: Sus scrofa

<400> SEQUENCE: 698

Arg Gly Gly Arg Leu Ser Tyr Ser Arg Arg Phe Ser Thr Ser Thr
1               5                   10                  15

Gly Arg

<210> SEQ ID NO 699
<211> LENGTH: 18
<212> TYPE: PRT
<213> ORGANISM: Sus scrofa

<400> SEQUENCE: 699

Arg Gly Gly Arg Leu Ser Tyr Ser Arg Arg Phe Ser Thr Ser Thr
1               5                   10                  15

Gly Arg

<210> SEQ ID NO 700
<211> LENGTH: 10
<212> TYPE: PRT
<213> ORGANISM: Sus scrofa

<400> SEQUENCE: 700

Arg Arg Leu Ser Tyr Ser Arg Arg Arg Phe
1               5                   10

<210> SEQ ID NO 701
<211> LENGTH: 10
<212> TYPE: PRT
<213> ORGANISM: Sus scrofa

<400> SEQUENCE: 701

Arg Arg Leu Ser Tyr Ser Arg Arg Arg Phe
1               5                   10

<210> SEQ ID NO 702
<211> LENGTH: 17
<212> TYPE: PRT
<213> ORGANISM: Sus scrofa

<400> SEQUENCE: 702

Arg Gly Gly Arg Leu Ala Tyr Leu Arg Arg Trp Ala Val Leu Gly
1               5                   10                  15

Arg

<210> SEQ ID NO 703
<211> LENGTH: 16
<212> TYPE: PRT
<213> ORGANISM: Drosophila melanogaster

<400> SEQUENCE: 703

Arg Gln Ile Lys Ile Trp Phe Gln Asn Arg Arg Met Lys Trp Lys Lys
1               5                   10                  15

<210> SEQ ID NO 704
<211> LENGTH: 28
<212> TYPE: PRT
<213> ORGANISM: Mus musculus

<400> SEQUENCE: 704

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 705
<211> LENGTH: 28
<212> TYPE: PRT
<213> ORGANISM: Homo sapiens

<400> SEQUENCE: 705

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro
            20                  25

<210> SEQ ID NO 706
<211> LENGTH: 30
<212> TYPE: PRT
<213> ORGANISM: Bos primigenius

<400> SEQUENCE: 706

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 707
<211> LENGTH: 38
<212> TYPE: PRT
<213> ORGANISM: Homo sapiens

<400> SEQUENCE: 707

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Cys
            35

<210> SEQ ID NO 708
<211> LENGTH: 16
<212> TYPE: PRT
<213> ORGANISM: Drosophila melanogaster

<400> SEQUENCE: 708

Arg Gln Ile Lys Ile Trp Phe Gln Asn Arg Arg Met Lys Trp Lys Lys
1               5                   10                  15

<210> SEQ ID NO 709
<211> LENGTH: 16
<212> TYPE: PRT
<213> ORGANISM: Rattus rattus

<400> SEQUENCE: 709

Arg Val Ile Arg Val Trp Phe Gln Asn Lys Arg Cys Lys Asp Lys Lys
1               5                   10                  15

<210> SEQ ID NO 710
<211> LENGTH: 23
<212> TYPE: PRT
<213> ORGANISM: Xenopus laevis

<400> SEQUENCE: 710

Gly Ile Gly Lys Phe Leu His Ser Ala Lys Lys Trp Gly Lys Ala Phe
1               5                   10                  15

Val Gly Gln Ile Met Asn Cys
            20

<210> SEQ ID NO 711
<211> LENGTH: 24
<212> TYPE: PRT
<213> ORGANISM: Bufo bufo

<400> SEQUENCE: 711

Thr Arg Ser Ser Arg Ala Gly Leu Gln Trp Pro Val Gly Arg Val His
1               5                   10                  15

Arg Leu Leu Arg Lys Gly Gly Cys
            20

<210> SEQ ID NO 712
<211> LENGTH: 11

-continued

```
<212> TYPE: PRT
<213> ORGANISM: Human immunodeficiency virus type 1

<400> SEQUENCE: 712

Tyr Gly Arg Lys Lys Arg Arg Gln Arg Arg
1               5                   10

<210> SEQ ID NO 713
<211> LENGTH: 16
<212> TYPE: PRT
<213> ORGANISM: Homo sapiens

<400> SEQUENCE: 713

Arg His Ile Lys Ile Trp Phe Gln Asn Arg Arg Met Lys Trp Lys Lys
1               5                   10                  15

<210> SEQ ID NO 714
<211> LENGTH: 9
<212> TYPE: PRT
<213> ORGANISM: Human immunodeficiency virus type 1

<400> SEQUENCE: 714

Arg Lys Lys Arg Arg Gln Arg Arg Arg
1               5

<210> SEQ ID NO 715
<211> LENGTH: 16
<212> TYPE: PRT
<213> ORGANISM: Drosophila melanogaster

<400> SEQUENCE: 715

Arg Gln Ile Lys Ile Trp Phe Gln Asn Arg Arg Met Lys Trp Lys Lys
1               5                   10                  15

<210> SEQ ID NO 716
<211> LENGTH: 60
<212> TYPE: PRT
<213> ORGANISM: Drosophila melanogaster

<400> SEQUENCE: 716

Ser Lys Arg Thr Arg Gln Thr Tyr Thr Arg Tyr Gln Thr Leu Glu Leu
1               5                   10                  15

Glu Lys Glu Phe His Phe Asn Arg Tyr Ile Thr Arg Arg Arg Ile
            20                  25                  30

Asp Ile Ala Asn Ala Leu Ser Leu Ser Glu Arg Gln Ile Lys Ile Trp
        35                  40                  45

Phe Gln Asn Arg Arg Met Lys Ser Lys Lys Asp Arg
    50                  55                  60

<210> SEQ ID NO 717
<211> LENGTH: 61
<212> TYPE: PRT
<213> ORGANISM: Drosophila melanogaster

<400> SEQUENCE: 717

Glu Lys Arg Pro Arg Thr Ala Phe Ser Ser Glu Gln Leu Ala Arg Leu
1               5                   10                  15

Lys Arg Glu Phe Asn Glu Asn Arg Tyr Leu Thr Glu Arg Arg Arg
            20                  25                  30

Gln Gln Leu Ser Ser Glu Leu Gly Leu Asn Glu Ala Gln Ile Lys Ile
        35                  40                  45

Trp Phe Gln Asn Lys Arg Ala Lys Ile Lys Lys Ser Thr
    50                  55
```

-continued

```
            50                  55                  60

<210> SEQ ID NO 718
<211> LENGTH: 13
<212> TYPE: PRT
<213> ORGANISM: Human immunodeficiency virus type 1

<400> SEQUENCE: 718

Gly Arg Arg Arg Arg Arg Arg Arg Arg Pro Pro Gln
1               5                   10

<210> SEQ ID NO 719
<211> LENGTH: 10
<212> TYPE: PRT
<213> ORGANISM: Homo sapiens

<400> SEQUENCE: 719

Met Leu Leu Leu Thr Arg Arg Arg Ser Thr
1               5                   10

<210> SEQ ID NO 720
<211> LENGTH: 16
<212> TYPE: PRT
<213> ORGANISM: Homo sapiens

<400> SEQUENCE: 720

Gly Leu Arg Lys Arg Leu Arg Lys Phe Arg Asn Lys Ile Lys Glu Lys
1               5                   10                  15

<210> SEQ ID NO 721
<211> LENGTH: 6
<212> TYPE: PRT
<213> ORGANISM: Zea mays

<400> SEQUENCE: 721

Val Arg Leu Pro Pro Pro
1               5

<210> SEQ ID NO 722
<211> LENGTH: 12
<212> TYPE: PRT
<213> ORGANISM: Zea mays

<400> SEQUENCE: 722

Val Arg Leu Pro Pro Pro Val Arg Leu Pro Pro Pro
1               5                   10

<210> SEQ ID NO 723
<211> LENGTH: 18
<212> TYPE: PRT
<213> ORGANISM: Zea mays

<400> SEQUENCE: 723

Val Arg Leu Pro Pro Pro Val Arg Leu Pro Pro Pro Val Arg Leu Pro
1               5                   10                  15

Pro Pro

<210> SEQ ID NO 724
<211> LENGTH: 6
<212> TYPE: PRT
<213> ORGANISM: Zea mays

<400> SEQUENCE: 724

Val His Leu Pro Pro Pro
```

```
<210> SEQ ID NO 725
<211> LENGTH: 12
<212> TYPE: PRT
<213> ORGANISM: Zea mays

<400> SEQUENCE: 725

Val His Leu Pro Pro Pro Val His Leu Pro Pro Pro
1               5                   10

<210> SEQ ID NO 726
<211> LENGTH: 18
<212> TYPE: PRT
<213> ORGANISM: Zea mays

<400> SEQUENCE: 726

Val His Leu Pro Pro Pro Val His Leu Pro Pro Pro Val His Leu Pro
1               5                   10                  15

Pro Pro

<210> SEQ ID NO 727
<211> LENGTH: 6
<212> TYPE: PRT
<213> ORGANISM: Zea mays

<400> SEQUENCE: 727

Val Lys Leu Pro Pro Pro
1               5

<210> SEQ ID NO 728
<211> LENGTH: 12
<212> TYPE: PRT
<213> ORGANISM: Zea mays

<400> SEQUENCE: 728

Val Lys Leu Pro Pro Pro Val Lys Leu Pro Pro Pro
1               5                   10

<210> SEQ ID NO 729
<211> LENGTH: 18
<212> TYPE: PRT
<213> ORGANISM: Zea mays

<400> SEQUENCE: 729

Val Lys Leu Pro Pro Pro Val Lys Leu Pro Pro Pro Val Lys Leu Pro
1               5                   10                  15

Pro Pro

<210> SEQ ID NO 730
<211> LENGTH: 16
<212> TYPE: PRT
<213> ORGANISM: Drosophila melanogaster

<400> SEQUENCE: 730

Arg Gln Ile Lys Ile Trp Phe Gln Asn Arg Arg Met Lys Trp Lys Lys
1               5                   10                  15

<210> SEQ ID NO 731
<211> LENGTH: 16
<212> TYPE: PRT
<213> ORGANISM: Drosophila melanogaster

<400> SEQUENCE: 731
```

Arg Gln Ile Lys Ile Phe Phe Gln Asn Arg Arg Met Lys Trp Lys Lys
1               5                   10                  15

<210> SEQ ID NO 732
<211> LENGTH: 21
<212> TYPE: PRT
<213> ORGANISM: Flock house virus

<400> SEQUENCE: 732

Ala Ser Met Trp Glu Arg Val Lys Ser Ile Ile Lys Ser Ser Leu Ala
1               5                   10                  15

Ala Ala Ser Asn Ile
            20

<210> SEQ ID NO 733
<211> LENGTH: 21
<212> TYPE: PRT
<213> ORGANISM: Flock house virus

<400> SEQUENCE: 733

Ala Ser Met Trp Glu Arg Val Lys Ser Ile Ile Lys Ser Ser Leu Ala
1               5                   10                  15

Ala Ala Ser Asn Ile
            20

<210> SEQ ID NO 734
<211> LENGTH: 16
<212> TYPE: PRT
<213> ORGANISM: Homo sapiens

<400> SEQUENCE: 734

Cys Ser Ile Pro Pro Glu Val Lys Phe Asn Pro Phe Val Tyr Leu Ile
1               5                   10                  15

<210> SEQ ID NO 735
<211> LENGTH: 16
<212> TYPE: PRT
<213> ORGANISM: Homo sapiens

<400> SEQUENCE: 735

Cys Ser Ile Pro Pro Glu Val Lys Phe Asn Pro Phe Val Tyr Leu Ile
1               5                   10                  15

<210> SEQ ID NO 736
<211> LENGTH: 6
<212> TYPE: PRT
<213> ORGANISM: Homo sapiens

<400> SEQUENCE: 736

Pro Phe Val Tyr Leu Ile
1               5

<210> SEQ ID NO 737
<211> LENGTH: 8
<212> TYPE: PRT
<213> ORGANISM: Homo sapiens

<400> SEQUENCE: 737

Asn Lys Pro Ile Leu Val Phe Tyr
1               5

<210> SEQ ID NO 738
<211> LENGTH: 14

```
<212> TYPE: PRT
<213> ORGANISM: Crotalus durissus

<400> SEQUENCE: 738

Tyr Lys Gln Cys His Lys Lys Gly Gly Lys Lys Gly Ser Gly
1               5                   10

<210> SEQ ID NO 739
<211> LENGTH: 15
<212> TYPE: PRT
<213> ORGANISM: Crotalus durissus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 739

Tyr Lys Gln Cys His Lys Lys Gly Gly Xaa Lys Lys Gly Ser Gly
1               5                   10                  15

<210> SEQ ID NO 740
<211> LENGTH: 14
<212> TYPE: PRT
<213> ORGANISM: Crotalus durissus

<400> SEQUENCE: 740

Gly Ser Gly Lys Lys Gly Gly Lys Lys His Cys Gln Lys Tyr
1               5                   10

<210> SEQ ID NO 741
<211> LENGTH: 14
<212> TYPE: PRT
<213> ORGANISM: Crotalus durissus

<400> SEQUENCE: 741

Gly Ser Gly Lys Lys Gly Gly Lys Lys Ile Cys Gln Lys Tyr
1               5                   10

<210> SEQ ID NO 742
<211> LENGTH: 23
<212> TYPE: PRT
<213> ORGANISM: Drosophila melanogaster

<400> SEQUENCE: 742

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 743
<211> LENGTH: 16
<212> TYPE: PRT
<213> ORGANISM: Homo sapiens

<400> SEQUENCE: 743

Ala Ala Val Ala Leu Leu Pro Ala Val Leu Leu Ala Leu Leu Ala Pro
1               5                   10                  15

<210> SEQ ID NO 744
<211> LENGTH: 23
<212> TYPE: PRT
<213> ORGANISM: Homo sapiens

<400> SEQUENCE: 744

Cys Gly Ala Tyr Asp Leu Arg Arg Arg Glu Arg Gln Ser Arg Leu Arg
```

```
1               5                  10                  15
Arg Arg Glu Arg Gln Ser Arg
                20

<210> SEQ ID NO 745
<211> LENGTH: 17
<212> TYPE: PRT
<213> ORGANISM: Homo sapiens

<400> SEQUENCE: 745

Arg Lys Lys Arg Arg Arg Glu Ser Arg Lys Lys Arg Arg Glu Ser
1               5                  10                  15

Cys

<210> SEQ ID NO 746
<211> LENGTH: 19
<212> TYPE: PRT
<213> ORGANISM: Homo sapiens

<400> SEQUENCE: 746

Cys Val Lys Arg Gly Leu Lys Leu Arg His Val Arg Pro Arg Val Thr
1               5                  10                  15

Arg Asp Val

<210> SEQ ID NO 747
<211> LENGTH: 17
<212> TYPE: PRT
<213> ORGANISM: Drosophila melanogaster

<400> SEQUENCE: 747

Cys Arg Gln Ile Lys Ile Trp Phe Gln Asn Arg Arg Met Lys Trp Lys
1               5                  10                  15

Lys

<210> SEQ ID NO 748
<211> LENGTH: 15
<212> TYPE: PRT
<213> ORGANISM: Homo sapiens

<400> SEQUENCE: 748

Pro Pro Lys Lys Ser Ala Gln Cys Leu Arg Tyr Lys Lys Pro Glu
1               5                  10                  15

<210> SEQ ID NO 749
<211> LENGTH: 15
<212> TYPE: PRT
<213> ORGANISM: Homo sapiens

<400> SEQUENCE: 749

Asp Pro Val Asp Thr Pro Asn Pro Thr Arg Arg Lys Pro Gly Lys
1               5                  10                  15

<210> SEQ ID NO 750
<211> LENGTH: 13
<212> TYPE: PRT
<213> ORGANISM: Homo sapiens

<400> SEQUENCE: 750

Lys Arg Val Ser Arg Asn Lys Ser Glu Lys Lys Arg Arg
1               5                  10

<210> SEQ ID NO 751
```

```
<211> LENGTH: 16
<212> TYPE: PRT
<213> ORGANISM: Homo sapiens

<400> SEQUENCE: 751

Gly Arg Arg His His Cys Arg Ser Lys Ala Lys Arg Ser Arg His His
1               5                   10                  15

<210> SEQ ID NO 752
<211> LENGTH: 16
<212> TYPE: PRT
<213> ORGANISM: Homo sapiens

<400> SEQUENCE: 752

Ser Ala Arg His His Cys Arg Ser Lys Ala Lys Arg Ser Arg His His
1               5                   10                  15

<210> SEQ ID NO 753
<211> LENGTH: 16
<212> TYPE: PRT
<213> ORGANISM: Homo sapiens

<400> SEQUENCE: 753

Ser Arg Ala His His Cys Arg Ser Lys Ala Lys Arg Ser Arg His His
1               5                   10                  15

<210> SEQ ID NO 754
<211> LENGTH: 16
<212> TYPE: PRT
<213> ORGANISM: Homo sapiens

<400> SEQUENCE: 754

Ser Arg Arg Ala His Cys Arg Ser Lys Ala Lys Arg Ser Arg His His
1               5                   10                  15

<210> SEQ ID NO 755
<211> LENGTH: 16
<212> TYPE: PRT
<213> ORGANISM: Homo sapiens

<400> SEQUENCE: 755

Ser Arg Arg His Ala Cys Arg Ser Lys Ala Lys Arg Ser Arg His His
1               5                   10                  15

<210> SEQ ID NO 756
<211> LENGTH: 16
<212> TYPE: PRT
<213> ORGANISM: Homo sapiens

<400> SEQUENCE: 756

Ser Arg Arg His His Ala Arg Ser Lys Ala Lys Arg Ser Arg His His
1               5                   10                  15

<210> SEQ ID NO 757
<211> LENGTH: 16
<212> TYPE: PRT
<213> ORGANISM: Homo sapiens

<400> SEQUENCE: 757

Ser Arg Arg His His Cys Arg Ala Lys Ala Lys Arg Ser Arg His His
1               5                   10                  15

<210> SEQ ID NO 758
<211> LENGTH: 16
<212> TYPE: PRT
```

<213> ORGANISM: Homo sapiens

<400> SEQUENCE: 758

Ser Arg Arg His His Cys Arg Ser Ala Ala Lys Arg Ser Arg His His
1               5                   10                  15

<210> SEQ ID NO 759
<211> LENGTH: 16
<212> TYPE: PRT
<213> ORGANISM: Homo sapiens

<400> SEQUENCE: 759

Ser Arg Arg His His Cys Arg Ser Lys Ala Ala Arg Ser Arg His His
1               5                   10                  15

<210> SEQ ID NO 760
<211> LENGTH: 16
<212> TYPE: PRT
<213> ORGANISM: Homo sapiens

<400> SEQUENCE: 760

Ser Arg Arg His His Cys Arg Ser Lys Ala Lys Ala Ser Arg His His
1               5                   10                  15

<210> SEQ ID NO 761
<211> LENGTH: 16
<212> TYPE: PRT
<213> ORGANISM: Homo sapiens

<400> SEQUENCE: 761

Ser Arg Arg His His Cys Arg Ser Lys Ala Lys Arg Ala Arg His His
1               5                   10                  15

<210> SEQ ID NO 762
<211> LENGTH: 16
<212> TYPE: PRT
<213> ORGANISM: Homo sapiens

<400> SEQUENCE: 762

Ser Arg Arg His His Cys Arg Ser Lys Ala Lys Arg Ser Ala His His
1               5                   10                  15

<210> SEQ ID NO 763
<211> LENGTH: 13
<212> TYPE: PRT
<213> ORGANISM: Homo sapiens

<400> SEQUENCE: 763

Arg Arg His His Cys Arg Ser Lys Ala Lys Arg Ser Arg
1               5                   10

<210> SEQ ID NO 764
<211> LENGTH: 12
<212> TYPE: PRT
<213> ORGANISM: Homo sapiens

<400> SEQUENCE: 764

Gly Arg Lys Gly Lys His Lys Arg Lys Lys Leu Pro
1               5                   10

<210> SEQ ID NO 765
<211> LENGTH: 18
<212> TYPE: PRT
<213> ORGANISM: Homo sapiens

```
<400> SEQUENCE: 765

Gly Lys Arg Val Ala Lys Arg Lys Leu Ile Glu Gln Asn Arg Glu Arg
1               5                   10                  15

Arg Arg

<210> SEQ ID NO 766
<211> LENGTH: 18
<212> TYPE: PRT
<213> ORGANISM: Homo sapiens

<400> SEQUENCE: 766

Gly Arg Lys Leu Lys Lys Lys Asn Glu Lys Glu Asp Lys Arg Pro
1               5                   10                  15

Arg Thr

<210> SEQ ID NO 767
<211> LENGTH: 17
<212> TYPE: PRT
<213> ORGANISM: Homo sapiens

<400> SEQUENCE: 767

Gly Lys Lys Thr Asn Leu Phe Ser Ala Leu Ile Lys Lys Lys Thr
1               5                   10                  15

Ala

<210> SEQ ID NO 768
<211> LENGTH: 18
<212> TYPE: PRT
<213> ORGANISM: Homo sapiens

<400> SEQUENCE: 768

Gly Arg Arg Glu Arg Asn Lys Met Ala Ala Ala Lys Cys Arg Asn Arg
1               5                   10                  15

Arg Arg

<210> SEQ ID NO 769
<211> LENGTH: 18
<212> TYPE: PRT
<213> ORGANISM: Homo sapiens

<400> SEQUENCE: 769

Gly Lys Arg Ala Arg Asn Thr Glu Ala Ala Arg Arg Ser Arg Ala Arg
1               5                   10                  15

Lys Leu

<210> SEQ ID NO 770
<211> LENGTH: 14
<212> TYPE: PRT
<213> ORGANISM: Homo sapiens

<400> SEQUENCE: 770

Gly Arg Arg Arg Arg Ala Thr Ala Lys Tyr Arg Thr Ala His
1               5                   10

<210> SEQ ID NO 771
<211> LENGTH: 15
<212> TYPE: PRT
<213> ORGANISM: Homo sapiens

<400> SEQUENCE: 771

Gly Lys Arg Arg Arg Arg Ala Thr Ala Lys Tyr Arg Ser Ala His
1               5                   10                  15
```

<210> SEQ ID NO 772
<211> LENGTH: 12
<212> TYPE: PRT
<213> ORGANISM: Homo sapiens

<400> SEQUENCE: 772

Gly Arg Arg Arg Arg Lys Arg Leu Ser His Arg Thr
1               5                   10

<210> SEQ ID NO 773
<211> LENGTH: 10
<212> TYPE: PRT
<213> ORGANISM: Homo sapiens

<400> SEQUENCE: 773

Gly Arg Arg Arg Arg Arg Glu Arg Asn Lys
1               5                   10

<210> SEQ ID NO 774
<211> LENGTH: 16
<212> TYPE: PRT
<213> ORGANISM: Homo sapiens

<400> SEQUENCE: 774

Gly Lys His Arg His Glu Arg Gly His His Arg Asp Arg Arg Glu Arg
1               5                   10                  15

<210> SEQ ID NO 775
<211> LENGTH: 17
<212> TYPE: PRT
<213> ORGANISM: Homo sapiens

<400> SEQUENCE: 775

Gly Lys Lys Lys Arg Lys Leu Ser Asn Arg Glu Ser Ala Lys Arg Ser
1               5                   10                  15

Arg

<210> SEQ ID NO 776
<211> LENGTH: 10
<212> TYPE: PRT
<213> ORGANISM: Homo sapiens

<400> SEQUENCE: 776

Met Ile Ile Tyr Arg Asp Leu Ile Ser His
1               5                   10

<210> SEQ ID NO 777
<211> LENGTH: 9
<212> TYPE: PRT
<213> ORGANISM: Homo sapiens

<400> SEQUENCE: 777

Met Ile Ile Tyr Arg Asp Leu Ile Ser
1               5

<210> SEQ ID NO 778
<211> LENGTH: 8
<212> TYPE: PRT
<213> ORGANISM: Homo sapiens

<400> SEQUENCE: 778

Met Ile Ile Tyr Arg Asp Leu Ile

```
<210> SEQ ID NO 779
<211> LENGTH: 9
<212> TYPE: PRT
<213> ORGANISM: Homo sapiens

<400> SEQUENCE: 779

Ile Ile Tyr Arg Asp Leu Ile Ser His
1               5

<210> SEQ ID NO 780
<211> LENGTH: 7
<212> TYPE: PRT
<213> ORGANISM: Homo sapiens

<400> SEQUENCE: 780

Met Ile Ile Tyr Arg Asp Leu
1               5

<210> SEQ ID NO 781
<211> LENGTH: 6
<212> TYPE: PRT
<213> ORGANISM: Homo sapiens

<400> SEQUENCE: 781

Met Ile Ile Tyr Arg Asp
1               5

<210> SEQ ID NO 782
<211> LENGTH: 8
<212> TYPE: PRT
<213> ORGANISM: Homo sapiens

<400> SEQUENCE: 782

Ile Tyr Arg Asp Leu Ile Ser His
1               5

<210> SEQ ID NO 783
<211> LENGTH: 9
<212> TYPE: PRT
<213> ORGANISM: Homo sapiens

<400> SEQUENCE: 783

Ala Ile Ile Tyr Arg Asp Leu Ile Ser
1               5

<210> SEQ ID NO 784
<211> LENGTH: 9
<212> TYPE: PRT
<213> ORGANISM: Homo sapiens

<400> SEQUENCE: 784

Met Ala Ile Tyr Arg Asp Leu Ile Ser
1               5

<210> SEQ ID NO 785
<211> LENGTH: 9
<212> TYPE: PRT
<213> ORGANISM: Homo sapiens

<400> SEQUENCE: 785

Met Ile Ala Tyr Arg Asp Leu Ile Ser
1               5
```

<210> SEQ ID NO 786
<211> LENGTH: 9
<212> TYPE: PRT
<213> ORGANISM: Homo sapiens

<400> SEQUENCE: 786

Met Ile Ile Ala Arg Asp Leu Ile Ser
1               5

<210> SEQ ID NO 787
<211> LENGTH: 9
<212> TYPE: PRT
<213> ORGANISM: Homo sapiens

<400> SEQUENCE: 787

Met Ile Ile Tyr Ala Asp Leu Ile Ser
1               5

<210> SEQ ID NO 788
<211> LENGTH: 9
<212> TYPE: PRT
<213> ORGANISM: Homo sapiens

<400> SEQUENCE: 788

Met Ile Ile Tyr Arg Ala Leu Ile Ser
1               5

<210> SEQ ID NO 789
<211> LENGTH: 9
<212> TYPE: PRT
<213> ORGANISM: Homo sapiens

<400> SEQUENCE: 789

Met Ile Ile Tyr Arg Asp Ala Ile Ser
1               5

<210> SEQ ID NO 790
<211> LENGTH: 9
<212> TYPE: PRT
<213> ORGANISM: Homo sapiens

<400> SEQUENCE: 790

Met Ile Ile Tyr Arg Asp Leu Ala Ser
1               5

<210> SEQ ID NO 791
<211> LENGTH: 9
<212> TYPE: PRT
<213> ORGANISM: Homo sapiens

<400> SEQUENCE: 791

Met Ile Ile Tyr Arg Asp Leu Ile Ala
1               5

<210> SEQ ID NO 792
<211> LENGTH: 11
<212> TYPE: PRT
<213> ORGANISM: Homo sapiens

<400> SEQUENCE: 792

Met Ile Ile Tyr Arg Asp Leu Ile Ser Lys Lys
1               5                   10

<210> SEQ ID NO 793

```
<211> LENGTH: 10
<212> TYPE: PRT
<213> ORGANISM: Homo sapiens

<400> SEQUENCE: 793

Met Ile Ile Tyr Arg Asp Lys Lys Ser His
1               5                   10

<210> SEQ ID NO 794
<211> LENGTH: 10
<212> TYPE: PRT
<213> ORGANISM: Homo sapiens

<400> SEQUENCE: 794

Met Ile Ile Phe Arg Asp Leu Ile Ser His
1               5                   10

<210> SEQ ID NO 795
<211> LENGTH: 10
<212> TYPE: PRT
<213> ORGANISM: Homo sapiens

<400> SEQUENCE: 795

Met Ile Ile Ser Arg Asp Leu Ile Ser His
1               5                   10

<210> SEQ ID NO 796
<211> LENGTH: 10
<212> TYPE: PRT
<213> ORGANISM: Homo sapiens

<400> SEQUENCE: 796

Gln Ile Ile Ser Arg Asp Leu Ile Ser His
1               5                   10

<210> SEQ ID NO 797
<211> LENGTH: 10
<212> TYPE: PRT
<213> ORGANISM: Homo sapiens

<400> SEQUENCE: 797

Cys Ile Ile Ser Arg Asp Leu Ile Ser His
1               5                   10

<210> SEQ ID NO 798
<211> LENGTH: 12
<212> TYPE: PRT
<213> ORGANISM: Homo sapiens

<400> SEQUENCE: 798

Met Ile Ile Tyr Arg Ala Leu Ile Ser His Lys Lys
1               5                   10

<210> SEQ ID NO 799
<211> LENGTH: 12
<212> TYPE: PRT
<213> ORGANISM: Homo sapiens

<400> SEQUENCE: 799

Met Ile Ile Tyr Arg Ile Ala Ala Ser His Lys Lys
1               5                   10

<210> SEQ ID NO 800
<211> LENGTH: 10
<212> TYPE: PRT
```

<213> ORGANISM: Homo sapiens

<400> SEQUENCE: 800

Met Ile Ile Arg Arg Asp Leu Ile Ser Glu
1               5                   10

<210> SEQ ID NO 801
<211> LENGTH: 10
<212> TYPE: PRT
<213> ORGANISM: Homo sapiens

<400> SEQUENCE: 801

Met Ile Ile Tyr Arg Ala Glu Ile Ser His
1               5                   10

<210> SEQ ID NO 802
<211> LENGTH: 10
<212> TYPE: PRT
<213> ORGANISM: Homo sapiens

<400> SEQUENCE: 802

Met Ile Ile Tyr Ala Arg Arg Ala Glu Glu
1               5                   10

<210> SEQ ID NO 803
<211> LENGTH: 12
<212> TYPE: PRT
<213> ORGANISM: Homo sapiens

<400> SEQUENCE: 803

Met Ile Ile Phe Arg Ile Ala Ala Ser His Lys Lys
1               5                   10

<210> SEQ ID NO 804
<211> LENGTH: 12
<212> TYPE: PRT
<213> ORGANISM: Homo sapiens

<400> SEQUENCE: 804

Met Ile Ile Phe Arg Ala Leu Ile Ser His Lys Lys
1               5                   10

<210> SEQ ID NO 805
<211> LENGTH: 12
<212> TYPE: PRT
<213> ORGANISM: Homo sapiens

<400> SEQUENCE: 805

Met Ile Ile Phe Arg Ala Ala Ala Ser His Lys Lys
1               5                   10

<210> SEQ ID NO 806
<211> LENGTH: 12
<212> TYPE: PRT
<213> ORGANISM: Homo sapiens

<400> SEQUENCE: 806

Phe Ile Ile Phe Arg Ile Ala Ala Ser His Lys Lys
1               5                   10

<210> SEQ ID NO 807
<211> LENGTH: 12
<212> TYPE: PRT
<213> ORGANISM: Homo sapiens

<400> SEQUENCE: 807

Leu Ile Ile Phe Arg Ile Ala Ala Ser His Lys Lys
1               5                   10

<210> SEQ ID NO 808
<211> LENGTH: 12
<212> TYPE: PRT
<213> ORGANISM: Homo sapiens

<400> SEQUENCE: 808

Trp Ile Ile Phe Arg Ile Ala Ala Ser His Lys Lys
1               5                   10

<210> SEQ ID NO 809
<211> LENGTH: 12
<212> TYPE: PRT
<213> ORGANISM: Homo sapiens

<400> SEQUENCE: 809

Trp Ile Ile Phe Arg Ala Ala Ala Ser His Lys Lys
1               5                   10

<210> SEQ ID NO 810
<211> LENGTH: 12
<212> TYPE: PRT
<213> ORGANISM: Homo sapiens

<400> SEQUENCE: 810

Trp Ile Ile Phe Arg Ala Leu Ile Ser His Lys Lys
1               5                   10

<210> SEQ ID NO 811
<211> LENGTH: 12
<212> TYPE: PRT
<213> ORGANISM: Homo sapiens

<400> SEQUENCE: 811

Met Ile Ile Phe Arg Ile Ala Ala Tyr His Lys Lys
1               5                   10

<210> SEQ ID NO 812
<211> LENGTH: 12
<212> TYPE: PRT
<213> ORGANISM: Homo sapiens

<400> SEQUENCE: 812

Trp Ile Ile Phe Arg Ile Ala Ala Tyr His Lys Lys
1               5                   10

<210> SEQ ID NO 813
<211> LENGTH: 12
<212> TYPE: PRT
<213> ORGANISM: Homo sapiens

<400> SEQUENCE: 813

Met Ile Ile Phe Arg Ile Ala Ala Thr His Lys Lys
1               5                   10

<210> SEQ ID NO 814
<211> LENGTH: 12
<212> TYPE: PRT
<213> ORGANISM: Homo sapiens

<400> SEQUENCE: 814

Trp Ile Ile Phe Arg Ile Ala Ala Thr His Lys Lys
1               5                   10

<210> SEQ ID NO 815
<211> LENGTH: 12
<212> TYPE: PRT
<213> ORGANISM: Homo sapiens

<400> SEQUENCE: 815

Met Ile Ile Phe Lys Ile Ala Ala Ser His Lys Lys
1               5                   10

<210> SEQ ID NO 816
<211> LENGTH: 12
<212> TYPE: PRT
<213> ORGANISM: Homo sapiens

<400> SEQUENCE: 816

Trp Ile Ile Phe Lys Ile Ala Ala Ser His Lys Lys
1               5                   10

<210> SEQ ID NO 817
<211> LENGTH: 12
<212> TYPE: PRT
<213> ORGANISM: Homo sapiens

<400> SEQUENCE: 817

Met Ile Ile Phe Ala Ile Ala Ala Ser His Lys Lys
1               5                   10

<210> SEQ ID NO 818
<211> LENGTH: 12
<212> TYPE: PRT
<213> ORGANISM: Homo sapiens

<400> SEQUENCE: 818

Leu Ile Ile Phe Arg Ile Leu Ile Ser His Lys Lys
1               5                   10

<210> SEQ ID NO 819
<211> LENGTH: 12
<212> TYPE: PRT
<213> ORGANISM: Homo sapiens

<400> SEQUENCE: 819

Met Ile Ile Phe Arg Ile Leu Ile Ser His Lys Lys
1               5                   10

<210> SEQ ID NO 820
<211> LENGTH: 12
<212> TYPE: PRT
<213> ORGANISM: Homo sapiens

<400> SEQUENCE: 820

Leu Ile Ile Phe Arg Ile Leu Ile Ser His Arg Arg
1               5                   10

<210> SEQ ID NO 821
<211> LENGTH: 12
<212> TYPE: PRT
<213> ORGANISM: Homo sapiens

<400> SEQUENCE: 821

Leu Ile Ile Phe Arg Ile Leu Ile Ser His His His
1               5                   10

<210> SEQ ID NO 822
<211> LENGTH: 11
<212> TYPE: PRT
<213> ORGANISM: Homo sapiens

<400> SEQUENCE: 822

Leu Ile Ile Phe Arg Ile Leu Ile Ser His Lys
1               5                   10

<210> SEQ ID NO 823
<211> LENGTH: 11
<212> TYPE: PRT
<213> ORGANISM: Homo sapiens

<400> SEQUENCE: 823

Leu Ile Ile Phe Arg Ile Leu Ile Ser His Arg
1               5                   10

<210> SEQ ID NO 824
<211> LENGTH: 10
<212> TYPE: PRT
<213> ORGANISM: Homo sapiens

<400> SEQUENCE: 824

Leu Ile Ile Phe Arg Ile Leu Ile Ser His
1               5                   10

<210> SEQ ID NO 825
<211> LENGTH: 12
<212> TYPE: PRT
<213> ORGANISM: Homo sapiens

<400> SEQUENCE: 825

Leu Ile Ile Phe Ala Ile Ala Ala Ser His Lys Lys
1               5                   10

<210> SEQ ID NO 826
<211> LENGTH: 12
<212> TYPE: PRT
<213> ORGANISM: Homo sapiens

<400> SEQUENCE: 826

Leu Ile Ile Phe Ala Ile Leu Ile Ser His Lys Lys
1               5                   10

<210> SEQ ID NO 827
<211> LENGTH: 16
<212> TYPE: PRT
<213> ORGANISM: Drosophila melanogaster

<400> SEQUENCE: 827

Arg Gln Ile Lys Ile Trp Phe Gln Asn Arg Arg Met Lys Trp Lys Lys
1               5                   10                  15

<210> SEQ ID NO 828
<211> LENGTH: 16
<212> TYPE: PRT
<213> ORGANISM: Homo sapiens

<400> SEQUENCE: 828

Ala Ala Val Ala Leu Leu Pro Ala Val Leu Leu Ala Leu Leu Ala Lys
1               5                   10                  15

```
<210> SEQ ID NO 829
<211> LENGTH: 26
<212> TYPE: PRT
<213> ORGANISM: Drosophila melanogaster

<400> SEQUENCE: 829

Ala His Ala Leu Cys Leu Thr Glu Arg Gln Ile Lys Ile Trp Phe Gln
1               5                   10                  15

Asn Arg Arg Met Lys Trp Lys Lys Glu Asn
            20                  25

<210> SEQ ID NO 830
<211> LENGTH: 26
<212> TYPE: PRT
<213> ORGANISM: Drosophila melanogaster

<400> SEQUENCE: 830

Ala His Ala Leu Cys Pro Pro Glu Arg Gln Ile Lys Ile Trp Phe Gln
1               5                   10                  15

Asn Arg Arg Met Lys Trp Lys Lys Glu Asn
            20                  25

<210> SEQ ID NO 831
<211> LENGTH: 26
<212> TYPE: PRT
<213> ORGANISM: Drosophila melanogaster

<400> SEQUENCE: 831

Ala Tyr Ala Leu Cys Leu Thr Glu Arg Gln Ile Lys Ile Trp Phe Ala
1               5                   10                  15

Asn Arg Arg Met Lys Trp Lys Lys Glu Asn
            20                  25

<210> SEQ ID NO 832
<211> LENGTH: 34
<212> TYPE: PRT
<213> ORGANISM: Momordica cochinchinensis

<400> SEQUENCE: 832

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 833
<211> LENGTH: 34
<212> TYPE: PRT
<213> ORGANISM: Momordica cochinchinensis

<400> SEQUENCE: 833

Gly Gly Val Cys Pro Lys Ile Leu Ala Ala Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 834
<211> LENGTH: 34
<212> TYPE: PRT
<213> ORGANISM: Momordica cochinchinensis
```

```
<400> SEQUENCE: 834

Gly Gly Val Cys Pro Ala Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 835
<211> LENGTH: 34
<212> TYPE: PRT
<213> ORGANISM: Momordica cochinchinensis

<400> SEQUENCE: 835

Gly Gly Val Cys Pro Lys Ile Leu Ala Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 836
<211> LENGTH: 34
<212> TYPE: PRT
<213> ORGANISM: Momordica cochinchinensis

<400> SEQUENCE: 836

Gly Gly Val Cys Pro Lys Ile Leu Lys Ala Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 837
<211> LENGTH: 29
<212> TYPE: PRT
<213> ORGANISM: Otocinclus affinis

<400> SEQUENCE: 837

Gly Leu Pro Val Cys Gly Glu Thr Cys Val Gly Gly Thr Cys Asn Thr
1               5                   10                  15

Pro Gly Cys Lys Cys Ser Trp Pro Val Cys Thr Arg Asn
            20                  25

<210> SEQ ID NO 838
<211> LENGTH: 29
<212> TYPE: PRT
<213> ORGANISM: Otocinclus affinis

<400> SEQUENCE: 838

Gly Leu Pro Val Cys Gly Glu Thr Cys Val Gly Gly Thr Cys Asn Thr
1               5                   10                  15

Pro Gly Cys Thr Cys Ser Trp Pro Lys Cys Thr Arg Asn
            20                  25

<210> SEQ ID NO 839
<211> LENGTH: 14
<212> TYPE: PRT
<213> ORGANISM: Helianthus annuus

<400> SEQUENCE: 839

Gly Arg Cys Thr Lys Ser Ile Pro Pro Ile Cys Phe Pro Asp
```

<210> SEQ ID NO 840
<211> LENGTH: 16
<212> TYPE: PRT
<213> ORGANISM: Drosophila melanogaster

<400> SEQUENCE: 840

Arg Gln Ile Lys Ile Trp Phe Gln Asn Arg Arg Met Lys Trp Lys Lys
1               5                   10                  15

<210> SEQ ID NO 841
<211> LENGTH: 33
<212> TYPE: PRT
<213> ORGANISM: Drosophila melanogaster

<400> SEQUENCE: 841

Arg Gln Ile Lys Ile Trp Phe Gln Asn Arg Arg Met Lys Trp Lys Lys
1               5                   10                  15

Thr Tyr Ala Asp Phe Ile Ala Ser Gly Arg Thr Gly Arg Arg Asn Ala
            20                  25                  30

Ile

<210> SEQ ID NO 842
<211> LENGTH: 13
<212> TYPE: PRT
<213> ORGANISM: Human immunodeficiency virus type 1

<400> SEQUENCE: 842

Gly Arg Lys Lys Arg Arg Gln Arg Arg Pro Pro Gln
1               5                   10

<210> SEQ ID NO 843
<211> LENGTH: 30
<212> TYPE: PRT
<213> ORGANISM: Human immunodeficiency virus type 1

<400> SEQUENCE: 843

Gly Arg Lys Lys Arg Arg Gln Arg Arg Pro Pro Gln Thr Tyr Ala
1               5                   10                  15

Asp Phe Ile Ala Ser Gly Arg Thr Gly Arg Arg Asn Ala Ile
            20                  25                  30

<210> SEQ ID NO 844
<211> LENGTH: 16
<212> TYPE: PRT
<213> ORGANISM: Drosophila melanogaster

<400> SEQUENCE: 844

Arg Gln Ile Lys Ile Trp Phe Gln Asn Arg Arg Met Lys Trp Lys Lys
1               5                   10                  15

<210> SEQ ID NO 845
<211> LENGTH: 16
<212> TYPE: PRT
<213> ORGANISM: Drosophila melanogaster

<400> SEQUENCE: 845

Arg Gln Ile Lys Ile Trp Phe Gln Asn Arg Arg Met Lys Trp Lys Lys
1               5                   10                  15

<210> SEQ ID NO 846
<211> LENGTH: 16

```
<212> TYPE: PRT
<213> ORGANISM: Drosophila melanogaster

<400> SEQUENCE: 846

Arg Gln Ile Lys Ile Trp Phe Gln Asn Arg Arg Met Lys Trp Lys Lys
1               5                   10                  15

<210> SEQ ID NO 847
<211> LENGTH: 16
<212> TYPE: PRT
<213> ORGANISM: Drosophila melanogaster

<400> SEQUENCE: 847

Arg Gln Ile Lys Ile Trp Phe Gln Asn Arg Arg Met Lys Trp Lys Lys
1               5                   10                  15

<210> SEQ ID NO 848
<211> LENGTH: 22
<212> TYPE: PRT
<213> ORGANISM: Homo sapiens

<400> SEQUENCE: 848

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 849
<211> LENGTH: 22
<212> TYPE: PRT
<213> ORGANISM: Homo sapiens

<400> SEQUENCE: 849

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 850
<211> LENGTH: 22
<212> TYPE: PRT
<213> ORGANISM: Homo sapiens

<400> SEQUENCE: 850

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 851
<211> LENGTH: 22
<212> TYPE: PRT
<213> ORGANISM: Homo sapiens

<400> SEQUENCE: 851

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 852
<211> LENGTH: 14
<212> TYPE: PRT
```

```
<213> ORGANISM: Human immunodeficiency virus type 1

<400> SEQUENCE: 852

Gly Arg Lys Lys Arg Gln Arg Arg Pro Pro Gln Cys
1               5                   10

<210> SEQ ID NO 853
<211> LENGTH: 19
<212> TYPE: PRT
<213> ORGANISM: Human immunodeficiency virus type 1

<400> SEQUENCE: 853

Thr Arg Gln Ala Arg Arg Asn Arg Arg Arg Trp Arg Glu Arg Gln
1               5                   10                  15

Arg Gly Cys

<210> SEQ ID NO 854
<211> LENGTH: 17
<212> TYPE: PRT
<213> ORGANISM: Flock house virus

<400> SEQUENCE: 854

Arg Arg Arg Arg Asn Arg Thr Arg Arg Asn Arg Arg Arg Val Arg Gly
1               5                   10                  15

Cys

<210> SEQ ID NO 855
<211> LENGTH: 21
<212> TYPE: PRT
<213> ORGANISM: Brome mosaic virus

<400> SEQUENCE: 855

Lys Met Thr Arg Ala Gln Arg Arg Ala Ala Ala Arg Arg Asn Arg Trp
1               5                   10                  15

Thr Ala Arg Gly Cys
                20

<210> SEQ ID NO 856
<211> LENGTH: 15
<212> TYPE: PRT
<213> ORGANISM: Human T-cell lymphotropic virus type 2

<400> SEQUENCE: 856

Thr Arg Arg Gln Arg Thr Arg Arg Ala Arg Arg Asn Arg Gly Cys
1               5                   10                  15

<210> SEQ ID NO 857
<211> LENGTH: 30
<212> TYPE: PRT
<213> ORGANISM: Homo sapiens

<400> SEQUENCE: 857

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg Gly Cys
                20                  25                  30

<210> SEQ ID NO 858
<211> LENGTH: 28
<212> TYPE: PRT
<213> ORGANISM: Homo sapiens

<400> SEQUENCE: 858
```

```
Lys Arg Arg Ile Arg Arg Glu Arg Asn Lys Met Ala Ala Ala Lys Ser
1               5                   10                  15

Arg Asn Arg Arg Arg Glu Leu Thr Asp Thr Gly Cys
            20                  25
```

<210> SEQ ID NO 859
<211> LENGTH: 23
<212> TYPE: PRT
<213> ORGANISM: Homo sapiens

<400> SEQUENCE: 859

```
Trp Leu Arg Arg Ile Lys Ala Trp Leu Arg Arg Ile Lys Ala Leu Asn
1               5                   10                  15

Arg Gln Leu Gly Val Ala Ala
            20
```

<210> SEQ ID NO 860
<211> LENGTH: 10
<212> TYPE: PRT
<213> ORGANISM: Human immunodeficiency virus type 1

<400> SEQUENCE: 860

```
Cys Arg Lys Lys Arg Arg Gln Arg Arg Arg
1               5                   10
```

<210> SEQ ID NO 861
<211> LENGTH: 12
<212> TYPE: PRT
<213> ORGANISM: Human immunodeficiency virus type 1

<400> SEQUENCE: 861

```
Gly Arg Lys Lys Arg Arg Gln Arg Arg Arg Pro Pro
1               5                   10
```

<210> SEQ ID NO 862
<211> LENGTH: 4
<212> TYPE: PRT
<213> ORGANISM: Artificial sequence
<220> FEATURE:
<223> OTHER INFORMATION: CPP

<400> SEQUENCE: 862

```
Arg Arg Arg Arg
1
```

<210> SEQ ID NO 863
<211> LENGTH: 5
<212> TYPE: PRT
<213> ORGANISM: Artificial sequence
<220> FEATURE:
<223> OTHER INFORMATION: CPP

<400> SEQUENCE: 863

```
Arg Arg Arg Arg Arg
1               5
```

<210> SEQ ID NO 864
<211> LENGTH: 6
<212> TYPE: PRT
<213> ORGANISM: Artificial sequence
<220> FEATURE:
<223> OTHER INFORMATION: CPP

<400> SEQUENCE: 864

Arg Arg Arg Arg Arg Arg
1               5

<210> SEQ ID NO 865
<211> LENGTH: 7
<212> TYPE: PRT
<213> ORGANISM: Artificial sequence
<220> FEATURE:
<223> OTHER INFORMATION: CPP

<400> SEQUENCE: 865

Arg Arg Arg Arg Arg Arg Arg
1               5

<210> SEQ ID NO 866
<211> LENGTH: 8
<212> TYPE: PRT
<213> ORGANISM: Artificial sequence
<220> FEATURE:
<223> OTHER INFORMATION: CPP

<400> SEQUENCE: 866

Arg Arg Arg Arg Arg Arg Arg Arg
1               5

<210> SEQ ID NO 867
<211> LENGTH: 9
<212> TYPE: PRT
<213> ORGANISM: Artificial sequence
<220> FEATURE:
<223> OTHER INFORMATION: CPP

<400> SEQUENCE: 867

Arg Arg Arg Arg Arg Arg Arg Arg Arg
1               5

<210> SEQ ID NO 868
<211> LENGTH: 11
<212> TYPE: PRT
<213> ORGANISM: Artificial sequence
<220> FEATURE:
<223> OTHER INFORMATION: CPP

<400> SEQUENCE: 868

Arg Arg Arg Arg Arg Arg Arg Arg Arg Arg Arg
1               5                   10

<210> SEQ ID NO 869
<211> LENGTH: 12
<212> TYPE: PRT
<213> ORGANISM: Artificial sequence
<220> FEATURE:
<223> OTHER INFORMATION: CPP

<400> SEQUENCE: 869

Arg Arg Arg Arg Arg Arg Arg Arg Arg Arg Arg Arg
1               5                   10

<210> SEQ ID NO 870
<211> LENGTH: 16
<212> TYPE: PRT
<213> ORGANISM: Artificial sequence
<220> FEATURE:
<223> OTHER INFORMATION: CPP

<400> SEQUENCE: 870

Arg Arg Arg Arg Arg Arg Arg Arg Arg Arg Arg Arg Arg Arg Arg Arg

```
<210> SEQ ID NO 871
<211> LENGTH: 18
<212> TYPE: PRT
<213> ORGANISM: Artificial sequence
<220> FEATURE:
<223> OTHER INFORMATION: CPP

<400> SEQUENCE: 871

Lys Leu Ala Leu Lys Leu Ala Leu Lys Ala Leu Lys Ala Ala Leu Lys
1               5                   10                  15

Leu Ala

<210> SEQ ID NO 872
<211> LENGTH: 18
<212> TYPE: PRT
<213> ORGANISM: Artificial sequence
<220> FEATURE:
<223> OTHER INFORMATION: CPP

<400> SEQUENCE: 872

Lys Leu Ala Leu Lys Leu Ala Leu Lys Ala Trp Lys Ala Ala Leu Lys
1               5                   10                  15

Leu Ala

<210> SEQ ID NO 873
<211> LENGTH: 18
<212> TYPE: PRT
<213> ORGANISM: Artificial sequence
<220> FEATURE:
<223> OTHER INFORMATION: CPP

<400> SEQUENCE: 873

Lys Leu Ala Leu Lys Ala Ala Leu Lys Ala Trp Lys Ala Ala Ala Lys
1               5                   10                  15

Leu Ala

<210> SEQ ID NO 874
<211> LENGTH: 18
<212> TYPE: PRT
<213> ORGANISM: Artificial sequence
<220> FEATURE:
<223> OTHER INFORMATION: CPP

<400> SEQUENCE: 874

Lys Leu Ala Leu Lys Ala Ala Ala Lys Ala Trp Lys Ala Ala Ala Lys
1               5                   10                  15

Ala Ala

<210> SEQ ID NO 875
<211> LENGTH: 18
<212> TYPE: PRT
<213> ORGANISM: Artificial sequence
<220> FEATURE:
<223> OTHER INFORMATION: CPP

<400> SEQUENCE: 875

Lys Ile Thr Leu Lys Leu Ala Ile Lys Ala Trp Lys Leu Ala Leu Lys
1               5                   10                  15

Ala Ala

<210> SEQ ID NO 876
```

```
<211> LENGTH: 18
<212> TYPE: PRT
<213> ORGANISM: Artificial sequence
<220> FEATURE:
<223> OTHER INFORMATION: CPP

<400> SEQUENCE: 876

Lys Ile Ala Ala Lys Ser Ile Ala Lys Ile Trp Lys Ser Ile Leu Lys
1               5                   10                  15

Ile Ala

<210> SEQ ID NO 877
<211> LENGTH: 18
<212> TYPE: PRT
<213> ORGANISM: Artificial sequence
<220> FEATURE:
<223> OTHER INFORMATION: CPP

<400> SEQUENCE: 877

Lys Ala Leu Ala Lys Ala Leu Ala Lys Leu Trp Lys Ala Leu Ala Lys
1               5                   10                  15

Ala Ala

<210> SEQ ID NO 878
<211> LENGTH: 18
<212> TYPE: PRT
<213> ORGANISM: Artificial sequence
<220> FEATURE:
<223> OTHER INFORMATION: CPP

<400> SEQUENCE: 878

Lys Leu Ala Leu Lys Leu Ala Leu Lys Trp Ala Lys Leu Ala Leu Lys
1               5                   10                  15

Ala Ala

<210> SEQ ID NO 879
<211> LENGTH: 18
<212> TYPE: PRT
<213> ORGANISM: Artificial sequence
<220> FEATURE:
<223> OTHER INFORMATION: CPP

<400> SEQUENCE: 879

Lys Leu Leu Ala Lys Ala Ala Lys Lys Trp Leu Leu Leu Ala Leu Lys
1               5                   10                  15

Ala Ala

<210> SEQ ID NO 880
<211> LENGTH: 18
<212> TYPE: PRT
<213> ORGANISM: Artificial sequence
<220> FEATURE:
<223> OTHER INFORMATION: CPP

<400> SEQUENCE: 880

Lys Leu Leu Ala Lys Ala Ala Leu Lys Trp Leu Leu Lys Ala Leu Lys
1               5                   10                  15

Ala Ala

<210> SEQ ID NO 881
<211> LENGTH: 18
<212> TYPE: PRT
<213> ORGANISM: Artificial sequence
<220> FEATURE:
```

<223> OTHER INFORMATION: CPP

<400> SEQUENCE: 881

Lys Ala Leu Lys Lys Leu Leu Ala Lys Trp Leu Ala Ala Ala Lys Ala
1               5                   10                  15

Leu Leu

<210> SEQ ID NO 882
<211> LENGTH: 18
<212> TYPE: PRT
<213> ORGANISM: Artificial sequence
<220> FEATURE:
<223> OTHER INFORMATION: CPP

<400> SEQUENCE: 882

Lys Leu Ala Ala Ala Leu Leu Lys Lys Trp Lys Lys Leu Ala Ala Ala
1               5                   10                  15

Leu Leu

<210> SEQ ID NO 883
<211> LENGTH: 18
<212> TYPE: PRT
<213> ORGANISM: Artificial sequence
<220> FEATURE:
<223> OTHER INFORMATION: CPP

<400> SEQUENCE: 883

Lys Ala Leu Ala Ala Leu Leu Lys Lys Trp Ala Lys Leu Leu Ala Ala
1               5                   10                  15

Leu Lys

<210> SEQ ID NO 884
<211> LENGTH: 18
<212> TYPE: PRT
<213> ORGANISM: Artificial sequence
<220> FEATURE:
<223> OTHER INFORMATION: CPP

<400> SEQUENCE: 884

Lys Ala Leu Ala Ala Leu Leu Lys Lys Leu Ala Lys Leu Leu Ala Ala
1               5                   10                  15

Leu Lys

<210> SEQ ID NO 885
<211> LENGTH: 16
<212> TYPE: PRT
<213> ORGANISM: Artificial sequence
<220> FEATURE:
<223> OTHER INFORMATION: CPP

<400> SEQUENCE: 885

Lys Leu Ala Leu Lys Leu Ala Leu Lys Ala Leu Lys Ala Ala Leu Lys
1               5                   10                  15

<210> SEQ ID NO 886
<211> LENGTH: 14
<212> TYPE: PRT
<213> ORGANISM: Artificial sequence
<220> FEATURE:
<223> OTHER INFORMATION: CPP

<400> SEQUENCE: 886

Lys Leu Ala Leu Lys Ala Leu Lys Ala Ala Leu Lys Leu Ala
1               5                   10

<210> SEQ ID NO 887
<211> LENGTH: 14
<212> TYPE: PRT
<213> ORGANISM: Artificial sequence
<220> FEATURE:
<223> OTHER INFORMATION: CPP

<400> SEQUENCE: 887

Lys Leu Ala Leu Lys Leu Ala Leu Lys Ala Leu Lys Ala Ala
1               5                   10

<210> SEQ ID NO 888
<211> LENGTH: 18
<212> TYPE: PRT
<213> ORGANISM: Artificial sequence
<220> FEATURE:
<223> OTHER INFORMATION: CPP

<400> SEQUENCE: 888

Lys Leu Gly Leu Lys Leu Gly Leu Lys Gly Leu Lys Gly Gly Leu Lys
1               5                   10                  15

Leu Gly

<210> SEQ ID NO 889
<211> LENGTH: 18
<212> TYPE: PRT
<213> ORGANISM: Artificial sequence
<220> FEATURE:
<223> OTHER INFORMATION: CPP

<400> SEQUENCE: 889

Lys Leu Ala Leu Lys Leu Ala Leu Lys Ala Leu Gln Ala Ala Leu Gln
1               5                   10                  15

Leu Ala

<210> SEQ ID NO 890
<211> LENGTH: 18
<212> TYPE: PRT
<213> ORGANISM: Artificial sequence
<220> FEATURE:
<223> OTHER INFORMATION: CPP

<400> SEQUENCE: 890

Lys Leu Ala Leu Gln Leu Ala Leu Gln Ala Leu Gln Ala Ala Leu Gln
1               5                   10                  15

Leu Ala

<210> SEQ ID NO 891
<211> LENGTH: 18
<212> TYPE: PRT
<213> ORGANISM: Artificial sequence
<220> FEATURE:
<223> OTHER INFORMATION: CPP

<400> SEQUENCE: 891

Gln Leu Ala Leu Gln Leu Ala Leu Gln Ala Leu Gln Ala Ala Leu Gln
1               5                   10                  15

Leu Ala

<210> SEQ ID NO 892
<211> LENGTH: 18
<212> TYPE: PRT
<213> ORGANISM: Artificial sequence

```
<220> FEATURE:
<223> OTHER INFORMATION: CPP

<400> SEQUENCE: 892

Glu Leu Ala Leu Glu Leu Ala Leu Glu Ala Leu Glu Ala Ala Leu Glu
1               5                   10                  15

Leu Ala

<210> SEQ ID NO 893
<211> LENGTH: 18
<212> TYPE: PRT
<213> ORGANISM: Artificial sequence
<220> FEATURE:
<223> OTHER INFORMATION: CPP

<400> SEQUENCE: 893

Leu Lys Thr Leu Ala Thr Ala Leu Thr Lys Leu Ala Lys Thr Leu Thr
1               5                   10                  15

Thr Leu

<210> SEQ ID NO 894
<211> LENGTH: 18
<212> TYPE: PRT
<213> ORGANISM: Artificial sequence
<220> FEATURE:
<223> OTHER INFORMATION: CPP

<400> SEQUENCE: 894

Leu Leu Lys Thr Thr Ala Leu Leu Lys Thr Thr Ala Leu Leu Lys Thr
1               5                   10                  15

Thr Ala

<210> SEQ ID NO 895
<211> LENGTH: 18
<212> TYPE: PRT
<213> ORGANISM: Artificial sequence
<220> FEATURE:
<223> OTHER INFORMATION: CPP

<400> SEQUENCE: 895

Leu Lys Thr Leu Thr Glu Thr Leu Lys Glu Leu Thr Lys Thr Leu Thr
1               5                   10                  15

Glu Leu

<210> SEQ ID NO 896
<211> LENGTH: 18
<212> TYPE: PRT
<213> ORGANISM: Artificial sequence
<220> FEATURE:
<223> OTHER INFORMATION: CPP

<400> SEQUENCE: 896

Leu Leu Lys Thr Thr Glu Leu Leu Lys Thr Thr Glu Leu Leu Lys Thr
1               5                   10                  15

Thr Glu

<210> SEQ ID NO 897
<211> LENGTH: 18
<212> TYPE: PRT
<213> ORGANISM: Artificial sequence
<220> FEATURE:
<223> OTHER INFORMATION: CPP

<400> SEQUENCE: 897
```

Lys Leu Ala Leu Lys Leu Ala Leu Lys Ala Leu Lys Ala Ala Leu Lys
1               5                   10                  15

Leu Ala

<210> SEQ ID NO 898
<211> LENGTH: 18
<212> TYPE: PRT
<213> ORGANISM: Artificial sequence
<220> FEATURE:
<223> OTHER INFORMATION: CPP

<400> SEQUENCE: 898

Lys Ala Leu Lys Leu Lys Leu Ala Leu Ala Leu Leu Ala Lys Leu Lys
1               5                   10                  15

Leu Ala

<210> SEQ ID NO 899
<211> LENGTH: 8
<212> TYPE: PRT
<213> ORGANISM: Artificial sequence
<220> FEATURE:
<223> OTHER INFORMATION: CPP

<400> SEQUENCE: 899

Arg Arg Arg Arg Arg Arg Arg Trp
1               5

<210> SEQ ID NO 900
<211> LENGTH: 15
<212> TYPE: PRT
<213> ORGANISM: Artificial sequence
<220> FEATURE:
<223> OTHER INFORMATION: CPP

<400> SEQUENCE: 900

Lys Leu Trp Met Arg Trp Tyr Ser Pro Thr Thr Arg Arg Tyr Gly
1               5                   10                  15

<210> SEQ ID NO 901
<211> LENGTH: 15
<212> TYPE: PRT
<213> ORGANISM: Artificial sequence
<220> FEATURE:
<223> OTHER INFORMATION: CPP

<400> SEQUENCE: 901

Asp Ser Leu Lys Ser Tyr Trp Tyr Leu Gln Lys Phe Ser Trp Arg
1               5                   10                  15

<210> SEQ ID NO 902
<211> LENGTH: 15
<212> TYPE: PRT
<213> ORGANISM: Artificial sequence
<220> FEATURE:
<223> OTHER INFORMATION: CPP

<400> SEQUENCE: 902

Arg Thr Leu Val Asn Glu Tyr Lys Asn Thr Leu Lys Phe Ser Lys
1               5                   10                  15

<210> SEQ ID NO 903
<211> LENGTH: 15
<212> TYPE: PRT
<213> ORGANISM: Artificial sequence
<220> FEATURE:

-continued

<223> OTHER INFORMATION: CPP

<400> SEQUENCE: 903

Ile Pro Ser Arg Trp Lys Asp Gln Phe Trp Lys Arg Trp His Tyr
1               5                   10                  15

<210> SEQ ID NO 904
<211> LENGTH: 15
<212> TYPE: PRT
<213> ORGANISM: Artificial sequence
<220> FEATURE:
<223> OTHER INFORMATION: CPP

<400> SEQUENCE: 904

Gly Tyr Gly Asn Cys Arg His Phe Lys Gln Lys Pro Arg Arg Asp
1               5                   10                  15

<210> SEQ ID NO 905
<211> LENGTH: 15
<212> TYPE: PRT
<213> ORGANISM: Artificial sequence
<220> FEATURE:
<223> OTHER INFORMATION: CPP

<400> SEQUENCE: 905

Lys Asn Ala Trp Lys His Ser Ser Cys His His Arg His Gln Ile
1               5                   10                  15

<210> SEQ ID NO 906
<211> LENGTH: 15
<212> TYPE: PRT
<213> ORGANISM: Artificial sequence
<220> FEATURE:
<223> OTHER INFORMATION: CPP

<400> SEQUENCE: 906

Arg Val Arg Glu Trp Trp Tyr Thr Ile Thr Leu Lys Gln Glu Ser
1               5                   10                  15

<210> SEQ ID NO 907
<211> LENGTH: 15
<212> TYPE: PRT
<213> ORGANISM: Artificial sequence
<220> FEATURE:
<223> OTHER INFORMATION: CPP

<400> SEQUENCE: 907

Gln Gln His Leu Leu Ile Ala Ile Asn Gly Tyr Pro Arg Tyr Asn
1               5                   10                  15

<210> SEQ ID NO 908
<211> LENGTH: 15
<212> TYPE: PRT
<213> ORGANISM: Artificial sequence
<220> FEATURE:
<223> OTHER INFORMATION: CPP

<400> SEQUENCE: 908

Trp Lys Cys Arg Arg Gln Cys Phe Arg Val Leu His His Trp Asn
1               5                   10                  15

<210> SEQ ID NO 909
<211> LENGTH: 15
<212> TYPE: PRT
<213> ORGANISM: Artificial sequence
<220> FEATURE:
<223> OTHER INFORMATION: CPP

<400> SEQUENCE: 909

Arg Leu Trp Met Arg Trp Tyr Ser Pro Thr Thr Arg Arg Tyr Gly
1               5                   10                  15

<210> SEQ ID NO 910
<211> LENGTH: 15
<212> TYPE: PRT
<213> ORGANISM: Artificial sequence
<220> FEATURE:
<223> OTHER INFORMATION: CPP

<400> SEQUENCE: 910

Lys Leu Trp Met Arg Trp Tyr Ser Ala Thr Thr Arg Arg Tyr Gly
1               5                   10                  15

<210> SEQ ID NO 911
<211> LENGTH: 15
<212> TYPE: PRT
<213> ORGANISM: Artificial sequence
<220> FEATURE:
<223> OTHER INFORMATION: CPP

<400> SEQUENCE: 911

Lys Leu Trp Met Arg Trp Tyr Ser Pro Trp Thr Arg Arg Tyr Gly
1               5                   10                  15

<210> SEQ ID NO 912
<211> LENGTH: 15
<212> TYPE: PRT
<213> ORGANISM: Artificial sequence
<220> FEATURE:
<223> OTHER INFORMATION: CPP

<400> SEQUENCE: 912

Arg Leu Trp Met Arg Trp Tyr Ser Pro Trp Thr Arg Arg Tyr Gly
1               5                   10                  15

<210> SEQ ID NO 913
<211> LENGTH: 15
<212> TYPE: PRT
<213> ORGANISM: Artificial sequence
<220> FEATURE:
<223> OTHER INFORMATION: CPP

<400> SEQUENCE: 913

Arg Leu Trp Met Arg Trp Tyr Ser Pro Trp Thr Arg Arg Trp Gly
1               5                   10                  15

<210> SEQ ID NO 914
<211> LENGTH: 15
<212> TYPE: PRT
<213> ORGANISM: Artificial sequence
<220> FEATURE:
<223> OTHER INFORMATION: CPP

<400> SEQUENCE: 914

Ala Leu Trp Met Arg Trp Tyr Ser Pro Thr Thr Arg Arg Tyr Gly
1               5                   10                  15

<210> SEQ ID NO 915
<211> LENGTH: 15
<212> TYPE: PRT
<213> ORGANISM: Artificial sequence
<220> FEATURE:
<223> OTHER INFORMATION: CPP

<400> SEQUENCE: 915

Arg Ala Trp Met Arg Trp Tyr Ser Pro Thr Thr Arg Arg Tyr Gly
1               5                   10                  15

<210> SEQ ID NO 916
<211> LENGTH: 15
<212> TYPE: PRT
<213> ORGANISM: Artificial sequence
<220> FEATURE:
<223> OTHER INFORMATION: CPP

<400> SEQUENCE: 916

Arg Leu Ala Met Arg Trp Tyr Ser Pro Thr Thr Arg Arg Tyr Gly
1               5                   10                  15

<210> SEQ ID NO 917
<211> LENGTH: 15
<212> TYPE: PRT
<213> ORGANISM: Artificial sequence
<220> FEATURE:
<223> OTHER INFORMATION: CPP

<400> SEQUENCE: 917

Arg Leu Trp Ala Arg Trp Tyr Ser Pro Thr Thr Arg Arg Tyr Gly
1               5                   10                  15

<210> SEQ ID NO 918
<211> LENGTH: 15
<212> TYPE: PRT
<213> ORGANISM: Artificial sequence
<220> FEATURE:
<223> OTHER INFORMATION: CPP

<400> SEQUENCE: 918

Arg Leu Trp Met Ala Trp Tyr Ser Pro Thr Thr Arg Arg Tyr Gly
1               5                   10                  15

<210> SEQ ID NO 919
<211> LENGTH: 15
<212> TYPE: PRT
<213> ORGANISM: Artificial sequence
<220> FEATURE:
<223> OTHER INFORMATION: CPP

<400> SEQUENCE: 919

Arg Leu Trp Met Arg Ala Tyr Ser Pro Thr Thr Arg Arg Tyr Gly
1               5                   10                  15

<210> SEQ ID NO 920
<211> LENGTH: 15
<212> TYPE: PRT
<213> ORGANISM: Artificial sequence
<220> FEATURE:
<223> OTHER INFORMATION: CPP

<400> SEQUENCE: 920

Arg Leu Trp Met Arg Trp Ala Ser Pro Thr Thr Arg Arg Tyr Gly
1               5                   10                  15

<210> SEQ ID NO 921
<211> LENGTH: 15
<212> TYPE: PRT
<213> ORGANISM: Artificial sequence
<220> FEATURE:
<223> OTHER INFORMATION: CPP

<400> SEQUENCE: 921

Arg Leu Trp Met Arg Trp Tyr Ala Pro Thr Thr Arg Tyr Gly
1               5                   10                  15

<210> SEQ ID NO 922
<211> LENGTH: 15
<212> TYPE: PRT
<213> ORGANISM: Artificial sequence
<220> FEATURE:
<223> OTHER INFORMATION: CPP

<400> SEQUENCE: 922

Arg Leu Trp Met Arg Trp Tyr Ser Pro Ala Thr Arg Arg Tyr Gly
1               5                   10                  15

<210> SEQ ID NO 923
<211> LENGTH: 15
<212> TYPE: PRT
<213> ORGANISM: Artificial sequence
<220> FEATURE:
<223> OTHER INFORMATION: CPP

<400> SEQUENCE: 923

Arg Leu Trp Met Arg Trp Tyr Ser Pro Thr Ala Arg Arg Tyr Gly
1               5                   10                  15

<210> SEQ ID NO 924
<211> LENGTH: 15
<212> TYPE: PRT
<213> ORGANISM: Artificial sequence
<220> FEATURE:
<223> OTHER INFORMATION: CPP

<400> SEQUENCE: 924

Arg Leu Trp Met Arg Trp Tyr Ser Pro Thr Thr Ala Arg Tyr Gly
1               5                   10                  15

<210> SEQ ID NO 925
<211> LENGTH: 15
<212> TYPE: PRT
<213> ORGANISM: Artificial sequence
<220> FEATURE:
<223> OTHER INFORMATION: CPP

<400> SEQUENCE: 925

Arg Leu Trp Met Arg Trp Tyr Ser Pro Thr Thr Arg Ala Tyr Gly
1               5                   10                  15

<210> SEQ ID NO 926
<211> LENGTH: 15
<212> TYPE: PRT
<213> ORGANISM: Artificial sequence
<220> FEATURE:
<223> OTHER INFORMATION: CPP

<400> SEQUENCE: 926

Arg Leu Trp Met Arg Trp Tyr Ser Pro Thr Thr Arg Arg Ala Gly
1               5                   10                  15

<210> SEQ ID NO 927
<211> LENGTH: 15
<212> TYPE: PRT
<213> ORGANISM: Artificial sequence
<220> FEATURE:
<223> OTHER INFORMATION: CPP

<400> SEQUENCE: 927

```
Arg Leu Trp Met Arg Trp Tyr Ser Pro Thr Thr Arg Arg Tyr Ala
1               5                   10                  15

<210> SEQ ID NO 928
<211> LENGTH: 15
<212> TYPE: PRT
<213> ORGANISM: Artificial sequence
<220> FEATURE:
<223> OTHER INFORMATION: CPP

<400> SEQUENCE: 928

Arg Leu Leu Met Arg Leu Tyr Ser Pro Thr Thr Arg Arg Tyr Gly
1               5                   10                  15

<210> SEQ ID NO 929
<211> LENGTH: 15
<212> TYPE: PRT
<213> ORGANISM: Artificial sequence
<220> FEATURE:
<223> OTHER INFORMATION: CPP

<400> SEQUENCE: 929

Arg Leu Phe Met Arg Phe Tyr Ser Pro Thr Thr Arg Arg Tyr Gly
1               5                   10                  15

<210> SEQ ID NO 930
<211> LENGTH: 15
<212> TYPE: PRT
<213> ORGANISM: Artificial sequence
<220> FEATURE:
<223> OTHER INFORMATION: CPP

<400> SEQUENCE: 930

Arg Leu Ile Met Arg Ile Tyr Ser Pro Thr Thr Arg Arg Tyr Gly
1               5                   10                  15

<210> SEQ ID NO 931
<211> LENGTH: 15
<212> TYPE: PRT
<213> ORGANISM: Artificial sequence
<220> FEATURE:
<223> OTHER INFORMATION: CPP

<400> SEQUENCE: 931

Arg Leu Val Met Arg Val Tyr Ser Pro Thr Thr Arg Arg Tyr Gly
1               5                   10                  15

<210> SEQ ID NO 932
<211> LENGTH: 15
<212> TYPE: PRT
<213> ORGANISM: Artificial sequence
<220> FEATURE:
<223> OTHER INFORMATION: CPP

<400> SEQUENCE: 932

Arg Leu Tyr Met Arg Tyr Tyr Ser Pro Thr Thr Arg Arg Tyr Gly
1               5                   10                  15

<210> SEQ ID NO 933
<211> LENGTH: 17
<212> TYPE: PRT
<213> ORGANISM: Artificial sequence
<220> FEATURE:
<223> OTHER INFORMATION: CPP

<400> SEQUENCE: 933

Asp Arg Asp Asp Arg Asp Asp Arg Asp Asp Arg Asp Asp Arg Asp Asp
```

```
1               5               10              15

Arg

<210> SEQ ID NO 934
<211> LENGTH: 14
<212> TYPE: PRT
<213> ORGANISM: Artificial sequence
<220> FEATURE:
<223> OTHER INFORMATION: CPP

<400> SEQUENCE: 934

Glu Arg Glu Arg Glu Arg Glu Arg Glu Arg Glu Arg Glu Arg
1               5                   10

<210> SEQ ID NO 935
<211> LENGTH: 14
<212> TYPE: PRT
<213> ORGANISM: Artificial sequence
<220> FEATURE:
<223> OTHER INFORMATION: CPP

<400> SEQUENCE: 935

Trp Arg Trp Arg Trp Arg Trp Arg Trp Arg Trp Arg Trp Arg
1               5                   10

<210> SEQ ID NO 936
<211> LENGTH: 10
<212> TYPE: PRT
<213> ORGANISM: Artificial sequence
<220> FEATURE:
<223> OTHER INFORMATION: CPP

<400> SEQUENCE: 936

Asp Arg Asp Arg Asp Arg Asp Arg Asp Arg
1               5                   10

<210> SEQ ID NO 937
<211> LENGTH: 27
<212> TYPE: PRT
<213> ORGANISM: Artificial sequence
<220> FEATURE:
<223> OTHER INFORMATION: CPP

<400> SEQUENCE: 937

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 938
<211> LENGTH: 4
<212> TYPE: PRT
<213> ORGANISM: Artificial sequence
<220> FEATURE:
<223> OTHER INFORMATION: CPP

<400> SEQUENCE: 938

Glu Glu Glu Ala
1

<210> SEQ ID NO 939
<211> LENGTH: 5
<212> TYPE: PRT
<213> ORGANISM: Artificial sequence
<220> FEATURE:
<223> OTHER INFORMATION: CPP
```

<400> SEQUENCE: 939

Glu Glu Glu Ala Ala
1               5

<210> SEQ ID NO 940
<211> LENGTH: 8
<212> TYPE: PRT
<213> ORGANISM: Artificial sequence
<220> FEATURE:
<223> OTHER INFORMATION: CPP

<400> SEQUENCE: 940

Glu Glu Glu Ala Ala Lys Lys Lys
1               5

<210> SEQ ID NO 941
<211> LENGTH: 16
<212> TYPE: PRT
<213> ORGANISM: Artificial sequence
<220> FEATURE:
<223> OTHER INFORMATION: CPP

<400> SEQUENCE: 941

Lys Thr Val Leu Leu Arg Lys Leu Leu Lys Leu Leu Val Arg Lys Ile
1               5                   10                  15

<210> SEQ ID NO 942
<211> LENGTH: 16
<212> TYPE: PRT
<213> ORGANISM: Artificial sequence
<220> FEATURE:
<223> OTHER INFORMATION: CPP

<400> SEQUENCE: 942

Leu Leu Lys Lys Arg Lys Val Val Arg Leu Ile Lys Phe Leu Leu Lys
1               5                   10                  15

<210> SEQ ID NO 943
<211> LENGTH: 9
<212> TYPE: PRT
<213> ORGANISM: Artificial sequence
<220> FEATURE:
<223> OTHER INFORMATION: CPP

<400> SEQUENCE: 943

Cys Gly Asn Lys Arg Thr Arg Gly Cys
1               5

<210> SEQ ID NO 944
<211> LENGTH: 12
<212> TYPE: PRT
<213> ORGANISM: Artificial sequence
<220> FEATURE:
<223> OTHER INFORMATION: CPP

<400> SEQUENCE: 944

Thr Ser Pro Leu Asn Ile His Asn Gly Gln Lys Leu
1               5                   10

<210> SEQ ID NO 945
<211> LENGTH: 13
<212> TYPE: PRT
<213> ORGANISM: Artificial sequence
<220> FEATURE:
<223> OTHER INFORMATION: CPP -continued

<400> SEQUENCE: 945

Cys Val Gln Trp Ser Leu Leu Arg Gly Tyr Gln Pro Cys
1               5                   10

<210> SEQ ID NO 946
<211> LENGTH: 26
<212> TYPE: PRT
<213> ORGANISM: Artificial sequence
<220> FEATURE:
<223> OTHER INFORMATION: CPP

<400> SEQUENCE: 946

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 947
<211> LENGTH: 16
<212> TYPE: PRT
<213> ORGANISM: Artificial sequence
<220> FEATURE:
<223> OTHER INFORMATION: CPP

<400> SEQUENCE: 947

Tyr Thr Ala Ile Ala Trp Val Lys Ala Phe Ile Arg Lys Leu Arg Lys
1               5                   10                  15

<210> SEQ ID NO 948
<211> LENGTH: 17
<212> TYPE: PRT
<213> ORGANISM: Artificial sequence
<220> FEATURE:
<223> OTHER INFORMATION: CPP

<400> SEQUENCE: 948

Ile Ala Trp Val Lys Ala Phe Ile Arg Lys Leu Arg Lys Gly Pro Leu
1               5                   10                  15

Gly

<210> SEQ ID NO 949
<211> LENGTH: 34
<212> TYPE: PRT
<213> ORGANISM: Artificial sequence
<220> FEATURE:
<223> OTHER INFORMATION: CPP

<400> SEQUENCE: 949

Lys Lys Lys Lys Lys Lys Gly Gly Phe Leu Gly Phe Trp Arg Gly Glu
1               5                   10                  15

Asn Gly Arg Lys Thr Arg Ser Ala Tyr Glu Arg Met Cys Ile Leu Lys
            20                  25                  30

Gly Lys

<210> SEQ ID NO 950
<211> LENGTH: 14
<212> TYPE: PRT
<213> ORGANISM: Artificial sequence
<220> FEATURE:
<223> OTHER INFORMATION: CPP

<400> SEQUENCE: 950

Arg Leu Ser Gly Met Asn Glu Val Leu Ser Phe Arg Trp Leu
1               5                   10

<210> SEQ ID NO 951
<211> LENGTH: 13
<212> TYPE: PRT
<213> ORGANISM: Artificial sequence
<220> FEATURE:
<223> OTHER INFORMATION: CPP

<400> SEQUENCE: 951

Gly Pro Phe His Phe Tyr Gln Phe Leu Phe Pro Pro Val
1               5                   10

<210> SEQ ID NO 952
<211> LENGTH: 13
<212> TYPE: PRT
<213> ORGANISM: Artificial sequence
<220> FEATURE:
<223> OTHER INFORMATION: CPP

<400> SEQUENCE: 952

Gly Ser Pro Trp Gly Leu Gln His His Pro Pro Arg Thr
1               5                   10

<210> SEQ ID NO 953
<211> LENGTH: 30
<212> TYPE: PRT
<213> ORGANISM: Artificial sequence
<220> FEATURE:
<223> OTHER INFORMATION: CPP

<400> SEQUENCE: 953

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 954
<211> LENGTH: 30
<212> TYPE: PRT
<213> ORGANISM: Artificial sequence
<220> FEATURE:
<223> OTHER INFORMATION: CPP

<400> SEQUENCE: 954

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 955
<211> LENGTH: 20
<212> TYPE: PRT
<213> ORGANISM: Artificial sequence
<220> FEATURE:
<223> OTHER INFORMATION: CPP

<400> SEQUENCE: 955

Gly Leu Phe Glu Ala Leu Leu Glu Leu Leu Glu Ser Leu Trp Glu Leu
1               5                   10                  15

Leu Leu Glu Ala
            20

<210> SEQ ID NO 956
<211> LENGTH: 20
<212> TYPE: PRT

```
<213> ORGANISM: Artificial sequence
<220> FEATURE:
<223> OTHER INFORMATION: CPP

<400> SEQUENCE: 956

Gly Leu Phe Lys Ala Leu Leu Lys Leu Leu Lys Ser Leu Trp Lys Leu
1               5                   10                  15

Leu Leu Lys Ala
            20

<210> SEQ ID NO 957
<211> LENGTH: 20
<212> TYPE: PRT
<213> ORGANISM: Artificial sequence
<220> FEATURE:
<223> OTHER INFORMATION: CPP

<400> SEQUENCE: 957

Gly Leu Phe Arg Ala Leu Leu Arg Leu Leu Arg Ser Leu Trp Arg Leu
1               5                   10                  15

Leu Leu Arg Ala
            20

<210> SEQ ID NO 958
<211> LENGTH: 11
<212> TYPE: PRT
<213> ORGANISM: Artificial sequence
<220> FEATURE:
<223> OTHER INFORMATION: CPP

<400> SEQUENCE: 958

Tyr Ala Arg Ala Ala Ala Arg Gln Ala Arg Ala
1               5                   10

<210> SEQ ID NO 959
<211> LENGTH: 10
<212> TYPE: PRT
<213> ORGANISM: Artificial sequence
<220> FEATURE:
<223> OTHER INFORMATION: CPP

<400> SEQUENCE: 959

Gly Lys Lys Lys Lys Lys Lys Lys Lys Lys
1               5                   10

<210> SEQ ID NO 960
<211> LENGTH: 20
<212> TYPE: PRT
<213> ORGANISM: Artificial sequence
<220> FEATURE:
<223> OTHER INFORMATION: CPP

<400> SEQUENCE: 960

Arg Ile Leu Gln Gln Leu Leu Phe Ile His Phe Arg Ile Gly Cys Arg
1               5                   10                  15

His Ser Arg Ile
            20

<210> SEQ ID NO 961
<211> LENGTH: 17
<212> TYPE: PRT
<213> ORGANISM: Artificial sequence
<220> FEATURE:
<223> OTHER INFORMATION: CPP

<400> SEQUENCE: 961
```

Arg Ile Leu Gln Gln Leu Leu Phe Ile His Phe Arg Ile Gly Cys Arg
1               5                   10                  15

His

<210> SEQ ID NO 962
<211> LENGTH: 15
<212> TYPE: PRT
<213> ORGANISM: Artificial sequence
<220> FEATURE:
<223> OTHER INFORMATION: CPP

<400> SEQUENCE: 962

Arg Ile Leu Gln Gln Leu Leu Phe Ile His Phe Arg Ile Gly Cys
1               5                   10                  15

<210> SEQ ID NO 963
<211> LENGTH: 10
<212> TYPE: PRT
<213> ORGANISM: Artificial sequence
<220> FEATURE:
<223> OTHER INFORMATION: CPP

<400> SEQUENCE: 963

Arg Ile Phe Ile His Phe Arg Ile Gly Cys
1               5                   10

<210> SEQ ID NO 964
<211> LENGTH: 8
<212> TYPE: PRT
<213> ORGANISM: Artificial sequence
<220> FEATURE:
<223> OTHER INFORMATION: CPP

<400> SEQUENCE: 964

Arg Ile Phe Ile Arg Ile Gly Cys
1               5

<210> SEQ ID NO 965
<211> LENGTH: 11
<212> TYPE: PRT
<213> ORGANISM: Artificial sequence
<220> FEATURE:
<223> OTHER INFORMATION: CPP

<400> SEQUENCE: 965

Arg Ile Leu Gln Gln Leu Leu Phe Ile His Phe
1               5                   10

<210> SEQ ID NO 966
<211> LENGTH: 6
<212> TYPE: PRT
<213> ORGANISM: Artificial sequence
<220> FEATURE:
<223> OTHER INFORMATION: CPP

<400> SEQUENCE: 966

Arg Ile Phe Ile Gly Cys
1               5

<210> SEQ ID NO 967
<211> LENGTH: 6
<212> TYPE: PRT
<213> ORGANISM: Artificial sequence
<220> FEATURE:
<223> OTHER INFORMATION: CPP

```
<400> SEQUENCE: 967

Phe Ile Arg Ile Gly Cys
1               5

<210> SEQ ID NO 968
<211> LENGTH: 22
<212> TYPE: PRT
<213> ORGANISM: Artificial sequence
<220> FEATURE:
<223> OTHER INFORMATION: CPP

<400> SEQUENCE: 968

Asp Thr Trp Ala Gly Val Glu Ala Ile Ile Arg Ile Leu Gln Gln Leu
1               5                   10                  15

Leu Phe Ile His Phe Arg
            20

<210> SEQ ID NO 969
<211> LENGTH: 5
<212> TYPE: PRT
<213> ORGANISM: Artificial sequence
<220> FEATURE:
<223> OTHER INFORMATION: CPP

<400> SEQUENCE: 969

Ile Gly Cys Arg His
1               5

<210> SEQ ID NO 970
<211> LENGTH: 23
<212> TYPE: PRT
<213> ORGANISM: Artificial sequence
<220> FEATURE:
<223> OTHER INFORMATION: CPP

<400> SEQUENCE: 970

Gly Tyr Gly Arg Lys Lys Arg Arg Gly Arg Arg Thr His Arg Leu
1               5                   10                  15

Pro Arg Arg Arg Arg Arg Arg
            20

<210> SEQ ID NO 971
<211> LENGTH: 12
<212> TYPE: PRT
<213> ORGANISM: Artificial sequence
<220> FEATURE:
<223> OTHER INFORMATION: CPP

<400> SEQUENCE: 971

Lys Arg Ile Ile Gln Arg Ile Leu Ser Arg Asn Ser
1               5                   10

<210> SEQ ID NO 972
<211> LENGTH: 12
<212> TYPE: PRT
<213> ORGANISM: Artificial sequence
<220> FEATURE:
<223> OTHER INFORMATION: CPP

<400> SEQUENCE: 972

Lys Arg Ile His Pro Arg Leu Thr Arg Ser Ile Arg
1               5                   10

<210> SEQ ID NO 973
<211> LENGTH: 12
```

```
<212> TYPE: PRT
<213> ORGANISM: Artificial sequence
<220> FEATURE:
<223> OTHER INFORMATION: CPP

<400> SEQUENCE: 973

Pro Pro Arg Leu Arg Lys Arg Arg Gln Leu Asn Met
1               5                   10

<210> SEQ ID NO 974
<211> LENGTH: 12
<212> TYPE: PRT
<213> ORGANISM: Artificial sequence
<220> FEATURE:
<223> OTHER INFORMATION: CPP

<400> SEQUENCE: 974

Pro Ile Arg Arg Arg Lys Lys Leu Arg Arg Leu Lys
1               5                   10

<210> SEQ ID NO 975
<211> LENGTH: 12
<212> TYPE: PRT
<213> ORGANISM: Artificial sequence
<220> FEATURE:
<223> OTHER INFORMATION: CPP

<400> SEQUENCE: 975

Arg Arg Gln Arg Arg Thr Ser Lys Leu Met Lys Arg
1               5                   10

<210> SEQ ID NO 976
<211> LENGTH: 12
<212> TYPE: PRT
<213> ORGANISM: Artificial sequence
<220> FEATURE:
<223> OTHER INFORMATION: CPP

<400> SEQUENCE: 976

Met His Lys Arg Pro Thr Thr Pro Ser Arg Lys Met
1               5                   10

<210> SEQ ID NO 977
<211> LENGTH: 12
<212> TYPE: PRT
<213> ORGANISM: Artificial sequence
<220> FEATURE:
<223> OTHER INFORMATION: CPP

<400> SEQUENCE: 977

Arg Gln Arg Ser Arg Arg Arg Pro Leu Asn Ile Arg
1               5                   10

<210> SEQ ID NO 978
<211> LENGTH: 12
<212> TYPE: PRT
<213> ORGANISM: Artificial sequence
<220> FEATURE:
<223> OTHER INFORMATION: CPP

<400> SEQUENCE: 978

Arg Ile Arg Met Ile Gln Asn Leu Ile Lys Lys Thr
1               5                   10

<210> SEQ ID NO 979
<211> LENGTH: 12
<212> TYPE: PRT
```

```
<213> ORGANISM: Artificial sequence
<220> FEATURE:
<223> OTHER INFORMATION: CPP

<400> SEQUENCE: 979

Ser Arg Arg Lys Arg Gln Arg Ser Asn Met Arg Ile
1               5                   10

<210> SEQ ID NO 980
<211> LENGTH: 12
<212> TYPE: PRT
<213> ORGANISM: Artificial sequence
<220> FEATURE:
<223> OTHER INFORMATION: CPP

<400> SEQUENCE: 980

Gln Arg Ile Arg Lys Ser Lys Ile Ser Arg Thr Leu
1               5                   10

<210> SEQ ID NO 981
<211> LENGTH: 12
<212> TYPE: PRT
<213> ORGANISM: Artificial sequence
<220> FEATURE:
<223> OTHER INFORMATION: CPP

<400> SEQUENCE: 981

Pro Ser Lys Arg Leu Leu His Asn Asn Leu Arg Arg
1               5                   10

<210> SEQ ID NO 982
<211> LENGTH: 12
<212> TYPE: PRT
<213> ORGANISM: Artificial sequence
<220> FEATURE:
<223> OTHER INFORMATION: CPP

<400> SEQUENCE: 982

His Arg His Ile Arg Arg Gln Ser Leu Ile Met Leu
1               5                   10

<210> SEQ ID NO 983
<211> LENGTH: 12
<212> TYPE: PRT
<213> ORGANISM: Artificial sequence
<220> FEATURE:
<223> OTHER INFORMATION: CPP

<400> SEQUENCE: 983

Pro Gln Asn Arg Leu Gln Ile Arg Arg His Ser Lys
1               5                   10

<210> SEQ ID NO 984
<211> LENGTH: 12
<212> TYPE: PRT
<213> ORGANISM: Artificial sequence
<220> FEATURE:
<223> OTHER INFORMATION: CPP

<400> SEQUENCE: 984

Pro Pro His Asn Arg Ile Gln Arg Arg Leu Asn Met
1               5                   10

<210> SEQ ID NO 985
<211> LENGTH: 12
<212> TYPE: PRT
<213> ORGANISM: Artificial sequence
```

<220> FEATURE:
<223> OTHER INFORMATION: CPP

<400> SEQUENCE: 985

Ser Met Leu Lys Arg Asn His Ser Thr Ser Asn Arg
1               5                   10

<210> SEQ ID NO 986
<211> LENGTH: 12
<212> TYPE: PRT
<213> ORGANISM: Artificial sequence
<220> FEATURE:
<223> OTHER INFORMATION: CPP

<400> SEQUENCE: 986

Gly Ser Arg His Pro Ser Leu Ile Ile Pro Arg Gln
1               5                   10

<210> SEQ ID NO 987
<211> LENGTH: 12
<212> TYPE: PRT
<213> ORGANISM: Artificial sequence
<220> FEATURE:
<223> OTHER INFORMATION: CPP

<400> SEQUENCE: 987

Ser Pro Met Gln Lys Thr Met Asn Leu Pro Pro Met
1               5                   10

<210> SEQ ID NO 988
<211> LENGTH: 12
<212> TYPE: PRT
<213> ORGANISM: Artificial sequence
<220> FEATURE:
<223> OTHER INFORMATION: CPP

<400> SEQUENCE: 988

Asn Lys Arg Ile Leu Ile Arg Ile Met Thr Arg Pro
1               5                   10

<210> SEQ ID NO 989
<211> LENGTH: 12
<212> TYPE: PRT
<213> ORGANISM: Artificial sequence
<220> FEATURE:
<223> OTHER INFORMATION: CPP

<400> SEQUENCE: 989

His Gly Trp Glx Ile His Gly Leu Leu His Arg Ala
1               5                   10

<210> SEQ ID NO 990
<211> LENGTH: 11
<212> TYPE: PRT
<213> ORGANISM: Artificial sequence
<220> FEATURE:
<223> OTHER INFORMATION: CPP

<400> SEQUENCE: 990

Ala Val Pro Ala Lys Lys Arg Glx Lys Ser Val
1               5                   10

<210> SEQ ID NO 991
<211> LENGTH: 11
<212> TYPE: PRT
<213> ORGANISM: Artificial sequence
<220> FEATURE:

```
<223> OTHER INFORMATION: CPP

<400> SEQUENCE: 991

Pro Asn Thr Arg Val Arg Pro Asp Val Ser Phe
1               5                   10

<210> SEQ ID NO 992
<211> LENGTH: 12
<212> TYPE: PRT
<213> ORGANISM: Artificial sequence
<220> FEATURE:
<223> OTHER INFORMATION: CPP

<400> SEQUENCE: 992

Leu Thr Arg Asn Tyr Glu Ala Trp Val Pro Thr Pro
1               5                   10

<210> SEQ ID NO 993
<211> LENGTH: 13
<212> TYPE: PRT
<213> ORGANISM: Artificial sequence
<220> FEATURE:
<223> OTHER INFORMATION: CPP

<400> SEQUENCE: 993

Ser Ala Glu Thr Val Glu Ser Cys Leu Ala Lys Ser His
1               5                   10

<210> SEQ ID NO 994
<211> LENGTH: 12
<212> TYPE: PRT
<213> ORGANISM: Artificial sequence
<220> FEATURE:
<223> OTHER INFORMATION: CPP

<400> SEQUENCE: 994

Tyr Ser His Ile Ala Thr Leu Pro Phe Thr Pro Thr
1               5                   10

<210> SEQ ID NO 995
<211> LENGTH: 12
<212> TYPE: PRT
<213> ORGANISM: Artificial sequence
<220> FEATURE:
<223> OTHER INFORMATION: CPP

<400> SEQUENCE: 995

Ser Tyr Ile Gln Arg Thr Pro Ser Thr Thr Leu Pro
1               5                   10

<210> SEQ ID NO 996
<211> LENGTH: 12
<212> TYPE: PRT
<213> ORGANISM: Artificial sequence
<220> FEATURE:
<223> OTHER INFORMATION: CPP

<400> SEQUENCE: 996

Ala Val Pro Ala Glu Asn Ala Leu Asn Asn Pro Phe
1               5                   10

<210> SEQ ID NO 997
<211> LENGTH: 12
<212> TYPE: PRT
<213> ORGANISM: Artificial sequence
<220> FEATURE:
<223> OTHER INFORMATION: CPP
```

<400> SEQUENCE: 997

Ser Phe His Gln Phe Ala Arg Ala Thr Leu Ala Ser
1               5                   10

<210> SEQ ID NO 998
<211> LENGTH: 12
<212> TYPE: PRT
<213> ORGANISM: Artificial sequence
<220> FEATURE:
<223> OTHER INFORMATION: CPP

<400> SEQUENCE: 998

Gln Ser Pro Thr Asp Phe Thr Phe Pro Asn Pro Leu
1               5                   10

<210> SEQ ID NO 999
<211> LENGTH: 12
<212> TYPE: PRT
<213> ORGANISM: Artificial sequence
<220> FEATURE:
<223> OTHER INFORMATION: CPP

<400> SEQUENCE: 999

His Phe Ala Ala Trp Gly Gly Trp Ser Leu Val His
1               5                   10

<210> SEQ ID NO 1000
<211> LENGTH: 12
<212> TYPE: PRT
<213> ORGANISM: Artificial sequence
<220> FEATURE:
<223> OTHER INFORMATION: CPP

<400> SEQUENCE: 1000

His Ile Gln Leu Ser Pro Phe Ser Gln Ser Trp Arg
1               5                   10

<210> SEQ ID NO 1001
<211> LENGTH: 12
<212> TYPE: PRT
<213> ORGANISM: Artificial sequence
<220> FEATURE:
<223> OTHER INFORMATION: CPP

<400> SEQUENCE: 1001

Leu Thr Met Pro Ser Asp Leu Gln Pro Val Leu Trp
1               5                   10

<210> SEQ ID NO 1002
<211> LENGTH: 12
<212> TYPE: PRT
<213> ORGANISM: Artificial sequence
<220> FEATURE:
<223> OTHER INFORMATION: CPP

<400> SEQUENCE: 1002

Phe Gln Pro Tyr Asp His Pro Ala Glu Val Ser Tyr
1               5                   10

<210> SEQ ID NO 1003
<211> LENGTH: 12
<212> TYPE: PRT
<213> ORGANISM: Artificial sequence
<220> FEATURE:
<223> OTHER INFORMATION: CPP

```
<400> SEQUENCE: 1003

Phe Asp Pro Phe Phe Trp Lys Tyr Ser Pro Arg Asp
1               5                   10

<210> SEQ ID NO 1004
<211> LENGTH: 12
<212> TYPE: PRT
<213> ORGANISM: Artificial sequence
<220> FEATURE:
<223> OTHER INFORMATION: CPP

<400> SEQUENCE: 1004

Phe Ala Pro Trp Asp Thr Ala Ser Phe Met Leu Gly
1               5                   10

<210> SEQ ID NO 1005
<211> LENGTH: 12
<212> TYPE: PRT
<213> ORGANISM: Artificial sequence
<220> FEATURE:
<223> OTHER INFORMATION: CPP

<400> SEQUENCE: 1005

Phe Thr Tyr Lys Asn Phe Phe Trp Leu Pro Glu Leu
1               5                   10

<210> SEQ ID NO 1006
<211> LENGTH: 12
<212> TYPE: PRT
<213> ORGANISM: Artificial sequence
<220> FEATURE:
<223> OTHER INFORMATION: CPP

<400> SEQUENCE: 1006

Ser Ala Thr Gly Ala Pro Trp Lys Met Trp Val Arg
1               5                   10

<210> SEQ ID NO 1007
<211> LENGTH: 12
<212> TYPE: PRT
<213> ORGANISM: Artificial sequence
<220> FEATURE:
<223> OTHER INFORMATION: CPP

<400> SEQUENCE: 1007

Ser Leu Gly Trp Met Leu Pro Phe Ser Pro Pro Phe
1               5                   10

<210> SEQ ID NO 1008
<211> LENGTH: 12
<212> TYPE: PRT
<213> ORGANISM: Artificial sequence
<220> FEATURE:
<223> OTHER INFORMATION: CPP

<400> SEQUENCE: 1008

Ser His Ala Phe Thr Trp Pro Thr Tyr Leu Gln Leu
1               5                   10

<210> SEQ ID NO 1009
<211> LENGTH: 12
<212> TYPE: PRT
<213> ORGANISM: Artificial sequence
<220> FEATURE:
<223> OTHER INFORMATION: CPP

<400> SEQUENCE: 1009
```

Ser His Asn Trp Leu Pro Leu Trp Pro Leu Arg Pro
1               5                   10

<210> SEQ ID NO 1010
<211> LENGTH: 12
<212> TYPE: PRT
<213> ORGANISM: Artificial sequence
<220> FEATURE:
<223> OTHER INFORMATION: CPP

<400> SEQUENCE: 1010

Ser Trp Leu Pro Tyr Pro Trp His Val Pro Ser Ser
1               5                   10

<210> SEQ ID NO 1011
<211> LENGTH: 12
<212> TYPE: PRT
<213> ORGANISM: Artificial sequence
<220> FEATURE:
<223> OTHER INFORMATION: CPP

<400> SEQUENCE: 1011

Ser Trp Trp Thr Pro Trp His Val His Ser Glu Ser
1               5                   10

<210> SEQ ID NO 1012
<211> LENGTH: 12
<212> TYPE: PRT
<213> ORGANISM: Artificial sequence
<220> FEATURE:
<223> OTHER INFORMATION: CPP

<400> SEQUENCE: 1012

Ser Trp Ala Gln His Leu Ser Leu Pro Pro Val Leu
1               5                   10

<210> SEQ ID NO 1013
<211> LENGTH: 12
<212> TYPE: PRT
<213> ORGANISM: Artificial sequence
<220> FEATURE:
<223> OTHER INFORMATION: CPP

<400> SEQUENCE: 1013

Ser Ser Ser Ile Phe Pro Pro Trp Leu Ser Phe Phe
1               5                   10

<210> SEQ ID NO 1014
<211> LENGTH: 12
<212> TYPE: PRT
<213> ORGANISM: Artificial sequence
<220> FEATURE:
<223> OTHER INFORMATION: CPP

<400> SEQUENCE: 1014

Leu Asn Val Pro Pro Ser Trp Phe Leu Ser Gln Arg
1               5                   10

<210> SEQ ID NO 1015
<211> LENGTH: 12
<212> TYPE: PRT
<213> ORGANISM: Artificial sequence
<220> FEATURE:
<223> OTHER INFORMATION: CPP

<400> SEQUENCE: 1015

```
Leu Asp Ile Thr Pro Phe Leu Ser Leu Thr Leu Pro
1               5                   10
```

<210> SEQ ID NO 1016
<211> LENGTH: 12
<212> TYPE: PRT
<213> ORGANISM: Artificial sequence
<220> FEATURE:
<223> OTHER INFORMATION: CPP

<400> SEQUENCE: 1016

```
Leu Pro His Pro Val Leu His Met Gly Pro Leu Arg
1               5                   10
```

<210> SEQ ID NO 1017
<211> LENGTH: 12
<212> TYPE: PRT
<213> ORGANISM: Artificial sequence
<220> FEATURE:
<223> OTHER INFORMATION: CPP

<400> SEQUENCE: 1017

```
Val Ser Lys Gln Pro Tyr Tyr Met Trp Asn Gly Asn
1               5                   10
```

<210> SEQ ID NO 1018
<211> LENGTH: 12
<212> TYPE: PRT
<213> ORGANISM: Artificial sequence
<220> FEATURE:
<223> OTHER INFORMATION: CPP

<400> SEQUENCE: 1018

```
Asn Tyr Thr Thr Tyr Lys Ser His Phe Gln Asp Arg
1               5                   10
```

<210> SEQ ID NO 1019
<211> LENGTH: 12
<212> TYPE: PRT
<213> ORGANISM: Artificial sequence
<220> FEATURE:
<223> OTHER INFORMATION: CPP

<400> SEQUENCE: 1019

```
Ala Ile Pro Asn Asn Gln Leu Gly Phe Pro Phe Lys
1               5                   10
```

<210> SEQ ID NO 1020
<211> LENGTH: 12
<212> TYPE: PRT
<213> ORGANISM: Artificial sequence
<220> FEATURE:
<223> OTHER INFORMATION: CPP

<400> SEQUENCE: 1020

```
Asn Ile Glu Asn Ser Thr Leu Ala Thr Pro Leu Ser
1               5                   10
```

<210> SEQ ID NO 1021
<211> LENGTH: 12
<212> TYPE: PRT
<213> ORGANISM: Artificial sequence
<220> FEATURE:
<223> OTHER INFORMATION: CPP

<400> SEQUENCE: 1021

Tyr Pro Tyr Asp Ala Asn His Thr Arg Ser Pro Thr

```
<210> SEQ ID NO 1022
<211> LENGTH: 12
<212> TYPE: PRT
<213> ORGANISM: Artificial sequence
<220> FEATURE:
<223> OTHER INFORMATION: CPP

<400> SEQUENCE: 1022

Asp Pro Ala Thr Asn Pro Gly Pro His Phe Pro Arg
1               5                   10

<210> SEQ ID NO 1023
<211> LENGTH: 12
<212> TYPE: PRT
<213> ORGANISM: Artificial sequence
<220> FEATURE:
<223> OTHER INFORMATION: CPP

<400> SEQUENCE: 1023

Thr Leu Pro Ser Pro Leu Ala Leu Leu Thr Val His
1               5                   10

<210> SEQ ID NO 1024
<211> LENGTH: 12
<212> TYPE: PRT
<213> ORGANISM: Artificial sequence
<220> FEATURE:
<223> OTHER INFORMATION: CPP

<400> SEQUENCE: 1024

His Pro Gly Ser Pro Phe Pro Pro Glu His Arg Pro
1               5                   10

<210> SEQ ID NO 1025
<211> LENGTH: 12
<212> TYPE: PRT
<213> ORGANISM: Artificial sequence
<220> FEATURE:
<223> OTHER INFORMATION: CPP

<400> SEQUENCE: 1025

Thr Ser His Thr Asp Ala Pro Pro Ala Arg Ser Pro
1               5                   10

<210> SEQ ID NO 1026
<211> LENGTH: 12
<212> TYPE: PRT
<213> ORGANISM: Artificial sequence
<220> FEATURE:
<223> OTHER INFORMATION: CPP

<400> SEQUENCE: 1026

Met Thr Pro Ser Ser Leu Ser Thr Leu Pro Trp Pro
1               5                   10

<210> SEQ ID NO 1027
<211> LENGTH: 12
<212> TYPE: PRT
<213> ORGANISM: Artificial sequence
<220> FEATURE:
<223> OTHER INFORMATION: CPP

<400> SEQUENCE: 1027

Val Leu Gly Gln Ser Gly Tyr Leu Met Pro Met Arg
1               5                   10
```

```
<210> SEQ ID NO 1028
<211> LENGTH: 12
<212> TYPE: PRT
<213> ORGANISM: Artificial sequence
<220> FEATURE:
<223> OTHER INFORMATION: CPP

<400> SEQUENCE: 1028

Gln Pro Ile Ile Ile Thr Ser Pro Tyr Leu Pro Ser
1               5                   10

<210> SEQ ID NO 1029
<211> LENGTH: 12
<212> TYPE: PRT
<213> ORGANISM: Artificial sequence
<220> FEATURE:
<223> OTHER INFORMATION: CPP

<400> SEQUENCE: 1029

Thr Pro Lys Thr Met Thr Gln Thr Tyr Asp Phe Ser
1               5                   10

<210> SEQ ID NO 1030
<211> LENGTH: 12
<212> TYPE: PRT
<213> ORGANISM: Artificial sequence
<220> FEATURE:
<223> OTHER INFORMATION: CPP

<400> SEQUENCE: 1030

Asn Ser Gly Thr Met Gln Ser Ala Ser Arg Ala Thr
1               5                   10

<210> SEQ ID NO 1031
<211> LENGTH: 12
<212> TYPE: PRT
<213> ORGANISM: Artificial sequence
<220> FEATURE:
<223> OTHER INFORMATION: CPP

<400> SEQUENCE: 1031

Gln Ala Ala Ser Arg Val Glu Asn Tyr Met His Arg
1               5                   10

<210> SEQ ID NO 1032
<211> LENGTH: 12
<212> TYPE: PRT
<213> ORGANISM: Artificial sequence
<220> FEATURE:
<223> OTHER INFORMATION: CPP

<400> SEQUENCE: 1032

His Gln His Lys Pro Pro Pro Leu Thr Asn Asn Trp
1               5                   10

<210> SEQ ID NO 1033
<211> LENGTH: 12
<212> TYPE: PRT
<213> ORGANISM: Artificial sequence
<220> FEATURE:
<223> OTHER INFORMATION: CPP

<400> SEQUENCE: 1033

Ser Asn Pro Trp Asp Ser Leu Leu Ser Val Ser Thr
1               5                   10
```

<210> SEQ ID NO 1034
<211> LENGTH: 12
<212> TYPE: PRT
<213> ORGANISM: Artificial sequence
<220> FEATURE:
<223> OTHER INFORMATION: CPP

<400> SEQUENCE: 1034

Lys Thr Ile Glu Ala His Pro Pro Tyr Tyr Ala Ser
1               5                   10

<210> SEQ ID NO 1035
<211> LENGTH: 12
<212> TYPE: PRT
<213> ORGANISM: Artificial sequence
<220> FEATURE:
<223> OTHER INFORMATION: CPP

<400> SEQUENCE: 1035

Glu Pro Asp Asn Trp Ser Leu Asp Phe Pro Arg Arg
1               5                   10

<210> SEQ ID NO 1036
<211> LENGTH: 12
<212> TYPE: PRT
<213> ORGANISM: Artificial sequence
<220> FEATURE:
<223> OTHER INFORMATION: CPP

<400> SEQUENCE: 1036

His Gln His Lys Pro Pro Pro Leu Thr Asn Asn Trp
1               5                   10

<210> SEQ ID NO 1037
<211> LENGTH: 20
<212> TYPE: PRT
<213> ORGANISM: Artificial sequence
<220> FEATURE:
<223> OTHER INFORMATION: CPP

<400> SEQUENCE: 1037

Gly Leu Trp Arg Ala Leu Trp Arg Leu Leu Arg Ser Leu Trp Arg Leu
1               5                   10                  15

Leu Trp Lys Ala
            20

<210> SEQ ID NO 1038
<211> LENGTH: 21
<212> TYPE: PRT
<213> ORGANISM: Artificial sequence
<220> FEATURE:
<223> OTHER INFORMATION: CPP

<400> SEQUENCE: 1038

Gly Leu Trp Arg Ala Leu Trp Arg Ala Leu Trp Arg Ser Leu Trp Lys
1               5                   10                  15

Leu Lys Arg Lys Val
            20

<210> SEQ ID NO 1039
<211> LENGTH: 20
<212> TYPE: PRT
<213> ORGANISM: Artificial sequence
<220> FEATURE:
<223> OTHER INFORMATION: CPP

```
<400> SEQUENCE: 1039

Gly Leu Trp Arg Ala Leu Trp Arg Ala Leu Arg Ser Leu Trp Lys Leu
1               5                   10                  15

Lys Arg Lys Val
            20

<210> SEQ ID NO 1040
<211> LENGTH: 20
<212> TYPE: PRT
<213> ORGANISM: Artificial sequence
<220> FEATURE:
<223> OTHER INFORMATION: CPP

<400> SEQUENCE: 1040

Gly Leu Trp Arg Ala Leu Trp Arg Gly Leu Arg Ser Leu Trp Lys Leu
1               5                   10                  15

Lys Arg Lys Val
            20

<210> SEQ ID NO 1041
<211> LENGTH: 20
<212> TYPE: PRT
<213> ORGANISM: Artificial sequence
<220> FEATURE:
<223> OTHER INFORMATION: CPP

<400> SEQUENCE: 1041

Gly Leu Trp Arg Ala Leu Trp Arg Gly Leu Arg Ser Leu Trp Lys Lys
1               5                   10                  15

Lys Arg Lys Val
            20

<210> SEQ ID NO 1042
<211> LENGTH: 21
<212> TYPE: PRT
<213> ORGANISM: Artificial sequence
<220> FEATURE:
<223> OTHER INFORMATION: CPP

<400> SEQUENCE: 1042

Gly Leu Trp Arg Ala Leu Trp Arg Ala Leu Trp Arg Ser Leu Trp Lys
1               5                   10                  15

Leu Lys Trp Lys Val
            20

<210> SEQ ID NO 1043
<211> LENGTH: 21
<212> TYPE: PRT
<213> ORGANISM: Artificial sequence
<220> FEATURE:
<223> OTHER INFORMATION: CPP

<400> SEQUENCE: 1043

Gly Leu Trp Arg Ala Leu Trp Arg Ala Leu Trp Arg Ser Leu Trp Lys
1               5                   10                  15

Ser Lys Arg Lys Val
            20

<210> SEQ ID NO 1044
<211> LENGTH: 21
<212> TYPE: PRT
<213> ORGANISM: Artificial sequence
<220> FEATURE:
<223> OTHER INFORMATION: CPP
```

```
<400> SEQUENCE: 1044

Gly Leu Trp Arg Ala Leu Trp Arg Ala Leu Trp Arg Ser Leu Trp Lys
1               5                   10                  15

Lys Lys Arg Lys Val
            20

<210> SEQ ID NO 1045
<211> LENGTH: 21
<212> TYPE: PRT
<213> ORGANISM: Artificial sequence
<220> FEATURE:
<223> OTHER INFORMATION: CPP

<400> SEQUENCE: 1045

Gly Leu Trp Arg Ala Leu Trp Arg Ala Leu Trp Arg Ser Leu Trp Lys
1               5                   10                  15

Leu Lys Arg Lys Val
            20

<210> SEQ ID NO 1046
<211> LENGTH: 27
<212> TYPE: PRT
<213> ORGANISM: Artificial sequence
<220> FEATURE:
<223> OTHER INFORMATION: CPP

<400> SEQUENCE: 1046

Gly Leu Trp Arg Ala Leu Trp Arg Leu Leu Arg Ser Leu Trp Arg Leu
1               5                   10                  15

Leu Trp Ser Gln Pro Lys Lys Arg Lys Val
            20                  25

<210> SEQ ID NO 1047
<211> LENGTH: 11
<212> TYPE: PRT
<213> ORGANISM: Artificial sequence
<220> FEATURE:
<223> OTHER INFORMATION: CPP

<400> SEQUENCE: 1047

Tyr Ala Arg Ala Ala Arg Arg Ala Ala Arg Arg
1               5                   10

<210> SEQ ID NO 1048
<211> LENGTH: 11
<212> TYPE: PRT
<213> ORGANISM: Artificial sequence
<220> FEATURE:
<223> OTHER INFORMATION: CPP

<400> SEQUENCE: 1048

Pro Ala Arg Ala Ala Arg Arg Ala Ala Arg Arg
1               5                   10

<210> SEQ ID NO 1049
<211> LENGTH: 11
<212> TYPE: PRT
<213> ORGANISM: Artificial sequence
<220> FEATURE:
<223> OTHER INFORMATION: CPP

<400> SEQUENCE: 1049

Tyr Pro Arg Ala Ala Arg Arg Ala Ala Arg Arg
1               5                   10
```

```
<210> SEQ ID NO 1050
<211> LENGTH: 11
<212> TYPE: PRT
<213> ORGANISM: Artificial sequence
<220> FEATURE:
<223> OTHER INFORMATION: CPP

<400> SEQUENCE: 1050

Tyr Arg Arg Ala Ala Arg Arg Ala Ala Arg Ala
1               5                   10

<210> SEQ ID NO 1051
<211> LENGTH: 11
<212> TYPE: PRT
<213> ORGANISM: Artificial sequence
<220> FEATURE:
<223> OTHER INFORMATION: CPP

<400> SEQUENCE: 1051

Tyr Gly Arg Ala Ala Arg Arg Ala Ala Arg Arg
1               5                   10

<210> SEQ ID NO 1052
<211> LENGTH: 11
<212> TYPE: PRT
<213> ORGANISM: Artificial sequence
<220> FEATURE:
<223> OTHER INFORMATION: CPP

<400> SEQUENCE: 1052

Tyr Ala Arg Glu Ala Arg Arg Ala Ala Arg Arg
1               5                   10

<210> SEQ ID NO 1053
<211> LENGTH: 11
<212> TYPE: PRT
<213> ORGANISM: Artificial sequence
<220> FEATURE:
<223> OTHER INFORMATION: CPP

<400> SEQUENCE: 1053

Tyr Glu Arg Glu Ala Arg Arg Ala Ala Arg Arg
1               5                   10

<210> SEQ ID NO 1054
<211> LENGTH: 11
<212> TYPE: PRT
<213> ORGANISM: Artificial sequence
<220> FEATURE:
<223> OTHER INFORMATION: CPP

<400> SEQUENCE: 1054

Tyr Lys Arg Ala Ala Arg Arg Ala Ala Arg Arg
1               5                   10

<210> SEQ ID NO 1055
<211> LENGTH: 11
<212> TYPE: PRT
<213> ORGANISM: Artificial sequence
<220> FEATURE:
<223> OTHER INFORMATION: CPP

<400> SEQUENCE: 1055

Tyr Ala Arg Lys Ala Arg Arg Ala Ala Arg Arg
1               5                   10
```

```
<210> SEQ ID NO 1056
<211> LENGTH: 11
<212> TYPE: PRT
<213> ORGANISM: Artificial sequence
<220> FEATURE:
<223> OTHER INFORMATION: CPP

<400> SEQUENCE: 1056

Tyr Lys Arg Lys Ala Arg Arg Ala Ala Arg Arg
1               5                   10

<210> SEQ ID NO 1057
<211> LENGTH: 11
<212> TYPE: PRT
<213> ORGANISM: Artificial sequence
<220> FEATURE:
<223> OTHER INFORMATION: CPP

<400> SEQUENCE: 1057

Tyr Gly Arg Arg Ala Arg Arg Ala Ala Arg Arg
1               5                   10

<210> SEQ ID NO 1058
<211> LENGTH: 11
<212> TYPE: PRT
<213> ORGANISM: Artificial sequence
<220> FEATURE:
<223> OTHER INFORMATION: CPP

<400> SEQUENCE: 1058

Tyr Gly Arg Arg Ala Arg Arg Arg Ala Arg Arg
1               5                   10

<210> SEQ ID NO 1059
<211> LENGTH: 11
<212> TYPE: PRT
<213> ORGANISM: Artificial sequence
<220> FEATURE:
<223> OTHER INFORMATION: CPP

<400> SEQUENCE: 1059

Tyr Gly Arg Arg Ala Arg Arg Arg Arg Arg Arg
1               5                   10

<210> SEQ ID NO 1060
<211> LENGTH: 11
<212> TYPE: PRT
<213> ORGANISM: Artificial sequence
<220> FEATURE:
<223> OTHER INFORMATION: CPP

<400> SEQUENCE: 1060

Tyr Gly Arg Arg Arg Arg Arg Arg Arg Arg Arg
1               5                   10

<210> SEQ ID NO 1061
<211> LENGTH: 11
<212> TYPE: PRT
<213> ORGANISM: Artificial sequence
<220> FEATURE:
<223> OTHER INFORMATION: CPP

<400> SEQUENCE: 1061

Tyr Arg Arg Arg Arg Arg Arg Arg Arg Arg Arg
1               5                   10
```

-continued

```
<210> SEQ ID NO 1062
<211> LENGTH: 16
<212> TYPE: PRT
<213> ORGANISM: Artificial sequence
<220> FEATURE:
<223> OTHER INFORMATION: CPP

<400> SEQUENCE: 1062

Gly Lys Ile Asn Leu Lys Ala Leu Ala Ala Leu Ala Lys Lys Ile Leu
1               5                   10                  15

<210> SEQ ID NO 1063
<211> LENGTH: 16
<212> TYPE: PRT
<213> ORGANISM: Artificial sequence
<220> FEATURE:
<223> OTHER INFORMATION: CPP

<400> SEQUENCE: 1063

Arg Val Ile Arg Val Trp Phe Gln Asn Lys Arg Cys Lys Asp Lys Lys
1               5                   10                  15

<210> SEQ ID NO 1064
<211> LENGTH: 39
<212> TYPE: PRT
<213> ORGANISM: Artificial sequence
<220> FEATURE:
<223> OTHER INFORMATION: CPP

<400> SEQUENCE: 1064

Gly Arg Lys Lys Arg Arg Gln Arg Arg Pro Pro Gln Gly Arg Lys
1               5                   10                  15

Lys Arg Arg Gln Arg Arg Pro Pro Gln Gly Arg Lys Lys Arg Arg
                20                  25                  30

Gln Arg Arg Pro Pro Gln
            35

<210> SEQ ID NO 1065
<211> LENGTH: 22
<212> TYPE: PRT
<213> ORGANISM: Artificial sequence
<220> FEATURE:
<223> OTHER INFORMATION: CPP

<400> SEQUENCE: 1065

Gly Glu Gln Ile Ala Gln Leu Ile Ala Gly Tyr Ile Asp Ile Ile Leu
1               5                   10                  15

Lys Lys Lys Lys Ser Lys
            20

<210> SEQ ID NO 1066
<211> LENGTH: 14
<212> TYPE: PRT
<213> ORGANISM: Artificial sequence
<220> FEATURE:
<223> OTHER INFORMATION: CPP

<400> SEQUENCE: 1066

Gly Arg Lys Lys Arg Arg Gln Arg Arg Arg Pro Pro Gln Cys
1               5                   10

<210> SEQ ID NO 1067
<211> LENGTH: 28
<212> TYPE: PRT
<213> ORGANISM: Artificial sequence
<220> FEATURE:
```

<223> OTHER INFORMATION: CPP

<400> SEQUENCE: 1067

Ala Ala Val Ala Leu Leu Pro Ala Val Leu Leu Ala Leu Leu Ala Pro
1               5                   10                  15

Arg Lys Lys Arg Arg Gln Arg Arg Pro Pro Gln
            20                  25

<210> SEQ ID NO 1068
<211> LENGTH: 29
<212> TYPE: PRT
<213> ORGANISM: Artificial sequence
<220> FEATURE:
<223> OTHER INFORMATION: CPP

<400> SEQUENCE: 1068

Ala Ala Val Ala Leu Leu Pro Ala Val Leu Leu Ala Leu Leu Ala Pro
1               5                   10                  15

Arg Lys Lys Arg Arg Gln Arg Arg Pro Pro Gln Cys
            20                  25

<210> SEQ ID NO 1069
<211> LENGTH: 28
<212> TYPE: PRT
<213> ORGANISM: Artificial sequence
<220> FEATURE:
<223> OTHER INFORMATION: CPP

<400> SEQUENCE: 1069

Ala Ala Val Ala Leu Leu Pro Ala Val Leu Leu Ala Leu Leu Ala Pro
1               5                   10                  15

Arg Lys Lys Arg Arg Gln Arg Arg Pro Pro Gln
            20                  25

<210> SEQ ID NO 1070
<211> LENGTH: 29
<212> TYPE: PRT
<213> ORGANISM: Artificial sequence
<220> FEATURE:
<223> OTHER INFORMATION: CPP

<400> SEQUENCE: 1070

Arg Lys Lys Arg Arg Gln Arg Arg Pro Pro Gln Cys Ala Ala Val
1               5                   10                  15

Ala Leu Leu Pro Ala Val Leu Leu Ala Leu Leu Ala Pro
            20                  25

<210> SEQ ID NO 1071
<211> LENGTH: 29
<212> TYPE: PRT
<213> ORGANISM: Artificial sequence
<220> FEATURE:
<223> OTHER INFORMATION: CPP

<400> SEQUENCE: 1071

Arg Arg Arg Gln Arg Arg Lys Arg Gly Gly Asp Ile Met Gly Glu Trp
1               5                   10                  15

Gly Asn Glu Ile Phe Gly Ala Ile Ala Gly Phe Leu Gly
            20                  25

<210> SEQ ID NO 1072
<211> LENGTH: 29
<212> TYPE: PRT
<213> ORGANISM: Artificial sequence

```
<220> FEATURE:
<223> OTHER INFORMATION: CPP

<400> SEQUENCE: 1072

Arg Arg Arg Gln Arg Arg Lys Arg Gly Gly Asp Ile Met Gly Glu Trp
1               5                   10                  15

Gly Asn Glu Ile Phe Gly Ala Ile Ala Gly Phe Leu Gly
            20                  25

<210> SEQ ID NO 1073
<211> LENGTH: 25
<212> TYPE: PRT
<213> ORGANISM: Artificial sequence
<220> FEATURE:
<223> OTHER INFORMATION: CPP

<400> SEQUENCE: 1073

Tyr Gly Arg Lys Lys Arg Arg Gln Arg Arg Gly Cys Tyr Gly Arg
1               5                   10                  15

Lys Lys Arg Arg Gln Arg Arg Gly
            20                  25

<210> SEQ ID NO 1074
<211> LENGTH: 13
<212> TYPE: PRT
<213> ORGANISM: Artificial sequence
<220> FEATURE:
<223> OTHER INFORMATION: CPP

<400> SEQUENCE: 1074

Gly Arg Lys Lys Arg Arg Gln Arg Arg Arg Pro Pro Gln
1               5                   10

<210> SEQ ID NO 1075
<211> LENGTH: 22
<212> TYPE: PRT
<213> ORGANISM: Artificial sequence
<220> FEATURE:
<223> OTHER INFORMATION: CPP

<400> SEQUENCE: 1075

Ala Ala Val Ala Leu Leu Pro Ala Val Leu Leu Ala Leu Leu Ala Pro
1               5                   10                  15

Arg Arg Arg Arg Arg Arg
            20

<210> SEQ ID NO 1076
<211> LENGTH: 16
<212> TYPE: PRT
<213> ORGANISM: Artificial sequence
<220> FEATURE:
<223> OTHER INFORMATION: CPP

<400> SEQUENCE: 1076

Arg Leu Trp Arg Ala Leu Pro Arg Val Leu Arg Leu Leu Arg Pro
1               5                   10                  15

<210> SEQ ID NO 1077
<211> LENGTH: 28
<212> TYPE: PRT
<213> ORGANISM: Artificial sequence
<220> FEATURE:
<223> OTHER INFORMATION: CPP

<400> SEQUENCE: 1077
```

-continued

```
Ala Ala Val Ala Leu Leu Pro Ala Val Leu Ala Leu Leu Ala Pro
1               5                   10                  15

Ser Gly Ala Ser Gly Leu Asp Lys Arg Asp Tyr Val
            20                  25
```

<210> SEQ ID NO 1078
<211> LENGTH: 33
<212> TYPE: PRT
<213> ORGANISM: Artificial sequence
<220> FEATURE:
<223> OTHER INFORMATION: CPP

<400> SEQUENCE: 1078

```
Leu Leu Glu Thr Leu Leu Lys Pro Phe Gln Cys Arg Ile Cys Met Arg
1               5                   10                  15

Asn Phe Ser Thr Arg Gln Ala Arg Arg Asn His Arg Arg His Arg
            20                  25                  30

Arg
```

<210> SEQ ID NO 1079
<211> LENGTH: 27
<212> TYPE: PRT
<213> ORGANISM: Artificial sequence
<220> FEATURE:
<223> OTHER INFORMATION: CPP

<400> SEQUENCE: 1079

```
Ala Ala Val Ala Cys Arg Ile Cys Met Arg Asn Phe Ser Thr Arg Gln
1               5                   10                  15

Ala Arg Arg Asn His Arg Arg His Arg Arg
            20                  25
```

<210> SEQ ID NO 1080
<211> LENGTH: 16
<212> TYPE: PRT
<213> ORGANISM: Artificial sequence
<220> FEATURE:
<223> OTHER INFORMATION: CPP

<400> SEQUENCE: 1080

```
Arg Gln Ile Lys Ile Trp Phe Gln Asn Arg Arg Met Lys Trp Lys Lys
1               5                   10                  15
```

<210> SEQ ID NO 1081
<211> LENGTH: 16
<212> TYPE: PRT
<213> ORGANISM: Artificial sequence
<220> FEATURE:
<223> OTHER INFORMATION: CPP

<400> SEQUENCE: 1081

```
Arg Gln Ile Lys Ile Trp Phe Gln Asn Arg Arg Met Lys Trp Lys Lys
1               5                   10                  15
```

<210> SEQ ID NO 1082
<211> LENGTH: 35
<212> TYPE: PRT
<213> ORGANISM: Artificial sequence
<220> FEATURE:
<223> OTHER INFORMATION: CPP

<400> SEQUENCE: 1082

```
Arg Gln Ile Lys Ile Trp Phe Gln Asn Arg Arg Met Lys Trp Lys Lys
1               5                   10                  15
```

```
Asp Ile Met Gly Glu Trp Gly Asn Glu Ile Phe Gly Ala Ile Ala Gly
            20                  25                  30

Phe Leu Gly
        35

<210> SEQ ID NO 1083
<211> LENGTH: 37
<212> TYPE: PRT
<213> ORGANISM: Artificial sequence
<220> FEATURE:
<223> OTHER INFORMATION: CPP

<400> SEQUENCE: 1083

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly
        35

<210> SEQ ID NO 1084
<211> LENGTH: 38
<212> TYPE: PRT
<213> ORGANISM: Artificial sequence
<220> FEATURE:
<223> OTHER INFORMATION: CPP

<400> SEQUENCE: 1084

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Cys
        35

<210> SEQ ID NO 1085
<211> LENGTH: 25
<212> TYPE: PRT
<213> ORGANISM: Artificial sequence
<220> FEATURE:
<223> OTHER INFORMATION: CPP

<400> SEQUENCE: 1085

Lys Lys Asp Gly Lys Lys Arg Lys Arg Ser Arg Lys Glu Ser Tyr Ser
1               5                   10                  15

Val Tyr Val Tyr Lys Val Leu Lys Gln
            20                  25

<210> SEQ ID NO 1086
<211> LENGTH: 36
<212> TYPE: PRT
<213> ORGANISM: Artificial sequence
<220> FEATURE:
<223> OTHER INFORMATION: CPP

<400> SEQUENCE: 1086

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
            20                  25                  30

Val Leu Lys Gln
        35
```

<210> SEQ ID NO 1087
<211> LENGTH: 27
<212> TYPE: PRT
<213> ORGANISM: Artificial sequence
<220> FEATURE:
<223> OTHER INFORMATION: CPP

<400> SEQUENCE: 1087

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1088
<211> LENGTH: 18
<212> TYPE: PRT
<213> ORGANISM: Artificial sequence
<220> FEATURE:
<223> OTHER INFORMATION: CPP

<400> SEQUENCE: 1088

Lys Leu Ala Leu Lys Leu Ala Leu Lys Ala Leu Lys Ala Ala Leu Lys
1               5                   10                  15

Leu Ala

<210> SEQ ID NO 1089
<211> LENGTH: 21
<212> TYPE: PRT
<213> ORGANISM: Artificial sequence
<220> FEATURE:
<223> OTHER INFORMATION: CPP

<400> SEQUENCE: 1089

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 1090
<211> LENGTH: 28
<212> TYPE: PRT
<213> ORGANISM: Artificial sequence
<220> FEATURE:
<223> OTHER INFORMATION: CPP

<400> SEQUENCE: 1090

Lys Glu Thr Trp Trp Glu Thr Trp Trp Thr Glu Trp Ser Gln Pro Gly
1               5                   10                  15

Arg Lys Lys Arg Arg Gln Arg Arg Pro Pro Gln
            20                  25

<210> SEQ ID NO 1091
<211> LENGTH: 15
<212> TYPE: PRT
<213> ORGANISM: Artificial sequence
<220> FEATURE:
<223> OTHER INFORMATION: CPP

<400> SEQUENCE: 1091

Arg Val Ile Arg Trp Phe Gln Asn Lys Arg Cys Lys Asp Lys Lys
1               5                   10                  15

<210> SEQ ID NO 1092
<211> LENGTH: 18

```
<212> TYPE: PRT
<213> ORGANISM: Artificial sequence
<220> FEATURE:
<223> OTHER INFORMATION: CPP

<400> SEQUENCE: 1092

Leu Gly Leu Leu Leu Arg His Leu Arg His His Ser Asn Leu Leu Ala
1               5                   10                  15

Asn Ile

<210> SEQ ID NO 1093
<211> LENGTH: 16
<212> TYPE: PRT
<213> ORGANISM: Artificial sequence
<220> FEATURE:
<223> OTHER INFORMATION: CPP

<400> SEQUENCE: 1093

Lys Leu Trp Ser Ala Trp Pro Ser Leu Trp Ser Ser Leu Trp Lys Pro
1               5                   10                  15

<210> SEQ ID NO 1094
<211> LENGTH: 22
<212> TYPE: PRT
<213> ORGANISM: Artificial sequence
<220> FEATURE:
<223> OTHER INFORMATION: CPP

<400> SEQUENCE: 1094

Gly Leu Gly Ser Leu Leu Lys Lys Ala Gly Lys Lys Leu Lys Gln Pro
1               5                   10                  15

Lys Ser Lys Arg Lys Val
            20

<210> SEQ ID NO 1095
<211> LENGTH: 12
<212> TYPE: PRT
<213> ORGANISM: Artificial sequence
<220> FEATURE:
<223> OTHER INFORMATION: CPP

<400> SEQUENCE: 1095

Phe Lys Gln Gln Gln Gln Gln Gln Gln Gln Gln Gln
1               5                   10

<210> SEQ ID NO 1096
<211> LENGTH: 4
<212> TYPE: PRT
<213> ORGANISM: Artificial sequence
<220> FEATURE:
<223> OTHER INFORMATION: CPP

<400> SEQUENCE: 1096

Tyr Arg Phe Lys
1

<210> SEQ ID NO 1097
<211> LENGTH: 13
<212> TYPE: PRT
<213> ORGANISM: Artificial sequence
<220> FEATURE:
<223> OTHER INFORMATION: CPP

<400> SEQUENCE: 1097

Tyr Arg Phe Lys Tyr Arg Phe Lys Tyr Arg Leu Phe Lys
1               5                   10
```

<210> SEQ ID NO 1098
<211> LENGTH: 10
<212> TYPE: PRT
<213> ORGANISM: Artificial sequence
<220> FEATURE:
<223> OTHER INFORMATION: CPP

<400> SEQUENCE: 1098

Trp Arg Phe Lys Lys Ser Lys Arg Lys Val
1               5                   10

<210> SEQ ID NO 1099
<211> LENGTH: 20
<212> TYPE: PRT
<213> ORGANISM: Artificial sequence
<220> FEATURE:
<223> OTHER INFORMATION: CPP

<400> SEQUENCE: 1099

Trp Arg Phe Lys Ala Ala Val Ala Leu Leu Pro Ala Val Leu Leu Ala
1               5                   10                  15

Leu Leu Ala Pro
            20

<210> SEQ ID NO 1100
<211> LENGTH: 8
<212> TYPE: PRT
<213> ORGANISM: Artificial sequence
<220> FEATURE:
<223> OTHER INFORMATION: CPP

<400> SEQUENCE: 1100

Trp Arg Phe Lys Trp Arg Phe Lys
1               5

<210> SEQ ID NO 1101
<211> LENGTH: 12
<212> TYPE: PRT
<213> ORGANISM: Artificial sequence
<220> FEATURE:
<223> OTHER INFORMATION: CPP

<400> SEQUENCE: 1101

Trp Arg Phe Lys Trp Arg Phe Lys Trp Arg Phe Lys
1               5                   10

<210> SEQ ID NO 1102
<211> LENGTH: 36
<212> TYPE: PRT
<213> ORGANISM: Artificial sequence
<220> FEATURE:
<223> OTHER INFORMATION: CPP

<400> SEQUENCE: 1102

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
                20                  25                  30

Val Leu Lys Gln
            35

<210> SEQ ID NO 1103
<211> LENGTH: 36
<212> TYPE: PRT

```
<213> ORGANISM: Artificial sequence
<220> FEATURE:
<223> OTHER INFORMATION: CPP

<400> SEQUENCE: 1103

Arg Gly Ser Arg Arg Ala Val Thr Arg Ala Gln Arg Arg Asp Gly Arg
1               5                   10                  15
Arg Arg Arg Arg Ser Arg Arg Glu Ser Tyr Ser Val Tyr Val Tyr Arg
                20                  25                  30
Val Leu Arg Gln
            35

<210> SEQ ID NO 1104
<211> LENGTH: 15
<212> TYPE: PRT
<213> ORGANISM: Artificial sequence
<220> FEATURE:
<223> OTHER INFORMATION: CPP

<400> SEQUENCE: 1104

Arg Val Ile Arg Trp Phe Gln Asn Lys Arg Ser Lys Asp Lys Lys
1               5                   10                  15

<210> SEQ ID NO 1105
<211> LENGTH: 27
<212> TYPE: PRT
<213> ORGANISM: Artificial sequence
<220> FEATURE:
<223> OTHER INFORMATION: CPP

<400> SEQUENCE: 1105

Gly Trp Thr Leu Asn Ser Ala Gly Tyr Leu Leu Gly Lys Ile Asn Leu
1               5                   10                  15
Lys Ala Leu Ala Ala Leu Ala Lys Lys Ile Leu
                20                  25

<210> SEQ ID NO 1106
<211> LENGTH: 28
<212> TYPE: PRT
<213> ORGANISM: Artificial sequence
<220> FEATURE:
<223> OTHER INFORMATION: CPP

<400> SEQUENCE: 1106

Ala Ala Val Ala Leu Leu Pro Ala Val Leu Leu Ala Leu Leu Ala Pro
1               5                   10                  15
Arg Lys Lys Arg Arg Gln Arg Arg Arg Pro Pro Gln
                20                  25

<210> SEQ ID NO 1107
<211> LENGTH: 5
<212> TYPE: PRT
<213> ORGANISM: Artificial sequence
<220> FEATURE:
<223> OTHER INFORMATION: CPP

<400> SEQUENCE: 1107

Cys Trp Lys Lys Lys
1               5

<210> SEQ ID NO 1108
<211> LENGTH: 10
<212> TYPE: PRT
<213> ORGANISM: Artificial sequence
<220> FEATURE:
```

-continued

```
<223> OTHER INFORMATION: CPP

<400> SEQUENCE: 1108

Cys Trp Lys Lys Lys Lys Lys Lys Lys
1               5                   10

<210> SEQ ID NO 1109
<211> LENGTH: 15
<212> TYPE: PRT
<213> ORGANISM: Artificial sequence
<220> FEATURE:
<223> OTHER INFORMATION: CPP

<400> SEQUENCE: 1109

Cys Trp Lys Lys Lys Lys Lys Lys Lys Lys Lys Lys Lys Lys Lys
1               5                   10                  15

<210> SEQ ID NO 1110
<211> LENGTH: 20
<212> TYPE: PRT
<213> ORGANISM: Artificial sequence
<220> FEATURE:
<223> OTHER INFORMATION: CPP

<400> SEQUENCE: 1110

Cys Trp Lys Lys Lys Lys Lys Lys Lys Lys Lys Lys Lys Lys Lys Lys
1               5                   10                  15

Lys Lys Lys Lys
            20

<210> SEQ ID NO 1111
<211> LENGTH: 19
<212> TYPE: PRT
<213> ORGANISM: Artificial sequence
<220> FEATURE:
<223> OTHER INFORMATION: CPP

<400> SEQUENCE: 1111

Lys Lys Lys Lys Lys Lys Lys Lys Lys Lys Lys Lys Lys Lys Lys Lys
1               5                   10                  15

Lys Lys Lys

<210> SEQ ID NO 1112
<211> LENGTH: 19
<212> TYPE: PRT
<213> ORGANISM: Artificial sequence
<220> FEATURE:
<223> OTHER INFORMATION: CPP

<400> SEQUENCE: 1112

Lys Lys Trp Lys Met Arg Arg Gly Ala Gly Arg Arg Arg Arg Arg Arg
1               5                   10                  15

Arg Arg Arg

<210> SEQ ID NO 1113
<211> LENGTH: 12
<212> TYPE: PRT
<213> ORGANISM: Artificial sequence
<220> FEATURE:
<223> OTHER INFORMATION: CPP

<400> SEQUENCE: 1113

Ala Pro Trp His Leu Ser Ser Gln Tyr Ser Arg Thr
1               5                   10
```

```
<210> SEQ ID NO 1114
<211> LENGTH: 11
<212> TYPE: PRT
<213> ORGANISM: Artificial sequence
<220> FEATURE:
<223> OTHER INFORMATION: CPP

<400> SEQUENCE: 1114

Arg Arg Arg Arg Arg Arg Arg Arg Arg Arg Arg
1               5                   10

<210> SEQ ID NO 1115
<211> LENGTH: 20
<212> TYPE: PRT
<213> ORGANISM: Artificial sequence
<220> FEATURE:
<223> OTHER INFORMATION: CPP

<400> SEQUENCE: 1115

Lys Leu Ala Leu Lys Leu Ala Leu Lys Ala Leu Lys Ala Ala Leu Lys
1               5                   10                  15

Leu Ala Gly Cys
            20

<210> SEQ ID NO 1116
<211> LENGTH: 15
<212> TYPE: PRT
<213> ORGANISM: Artificial sequence
<220> FEATURE:
<223> OTHER INFORMATION: CPP

<400> SEQUENCE: 1116

Lys Leu Leu Lys Leu Leu Lys Leu Lys Ala Leu Lys Leu Gly Cys
1               5                   10                  15

<210> SEQ ID NO 1117
<211> LENGTH: 35
<212> TYPE: PRT
<213> ORGANISM: Artificial sequence
<220> FEATURE:
<223> OTHER INFORMATION: CPP

<400> SEQUENCE: 1117

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala
        35

<210> SEQ ID NO 1118
<211> LENGTH: 10
<212> TYPE: PRT
<213> ORGANISM: Artificial sequence
<220> FEATURE:
<223> OTHER INFORMATION: CPP

<400> SEQUENCE: 1118

Cys Arg Arg Arg Arg Arg Arg Arg Arg Arg
1               5                   10

<210> SEQ ID NO 1119
<211> LENGTH: 10
<212> TYPE: PRT
<213> ORGANISM: Artificial sequence
```

```
<220> FEATURE:
<223> OTHER INFORMATION: CPP

<400> SEQUENCE: 1119

Cys Lys Lys Lys Lys Lys Lys Lys Lys
1               5                   10

<210> SEQ ID NO 1120
<211> LENGTH: 27
<212> TYPE: PRT
<213> ORGANISM: Artificial sequence
<220> FEATURE:
<223> OTHER INFORMATION: CPP

<400> SEQUENCE: 1120

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1121
<211> LENGTH: 27
<212> TYPE: PRT
<213> ORGANISM: Artificial sequence
<220> FEATURE:
<223> OTHER INFORMATION: CPP

<400> SEQUENCE: 1121

Gly Trp Thr Leu Asn Ser Ala Gly Tyr Leu Leu Gly Lys Ile Asn Leu
1               5                   10                  15

Lys Ala Leu Ala Ala Leu Ala Lys Lys Leu Leu
            20                  25

<210> SEQ ID NO 1122
<211> LENGTH: 26
<212> TYPE: PRT
<213> ORGANISM: Artificial sequence
<220> FEATURE:
<223> OTHER INFORMATION: CPP

<400> SEQUENCE: 1122

Gly Trp Thr Leu Asn Ser Ala Gly Tyr Leu Leu Gly Lys Phe Leu Pro
1               5                   10                  15

Leu Ile Leu Arg Lys Ile Val Thr Ala Leu
            20                  25

<210> SEQ ID NO 1123
<211> LENGTH: 27
<212> TYPE: PRT
<213> ORGANISM: Artificial sequence
<220> FEATURE:
<223> OTHER INFORMATION: CPP

<400> SEQUENCE: 1123

Gly Trp Thr Leu Asn Pro Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1124
<211> LENGTH: 27
<212> TYPE: PRT
<213> ORGANISM: Artificial sequence
<220> FEATURE:
<223> OTHER INFORMATION: CPP
```

<400> SEQUENCE: 1124

Gly Trp Thr Leu Asn Pro Pro Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 1125
<211> LENGTH: 24
<212> TYPE: PRT
<213> ORGANISM: Artificial sequence
<220> FEATURE:
<223> OTHER INFORMATION: CPP

<400> SEQUENCE: 1125

Leu Asn Ser Ala Gly Tyr Leu Leu Gly Lys Ile Asn Leu Lys Ala Leu
1               5                   10                  15

Ala Ala Leu Ala Lys Lys Ile Leu
            20

<210> SEQ ID NO 1126
<211> LENGTH: 18
<212> TYPE: PRT
<213> ORGANISM: Artificial sequence
<220> FEATURE:
<223> OTHER INFORMATION: CPP

<400> SEQUENCE: 1126

Leu Leu Gly Lys Ile Asn Leu Lys Ala Leu Ala Ala Leu Ala Lys Lys
1               5                   10                  15

Ile Leu

<210> SEQ ID NO 1127
<211> LENGTH: 25
<212> TYPE: PRT
<213> ORGANISM: Artificial sequence
<220> FEATURE:
<223> OTHER INFORMATION: CPP

<400> SEQUENCE: 1127

Gly Trp Thr Leu Asn Ser Ala Gly Tyr Leu Leu Gly Lys Leu Lys Ala
1               5                   10                  15

Leu Ala Ala Leu Ala Lys Lys Ile Leu
            20                  25

<210> SEQ ID NO 1128
<211> LENGTH: 21
<212> TYPE: PRT
<213> ORGANISM: Artificial sequence
<220> FEATURE:
<223> OTHER INFORMATION: CPP

<400> SEQUENCE: 1128

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 1129
<211> LENGTH: 21
<212> TYPE: PRT
<213> ORGANISM: Artificial sequence
<220> FEATURE:
<223> OTHER INFORMATION: CPP

<400> SEQUENCE: 1129

Gly Trp Thr Leu Asn Ser Lys Ile Asn Leu Lys Ala Leu Ala Ala Leu
1               5                   10                  15

Ala Lys Lys Ile Leu
            20

<210> SEQ ID NO 1130
<211> LENGTH: 21
<212> TYPE: PRT
<213> ORGANISM: Artificial sequence
<220> FEATURE:
<223> OTHER INFORMATION: CPP

<400> SEQUENCE: 1130

Leu Asn Ser Ala Gly Tyr Leu Leu Gly Lys Leu Lys Ala Leu Ala Ala
1               5                   10                  15

Leu Ala Lys Ile Leu
            20

<210> SEQ ID NO 1131
<211> LENGTH: 20
<212> TYPE: PRT
<213> ORGANISM: Artificial sequence
<220> FEATURE:
<223> OTHER INFORMATION: CPP

<400> SEQUENCE: 1131

Leu Asn Ser Ala Gly Tyr Leu Leu Gly Lys Ala Leu Ala Ala Leu Ala
1               5                   10                  15

Lys Lys Ile Leu
            20

<210> SEQ ID NO 1132
<211> LENGTH: 19
<212> TYPE: PRT
<213> ORGANISM: Artificial sequence
<220> FEATURE:
<223> OTHER INFORMATION: CPP

<400> SEQUENCE: 1132

Ala Gly Tyr Leu Leu Gly Lys Leu Lys Ala Leu Ala Ala Leu Ala Lys
1               5                   10                  15

Lys Ile Leu

<210> SEQ ID NO 1133
<211> LENGTH: 19
<212> TYPE: PRT
<213> ORGANISM: Artificial sequence
<220> FEATURE:
<223> OTHER INFORMATION: CPP

<400> SEQUENCE: 1133

Leu Asn Ser Ala Gly Tyr Leu Leu Gly Lys Leu Lys Ala Leu Ala Ala
1               5                   10                  15

Leu Ala Lys

<210> SEQ ID NO 1134
<211> LENGTH: 27
<212> TYPE: PRT
<213> ORGANISM: Artificial sequence
<220> FEATURE:
<223> OTHER INFORMATION: CPP

<400> SEQUENCE: 1134

Gly Trp Thr Leu Asn Ser Ala Gly Tyr Leu Leu Gly Lys Ile Asn Leu
1               5                   10                  15

Lys Ala Pro Ala Ala Leu Ala Lys Lys Ile Leu
            20                  25

<210> SEQ ID NO 1135
<211> LENGTH: 21
<212> TYPE: PRT
<213> ORGANISM: Artificial sequence
<220> FEATURE:
<223> OTHER INFORMATION: CPP

<400> SEQUENCE: 1135

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 1136
<211> LENGTH: 21
<212> TYPE: PRT
<213> ORGANISM: Artificial sequence
<220> FEATURE:
<223> OTHER INFORMATION: CPP

<400> SEQUENCE: 1136

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 1137
<211> LENGTH: 21
<212> TYPE: PRT
<213> ORGANISM: Artificial sequence
<220> FEATURE:
<223> OTHER INFORMATION: CPP

<400> SEQUENCE: 1137

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 1138
<211> LENGTH: 15
<212> TYPE: PRT
<213> ORGANISM: Artificial sequence
<220> FEATURE:
<223> OTHER INFORMATION: CPP

<400> SEQUENCE: 1138

Lys Trp Phe Glu Thr Trp Phe Thr Glu Trp Pro Lys Lys Arg Lys
1               5                   10                  15

<210> SEQ ID NO 1139
<211> LENGTH: 27
<212> TYPE: PRT
<213> ORGANISM: Artificial sequence
<220> FEATURE:
<223> OTHER INFORMATION: CPP

<400> SEQUENCE: 1139

-continued

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 1140
<211> LENGTH: 27
<212> TYPE: PRT
<213> ORGANISM: Artificial sequence
<220> FEATURE:
<223> OTHER INFORMATION: CPP

<400> SEQUENCE: 1140

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 1141
<211> LENGTH: 20
<212> TYPE: PRT
<213> ORGANISM: Artificial sequence
<220> FEATURE:
<223> OTHER INFORMATION: CPP

<400> SEQUENCE: 1141

Ala Leu Trp Lys Thr Leu Leu Lys Lys Val Leu Lys Ala Pro Lys Lys
1               5                   10                  15

Lys Arg Lys Val
            20

<210> SEQ ID NO 1142
<211> LENGTH: 20
<212> TYPE: PRT
<213> ORGANISM: Artificial sequence
<220> FEATURE:
<223> OTHER INFORMATION: CPP

<400> SEQUENCE: 1142

Pro Lys Lys Lys Arg Lys Val Ala Leu Trp Lys Thr Leu Leu Lys Lys
1               5                   10                  15

Val Leu Lys Ala
            20

<210> SEQ ID NO 1143
<211> LENGTH: 20
<212> TYPE: PRT
<213> ORGANISM: Artificial sequence
<220> FEATURE:
<223> OTHER INFORMATION: CPP

<400> SEQUENCE: 1143

Val Lys Arg Lys Lys Lys Pro Ala Leu Trp Lys Thr Leu Leu Lys Lys
1               5                   10                  15

Val Leu Lys Ala
            20

<210> SEQ ID NO 1144
<211> LENGTH: 22
<212> TYPE: PRT
<213> ORGANISM: Artificial sequence
<220> FEATURE:
<223> OTHER INFORMATION: CPP

<400> SEQUENCE: 1144

```
Arg Gln Ala Arg Arg Asn Arg Arg Ala Leu Trp Lys Thr Leu Leu
1               5                   10                  15

Lys Lys Val Leu Lys Ala
            20

<210> SEQ ID NO 1145
<211> LENGTH: 13
<212> TYPE: PRT
<213> ORGANISM: Artificial sequence
<220> FEATURE:
<223> OTHER INFORMATION: CPP

<400> SEQUENCE: 1145

Glu Glu Glu Ala Ala Gly Arg Lys Arg Lys Lys Arg Thr
1               5                   10

<210> SEQ ID NO 1146
<211> LENGTH: 13
<212> TYPE: PRT
<213> ORGANISM: Artificial sequence
<220> FEATURE:
<223> OTHER INFORMATION: CPP

<400> SEQUENCE: 1146

Phe Phe Phe Ala Ala Gly Arg Lys Arg Lys Lys Arg Thr
1               5                   10

<210> SEQ ID NO 1147
<211> LENGTH: 13
<212> TYPE: PRT
<213> ORGANISM: Artificial sequence
<220> FEATURE:
<223> OTHER INFORMATION: CPP

<400> SEQUENCE: 1147

Asn Asn Asn Ala Ala Gly Arg Lys Arg Lys Lys Arg Thr
1               5                   10

<210> SEQ ID NO 1148
<211> LENGTH: 13
<212> TYPE: PRT
<213> ORGANISM: Artificial sequence
<220> FEATURE:
<223> OTHER INFORMATION: CPP

<400> SEQUENCE: 1148

Tyr Tyr Tyr Ala Ala Gly Arg Lys Arg Lys Lys Arg Thr
1               5                   10

<210> SEQ ID NO 1149
<211> LENGTH: 21
<212> TYPE: PRT
<213> ORGANISM: Artificial sequence
<220> FEATURE:
<223> OTHER INFORMATION: CPP

<400> SEQUENCE: 1149

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 1150
<211> LENGTH: 27
<212> TYPE: PRT
```

```
<213> ORGANISM: Artificial sequence
<220> FEATURE:
<223> OTHER INFORMATION: CPP

<400> SEQUENCE: 1150

Gly Ala Leu Phe Leu Gly Phe Leu Gly Ala Ala Gly Ser Thr Met Gly
1               5                   10                  15

Ala Trp Ser Gln Pro Lys Lys Arg Lys Val
            20                  25

<210> SEQ ID NO 1151
<211> LENGTH: 27
<212> TYPE: PRT
<213> ORGANISM: Artificial sequence
<220> FEATURE:
<223> OTHER INFORMATION: CPP

<400> SEQUENCE: 1151

Gly Ala Leu Phe Leu Ala Phe Leu Ala Ala Ala Leu Ser Leu Met Gly
1               5                   10                  15

Leu Trp Ser Gln Pro Lys Lys Arg Arg Val
            20                  25

<210> SEQ ID NO 1152
<211> LENGTH: 27
<212> TYPE: PRT
<213> ORGANISM: Artificial sequence
<220> FEATURE:
<223> OTHER INFORMATION: CPP

<400> SEQUENCE: 1152

Gly Leu Leu Glu Ala Leu Ala Glu Leu Leu Glu Gly Leu Arg Lys Arg
1               5                   10                  15

Leu Arg Lys Phe Arg Asn Lys Ile Lys Glu Lys
            20                  25

<210> SEQ ID NO 1153
<211> LENGTH: 41
<212> TYPE: PRT
<213> ORGANISM: Artificial sequence
<220> FEATURE:
<223> OTHER INFORMATION: CPP

<400> SEQUENCE: 1153

Ala Ala Val Ala Leu Leu Pro Ala Val Leu Leu Ala Leu Leu Ala Pro
1               5                   10                  15

Glu Ile Leu Leu Pro Asn Asn Tyr Asn Ala Tyr Glu Ser Tyr Lys Tyr
            20                  25                  30

Pro Gly Met Phe Ile Ala Leu Ser Lys
        35                  40

<210> SEQ ID NO 1154
<211> LENGTH: 26
<212> TYPE: PRT
<213> ORGANISM: Artificial sequence
<220> FEATURE:
<223> OTHER INFORMATION: CPP

<400> SEQUENCE: 1154

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25
```

```
<210> SEQ ID NO 1155
<211> LENGTH: 27
<212> TYPE: PRT
<213> ORGANISM: Artificial sequence
<220> FEATURE:
<223> OTHER INFORMATION: CPP

<400> SEQUENCE: 1155

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 1156
<211> LENGTH: 23
<212> TYPE: PRT
<213> ORGANISM: Artificial sequence
<220> FEATURE:
<223> OTHER INFORMATION: CPP

<400> SEQUENCE: 1156

Met Gly Leu Gly Leu His Leu Leu Val Leu Ala Ala Ala Leu Gln Gly
1               5                   10                  15

Ala Lys Lys Lys Arg Lys Val
            20

<210> SEQ ID NO 1157
<211> LENGTH: 26
<212> TYPE: PRT
<213> ORGANISM: Artificial sequence
<220> FEATURE:
<223> OTHER INFORMATION: CPP

<400> SEQUENCE: 1157

Ala Ala Val Ala Leu Leu Pro Ala Val Leu Leu Ala Leu Leu Ala Lys
1               5                   10                  15

Lys Asn Asn Leu Lys Asp Cys Gly Leu Phe
            20                  25

<210> SEQ ID NO 1158
<211> LENGTH: 26
<212> TYPE: PRT
<213> ORGANISM: Artificial sequence
<220> FEATURE:
<223> OTHER INFORMATION: CPP

<400> SEQUENCE: 1158

Ala Ala Val Ala Leu Leu Pro Ala Val Leu Leu Ala Leu Leu Ala Lys
1               5                   10                  15

Lys Asn Asn Leu Lys Glu Cys Gly Leu Tyr
            20                  25

<210> SEQ ID NO 1159
<211> LENGTH: 43
<212> TYPE: PRT
<213> ORGANISM: Artificial sequence
<220> FEATURE:
<223> OTHER INFORMATION: CPP

<400> SEQUENCE: 1159

Ala Ala Val Ala Leu Leu Pro Ala Val Leu Leu Ala Leu Leu Ala Val
1               5                   10                  15

Thr Asp Gln Leu Gly Glu Asp Phe Phe Ala Val Asp Leu Glu Ala Phe
            20                  25                  30
```

Leu Gln Glu Phe Gly Leu Leu Pro Glu Lys Glu
          35                  40

<210> SEQ ID NO 1160
<211> LENGTH: 21
<212> TYPE: PRT
<213> ORGANISM: Artificial sequence
<220> FEATURE:
<223> OTHER INFORMATION: CPP

<400> SEQUENCE: 1160

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 1161
<211> LENGTH: 38
<212> TYPE: PRT
<213> ORGANISM: Artificial sequence
<220> FEATURE:
<223> OTHER INFORMATION: CPP

<400> SEQUENCE: 1161

Ala Gly Tyr Leu Leu Gly Lys Ile Asn Leu Lys Ala Leu Ala Ala Leu
1               5                   10                  15

Ala Lys Lys Ile Leu Thr Tyr Ala Asp Phe Ile Ala Ser Gly Arg Thr
            20                  25                  30

Gly Arg Arg Asn Ala Ile
        35

<210> SEQ ID NO 1162
<211> LENGTH: 28
<212> TYPE: PRT
<213> ORGANISM: Artificial sequence
<220> FEATURE:
<223> OTHER INFORMATION: CPP

<400> SEQUENCE: 1162

Arg Arg Arg Arg Arg Arg Arg Arg Arg Arg Thr Tyr Ala Asp Phe
1               5                   10                  15

Ile Ala Ser Gly Arg Thr Gly Arg Arg Asn Ala Ile
            20                  25

<210> SEQ ID NO 1163
<211> LENGTH: 4
<212> TYPE: PRT
<213> ORGANISM: Artificial sequence
<220> FEATURE:
<223> OTHER INFORMATION: NLS

<400> SEQUENCE: 1163

Arg Lys Arg His
1

<210> SEQ ID NO 1164
<211> LENGTH: 7
<212> TYPE: PRT
<213> ORGANISM: Artificial sequence
<220> FEATURE:
<223> OTHER INFORMATION: SV40 large T antigen NLS

<400> SEQUENCE: 1164

Pro Lys Lys Lys Arg Lys Val

```
<210> SEQ ID NO 1165
<211> LENGTH: 16
<212> TYPE: PRT
<213> ORGANISM: Artificial sequence
<220> FEATURE:
<223> OTHER INFORMATION: Nucleoplasmin NLS

<400> SEQUENCE: 1165

Lys Arg Pro Ala Ala Thr Lys Lys Ala Gly Gln Ala Lys Lys Lys Lys
1               5                   10                  15

<210> SEQ ID NO 1166
<211> LENGTH: 4
<212> TYPE: PRT
<213> ORGANISM: Artificial sequence
<220> FEATURE:
<223> OTHER INFORMATION: NLS consensus sequence
<220> FEATURE:
<221> NAME/KEY: variant
<222> LOCATION: (2)..(2)
<223> OTHER INFORMATION: /REPLACE= "Arg" or "Lys"
<220> FEATURE:
<221> NAME/KEY: variant
<222> LOCATION: (3)..(3)
<223> OTHER INFORMATION: /REPLACE= any amino acid
<220> FEATURE:
<221> NAME/KEY: variant
<222> LOCATION: (4)..(4)
<223> OTHER INFORMATION: /REPLACE= "Arg" or "Lys"

<400> SEQUENCE: 1166

Lys Xaa Xaa Xaa
1

<210> SEQ ID NO 1167
<211> LENGTH: 7
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (3)..(3)
<223> OTHER INFORMATION: /REPLACE= any amino acid
<220> FEATURE:
<221> NAME/KEY: repeat
<222> LOCATION: (3)..(3)
<223> OTHER INFORMATION: X can be 5 to 20 residues

<400> SEQUENCE: 1167

Lys Arg Xaa Lys Lys Lys Lys
1               5

<210> SEQ ID NO 1168
<211> LENGTH: 16
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (3)..(12)
<223> OTHER INFORMATION: /REPLACE= any amino acid

<400> SEQUENCE: 1168

Lys Arg Xaa Xaa Xaa Xaa Xaa Xaa Xaa Xaa Xaa Xaa Lys Lys Lys Lys
1               5                   10                  15
```

```
<210> SEQ ID NO 1169
<211> LENGTH: 7
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (5)..(5)
<223> OTHER INFORMATION: /REPLACE= any amino acid
<220> FEATURE:
<221> NAME/KEY: repeat
<222> LOCATION: (5)..(5)
<223> OTHER INFORMATION: 2 to 10
<220> FEATURE:
<221> NAME/KEY: repeat
<222> LOCATION: (5)..(5)
<223> OTHER INFORMATION: X can be 2 to 10 residues

<400> SEQUENCE: 1169

Arg Lys Arg His Xaa Lys Lys
1               5

<210> SEQ ID NO 1170
<211> LENGTH: 8
<212> TYPE: PRT
<213> ORGANISM: Artificial sequence
<220> FEATURE:
<223> OTHER INFORMATION: NLS variant
<220> FEATURE:
<221> NAME/KEY: variant
<222> LOCATION: (5)..(6)
<223> OTHER INFORMATION: /REPLACE= any amino acid

<400> SEQUENCE: 1170

Arg Lys Arg His Xaa Xaa Lys Lys
1               5

<210> SEQ ID NO 1171
<211> LENGTH: 8
<212> TYPE: PRT
<213> ORGANISM: Artificial sequence
<220> FEATURE:
<223> OTHER INFORMATION: NLS variant

<400> SEQUENCE: 1171

Arg Lys Arg His Ile Ile Lys Lys
1               5

<210> SEQ ID NO 1172
<211> LENGTH: 9
<212> TYPE: PRT
<213> ORGANISM: Artificial sequence
<220> FEATURE:
<223> OTHER INFORMATION: Oncoprotein c-myc NLS

<400> SEQUENCE: 1172

Pro Ala Ala Lys Arg Val Lys Leu Asp
1               5

<210> SEQ ID NO 1173
<211> LENGTH: 4
<212> TYPE: PRT
<213> ORGANISM: Artificial sequence
<220> FEATURE:
<223> OTHER INFORMATION: NLS cluster of basic amino acids

<400> SEQUENCE: 1173

Lys Lys Lys Lys
1
```

```
<210> SEQ ID NO 1174
<211> LENGTH: 8
<212> TYPE: PRT
<213> ORGANISM: Artificial sequence
<220> FEATURE:
<223> OTHER INFORMATION: NLS variant

<400> SEQUENCE: 1174

Pro Ala Ala Lys Lys Lys Leu Asp
1               5

<210> SEQ ID NO 1175
<211> LENGTH: 8
<212> TYPE: PRT
<213> ORGANISM: Artificial sequence
<220> FEATURE:
<223> OTHER INFORMATION: NLS variant

<400> SEQUENCE: 1175

Pro Lys Lys Lys Arg Lys Val Leu
1               5

<210> SEQ ID NO 1176
<211> LENGTH: 5
<212> TYPE: PRT
<213> ORGANISM: Artificial sequence
<220> FEATURE:
<223> OTHER INFORMATION: NLS variant

<400> SEQUENCE: 1176

Lys Lys Lys Arg Lys
1               5

<210> SEQ ID NO 1177
<211> LENGTH: 6
<212> TYPE: PRT
<213> ORGANISM: Artificial sequence
<220> FEATURE:
<223> OTHER INFORMATION: NLS variant

<400> SEQUENCE: 1177

Lys Lys Lys Arg Val Lys
1               5

<210> SEQ ID NO 1178
<211> LENGTH: 7
<212> TYPE: PRT
<213> ORGANISM: Artificial sequence
<220> FEATURE:
<223> OTHER INFORMATION: NLS variant

<400> SEQUENCE: 1178

Lys Lys Lys Arg Lys Val Leu
1               5

<210> SEQ ID NO 1179
<211> LENGTH: 7
<212> TYPE: PRT
<213> ORGANISM: Artificial sequence
<220> FEATURE:
<223> OTHER INFORMATION: NLS variant

<400> SEQUENCE: 1179

Arg Lys Lys Arg Lys Val Leu
1               5
```

<210> SEQ ID NO 1180
<211> LENGTH: 5
<212> TYPE: PRT
<213> ORGANISM: Artificial Sequence
<220> FEATURE:
<223> OTHER INFORMATION: Linker

<400> SEQUENCE: 1180

Ile Ile Leu Val Ile
1               5

<210> SEQ ID NO 1181
<211> LENGTH: 7
<212> TYPE: PRT
<213> ORGANISM: Artificial sequence
<220> FEATURE:
<223> OTHER INFORMATION: Linker

<400> SEQUENCE: 1181

Ile Ile Leu Val Ile Ile Ile
1               5

<210> SEQ ID NO 1182
<211> LENGTH: 26
<212> TYPE: PRT
<213> ORGANISM: Artificial Sequence
<220> FEATURE:
<223> OTHER INFORMATION: APIM Oligopeptidic compound

<400> SEQUENCE: 1182

Met Asp Arg Phe Phe Leu Val Lys Trp Lys Lys Lys Arg Lys Ile Arg
1               5                   10                  15

Arg Arg Arg Arg Arg Arg Arg Arg Arg Arg
            20                  25

<210> SEQ ID NO 1183
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1183

Met Asp Arg Phe Tyr Leu Val Lys Trp Lys Lys Lys Arg Lys Ile Arg
1               5                   10                  15

Arg Arg Arg Arg Arg Arg Arg Arg Arg Arg
            20                  25

<210> SEQ ID NO 1184
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1184

Met Asp Arg Trp Tyr Leu Val Lys Trp Lys Lys Lys Arg Lys Ile Arg
1               5                   10                  15

Arg Arg Arg Arg Arg Arg Arg Arg Arg Arg
            20                  25

<210> SEQ ID NO 1185
<211> LENGTH: 26
<212> TYPE: PRT
<213> ORGANISM: Artificial sequence

```
<220> FEATURE:
<223> OTHER INFORMATION: APIM Oligopeptidic compound

<400> SEQUENCE: 1185

Met Asp Arg Phe Val Leu Val Lys Trp Lys Lys Lys Arg Lys Ile Arg
1               5                   10                  15

Arg Arg Arg Arg Arg Arg Arg Arg Arg Arg
            20                  25

<210> SEQ ID NO 1186
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1186

Met Asp Arg Phe Ile Leu Val Lys Trp Lys Lys Lys Arg Lys Ile Arg
1               5                   10                  15

Arg Arg Arg Arg Arg Arg Arg Arg Arg Arg
            20                  25

<210> SEQ ID NO 1187
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1187

Met Asp Arg Phe Leu Leu Val Lys Trp Lys Lys Lys Arg Lys Ile Arg
1               5                   10                  15

Arg Arg Arg Arg Arg Arg Arg Arg Arg Arg
            20                  25

<210> SEQ ID NO 1188
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1188

Met Asp Arg Trp Phe Leu Val Lys Trp Lys Lys Lys Arg Lys Ile Arg
1               5                   10                  15

Arg Arg Arg Arg Arg Arg Arg Arg Arg Arg
            20                  25

<210> SEQ ID NO 1189
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1189

Met Asp Arg Phe Trp Leu Val Lys Trp Lys Lys Lys Arg Lys Ile Arg
1               5                   10                  15

Arg Arg Arg Arg Arg Arg Arg Arg Arg Arg
            20                  25

<210> SEQ ID NO 1190
<211> LENGTH: 26
<212> TYPE: PRT
```

-continued

```
<213> ORGANISM: Artificial sequence
<220> FEATURE:
<223> OTHER INFORMATION: APIM Oligopeptidic compound

<400> SEQUENCE: 1190

Met Asp Arg Phe Met Leu Val Lys Trp Lys Lys Lys Arg Lys Ile Arg
1               5                   10                  15
Arg Arg Arg Arg Arg Arg Arg Arg Arg Arg
            20                  25

<210> SEQ ID NO 1191
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1191

Met Asp Arg Trp Ile Leu Val Lys Trp Lys Lys Lys Arg Lys Ile Arg
1               5                   10                  15
Arg Arg Arg Arg Arg Arg Arg Arg Arg Arg
            20                  25

<210> SEQ ID NO 1192
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1192

Met Asp Arg Trp Leu Leu Val Lys Trp Lys Lys Lys Arg Lys Ile Arg
1               5                   10                  15
Arg Arg Arg Arg Arg Arg Arg Arg Arg Arg
            20                  25

<210> SEQ ID NO 1193
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1193

Met Asp Arg Trp Val Leu Val Lys Trp Lys Lys Lys Arg Lys Ile Arg
1               5                   10                  15
Arg Arg Arg Arg Arg Arg Arg Arg Arg Arg
            20                  25

<210> SEQ ID NO 1194
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1194

Met Asp Arg Trp Met Leu Val Lys Trp Lys Lys Lys Arg Lys Ile Arg
1               5                   10                  15
Arg Arg Arg Arg Arg Arg Arg Arg Arg Arg
            20                  25

<210> SEQ ID NO 1195
<211> LENGTH: 26
```

<212> TYPE: PRT
<213> ORGANISM: Artificial sequence
<220> FEATURE:
<223> OTHER INFORMATION: APIM Oligopeptidic compound

<400> SEQUENCE: 1195

Met Asp Arg Tyr Phe Leu Val Lys Trp Lys Lys Lys Arg Lys Ile Arg
1               5                   10                  15

Arg Arg Arg Arg Arg Arg Arg Arg Arg
            20                  25

<210> SEQ ID NO 1196
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1196

Met Asp Arg Tyr Ile Leu Val Lys Trp Lys Lys Lys Arg Lys Ile Arg
1               5                   10                  15

Arg Arg Arg Arg Arg Arg Arg Arg Arg
            20                  25

<210> SEQ ID NO 1197
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1197

Met Asp Arg Tyr Leu Leu Val Lys Trp Lys Lys Lys Arg Lys Ile Arg
1               5                   10                  15

Arg Arg Arg Arg Arg Arg Arg Arg Arg
            20                  25

<210> SEQ ID NO 1198
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1198

Met Asp Arg Tyr Val Leu Val Lys Trp Lys Lys Lys Arg Lys Ile Arg
1               5                   10                  15

Arg Arg Arg Arg Arg Arg Arg Arg Arg
            20                  25

<210> SEQ ID NO 1199
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1199

Met Asp Arg Tyr Met Leu Val Lys Trp Lys Lys Lys Arg Lys Ile Arg
1               5                   10                  15

Arg Arg Arg Arg Arg Arg Arg Arg Arg
            20                  25

<210> SEQ ID NO 1200

-continued

```
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1200

Met Asp Arg Tyr Tyr Leu Val Lys Trp Lys Lys Lys Arg Lys Ile Arg
1               5                   10                  15
Arg Arg Arg Arg Arg Arg Arg Arg Arg Arg
            20                  25

<210> SEQ ID NO 1201
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1201

Met Asp Arg Tyr Trp Leu Val Lys Trp Lys Lys Lys Arg Lys Ile Arg
1               5                   10                  15
Arg Arg Arg Arg Arg Arg Arg Arg Arg Arg
            20                  25

<210> SEQ ID NO 1202
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1202

Met Asp Arg Trp Leu Val Ile Lys Trp Lys Lys Lys Arg Lys Ile Arg
1               5                   10                  15
Arg Arg Arg Arg Arg Arg Arg Arg Arg Arg
            20                  25

<210> SEQ ID NO 1203
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1203

Met Asp Arg Trp Phe Val Ile Lys Trp Lys Lys Lys Arg Lys Ile Arg
1               5                   10                  15
Arg Arg Arg Arg Arg Arg Arg Arg Arg Arg
            20                  25

<210> SEQ ID NO 1204
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1204

Met Asp Arg Trp Tyr Val Ile Lys Trp Lys Lys Lys Arg Lys Ile Arg
1               5                   10                  15
Arg Arg Arg Arg Arg Arg Arg Arg Arg Arg
            20                  25
```

```
<210> SEQ ID NO 1205
<211> LENGTH: 8
<212> TYPE: PRT
<213> ORGANISM: Artificial sequence
<220> FEATURE:
<223> OTHER INFORMATION: PIP-box
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: variant
<222> LOCATION: (4)..(4)
<223> OTHER INFORMATION: /REPLACE: "Leu" or "Ile" or "Met"
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: variant
<222> LOCATION: (7)..(7)
<223> OTHER INFORMATION: /REPLACE: "Phe" or "Asp"
<220> FEATURE:
<221> NAME/KEY: variant
<222> LOCATION: (8)..(8)
<223> OTHER INFORMATION: /REPLACE: "Phe" or "Tyr"

<400> SEQUENCE: 1205

Gln Xaa Xaa Xaa Xaa Xaa Xaa Xaa
1               5

<210> SEQ ID NO 1206
<211> LENGTH: 25
<212> TYPE: PRT
<213> ORGANISM: Artificial sequence
<220> FEATURE:
<223> OTHER INFORMATION: APIM negative control peptide

<400> SEQUENCE: 1206

Met Asp Arg Ala Leu Val Lys Trp Lys Lys Arg Lys Ile Arg Arg
1               5                   10                  15

Arg Arg Arg Arg Arg Arg Arg Arg Arg
            20                  25

<210> SEQ ID NO 1207
<211> LENGTH: 6
<212> TYPE: PRT
<213> ORGANISM: Artificial sequence
<220> FEATURE:
<223> OTHER INFORMATION: APIM negative control motif
<220> FEATURE:
<221> NAME/KEY: VARIANT
<222> LOCATION: (3)..(3)
<223> OTHER INFORMATION: X is W, Y, F, L, I, V or M

<400> SEQUENCE: 1207

Arg Phe Xaa Ser Leu Lys
1               5

<210> SEQ ID NO 1208
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1208

Met Asp Arg Trp Ile Val Ile Lys Trp Lys Lys Arg Lys Ile Arg
1               5                   10                  15

Arg Arg Arg Arg Arg Arg Arg Arg Arg Arg
```

```
            20              25

<210> SEQ ID NO 1209
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: VARIANT
<222> LOCATION: (3)..(3)
<223> OTHER INFORMATION: X is W, F, Y, L, I, V or M

<400> SEQUENCE: 1209

Arg Trp Xaa Leu Val Pro
1               5

<210> SEQ ID NO 1210
<211> LENGTH: 22
<212> TYPE: PRT
<213> ORGANISM: Artificial sequence
<220> FEATURE:
<223> OTHER INFORMATION: R41
<220> FEATURE:
<221> NAME/KEY: MISC_FEATURE
<222> LOCATION: (22)..(22)
<223> OTHER INFORMATION: Amide

<400> SEQUENCE: 1210

Phe Ile Leu Phe Ile Leu Phe Ile Leu Gly Gly Lys His Lys His Lys
1               5                   10                  15

His Lys His Lys His Lys
            20

<210> SEQ ID NO 1211
<211> LENGTH: 22
<212> TYPE: PRT
<213> ORGANISM: Artificial sequence
<220> FEATURE:
<223> OTHER INFORMATION: R8
<220> FEATURE:
<221> NAME/KEY: MISC_FEATURE
<222> LOCATION: (22)..(22)
<223> OTHER INFORMATION: Amide

<400> SEQUENCE: 1211

Gly Pro Pro Arg Phe Pro Pro Arg Phe Pro Pro Arg Phe Pro Pro Arg
1               5                   10                  15

Phe Pro Pro Arg Phe Pro
            20

<210> SEQ ID NO 1212
<211> LENGTH: 22
<212> TYPE: PRT
<213> ORGANISM: Artificial sequence
<220> FEATURE:
<223> OTHER INFORMATION: M918
<220> FEATURE:
<221> NAME/KEY: MISC_FEATURE
<222> LOCATION: (22)..(22)
<223> OTHER INFORMATION: amide

<400> SEQUENCE: 1212

Met Val Thr Val Leu Phe Arg Arg Leu Arg Ile Arg Arg Ala Ser Gly
1               5                   10                  15

Pro Pro Arg Val Arg Val
            20
```

```
<210> SEQ ID NO 1213
<211> LENGTH: 17
<212> TYPE: PRT
<213> ORGANISM: Artificial sequence
<220> FEATURE:
<223> OTHER INFORMATION: YTA-4
<220> FEATURE:
<221> NAME/KEY: MISC_FEATURE
<222> LOCATION: (1)..(1)
<223> OTHER INFORMATION: Acetyl
<220> FEATURE:
<221> NAME/KEY: MISC_FEATURE
<222> LOCATION: (17)..(17)
<223> OTHER INFORMATION: amide

<400> SEQUENCE: 1213

Ile Ala Trp Val Lys Ala Phe Ile Arg Lys Leu Arg Lys Gly Pro Leu
1               5                   10                  15

Gly

<210> SEQ ID NO 1214
<211> LENGTH: 8
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(8)
<223> OTHER INFORMATION: cyclic
<220> FEATURE:
<221> NAME/KEY: MISC_FEATURE
<222> LOCATION: (1)..(8)
<223> OTHER INFORMATION: may be cyclic

<400> SEQUENCE: 1214

Arg Arg Arg Arg Trp Trp Trp Trp
1               5

<210> SEQ ID NO 1215
<211> LENGTH: 7
<212> TYPE: PRT
<213> ORGANISM: Artificial sequence
<220> FEATURE:
<223> OTHER INFORMATION: Cyclic CPP
<220> FEATURE:
<221> NAME/KEY: MISC_FEATURE
<222> LOCATION: (1)..(7)
<223> OTHER INFORMATION: may be cyclic

<400> SEQUENCE: 1215

Arg Arg Arg Arg Trp Trp Trp
1               5

<210> SEQ ID NO 1216
<211> LENGTH: 8
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(8)
<223> OTHER INFORMATION: cyclic

<400> SEQUENCE: 1216

Glu Glu Glu Glu Trp Trp Trp Trp
1               5
```

```
<210> SEQ ID NO 1217
<211> LENGTH: 7
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(7)
<223> OTHER INFORMATION: cyclic

<400> SEQUENCE: 1217

Glu Glu Glu Glu Trp Trp Trp
1               5

<210> SEQ ID NO 1218
<211> LENGTH: 6
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(1)
<223> OTHER INFORMATION: may comprise a fatty acyl group containing at
      least 8 carbons
<220> FEATURE:
<221> NAME/KEY: MISC_FEATURE
<222> LOCATION: (1)..(6)
<223> OTHER INFORMATION: may be cyclic

<400> SEQUENCE: 1218

Lys Arg Arg Arg Arg Arg
1               5

<210> SEQ ID NO 1219
<211> LENGTH: 7
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(1)
<223> OTHER INFORMATION: may comprise a fatty acyl group containing at
      least 8 carbons
<220> FEATURE:
<221> NAME/KEY: MISC_FEATURE
<222> LOCATION: (1)..(7)
<223> OTHER INFORMATION: cyclic

<400> SEQUENCE: 1219

Lys Arg Arg Arg Arg Arg Arg
1               5

<210> SEQ ID NO 1220
<211> LENGTH: 10
<212> TYPE: PRT
<213> ORGANISM: Artificial sequence
<220> FEATURE:
<223> OTHER INFORMATION: cyclic CPP
<220> FEATURE:
<221> NAME/KEY: MISC_FEATURE
<222> LOCATION: (1)..(10)
<223> OTHER INFORMATION: cyclic
<220> FEATURE:
<221> NAME/KEY: MISC_FEATURE
<222> LOCATION: (1)..(1)
<223> OTHER INFORMATION: N-acetyl

<400> SEQUENCE: 1220

Trp Trp Trp Trp Lys Arg Arg Arg Arg Arg
```

-continued

```
1               5               10
```

```
<210> SEQ ID NO 1221
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is L, I or V
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, I, V, A, S or T
<220> FEATURE:
<221> NAME/KEY: variant
<222> LOCATION: (6)..(6)
<223> OTHER INFORMATION: X is R or K

<400> SEQUENCE: 1221

Xaa Xaa Xaa Xaa Xaa Xaa
1               5

<210> SEQ ID NO 1222
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I or V
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, V, A, M, S or T
<220> FEATURE:
<221> NAME/KEY: variant
<222> LOCATION: (6)..(6)
<223> OTHER INFORMATION: X is R or K

<400> SEQUENCE: 1222

Arg Xaa Xaa Xaa Xaa Xaa
1               5

<210> SEQ ID NO 1223
<211> LENGTH: 6
<212> TYPE: PRT
<213> ORGANISM: Artificial sequence
<220> FEATURE:
<223> OTHER INFORMATION: APIM variant
```

```
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I or V
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, I, V, A, M, S or T

<400> SEQUENCE: 1223

Arg Xaa Xaa Xaa Xaa Lys
1               5

<210> SEQ ID NO 1224
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is Y or F
<220> FEATURE:
<221> NAME/KEY: variant
<222> LOCATION: (3)..(3)
<223> OTHER INFORMATION: X is L, I or V
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, I, V, A or M
<220> FEATURE:
<221> NAME/KEY: variant
<222> LOCATION: (6)..(6)
<223> OTHER INFORMATION: X is R or K

<400> SEQUENCE: 1224

Xaa Xaa Xaa Xaa Xaa Xaa
1               5

<210> SEQ ID NO 1225
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I or V
<220> FEATURE:
```

```
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, I, V or A
<220> FEATURE:
<221> NAME/KEY: variant
<222> LOCATION: (6)..(6)
<223> OTHER INFORMATION: X is R or K

<400> SEQUENCE: 1225

Xaa Xaa Xaa Xaa Xaa Xaa
1               5

<210> SEQ ID NO 1226
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or Y
<220> FEATURE:
<221> NAME/KEY: variant
<222> LOCATION: (3)..(3)
<223> OTHER INFORMATION: X is L, I or V
<220> FEATURE:
<221> NAME/KEY: variant
<222> LOCATION: (4)..(4)
<223> OTHER INFORMATION: X is L, I, V, A, S or T
<220> FEATURE:
<221> NAME/KEY: variant
<222> LOCATION: (5)..(5)
<223> OTHER INFORMATION: X is L, V, A, M, S or T
<220> FEATURE:
<221> NAME/KEY: variant
<222> LOCATION: (6)..(6)
<223> OTHER INFORMATION: X is R or K

<400> SEQUENCE: 1226

Xaa Xaa Xaa Xaa Xaa Xaa
1               5

<210> SEQ ID NO 1227
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I or V
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, I, V, A, M, S or T

<400> SEQUENCE: 1227
```

Lys Xaa Xaa Xaa Xaa Lys
1               5

<210> SEQ ID NO 1228
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F or Y
<220> FEATURE:
<221> NAME/KEY: variant
<222> LOCATION: (4)..(4)
<223> OTHER INFORMATION: X is L, I, V, A, M, S, T, N or Q
<220> FEATURE:
<221> NAME/KEY: variant
<222> LOCATION: (5)..(5)
<223> OTHER INFORMATION: X is L, I, V, A, M, G, S, T, N, Q, R, H or K
<220> FEATURE:
<221> NAME/KEY: variant
<222> LOCATION: (6)..(6)
<223> OTHER INFORMATION: X is L, I, V, A, M, G, S, T, N, Q, R, H, K, C
      or P

<400> SEQUENCE: 1228

Xaa Xaa Xaa Xaa Xaa Xaa
1               5

<210> SEQ ID NO 1229
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F or Y
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S, T, N, Q, R, H or K
<220> FEATURE:
<221> NAME/KEY: variant
<222> LOCATION: (6)..(6)
<223> OTHER INFORMATION: X is L, I, V, A, M, G, S, T, N, Q, R, H, K, C
      or P

<400> SEQUENCE: 1229

Xaa Xaa Xaa Xaa Xaa Xaa
1               5

```
<210> SEQ ID NO 1230
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F or Y
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S, T, N, Q, R, H or K
<220> FEATURE:
<221> NAME/KEY: variant
<222> LOCATION: (6)..(6)
<223> OTHER INFORMATION: X is L, I, V, A, M, G, S, T, R, H, K or P

<400> SEQUENCE: 1230

Xaa Xaa Xaa Xaa Xaa Xaa
1               5

<210> SEQ ID NO 1231
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F or Y
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S, T, N, Q, R, H or K
<220> FEATURE:
<221> NAME/KEY: variant
<222> LOCATION: (6)..(6)
<223> OTHER INFORMATION: X is L, I, V, A, M, R, H, K or P

<400> SEQUENCE: 1231

Xaa Xaa Xaa Xaa Xaa Xaa
1               5

<210> SEQ ID NO 1232
<211> LENGTH: 6
<212> TYPE: PRT
```

```
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F or Y
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S, T, N, Q, R, H or K
<220> FEATURE:
<221> NAME/KEY: variant
<222> LOCATION: (6)..(6)
<223> OTHER INFORMATION: X is R, H, K or P

<400> SEQUENCE: 1232

Xaa Xaa Xaa Xaa Xaa Xaa
1               5

<210> SEQ ID NO 1233
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F or Y
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S, T, R or K
<220> FEATURE:
<221> NAME/KEY: variant
<222> LOCATION: (6)..(6)
<223> OTHER INFORMATION: X is R, H or K

<400> SEQUENCE: 1233

Xaa Xaa Xaa Xaa Xaa Xaa
1               5

<210> SEQ ID NO 1234
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
```

```
<222> LOCATION: (1)..(1)
<223> OTHER INFORMATION: X is R, K or H
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S or T
<220> FEATURE:
<221> NAME/KEY: variant
<222> LOCATION: (6)..(6)
<223> OTHER INFORMATION: X is R, H or K

<400> SEQUENCE: 1234

Xaa Xaa Xaa Xaa Xaa Xaa
1               5

<210> SEQ ID NO 1235
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S or T
<220> FEATURE:
<221> NAME/KEY: variant
<222> LOCATION: (6)..(6)
<223> OTHER INFORMATION: X is R or K

<400> SEQUENCE: 1235

Xaa Xaa Xaa Xaa Xaa Xaa
1               5

<210> SEQ ID NO 1236
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
```

```
<223> OTHER INFORMATION: X is W or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, G, S or T
<220> FEATURE:
<221> NAME/KEY: variant
<222> LOCATION: (6)..(6)
<223> OTHER INFORMATION: X is R or K

<400> SEQUENCE: 1236

Xaa Xaa Xaa Xaa Xaa Xaa
1               5

<210> SEQ ID NO 1237
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M or T
<220> FEATURE:
<221> NAME/KEY: variant
<222> LOCATION: (5)..(5)
<223> OTHER INFORMATION: X is L, I, V, A, M, G, S or T
<220> FEATURE:
<221> NAME/KEY: variant
<222> LOCATION: (6)..(6)
<223> OTHER INFORMATION: X is R or K

<400> SEQUENCE: 1237

Xaa Xaa Xaa Xaa Xaa Xaa
1               5

<210> SEQ ID NO 1238
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is W, F, Y, L, I, V or M
```

```
<220> FEATURE:
<221> NAME/KEY: variant
<222> LOCATION: (4)..(4)
<223> OTHER INFORMATION: X is L, I, V, A, M or T
<220> FEATURE:
<221> NAME/KEY: variant
<222> LOCATION: (5)..(5)
<223> OTHER INFORMATION: X is L, I, V, A, M, S or T
<220> FEATURE:
<221> NAME/KEY: variant
<222> LOCATION: (6)..(6)
<223> OTHER INFORMATION: X is R or K

<400> SEQUENCE: 1238

Xaa Xaa Xaa Xaa Xaa Xaa
1               5

<210> SEQ ID NO 1239
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M or G
<220> FEATURE:
<221> NAME/KEY: variant
<222> LOCATION: (6)..(6)
<223> OTHER INFORMATION: X is R or K

<400> SEQUENCE: 1239

Xaa Xaa Xaa Xaa Xaa Xaa
1               5

<210> SEQ ID NO 1240
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M or T
<220> FEATURE:
```

```
<221> NAME/KEY: variant
<222> LOCATION: (5)..(5)
<223> OTHER INFORMATION: X is L, I, V, A, M, S or T
<220> FEATURE:
<221> NAME/KEY: variant
<222> LOCATION: (6)..(6)
<223> OTHER INFORMATION: X is R or K

<400> SEQUENCE: 1240

Xaa Xaa Xaa Xaa Xaa Xaa
1               5

<210> SEQ ID NO 1241
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, M, S or T
<220> FEATURE:
<221> NAME/KEY: variant
<222> LOCATION: (6)..(6)
<223> OTHER INFORMATION: X is R or K

<400> SEQUENCE: 1241

Xaa Xaa Xaa Xaa Xaa Xaa
1               5

<210> SEQ ID NO 1242
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, V, A, I, S or T
<220> FEATURE:
<221> NAME/KEY: variant
```

```
<222> LOCATION: (6)..(6)
<223> OTHER INFORMATION: X is R or K

<400> SEQUENCE: 1242

Xaa Xaa Xaa Xaa Xaa Xaa
1               5

<210> SEQ ID NO 1243
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, V, A, M, S or T
<220> FEATURE:
<221> NAME/KEY: variant
<222> LOCATION: (6)..(6)
<223> OTHER INFORMATION: X is R or K

<400> SEQUENCE: 1243

Arg Xaa Xaa Xaa Xaa Xaa
1               5

<210> SEQ ID NO 1244
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, V, A, M, S or T

<400> SEQUENCE: 1244

Arg Xaa Xaa Xaa Xaa Lys
1               5

<210> SEQ ID NO 1245
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
```

```
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is Y or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, I, V, A or M
<220> FEATURE:
<221> NAME/KEY: variant
<222> LOCATION: (6)..(6)
<223> OTHER INFORMATION: X is R or K

<400> SEQUENCE: 1245

Xaa Xaa Xaa Xaa Xaa Xaa
1               5

<210> SEQ ID NO 1246
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, I, V or A
<220> FEATURE:
<221> NAME/KEY: variant
<222> LOCATION: (6)..(6)
<223> OTHER INFORMATION: X is R or K

<400> SEQUENCE: 1246

Xaa Xaa Xaa Xaa Xaa Xaa
1               5

<210> SEQ ID NO 1247
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
```

-continued

```
<223> OTHER INFORMATION: X is W or Y
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A, S or T
<220> FEATURE:
<221> NAME/KEY: variant
<222> LOCATION: (5)..(5)
<223> OTHER INFORMATION: X is L, V, A, M S or T
<220> FEATURE:
<221> NAME/KEY: variant
<222> LOCATION: (6)..(6)
<223> OTHER INFORMATION: X is R or K

<400> SEQUENCE: 1247

Xaa Xaa Xaa Xaa Xaa Xaa
1               5

<210> SEQ ID NO 1248
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is W, F, Y, L, I, V or M
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, I, V, A, M, S or T

<400> SEQUENCE: 1248

Lys Xaa Xaa Xaa Xaa Lys
1               5

<210> SEQ ID NO 1249
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is W, F, Y, L, I or V
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, S or T
```

```
<220> FEATURE:
<221> NAME/KEY: variant
<222> LOCATION: (6)..(6)
<223> OTHER INFORMATION: X is R or K

<400> SEQUENCE: 1249

Xaa Xaa Xaa Xaa Xaa Xaa
1               5

<210> SEQ ID NO 1250
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is F, Y, L, I, V or M
<220> FEATURE:
<221> NAME/KEY: variant
<222> LOCATION: (4)..(4)
<223> OTHER INFORMATION: X is L, I, V, A, M, S or T
<220> FEATURE:
<221> NAME/KEY: variant
<222> LOCATION: (5)..(5)
<223> OTHER INFORMATION: X is L, I, V, A, S or T
<220> FEATURE:
<221> NAME/KEY: variant
<222> LOCATION: (6)..(6)
<223> OTHER INFORMATION: X is R or K

<400> SEQUENCE: 1250

Xaa Xaa Xaa Xaa Xaa Xaa
1               5

<210> SEQ ID NO 1251
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or F
<220> FEATURE:
<221> NAME/KEY: variant
<222> LOCATION: (3)..(3)
<223> OTHER INFORMATION: X is W, F, Y, L, I or V
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, I, V, A, S or T
<220> FEATURE:
<221> NAME/KEY: variant
<222> LOCATION: (6)..(6)
<223> OTHER INFORMATION: X is R or K
```

```
<400> SEQUENCE: 1251

Xaa Xaa Xaa Xaa Xaa Xaa
1               5

<210> SEQ ID NO 1252
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is W, F, Y, L, I or V
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, V, A, M, S or T
<220> FEATURE:
<221> NAME/KEY: variant
<222> LOCATION: (6)..(6)
<223> OTHER INFORMATION: X is R or K

<400> SEQUENCE: 1252

Arg Xaa Xaa Xaa Xaa Xaa
1               5

<210> SEQ ID NO 1253
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is W, F, Y, L, I or V
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, V, A, M, S or T

<400> SEQUENCE: 1253

Arg Xaa Xaa Xaa Xaa Lys
1               5

<210> SEQ ID NO 1254
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
```

```
<221> NAME/KEY: variant
<222> LOCATION: (2)..(2)
<223> OTHER INFORMATION: X is Y or F
<220> FEATURE:
<221> NAME/KEY: variant
<222> LOCATION: (3)..(3)
<223> OTHER INFORMATION: X is W, F, Y, L, I or V
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, I, V, A or M
<220> FEATURE:
<221> NAME/KEY: variant
<222> LOCATION: (6)..(6)
<223> OTHER INFORMATION: X is R or K

<400> SEQUENCE: 1254

Xaa Xaa Xaa Xaa Xaa Xaa
1               5

<210> SEQ ID NO 1255
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W, F or Y
<220> FEATURE:
<221> NAME/KEY: variant
<222> LOCATION: (3)..(3)
<223> OTHER INFORMATION: X is W, F, Y, L, I or V
<220> FEATURE:
<221> NAME/KEY: variant
<222> LOCATION: (4)..(4)
<223> OTHER INFORMATION: X is L, I, V or A
<220> FEATURE:
<221> NAME/KEY: variant
<222> LOCATION: (5)..(5)
<223> OTHER INFORMATION: X is L, I, V or A
<220> FEATURE:
<221> NAME/KEY: variant
<222> LOCATION: (6)..(6)
<223> OTHER INFORMATION: X is R or K

<400> SEQUENCE: 1255

Xaa Xaa Xaa Xaa Xaa Xaa
1               5

<210> SEQ ID NO 1256
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W or Y
<220> FEATURE:
<221> NAME/KEY: variant
```

```
<222> LOCATION: (3)..(3)
<223> OTHER INFORMATION: X is W, F, Y, L, I or V
<220> FEATURE:
<221> NAME/KEY: variant
<222> LOCATION: (4)..(4)
<223> OTHER INFORMATION: X is L, I, V, A, S or T
<220> FEATURE:
<221> NAME/KEY: variant
<222> LOCATION: (5)..(5)
<223> OTHER INFORMATION: X is L, V, A, M, S or T
<220> FEATURE:
<221> NAME/KEY: variant
<222> LOCATION: (6)..(6)
<223> OTHER INFORMATION: X is R or K

<400> SEQUENCE: 1256

Xaa Xaa Xaa Xaa Xaa Xaa
1               5

<210> SEQ ID NO 1257
<211> LENGTH: 6
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is W, F, Y, L, I or V
<220> FEATURE:
<221> NAME/KEY: variant
<222> LOCATION: (4)..(4)
<223> OTHER INFORMATION: X is L, I, V, A or T
<220> FEATURE:
<221> NAME/KEY: variant
<222> LOCATION: (5)..(5)
<223> OTHER INFORMATION: X is L, I, V, A, M, S or T

<400> SEQUENCE: 1257

Lys Xaa Xaa Xaa Xaa Lys
1               5

<210> SEQ ID NO 1258
<211> LENGTH: 6
<212> TYPE: PRT
<213> ORGANISM: Artificial sequence
<220> FEATURE:
<223> OTHER INFORMATION: APIM variant

<400> SEQUENCE: 1258

Arg Trp Phe Leu Val Lys
1               5

<210> SEQ ID NO 1259
<211> LENGTH: 6
<212> TYPE: PRT
<213> ORGANISM: Artificial sequence
<220> FEATURE:
<223> OTHER INFORMATION: APIM variant

<400> SEQUENCE: 1259

Arg Trp Tyr Leu Val Lys
1               5

<210> SEQ ID NO 1260
<211> LENGTH: 6
<212> TYPE: PRT
```

```
<213> ORGANISM: Artificial sequence
<220> FEATURE:
<223> OTHER INFORMATION: APIM variant

<400> SEQUENCE: 1260

Arg Trp Leu Leu Val Lys
1               5

<210> SEQ ID NO 1261
<211> LENGTH: 6
<212> TYPE: PRT
<213> ORGANISM: Artificial sequence
<220> FEATURE:
<223> OTHER INFORMATION: APIM variant

<400> SEQUENCE: 1261

Arg Trp Ile Leu Val Lys
1               5

<210> SEQ ID NO 1262
<211> LENGTH: 6
<212> TYPE: PRT
<213> ORGANISM: Artificial sequence
<220> FEATURE:
<223> OTHER INFORMATION: APIM variant

<400> SEQUENCE: 1262

Arg Trp Val Leu Val Lys
1               5

<210> SEQ ID NO 1263
<211> LENGTH: 6
<212> TYPE: PRT
<213> ORGANISM: Artificial sequence
<220> FEATURE:
<223> OTHER INFORMATION: APIM variant

<400> SEQUENCE: 1263

Arg Trp Met Leu Val Lys
1               5

<210> SEQ ID NO 1264
<211> LENGTH: 6
<212> TYPE: PRT
<213> ORGANISM: Artificial sequence
<220> FEATURE:
<223> OTHER INFORMATION: APIM variant

<400> SEQUENCE: 1264

Arg Phe Trp Leu Val Lys
1               5

<210> SEQ ID NO 1265
<211> LENGTH: 6
<212> TYPE: PRT
<213> ORGANISM: Artificial sequence
<220> FEATURE:
<223> OTHER INFORMATION: APIM variant

<400> SEQUENCE: 1265

Arg Phe Phe Leu Val Lys
1               5

<210> SEQ ID NO 1266
<211> LENGTH: 6
<212> TYPE: PRT
<213> ORGANISM: Artificial sequence
```

-continued

```
<220> FEATURE:
<223> OTHER INFORMATION: APIM variant

<400> SEQUENCE: 1266

Arg Phe Tyr Leu Val Lys
1               5

<210> SEQ ID NO 1267
<211> LENGTH: 6
<212> TYPE: PRT
<213> ORGANISM: Artificial sequence
<220> FEATURE:
<223> OTHER INFORMATION: APIM variant

<400> SEQUENCE: 1267

Arg Phe Leu Leu Val Lys
1               5

<210> SEQ ID NO 1268
<211> LENGTH: 6
<212> TYPE: PRT
<213> ORGANISM: Artificial sequence
<220> FEATURE:
<223> OTHER INFORMATION: APIM variant

<400> SEQUENCE: 1268

Arg Phe Ile Leu Val Lys
1               5

<210> SEQ ID NO 1269
<211> LENGTH: 6
<212> TYPE: PRT
<213> ORGANISM: Artificial sequence
<220> FEATURE:
<223> OTHER INFORMATION: APIM variant

<400> SEQUENCE: 1269

Arg Phe Val Leu Val Lys
1               5

<210> SEQ ID NO 1270
<211> LENGTH: 6
<212> TYPE: PRT
<213> ORGANISM: Artificial sequence
<220> FEATURE:
<223> OTHER INFORMATION: APIM variant

<400> SEQUENCE: 1270

Arg Phe Met Leu Val Lys
1               5

<210> SEQ ID NO 1271
<211> LENGTH: 6
<212> TYPE: PRT
<213> ORGANISM: Artificial sequence
<220> FEATURE:
<223> OTHER INFORMATION: APIM variant

<400> SEQUENCE: 1271

Arg Tyr Trp Leu Val Lys
1               5

<210> SEQ ID NO 1272
<211> LENGTH: 6
<212> TYPE: PRT
<213> ORGANISM: Artificial sequence
<220> FEATURE:
```

```
<223> OTHER INFORMATION: APIM variant

<400> SEQUENCE: 1272

Arg Tyr Phe Leu Val Lys
1               5

<210> SEQ ID NO 1273
<211> LENGTH: 6
<212> TYPE: PRT
<213> ORGANISM: Artificial sequence
<220> FEATURE:
<223> OTHER INFORMATION: APIM variant

<400> SEQUENCE: 1273

Arg Tyr Tyr Leu Val Lys
1               5

<210> SEQ ID NO 1274
<211> LENGTH: 6
<212> TYPE: PRT
<213> ORGANISM: Artificial sequence
<220> FEATURE:
<223> OTHER INFORMATION: APIM variant

<400> SEQUENCE: 1274

Arg Tyr Leu Leu Val Lys
1               5

<210> SEQ ID NO 1275
<211> LENGTH: 6
<212> TYPE: PRT
<213> ORGANISM: Artificial sequence
<220> FEATURE:
<223> OTHER INFORMATION: APIM variant

<400> SEQUENCE: 1275

Arg Tyr Ile Leu Val Lys
1               5

<210> SEQ ID NO 1276
<211> LENGTH: 6
<212> TYPE: PRT
<213> ORGANISM: Artificial sequence
<220> FEATURE:
<223> OTHER INFORMATION: APIM variant

<400> SEQUENCE: 1276

Arg Tyr Val Leu Val Lys
1               5

<210> SEQ ID NO 1277
<211> LENGTH: 6
<212> TYPE: PRT
<213> ORGANISM: Artificial sequence
<220> FEATURE:
<223> OTHER INFORMATION: APIM variant

<400> SEQUENCE: 1277

Arg Tyr Met Leu Val Lys
1               5

<210> SEQ ID NO 1278
<211> LENGTH: 6
<212> TYPE: PRT
<213> ORGANISM: Artificial sequence
<220> FEATURE:
<223> OTHER INFORMATION: APIM variant
```

```
<400> SEQUENCE: 1278

Arg Trp Phe Val Ile Lys
1               5

<210> SEQ ID NO 1279
<211> LENGTH: 6
<212> TYPE: PRT
<213> ORGANISM: Artificial sequence
<220> FEATURE:
<223> OTHER INFORMATION: APIM variant

<400> SEQUENCE: 1279

Arg Trp Tyr Val Ile Lys
1               5

<210> SEQ ID NO 1280
<211> LENGTH: 6
<212> TYPE: PRT
<213> ORGANISM: Artificial sequence
<220> FEATURE:
<223> OTHER INFORMATION: APIM variant

<400> SEQUENCE: 1280

Arg Trp Leu Val Ile Lys
1               5

<210> SEQ ID NO 1281
<211> LENGTH: 6
<212> TYPE: PRT
<213> ORGANISM: Artificial sequence
<220> FEATURE:
<223> OTHER INFORMATION: APIM variant

<400> SEQUENCE: 1281

Arg Trp Ile Val Ile Lys
1               5

<210> SEQ ID NO 1282
<211> LENGTH: 6
<212> TYPE: PRT
<213> ORGANISM: Artificial sequence
<220> FEATURE:
<223> OTHER INFORMATION: APIM variant

<400> SEQUENCE: 1282

Arg Trp Val Val Ile Lys
1               5

<210> SEQ ID NO 1283
<211> LENGTH: 6
<212> TYPE: PRT
<213> ORGANISM: Artificial sequence
<220> FEATURE:
<223> OTHER INFORMATION: APIM variant

<400> SEQUENCE: 1283

Arg Trp Met Val Ile Lys
1               5

<210> SEQ ID NO 1284
<211> LENGTH: 6
<212> TYPE: PRT
<213> ORGANISM: Artificial sequence
<220> FEATURE:
<223> OTHER INFORMATION: APIM variant
```

```
<400> SEQUENCE: 1284

Arg Phe Trp Val Ile Lys
1               5

<210> SEQ ID NO 1285
<211> LENGTH: 6
<212> TYPE: PRT
<213> ORGANISM: Artificial sequence
<220> FEATURE:
<223> OTHER INFORMATION: APIM variant

<400> SEQUENCE: 1285

Arg Phe Phe Val Ile Lys
1               5

<210> SEQ ID NO 1286
<211> LENGTH: 6
<212> TYPE: PRT
<213> ORGANISM: Artificial sequence
<220> FEATURE:
<223> OTHER INFORMATION: APIM variant

<400> SEQUENCE: 1286

Arg Phe Tyr Val Ile Lys
1               5

<210> SEQ ID NO 1287
<211> LENGTH: 6
<212> TYPE: PRT
<213> ORGANISM: Artificial sequence
<220> FEATURE:
<223> OTHER INFORMATION: APIM variant

<400> SEQUENCE: 1287

Arg Phe Leu Val Ile Lys
1               5

<210> SEQ ID NO 1288
<211> LENGTH: 6
<212> TYPE: PRT
<213> ORGANISM: Artificial sequence
<220> FEATURE:
<223> OTHER INFORMATION: APIM variant

<400> SEQUENCE: 1288

Arg Phe Ile Val Ile Lys
1               5

<210> SEQ ID NO 1289
<211> LENGTH: 25
<212> TYPE: PRT
<213> ORGANISM: Artificial sequence
<220> FEATURE:
<223> OTHER INFORMATION: APIM peptide

<400> SEQUENCE: 1289

Met Asp Arg Trp Leu Val Lys Trp Lys Lys Arg Lys Ile Arg Arg
1               5                   10                  15

Arg Arg Arg Arg Arg Arg Arg Arg Arg
                20                  25

<210> SEQ ID NO 1290
<211> LENGTH: 5
<212> TYPE: PRT
<213> ORGANISM: Artificial sequence
<220> FEATURE:
```

<223> OTHER INFORMATION: APIM

<400> SEQUENCE: 1290

Arg Trp Leu Val Lys
1               5

<210> SEQ ID NO 1291
<211> LENGTH: 5
<212> TYPE: PRT
<213> ORGANISM: Artificial sequence
<220> FEATURE:
<223> OTHER INFORMATION: APIM variant

<400> SEQUENCE: 1291

Arg Phe Ser Leu Lys
1               5

<210> SEQ ID NO 1292
<211> LENGTH: 5
<212> TYPE: PRT
<213> ORGANISM: Artificial sequence
<220> FEATURE:
<223> OTHER INFORMATION: APIM variant

<400> SEQUENCE: 1292

Arg Trp Leu Val Pro
1               5

<210> SEQ ID NO 1293
<211> LENGTH: 5
<212> TYPE: PRT
<213> ORGANISM: Artificial sequence
<220> FEATURE:
<223> OTHER INFORMATION: APIM variant

<400> SEQUENCE: 1293

Arg Trp Leu Thr Lys
1               5

<210> SEQ ID NO 1294
<211> LENGTH: 5
<212> TYPE: PRT
<213> ORGANISM: Artificial sequence
<220> FEATURE:
<223> OTHER INFORMATION: APIM variant

<400> SEQUENCE: 1294

Arg Trp Leu Ser Lys
1               5

<210> SEQ ID NO 1295
<211> LENGTH: 5
<212> TYPE: PRT
<213> ORGANISM: Artificial sequence
<220> FEATURE:
<223> OTHER INFORMATION: APIM variant

<400> SEQUENCE: 1295

Arg Phe Leu Ser Lys
1               5

<210> SEQ ID NO 1296
<211> LENGTH: 5
<212> TYPE: PRT
<213> ORGANISM: Artificial sequence
<220> FEATURE:
<223> OTHER INFORMATION: APIM variant -continued

```
<400> SEQUENCE: 1296

Arg Trp Ser Val Lys
1               5

<210> SEQ ID NO 1297
<211> LENGTH: 5
<212> TYPE: PRT
<213> ORGANISM: Artificial sequence
<220> FEATURE:
<223> OTHER INFORMATION: APIM variant

<400> SEQUENCE: 1297

Arg Trp Ala Val Lys
1               5

<210> SEQ ID NO 1298
<211> LENGTH: 25
<212> TYPE: PRT
<213> ORGANISM: Artificial sequence
<220> FEATURE:
<223> OTHER INFORMATION: APIM peptide

<400> SEQUENCE: 1298

Met Asp Arg Trp Ser Val Lys Trp Lys Lys Arg Lys Ile Arg Arg
1               5                   10                  15

Arg Arg Arg Arg Arg Arg Arg Arg Arg
            20                  25

<210> SEQ ID NO 1299
<211> LENGTH: 25
<212> TYPE: PRT
<213> ORGANISM: Artificial sequence
<220> FEATURE:
<223> OTHER INFORMATION: APIM peptide

<400> SEQUENCE: 1299

Met Asp Arg Trp Ala Val Lys Trp Lys Lys Arg Lys Ile Arg Arg
1               5                   10                  15

Arg Arg Arg Arg Arg Arg Arg Arg Arg
            20                  25

<210> SEQ ID NO 1300
<211> LENGTH: 25
<212> TYPE: PRT
<213> ORGANISM: Artificial sequence
<220> FEATURE:
<223> OTHER INFORMATION: APIM peptide

<400> SEQUENCE: 1300

Met Asp Arg Trp Leu Thr Lys Trp Lys Lys Arg Lys Ile Arg Arg
1               5                   10                  15

Arg Arg Arg Arg Arg Arg Arg Arg Arg
            20                  25

<210> SEQ ID NO 1301
<211> LENGTH: 25
<212> TYPE: PRT
<213> ORGANISM: Artificial sequence
<220> FEATURE:
<223> OTHER INFORMATION: APIM peptide

<400> SEQUENCE: 1301

Met Asp Arg Phe Leu Ser Lys Trp Lys Lys Arg Lys Ile Arg Arg
1               5                   10                  15
```

Arg Arg Arg Arg Arg Arg Arg Arg Arg
            20                  25

<210> SEQ ID NO 1302
<211> LENGTH: 25
<212> TYPE: PRT
<213> ORGANISM: Artificial sequence
<220> FEATURE:
<223> OTHER INFORMATION: APIM peptide

<400> SEQUENCE: 1302

Met Asp Arg Trp Leu Ser Lys Trp Lys Lys Arg Lys Ile Arg Arg
1               5                   10                  15

Arg Arg Arg Arg Arg Arg Arg Arg Arg
            20                  25

<210> SEQ ID NO 1303
<211> LENGTH: 25
<212> TYPE: PRT
<213> ORGANISM: Artificial sequence
<220> FEATURE:
<223> OTHER INFORMATION: APIM peptide

<400> SEQUENCE: 1303

Met Asp Arg Trp Leu Val Pro Trp Lys Lys Arg Lys Ile Arg Arg
1               5                   10                  15

Arg Arg Arg Arg Arg Arg Arg Arg Arg
            20                  25

<210> SEQ ID NO 1304
<211> LENGTH: 25
<212> TYPE: PRT
<213> ORGANISM: Artificial sequence
<220> FEATURE:
<223> OTHER INFORMATION: APIM peptide

<400> SEQUENCE: 1304

Met Asp Arg Phe Ser Leu Lys Trp Lys Lys Arg Lys Ile Arg Arg
1               5                   10                  15

Arg Arg Arg Arg Arg Arg Arg Arg Arg
            20                  25

<210> SEQ ID NO 1305
<211> LENGTH: 5
<212> TYPE: PRT
<213> ORGANISM: Artificial sequence
<220> FEATURE:
<223> OTHER INFORMATION: APIM variant

<400> SEQUENCE: 1305

Arg Trp Leu Ala Lys
1               5

<210> SEQ ID NO 1306
<211> LENGTH: 5
<212> TYPE: PRT
<213> ORGANISM: Artificial sequence
<220> FEATURE:
<223> OTHER INFORMATION: APIM variant

<400> SEQUENCE: 1306

Arg Trp Leu Gly Lys
1               5

```
<210> SEQ ID NO 1307
<211> LENGTH: 5
<212> TYPE: PRT
<213> ORGANISM: Artificial sequence
<220> FEATURE:
<223> OTHER INFORMATION: APIM variant

<400> SEQUENCE: 1307

Lys Phe Ile Val Lys
1               5

<210> SEQ ID NO 1308
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is R or K
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(4)
<223> OTHER INFORMATION: X is L, I, V or A
<220> FEATURE:
<221> NAME/KEY: variant
<222> LOCATION: (5)..(5)
<223> OTHER INFORMATION: X is R or K

<400> SEQUENCE: 1308

Xaa Xaa Xaa Xaa Xaa
1               5

<210> SEQ ID NO 1309
<211> LENGTH: 5
<212> TYPE: PRT
<213> ORGANISM: Artificial sequence
<220> FEATURE:
<223> OTHER INFORMATION: APIM variant
<220> FEATURE:
<221> NAME/KEY: variant
<222> LOCATION: (1)..(1)
<223> OTHER INFORMATION: X is K, R or H
<220> FEATURE:
<221> NAME/KEY: variant
<222> LOCATION: (2)..(2)
<223> OTHER INFORMATION: X is W, Y or F
<220> FEATURE:
<221> NAME/KEY: variant
<222> LOCATION: (3)..(3)
<223> OTHER INFORMATION: X is L, I, V, A, M, S, T, N, Q or C
<220> FEATURE:
<221> NAME/KEY: variant
<222> LOCATION: (4)..(4)
<223> OTHER INFORMATION: X is L, I, V, A, M, S, T, N, Q, C, G, K, H or R
<220> FEATURE:
<221> NAME/KEY: variant
<222> LOCATION: (5)..(5)
<223> OTHER INFORMATION: X is K, R, H or P

<400> SEQUENCE: 1309

Xaa Xaa Xaa Xaa Xaa
1               5

<210> SEQ ID NO 1310
<211> LENGTH: 6
<212> TYPE: PRT
<213> ORGANISM: Artificial sequence
```

```
<220> FEATURE:
<223> OTHER INFORMATION: APIM variant

<400> SEQUENCE: 1310

Arg Trp Trp Leu Val Lys
1               5

<210> SEQ ID NO 1311
<211> LENGTH: 26
<212> TYPE: PRT
<213> ORGANISM: Artificial sequence
<220> FEATURE:
<223> OTHER INFORMATION: APIM Oligopeptidic compound

<400> SEQUENCE: 1311

Met Asp Arg Trp Trp Leu Val Lys Trp Lys Lys Arg Lys Ile Arg
1               5                   10                  15

Arg Arg Arg Arg Arg Arg Arg Arg Arg Arg
                20                  25

<210> SEQ ID NO 1312
<211> LENGTH: 4
<212> TYPE: PRT
<213> ORGANISM: Artificial sequence
<220> FEATURE:
<223> OTHER INFORMATION: negative control peptide

<400> SEQUENCE: 1312

Arg Trp Leu Lys
1

<210> SEQ ID NO 1313
<211> LENGTH: 25
<212> TYPE: PRT
<213> ORGANISM: Artificial sequence
<220> FEATURE:
<223> OTHER INFORMATION: APIM peptide

<400> SEQUENCE: 1313

Met Asp Arg Tyr Leu Val Lys Trp Lys Lys Arg Lys Ile Arg Arg
1               5                   10                  15

Arg Arg Arg Arg Arg Arg Arg Arg Arg
                20                  25

<210> SEQ ID NO 1314
<211> LENGTH: 30
<212> TYPE: PRT
<213> ORGANISM: Artificial sequence
<220> FEATURE:
<223> OTHER INFORMATION: APIM peptide

<400> SEQUENCE: 1314

Met Asp Arg Trp Leu Val Lys Trp Lys Lys Arg Lys Ile Arg Gln
1               5                   10                  15

Ile Lys Ile Trp Phe Gln Asn Arg Arg Met Lys Trp Lys Lys
                20                  25                  30

<210> SEQ ID NO 1315
<211> LENGTH: 31
<212> TYPE: PRT
<213> ORGANISM: Artificial sequence
<220> FEATURE:
<223> OTHER INFORMATION: APIM peptide

<400> SEQUENCE: 1315
```

-continued

Met Asp Arg Trp Trp Leu Val Lys Trp Lys Lys Arg Lys Ile Arg
1               5                   10                  15

Gln Ile Lys Ile Trp Phe Gln Asn Arg Arg Met Lys Trp Lys Lys
            20                  25                  30

<210> SEQ ID NO 1316
<211> LENGTH: 31
<212> TYPE: PRT
<213> ORGANISM: Artificial sequence
<220> FEATURE:
<223> OTHER INFORMATION: APIM peptide

<400> SEQUENCE: 1316

Met Asp Arg Phe Phe Leu Val Lys Trp Lys Lys Arg Lys Ile Arg
1               5                   10                  15

Gln Ile Lys Ile Trp Phe Gln Asn Arg Arg Met Lys Trp Lys Lys
            20                  25                  30

<210> SEQ ID NO 1317
<211> LENGTH: 25
<212> TYPE: PRT
<213> ORGANISM: Artificial sequence
<220> FEATURE:
<223> OTHER INFORMATION: APIM peptide

<400> SEQUENCE: 1317

Met Asp Arg Trp Leu Val Lys Gly Ala Gln Pro Lys Val Leu Arg Arg
1               5                   10                  15

Arg Arg Arg Arg Arg Arg Arg Arg Arg
            20                  25

<210> SEQ ID NO 1318
<211> LENGTH: 24
<212> TYPE: PRT
<213> ORGANISM: Artificial sequence
<220> FEATURE:
<223> OTHER INFORMATION: APIM peptide

<400> SEQUENCE: 1318

Met Asp Arg Trp Leu Lys Trp Lys Lys Lys Arg Lys Ile Arg Arg
1               5                   10                  15

Arg Arg Arg Arg Arg Arg Arg Arg
            20

<210> SEQ ID NO 1319
<211> LENGTH: 72
<212> TYPE: DNA
<213> ORGANISM: Escherichia coli

<400> SEQUENCE: 1319
agccagctgt ctcagtttat ggaccagaac aacccgctgt ctgagattac gcacaaacgt     60
cgtatctccg ca                                                         72

<210> SEQ ID NO 1320
<211> LENGTH: 33
<212> TYPE: DNA
<213> ORGANISM: Escherichia coli

<400> SEQUENCE: 1320
cctgaaggtc cgaacatcgg tctgatcaac tct                                  33

ANTI-BACTERIAL AGENTS AND THEIR USE IN THERAPY

The present invention relates to novel agents, particularly peptides or mimetics thereof and their encoding nucleic acids, pharmaceutical compositions comprising at least one of said agents, and their use as antibacterials, e.g. in the treatment or prevention of bacterial infections. The agents may be useful alone or in combination with other compounds, such as cytotoxic and/or cytostatic compounds, e.g., antibiotics etc. Also provided are therapeutic methods which comprise the use of said agents and compositions for the aforementioned uses. The agents may also be used in the manufacture or preparation of medicaments for the aforementioned therapies. Furthermore, the agents may be used in in vitro methods, e.g. in cell culture methods (to prevent or inhibit bacterial growth or to prevent or reduce unwanted bacterial colonisation or contamination in a non-medical (e.g. in vitro or vivo) setting, for example for sterilisation or antiseptic purposes) and in the production of products coated with the agent (e.g., medical devices, implants etc.). Thus, products coated with the agent are also provided.

APIM peptides are a group of peptides that interact with PCNA (proliferating cell nuclear antigen) via a novel PCNA interacting motif (Gilliam et al., 2009. Identification of a novel, widespread, and functionally important PCNA-binding motif, J. Cell Biol, 186(5), pp. 645-654). The motif has been termed APIM (AlkB homologue 2 (hABH2) PCNA-interacting motif) since it was first identified as mediating the interaction between hABH2 and PCNA, but as will be clear from the disclosure below, APIM motifs have now been identified in a wide range of proteins. The PCNA binding motif found in APIM peptides typically is defined using the consensus sequence, [R/K]-[F/W/Y]-[L/I/V/A]-[L/I/V/A]-[K/R] (SEQ ID NO: 1308), and it has been determined that a more diverse motif, [R/K/H]-[W/F/Y]-[L/I/V/A/M/S/T/N/Q/C]-[L/I/V/A/M/G/S/T/N/Q/R/H/K/C]-[K/R/H/P](SEQ ID NO: 1309), is present in various proteins that interact with PCNA (see international application No. PCT/EP2014/073967).

PCNA is a member of the sliding clamp family of proteins, which is known to be involved in both DNA replication and DNA repair. The main function of PCNA is to provide replicative polymerases with the high processivity needed for duplication of the genome. In live S-phase cells, PCNA tagged with green fluorescent protein (GFP) forms distinct foci representing sites of replication. It can therefore be used as an S-phase marker.

Numerous proteins involved in cellular processes such as DNA repair, chromatin assembly, epigenetic and chromatin remodelling, sister-chromatid cohesion, cell cycle control and survival are localised in so-called replication factories which contain more than a dozen replication forks. Many of these proteins interact with PCNA and have been shown to co-localise with PCNA in replication foci.

Thus, various proteins interact with PCNA and it is thought that many of these interactions are mediated via a conserved PCNA interacting peptide sequence called the PIP-box (QxxL/I/MxxF/DF/Y [SEQ ID NO: 1205]), wherein x can be any amino acid. Peptides that contain a PIP-box typically are extremely cytotoxic to human and animal cells and therefore unsuitable for use in therapy.

However, APIM peptides have been shown to be useful in therapy. Specifically APIM peptides have been shown to be effective in sensitizing cell cytotoxic and cytostatic agents, particularly DNA-damaging agents (WO 2009/104001) and indeed as an apoptosis-inducing cytotoxic agent in its own right (Müller et al., 2013. Targeting Proliferating Cell Nuclear Antigen and its Protein Interactions Induces Apoptosis in Multiple Myeloma Cells, PLOS One, 8(7), e70430, pp 1-12). Thus, APIM peptides have been shown to be useful in combination with cytotoxic and/or cytostatic agents in the treatment of a disorder or condition where it is desirable to inhibit the growth of cells, or in a treatment which involves cytostatic therapy, i.e. to prevent or inhibit the unwanted proliferation of cells.

In work leading up to the present invention, the inventors have surprisingly determined that APIM peptides have a direct effect on bacteria, i.e. APIM peptides have direct cytotoxic effects on a variety of bacterial cells and also potentiate or enhance the effect of cytotoxic and/or cytostatic agents on bacterial cells, i.e. sensitize bacterial cells to various cytotoxic and/or cytostatic agents, e.g. antibiotics, particularly agents that act intracellularly rather than agents that function at the cell membrane or cell wall, e.g. to permeabilize cells. Whilst not wishing to be bound by any specific theory it is hypothesized that APIM peptides may interact with sliding clamp DNA proteins in bacteria, thereby effecting DNA replication and repair in bacterial cells, resulting cytotoxicity and/or reduction in cell growth. Thus, it is thought that the oligopeptidic compounds disclosed herein may be able to interfere with the interaction of e.g. TLS polymerases, and other DNA repair proteins, and sliding-clamp proteins (e.g. the β-clamp), thereby inhibiting essential cellular functions, particularly DNA synthesis and repair, resulting in the stimulation of apoptosis or apoptosis-like cell death; or increased sensitivity of the bacterial cells to other cytotoxic and/or cytostatic agents.

Infectious diseases, also known as transmissible diseases or communicable diseases, comprise clinically evident illness symptoms of disease, resulting from the infection, presence and growth of pathogenic biological agents, e.g. microbial organisms such as bacteria and fungi, in an individual host organism. In certain cases, infectious diseases may be asymptomatic for much or even all of their course in a given host. In the latter case, the disease may only be defined as a "disease" (which by definition means an illness) in hosts who secondarily become ill after contact with an asymptomatic carrier.

Microbial infections do not always result in, or progress to, a clinically overt or symptomatic disease or disease state. For instance, a wound may become infected by one or more microbes, without resulting in a infectious disease. Furthermore, microbial growth in and on a subject may occur naturally, e.g. commensal growth, such as gastrointestinal microbial flora. Thus, a microbial, e.g. bacterial, infection may be viewed as any atypical, unwanted, undesirable, excessive and/or harmful infection and does not necessarily involve or result in a disease.

Transmission of a microbial pathogen can occur in various ways including physical contact, contaminated food, body fluids, objects, airborne inhalation, or through vector organisms. Infectious diseases are sometimes called "contagious" when they are easily transmitted by contact with an ill person or their secretions. Thus, a contagious disease is a subset of infectious disease that is especially infective or easily transmitted.

Although only a relatively small proportion of microorganisms cause disease in otherwise healthy individuals, infectious diseases are one of the main contributors to global mortality and morbidity and a huge amount of effort has gone into the discovery and development of antimicrobial compounds, for both the treatment and prevention of infectious diseases.

However, ever since antimicrobials, particularly antibiotics, were first used it was found that microbes, e.g., bacteria, could display intrinsic resistance to these drugs or could develop resistance to these drugs. Resistance of a microbe, e.g. bacterium or fungus, to an antibiotic or antimycotic can be viewed as a substantially greater tolerance, or reduced susceptibility, to the antibiotic or antimycotic compared to a sensitive microbe or atypical or a wild type version of the microbe. In some cases a microbe can be completely unaffected by exposure to an antibiotic or antimycotic. In this instance the microbe can be considered fully resistant to that antibiotic or antimycotic.

Multidrug resistance (MDR) in bacteria describes the situation where a bacterium is resistant to at least three classes of drugs, specifically in the context of bacteria, at least three classes of anti-microbial (or more specifically anti-bacterial) agents. Antibiotics in one class are functionally unrelated, structurally unrelated, or both, to antibiotics in a different class. MDR in bacteria is thus often termed multiple anti-bacterial drug resistance or multiple antibiotic resistance. The terms are used interchangeably in the art and herein. Bacteria displaying multidrug resistance phenotypes (or multiple antibacterial/antibiotic drug resistance phenotypes) are referred to as MDR bacteria (or sometimes MAR bacteria). Again, these terms are used interchangeably in the art and herein.

Antimicrobial, e.g. antibiotic/antimycotic, resistance mechanisms are numerous. For instance, resistance may arise from cell impermeability, which physically prevents the antimicrobial from reaching its site of action in or on the cell; efflux mechanisms which prevent effective amounts of the antimicrobial reaching its site of action in or on the microbe by rapidly removing the antimicrobial from the cell; metabolic mechanisms which breakdown the antimicrobial or convert the antimicrobial into a harmless (or less harmful) compound, or a compound more easily excreted; bypass mechanisms in which the microbe uses alternative pathways to those inhibited by the antimicrobial; or through the microbe having a form of the antimicrobial target (e.g. enzyme) that is less sensitive to the antimicrobial or not having the target at all.

Development (or acquisition) of resistance can be through mutation. For instance, this may involve changes in the structure of the target of the antimicrobial that reduces the sensitivity of the target to the antimicrobial. It can also be a mutation in a pathway involved in the regulation of the cellular machinery involved in the metabolism or efflux of the antimicrobial. It can also be a mutation in the constituents of the outer layers (e.g. the membranes/walls) of the microbe that effects the permeability of the antimicrobial into the microbe. In some instances multiple mutations must accumulate in order for a microbe to become resistant to a particular antimicrobial or class thereof.

Recent studies have indicated that the process of translesion synthesis (TLS) in bacteria contributes to acquisition of antibiotic resistance, e.g. in MDR strains. TLS is a cellular mechanism to tolerate DNA damage in which specific DNA polymerases (TLS polymerases) are expressed that are capable of by-passing and leaving the DNA lesions in DNA for the possibility of removal later, thereby enabling the cell to complete the duplication of its genome. However, this damage tolerance mechanism is error-prone because TLS polymerases are commonly low-fidelity enzymes and insert bases in a non-Watson Crick manner opposite the lesion and opposite undamaged DNA, and thus their inaccurate synthesis introduces mutations. It is thought that these mutations contribute to genetic diversity in bacteria and facilitate the acquisition of antibiotic resistance, particularly in MDR strains.

Many MDR species and strains of microbe exist day. For instance, bacterial genera from which MDR species and strains pose significant problems for human and animal health include, but are not limited to *Pseudomonas, Acinetobacter, Burkholderia, Klebsiella, Providencia, Enterococcus* and *Staphylococcus*.

Accordingly, there remains a need for effective therapies suitable for the treatment of bacterial infections, particularly diseases, disorders or conditions caused by, or associated with, bacterial infections (e.g. infectious diseases caused by, associated with, or exacerbated by, a bacterial), which also have minimal side effects.

As mentioned above, the inventors have surprisingly found that APIM peptides have a direct effect on bacteria, i.e. APIM peptides have direct cytotoxic effects on a variety of bacterial cells and also potentiate or enhance the effect of cytotoxic and/or cytostatic agents, e.g. antibiotics, on bacterial cells. As discussed in more detail in the Examples, the inventors have unexpectedly determined that oligopeptidic compounds comprising a PCNA interacting motif (APIM motif) and an uptake peptide can be imported into bacterial cells (exemplified with both gram negative and gram positive bacteria), wherein the compounds have a cytotoxic and/or cytostatic effect, i.e. an anti-bacterial effect, e.g., bactericidal (antibiotic). Thus, the oligopeptidic compounds described herein may find utility as anti-bacteria agents alone and/or may enhance the effect of other cytotoxic and/or cytostatic agents, e.g. anti-bacterial agents. Thus, for instance, the introduction of the agents described herein, e.g. intravenously, may be useful in the treatment septicaemia (an infection of the blood) or oral administration may be useful in the treatment e.g. gastric ulcers caused by a bacterial infection, such *Helicobacter pylori* (a gram negative bacterium), or other infected wounds etc. Thus, it may be expected that the agents defined herein may be effective in the treatment of a number of bacterial infections including various infectious diseases, e.g. bacterial infections, or conditions caused or exacerbated by, or associated with, an infectious disease.

Even more unexpectedly, the inventors have also determined that the PCNA binding motif found in APIM peptides may be modified substantially (primarily by the internal insertion of an additional aromatic amino acid or "large" hydrophobic amino acid (having an R group with at least 3 carbon atoms)) without reducing the capacity of the peptide to bind to PCNA, i.e. the "conventional" APIM sequence that is found in naturally-occurring proteins that interacts with PCNA may be modified. Indeed, as shown in the Examples below, it can be seen that these "longer" or "extended" APIM peptides (i.e. peptides containing, a longer or extended APIM sequence) may in some instances have improved affinity for PCNA relative to peptides containing the conventional or naturally-occurring APIM sequence. Nevertheless, the longer APIM peptides are not cytotoxic to normal human cells. Accordingly, the longer or extended APIM peptides are expected to be at least as effective at inhibiting protein interactions with sliding clamp DNA proteins in bacteria as peptides containing the conventional or naturally-occurring APIM sequence discussed above (SEQ ID NOs: 1308 and 1309).

These surprising findings have led the inventors to propose new therapeutic uses for APIM peptides, i.e. peptides comprising a PCNA binding motif (particularly peptides containing a longer or extended APIM sequence), namely for use in treating a bacterial infectious disease or infection or a disease or condition exacerbated or caused by a bacterial infection, e.g. by acting directly on the infecting bacteria and/or acting indirectly by potentiating the effects of other anti-bacterial compounds, particularly cytotoxic or cytostatic agents, e.g. antibiotics. Furthermore, the inventors have also demonstrated that APIM peptides may also potentiate the effects of DNA damaging radiation, particularly UV radiation.

As mentioned above, it is thought that the peptides of the invention act, by interfering with DNA replication and repair mechanisms. This is different to mechanism of action for many known anti-bacterials, which commonly act by inhibiting cell wall synthesis, e.g. beta-lactams (such as penicillins, cephalosporins, carbapenems, monobactams), polymyxins, or by inhibiting protein syntheses, e.g. microlides, aminoglycosides, tetracyclines etc. Whilst not wishing to be bound by theory it is hypothesised that APIM peptides may function by inferring with protein interactions between the sliding clamp (e.g. the β-clamp in bacteria, such as E. coli and DNA polymerases and other proteins involved in DNA repair, including TLS polymerases. This is particularly surprising in view of the differences between the conserved motif that mediates the interactions between the β-clamp and polymerases in bacteria, QL[S/D]LF, and the APIM sequence. Thus, the antibacterial agents of the present invention may be particularly useful in combating diseases or conditions caused by MDR bacteria, because the agents act on a different part of the cellular machinery to which resistance mechanisms have not yet evolved. Moreover, the antibacterial agents of the present invention may interfere with the mechanisms associated with the acquisition of MDR.

The inventors have also determined that the peptides of the invention are particularly effective at combating bacterial biofilms. In general terms a biofilm is a collection, or community, of microorganisms, e.g. bacteria, surrounded by a matrix of extracellular polymers (also known in the art as a glycocalyx). These extracellular polymers are typically polysaccharides, notably polysaccharides produced by the organisms themselves, but they can contain other biopolymers as well. A biofilm will typically be attached to a surface, which may be inert or living, but it has also been observed that biofilms may form from microorganisms attached to each other or at any interface. Generally, therefore, a biofilm is characterised as a highly organised multi-cellular community of microorganisms, e.g. bacteria, encased in, or surrounded by, an extracellular polymer matrix, generally a polysaccharide matrix, and typically in close association with a surface or interface. Such a mode of growth is protective to the microorganisms, e.g., bacteria, and renders them difficult to remove or eradicate (for example, as discussed further below, recalcitrant or resistant to anti-bacterial agents or host defence or clearance mechanisms).

Biofilms cause significant commercial, industrial and medical problems, in terms of infections, contamination, fouling and spoilage etc., and thus the present invention provides a significant advantage in enabling or facilitating the combating of such biofilms, including both reducing or preventing their formation, and rendering them more susceptible to removal or reduction, e.g. more susceptible to the effect of anti-bacterial agents (including disinfectants or antibiotics) or indeed in the case of an infection, to the immune response of the infected host. The efficacy of anti-bacterial agents, both therapeutic and non-therapeutic and including particularly antibiotics, may thus be enhanced.

Biofilms are found ubiquitously on a wide variety of surfaces or interfaces (e.g. water/solid and water/gas (for example water/air) interfaces) if conditions conducive to bacterial colonisation exist. Basically a biofilm will form wherever there are bacteria and an interface or surface, particularly a surface exposed to water or moisture and biofilms are now recognised as the natural state of bacterial growth on such surfaces or interfaces.

The bacteria in a biofilm community display properties at the cellular level (phenotype) that are not shared by their planktonic (free-floating) equivalents. In fact, it is believed that bacteria in a biofilm are profoundly different from planktonic free-floating cells. Further differences can also be observed at the community level and are attributed to the effects of the extracellular matrix. Perhaps most notable is the commonly observed phenomenon that bacteria in a biofilm environment do not display the same susceptibilities to anti-bacterial agents, e.g., antibiotics and microbicides, and host immune defences or clearance mechanisms.

It is now becoming evident and increasingly documented that biofilms may form in the case of bacterial infections i.e. within or on an infected host. Thus biofilm formation may also occur on a "physiological" or "biological" surface, that is on an animate or biotic surface, or a surface on or in an infected host organism (e.g., a human or non-human animal subject), for example on an internal or external body or tissue surface. Such biofilm formation (or infection) on body tissues is increasingly believed to contribute to various infective diseases, including for example native valve endocarditis (mitral, aortic, tricupsid, pulmonic heart valves), acute otitis media (middle ear), chronic bacterial prostatitis (prostate), cystic fibrosis (lungs), pneumonia (respiratory tract), periodontitis (tissues supporting the teeth, e.g. gingiva, periodontal ligament, alvelor bone).

Biofilm niches are also present when medical devices are implanted and the formation of biofilm on such implanted ("in-dwelling") devices can lead to clinical problems with bacterial infection at such sites, such as prosthetic valve endocarditis and device-related infection, for example with intrauterine devices, contact lenses, prostheses (e.g. prosthetic joints) and at catheterisation sites, for example with central venous or urinary catheters.

A significant problem and risk with such biofilm infections is that bacteria (or more particularly microcolonies) may break off or detach from the biofilm, and enter other tissues, including significantly the circulation. Such circulating biofilm-derived bacteria can cause further infections and lead to significant clinical problems, particularly as the detached circulating bacteria may have all the resistance characteristics of the parent community.

Body or tissue surfaces which are dead or damaged (e.g., necrotic or inflamed) are particularly susceptible to biofilm infection. Wounds are susceptible to infection and biofilm formation can occur in wounds that do not heal in a short amount of time. Wounds are an ideal environment for the formation of biofilms due to their susceptibility to bacterial colonisation and the availability of substrate and surface for biofilm attachment. Problematically, infection of a wound often delays healing further and thus renders that wound more susceptible to biofilm formation and established infection. Wounds in which healing is delayed (so called chronic wounds) represent sites of particular concern with respect to biofilm formation. However, evidence is increasingly growing that both chronic and acute wounds may be sites of biofilm infection, with evidence of diverse bacterial communities or populations in wounds, particularly chronic wounds, including anaerobic bacteria within chronic wounds.

Biofilm based infection is very difficult to treat and biofilm contamination is very difficult to eradicate. Given the widespread occurrence of biofilms and the medical, environmental, industrial or other commercial problems they cause, any means of improving or enabling the combating of biofilms would be very important, both clinically and commercially. A need therefore exists for new methods of combating biofilms, both in clinical and industrial or commercial situations.

As noted above, it has been found that the peptides of the invention are effective as anti-biofilm agents, e.g., capable of inhibiting or preventing the formation of (bacterial) biofilms. Accordingly, the present invention may be seen also to provide new methods and means for combating (bacterial) biofilm, in vitro (e.g. on a product, material, device or implant), in vivo (e.g. at a wound site, including a surgical wound, a implant site etc.), or ex vivo.

Thus, at is broadest, the invention can be seen to provide a method of treating or preventing a bacterial infection, more particularly a bacterial infectious disease or a disease or condition exacerbated or caused by a bacterial infection, said method comprising administering (particularly administering an effective amount of) an agent comprising or encoding a peptide comprising an APIM motif (particularly a peptide containing a linger or extended APIM sequence) or a composition (e.g. a pharmaceutical composition) containing an agent comprising encoding a peptide comprising an APIM motif (particularly a peptide containing a longer or extended APIM sequence) to a subject in need thereof.

Thus, the invention provides an agent comprising or encoding a peptide comprising an APIM motif (particularly a peptide containing a longer or extended APIM sequence) or a composition (e.g. a pharmaceutical composition) containing an agent comprising or encoding a peptide comprising an APIM motif (particularly a peptide containing a longer or extended APIM sequence), for use in treating or preventing a bacterial infection, more particularly a bacterial infectious disease or a disease or condition exacerbated or caused by a bacterial infection.

In another aspect, there is provided the use of an agent comprising or encoding a peptide comprising an APIM motif (particularly a peptide containing a longer or extended APIM sequence) in the manufacture of a medicament for the treatment or prevention of a bacterial infection, more particularly a bacterial infectious disease or a disease or condition exacerbated or caused by a bacterial infection.

More particularly, the invention provides a method of treating or preventing a bacterial infection, more particularly a bacterial infectious disease or a disease or condition exacerbated or caused by a bacterial infection, said method comprising administering (particularly administering an effective amount of) an agent or a composition (e.g. a pharmaceutical composition) containing an agent to a subject need thereof, wherein said agent comprises:

(i) an oligopeptidic compound comprising a PCNA interacting motif and a domain that facilitates the cellular uptake of said compound,
wherein the PCNA interacting motif is $X_1X_2X_3X_4X_5X_6$ (SEQ ID NO: 1) and wherein
  $X_1$ is a basic amino acid;
  $X_2$ is an aromatic amino acid;
  $X_3$ is an aromatic amino acid or a hydrophobic amino acid that has an R group comprising at least three carbon atoms;
  $X_4$ is an uncharged amino acid other than an aromatic amino acid, Glycine (G) and Proline (P);
  $X_5$ is any amino acid other than an acidic amino acid or are aromatic amino acid; and
  $X_6$ is any amino acid other than an acidic amino acid or an aromatic amino acid, preferably a basic amino acid or Proline (P),
wherein when $X_3$ is not an aromatic amino acid, $X_5$ is not lysine (k) and $X_6$ is a basic amino acid or Proline (P); or
  ii) a nucleic acid molecule comprising a sequence encoding the oligopeptidic compound of (i).

In another aspect, there is provided an agent or a composition (e.g., a pharmaceutical composition) containing an agent for use in treating or preventing a bacterial infection, more particularly a bacterial infectious disease or a disease or condition exacerbated or caused by a bacterial infection, wherein said agent comprises:

(i) an oligopeptidic compound comprising a PCNA interacting motif and a domain that facilitates the cellular uptake of said compound,
wherein the PCNA interacting motif is $X_1X_2X_3X_4X_5X_6$ (SEQ ID NO: 1) and wherein:
  $X_1$ is a basic amino acid;
  $X_2$ is an aromatic amino acid;
  $X_3$ is an aromatic amino acid or a hydrophobic amino acid that has an R group comprising at least three carbon atoms;
  $X_4$ is an uncharged amino acid other than an aromatic amino acid, Glycine (G) and Proline (P);
  $X_5$ is any amino acid other than an acidic amino acid or an aromatic amino acid; and
  $X_6$ is any amino acid other than an acidic amino acid or an aromatic amino acid, preferably a basic amino acid or Proline (P),
wherein when $X_3$ is not an aromatic amino acid, $X_5$ is not lysine (K) and is a basic amino acid or Proline (P), or
  (ii) a nucleic acid molecule comprising a sequence encoding the oligopeptidic compound of (i).

In a further aspect, there is provided the use of an agent in the manufacture of a medicament for the treatment or prevention of a bacterial infection, more particularly a bacterial infectious disease or a disease or condition exacerbated or caused by a bacterial infection, wherein said agent comprises:

(i) an oligopeptidic compound comprising a PCNA interacting motif and a domain that facilitates the cellular uptake of said compound,
wherein the PCNA interacting motif is $X_1X_2X_3X_4X_5X_6$ (SEQ ID NO: 1) and wherein:
  $X_1$ is a basic amino acid;
  $X_2$ is an aromatic amino acid:
  $X_3$ is an aromatic amino acid or a hydrophobic amino acid that has an R group comprising at least three carbon atoms;
  $X_4$ is an uncharged amino acid other than an aromatic amino acid, Glycine (G) and Proline (P):
  $X_5$ is any amino acid other than an acidic amino acid or an aromatic amino acid; and
  $X_6$ is any amino acid other than an acidic amino acid or an aromatic amino acid, preferably a basic amino acid or Proline (P),
wherein when $X_3$ is not an aromatic amino acid, $X_5$ is not lysine (K) and $X_6$ is a basic amino acid or Proline (P); or
  (ii) a nucleic acid molecule comprising a sequence encoding the oligopeptidic compound of (i).

In particular embodiments the invention provides a method of treating or preventing a bacterial infection, said method comprising administering an agent, or a composition containing an agent, to a subject in need thereof, wherein said agent comprises:

(i) an oligopeptidic compound comprising a PCNA interacting motif and a domain that facilitates the cellular uptake of said compound, wherein the PCNA interacting motif is $X_1X_2X_3X_4X_5X_6$ (SEQ ID NO: 1) and wherein:

$X_1$ basic amino acid;

$X_2$ is an aromatic amino acid;

$X_3$ is an aromatic amino acid or a hydrophobic amino acid that has an R group comprising at least three carbon atoms;

$X_4$ is an unchanged amino acid other than an aromatic amino acid, Glycine (G) and Proline (P);

$X_5$ is any amino acid other than an acidic amino acid or an aromatic amino acid; and $X_6$ is any amino acid other than an acidic amino acid or an aromatic amino acid, preferably a basic amino acid or Proline (P), wherein when $X_3$ is not an aromatic amino acid, $X_5$ is not lysine (K) and $X_6$ is a basic amino acid or Proline (P); or (ii) a nucleic acid molecule comprising a sequence encoding the oligopeptidic compound of (i).

In a further embodiment, the invention provides an agent, or a composition containing an agent, for use in treating or preventing a bacterial infection in a subject, wherein said agent comprises:

(i) an oligopeptidic compound comprising a PCNA interacting motif and a domain that facilitates the cellular uptake of said compound, wherein the PCNA interacting motif is $X_1X_2X_3X_4X_5X_6$ (SEQ ID NO: 1) and wherein:

$X_1$ is a basic amino acid;

$X_2$ is an aromatic amino acid;

$X_3$ is an aromatic amino acid or a hydrophobic amino acid that has an R group comprising at least three carbon atoms;

$X_4$ is an unchanged amino acid other than an aromatic amino acid, Glycine (G) and Proline (P);

$X_5$ is any amino acid other than an acidic amino acid or a aromatic amino acid; and $X_6$ is any amino acid other than an acidic amino acid or an aromatic amino acid, preferably a basic amino acid or Proline (P), wherein when $X_3$ is not an aromatic amino acid, $X_5$ is not lysine (K) and $X_6$ is a bas amino acid or Proline (P); or (ii) a nucleic acid molecule comprising a sequence encoding the oligopeptidic compound of (i).

In still further embodiments, the invention provides the use of an agent in the manufacture of a medicament for the treatment or prevention of a bacterial, infection in a subject, wherein said agent comprises:

(i) an oligopeptidic compound comprising a PCNA interacting motif and a domain that facilitates the cellular uptake of said compound, wherein the PCNA interacting motif is $X_1X_2X_3X_4X_5X_6$ (SEQ ID NO: 1) and wherein:

$X_1$ is a basic amino acid;

$X_2$ is an aromatic amino acid;

$X_3$ is an aromatic amino acid or a hydrophobic amino acid that has an R group comprising at least three carbon atoms;

$X_4$ is an unchanged amino acid other than an aromatic amino acid, Glycine (G) and Proline (P);

$X_5$ is any amino acid other than an amino acid an aromatic amino acid; and $X_6$ is any amino acid other than acidic amino acid or an aromatic amino acid, preferably basic amino acid or Proline (P), wherein when $X_3$ is not an aromatic amino acid, $X_5$ is not lysine (K) and $X_6$ is a basic amino acid or Proline (P); or (ii) a nucleic acid molecule comprising a sequence encoding the oligopeptidic compound of (i).

As noted above, in some embodiments the agent may be used in combination with one or more additional active agents, e.g. a cytostatic or cytotoxic agent, in order to enhance the effect of that additional active agent, or to sensitise cells to the effect of said additional active agent, e.g. cytostatic or cytotoxic agent. However, in some embodiments, the agent as defined herein may be used alone, i.e., as the only active agent capable of preventing or inhibiting bacterial growth (e.g. having anti-bacterial activity) in a composition and/or medicament.

Accordingly, in yet another aspect, there is provided a method of treating or preventing a bacterial infection, more particularly a bacterial infectious disease or a disease or condition exacerbated or caused by a bacterial infection, said method comprising administering an agent or composition as defined herein, and separately, simultaneously or sequentially administering of one or more additional active agents, e.g. a cytostatic or cytotoxic agent, to a subject in need thereof.

Alternatively viewed, there is provided an agent or composition as defined herein for use in combination with one or more additional active agents, e.g., a cytostatic or cytotoxic agent, in the treatment or prevention of a bacterial infection, more particularly a bacterial infectious disease or a disease or condition exacerbated or caused by a bacterial infection.

Thus, there is provided the use of an agent as defined herein in the manufacture of a medicament for use in combination with one or more additional active agents, e.g. a cytostatic or cytotoxic agent, in the treatment or prevention of a bacterial infection, more particularly a bacterial infectious disease or a disease or condition exacerbated or caused by a bacterial infection.

In a particular embodiment, the invention provides a method of treating or preventing a bacterial infection, said method comprising administering an agent or composition as defined herein, and separately, simultaneously or sequentially administering of one or more additional active agents, e.g. a cytostatic or cytotoxic agent, to a subject in need thereof.

Alternatively viewed, there is provided an agent or composition as defined herein for use in combination with one or more additional active agents, e.g. an antibiotic, in the treatment or prevention of a bacterial infection.

Thus, there is provided the use of an agent as defined herein in the manufacture of a medicament for use in combination with one or more additional active agents, e.g. an antibiotic, in the treatment or prevention of a bacterial infection.

Thus, in one embodiment the medicament may further comprise one or more additional active agents, such as a cytostatic or cytotoxic agent, e.g. an antibiotic.

The medicament may be in the form of a single composition comprising both the agent as defined herein and the one or more additional active agents, e.g. cytostatic or cytotoxic agent, or it may be in the form of a kit or product containing them for separate (e.g. simultaneous or sequential) administration.

There is thus also provided the use of an agent as defined herein in the manufacture of a medicament for the treatment or prevention of a bacterial infection, more particularly a bacterial infectious disease or a disease or condition exacerbated or caused by a bacterial infection, wherein the medicament is administered separately, simultaneously or sequentially with one or more additional active agents, e.g. a cytostatic or cytotoxic agent.

In another aspect, the invention provides a product containing an agent as defined herein together with one or more additional active agents, e.g. a cytostatic or cytotoxic agent, as a combined preparation for separate, simultaneous or sequential use in the treatment or prevention of a bacterial infection, more particularly a bacterial infectious disease or a disease or condition exacerbated or caused by a bacterial infection.

In still further embodiments, there is provided the use of an agent as defined herein in the manufacture of a medicament for the treatment or prevention of a bacterial infection, wherein the medicament is administered separately. simultaneous or sequentially with one or more additional active agents e.g. an antibiotic.

In another aspect, the invention provides a product containing an agent as defined herein together with one or more additional active agents, e.g. an antibiotic, as a combined preparation for separate, simultaneous or sequential use in the treatment or prevention of a bacterial infection.

The agent as defined herein may be used to modulate or potentiate the effect of one or more additional active agents, e.g. cytostatic or cytotoxic agent. For instance, the agent may sensitize the bacterial cell to the one or more additional active agents, e.g. a cytostatic or cytotoxic agent, e.g., antibiotic. Alternatively viewed, the one or more additional active agents, such as a cytostatic or cytotoxic agent, may enhance, augment or improve the anti-bacterial effect of the agent defined herein. Thus, the agents defined herein may have the advantage of enabling lower doses of anti-bacterial agents to be effective and/or improving the efficacy of anti-bacterials against resistant strains.

In some embodiments the agent may be used in combination with DNA damaging radiation, e.g. UV radiation, in order to enhance the effect of the radiation, or to sensitize cells to the effect of said radiation, e.g., UV radiation.

UV radiotherapy (also known as UV radiation therapy or UV light therapy), may be used in the treatment of various bacterial infections. By "UV radiotherapy" is meant the use of UV radiation, preferably UVC radiation, i.e. radiation with a wavelength of 200 nm to 290 nm.

Unfortunately UV radiotherapy is often unsuccessful at completely eradicating bacterial cells from a patient because it is often not possible to deliver a sufficiently high dose of local radiation to kill bacterial cells without an unacceptably high risk of damage to the surrounding normal tissue at the site of infection. It is also known that bacterial cells show widely varying susceptibilities to radiation-induced cell death and ionizing radiation may only inhibit further cell growth, rather than eradicating the bacterial cells as such. Thus, there is a need to enhance the efficacy of radiotherapy by sensitizing bacterial cells to the effects of ionizing UV radiation.

Accordingly, the agents and compositions of the invention may be used to provide such a sensitizing effect, in other words to enhance (or alternatively put to increase, augment, or potentiate) the effects of UV radiotherapy, particularly UVC radiotherapy, or to render bacterial cells, which may be present in an infection site in a subject, more susceptible to the effects of radiotherapy. Thus, they may find utility in any anti-bacterial application where radiotherapy is used. This may include any situation where it is desired to kill, inhibit or eradicate bacterial cells, e.g. at an infection site or in vitro.

The agents and compositions of the invention may thus be used as sensitizer of bacterial cells, to the effects of UV radiation. By "sensitizer" is meant the use of the agents and compositions of the invention to enhance the effect of UV radiation on bacterial cells. This may be achieved by the inhibition of the endogenous cellular DNA repair mechanisms, e.g. the TLS pathway.

Thus, the present invention encompasses an agent, or a composition containing an agent, for use as a sensitizer for UV radiotherapy in the treatment or prevention of a bacterial infection in a subject, or in the treatment or prevention of a bacterial infection in subject which involves UV radiotherapy (e.g. UVC radiotherapy), wherein said agent comprises:

(i) an oligopeptidic compound comprising a PCNA interacting motif and a domain that facilitates the cellular uptake of said compound, wherein the PCNA interacting motif is $X_1X_2X_3X_4X_5X_6$ (SEQ ID NO: 1) and wherein:

$X_1$ is a basic amino acid;

$X_2$ is an aromatic amino acid;

$X_3$ is an aromatic amino acid or a hydrophobic amino acid that has an R group comprising at least three carbon atoms;

$X_4$ is an uncharged amino acid other than an aromatic amino acid, Glycine (G) and Proline (P);

$X_5$ is any amino acid other than an acidic amino acid or an aromatic amino acid; and $X_6$ is any amino acid other than an acidic amino or an aromatic amino acid, preferably a basic amino acid or Proline (P), wherein when $X_3$ is not an aromatic amino acid, $X_5$ is not lysine (K) and $X_6$ is a basic amino acid or Proline (P); or (ii) a nucleic acid molecule comprising a sequence coding the oligopeptidic compound of (i).

In further embodiments, the methods of treatment defined above may comprise UV radiotherapy (e.g. UVC radiotherapy), which may be administered simultaneously, sequentially or separately to said agent or composition.

It will be evident that therapies involving the administration of UV radiation (UV radiotherapy) may be particularly useful for the treatment of topical infections, e.g. infections of the skin or mucosal membranes, such as the oral cavity, oesophagus and/or eye. Thus, in some embodiments, the agent or composition for use as a sensitizer for UV radiation, or for use in methods comprising UV radiotherapy, may be formulated for topical administration, e.g. to the skin and/or muscosal membrane. However, the invention is not limited to this aspect, as the agents and compositions of the invention may be combined with UV radiation to treat infections by other means, e.g. endoscopically or ex vivo. For instance, a blood infection may be treated by administering the agent or composition of the invention to a subject and subsequently or contemporaneously irradiating the blood of said subject by circulating the blood through an external tube exposed to UV radiation, i.e. akin to a dialysis machine.

The agents and compositions as defined herein thus have a therapeutic utility in any condition or clinical situation where it is desirable (or where it may be of benefit) to prevent or inhibit the growth of bacterial cells.

A bacterial infection includes any bacterial infectious disease or a disease or condition exacerbated or caused by a bacterial infection. However, as noted above, bacterial infections do not always result in, or progress to, a disease or disease state. Thus, in some embodiments, a bacterial infection may be viewed specifically as a bacterial infection that is not associated with a disease or condition. Hence, the above therapeutic uses and methods may be viewed as the treatment or prevention of an atypical, unwanted, undesirable, excessive and/or harmful bacterial infection and/or a bacterial infectious disease or a disease or condition exacerbated or caused by a bacterial infection.

Thus, in yet another embodiment, the agent or composition as define herein may be used as an anti-bacterial agent in in vitro or ex vivo methods, e.g. in methods of cell culture or where the agent is used in the context of an abiotic or inanimate setting, e.g. to treat an inanimate surface to prevent, inhibit or reduce bacterial colonisation and/or growth, e.g. for decontamination, antiseptic or sterilisation purposes, or is applied to or contacted with a surface, material, substrate, product, device or system susceptible to bacterial growth, e.g. contamination, such as in the preparation of a medical device or implant.

Thus, the invention also provides an in vitro or ex vivo method of administering an agent or composition as defined herein to a bacterial cell or cell culture, i.e. to inhibit or prevent the growth of one or more bacteria. This may allow the identification and/or characterisation of agents as defined, e.g. to determine the dose at which the agent is effective or determine which bacteria are particularly susceptible. Furthermore, the in vitro methods may be useful to identify other anti-bacterial compounds, e.g. compounds that are weakly anti-bacterial when used on their own, but which have useful anti-bacterial activity when used in combination with the agent of the invention. Alternatively viewed, the invention provides the use of an agent or composition as defined herein in in vitro or ex vivo methods, e.g. bacterial cell culture or in the context of an abiotic or inanimate setting, e.g. to treat an inanimate surface (or product or material etc., e.g., as listed above) to prevent, inhibit or reduce bacterial colonisation and/or growth, e.g., for decontamination, antiseptic or sterilisation purposes, or for application or administration to a surface or system (etc., as above) susceptible to bacterial growth, e.g. contamination.

Thus, in a particular embodiment, the invention provides an in vitro method of:
(i) preventing, inhibiting or reducing bacterial colonisation and/or growth in or on a surface, product or material; or
(ii) preventing, inhibiting or reducing unwanted or undesirable bacterial colonisation and/or growth of a bacterial cell,
comprising administering an agent or composition as defined herein to a surface, product or material susceptible to bacterial growth or a bacterial cell or a cell culture, optionally simultaneously, sequentially or separately administering one or more additional active agents to said surface, product or material, cell or cell culture.

In some embodiments, the method further comprises a step of exposing said surface, product or material to UV radiation, prior to, contemporaneously with, or after administering said agent or composition.

As noted above, the agent or composition as defined herein is used to prevent a bacterial infection or contamination, e.g. in circumstances where there is an increased probability of an infection, such as in surgery or in the treatment of a wound. Thus, in some embodiments the agent or composition as defined herein may be provided or administered via a product, device, implant or material to which the agent or composition has been applied, impregnated or chemically bonded. In this respect, the oligopeptidic compounds defined herein are commonly positively charged and such compounds will readily adhere to various surfaces without the need for additional adhesives. However, the use of adhesives or other methods of bonding the agents of the invention to products, devices, implants or materials is contemplated herein.

Hence, a further aspect of the invention comprises the provision of a product, material, device or implant which is coated, impregnated or chemically bonded with an agent or composition as described herein. The invention also extends to the use of such products, materials, devices or implants in the methods and uses as described herein.

Thus, yet another aspect of the invention comprises a method of producing product, material, device or implant (e.g. an aseptic product, material, device or implant) which is coated, impregnated or chemically bonded with an agent or composition as defined herein, comprising providing a product, material, device or implant and coating or impregnating said device with said agent or composition, or chemically bonding said agent or composition to said product, material, device or implant. Alternatively viewed, the invention may be seen to provide the use of an agent or composition as defined herein in the production of a product, material, device or implant, particularly in the production of an aseptic product, material, device or implant.

As discussed above, the agents and compositions of the invention may also be used to combat bacterial biofilms, including both on biotic and abiotic surfaces. Thus, the methods and uses discussed above may be for use in combating bacterial biofilm infection or to combat bacterial biofilm formation on inanimate surfaces e.g. for disinfection and cleaning purposes. Alternatively viewed, the bacterial infection or bacterial colonisation and/or growth may be a biofilm.

Thus, in some embodiments, the invention may provide a method of preventing or inhibiting the formation of a bacterial biofilm on a product, material, device or implant, said method comprising:
(i) providing a product, material, device or implant; and
(ii) coating or impregnating said device with said agent or composition, or chemically bonding said agent or composition to said product, material, device or implant.

Thus, in yet a further embodiment, the invention provides n oligopeptidic compound (an agent) (e.g. a peptide) comprising a PCNA interacting motif and a domain that facilitates the cellular uptake of said compound, wherein the PCNA interacting motif is $X_1X_2X_3X_4X_5X_6$ (SEQ ID NO: 1), wherein:
$X_1$ is a basic amino acid:
$X_2$ is an aromatic amino acid;
$X_3$ is an aromatic amino acid or a hydrophobic amino acid that has an R group comprising at least three carbon atoms:
$X_4$ is an uncharged amino acid other than an aromatic amino acid, Glycine (G) and Proline (P),
$X_5$ is any amino acid other than an acidic amino acid or an aromatic amino acid; and
$X_6$ is any amino acid other than an acidic amino acid or an aromatic amino acid, preferably a basic amino acid or Proline (P),
wherein when $X_3$ is not an aromatic amino acid, $X_5$ is not lysine (K) and basic amino acid or Proline (P).

In a further aspect, the invention provides a nucleic acid molecule encoding an oligopeptidic compound (e.g. a peptide) as defined above. Also provided is the complement of such a nucleic acid molecule. A further aspect relates to a vector comprising said nucleic acid molecule or complement, which is defined further below.

In order that the oligopeptidic compound, which is capable of interacting with PCNA, or its encoding nucleic acid, may function in the methods and uses of the invention, the compound must be capable of entering the cell, i.e. crossing the, cell membrane and cell wall, if present, into the cytosol (cytoplasm), and optionally into one or more other cellular locations, e.g. the nucleus. Whilst this may be achieved using any convenient mechanism, such as with a liposome, as noted above, the inventors have surprisingly and advantageously found that uptake of the oligopeptidic compound may be achieved by associating the oligopeptidic compound with one or more molecules that are known to be capable of facilitating the uptake of molecules into animal cells, e.g. an import peptide.

Thus, the inventors have determined that is it particularly advantageous to generate an oligopeptidic compound that comprises a domain that assists the transit of the compound across the cell membrane, i.e. to generate a fusion peptide or chimeric peptide (a peptide formed from two or more domains that are not normally found together in nature). For instance, a peptide comprising a cell membrane permeable motif, e.g. a cell penetrating peptide (an uptake or import peptide, or a peptide transduction domain). In some embodiments the fusion peptide (an oligopeptidic compound) may optionally comprise further sequences to facilitate the targeting of the peptide (i.e. to direct e peptide) to a particular sub-cellular location, e.g. a target peptide, signal peptide or transit peptide. Whilst not wishing to be bound by theory, it is thought that it is the specific combination of a domain capable of interacting with PCNA and a domain that facilitates the uptake of the oligopeptidic compound that results in the anti-bacterial properties of the oligopeptidic compounds disclosed herein.

As the oligopeptidic compound comprises a PCNA interacting motif and a domain that facilitates its uptake, it will be evident that the compound comprises at least 6 residues and the final size of the compound will be dependent on the size and number of the domains that make up said compound, i.e. the PCNA interacting motif and uptake (import) peptide may be viewed as domains of the oligopeptidic compound. Thus, a domain may be viewed as a distinct portion (i.e. a sequence within the full-length peptidic sequence) of the oligopeptidic compound that can be assigned or ascribed a particular function or property.

In one embodiments, the oligopeptidic compound for use in the methods and uses of the invention comprises at least 2 domains, i.e. the PCNA interacting motif domain and the domain that facilitates the cellular uptake of said compound, e.g. uptake (import) peptide sequence domain. However, the oligopeptidic compound may comprise additional domains that may facilitate its function and/or stability, e.g. the capacity of the peptide to interact with its target, i.e. PCNA or an equivalent protein, such as the β-clamp protein from bacteria, e.g. E. coli. Thus, the oligopeptidic compound may comprise at least 2, 3, 4 or 5 domains, e.g. 6, 7, 8, 9, 10, 12, 15 or more domains. For example, in some embodiments the oligopeptidic compound may comprise one or more linker domains, i.e. a domain that interspaces between two other domains, i.e. occupies the space in between and connects two domains of the oligopeptidic compound. In further embodiments, the oligopeptidic compound may comprise a domain that is capable of directing the oligopeptidic compound to a cellular or subcellular location, e.g. signal peptide (also known as a target or transit peptide), such as a nuclear localization signal (NLS) sequence. In still further embodiments, the one or more linker domains may have an additional function, i.e., a linker domain may also function as a signal peptide, e.g. a NLS. Alternatively put, a signal peptide domain may function as a linker domain in some embodiments, e.g. an NLS sequence may be used as linker domain.

In an exemplary embodiment, the oligopeptidic compound may comprise a PCNA interacting motif domain, a domain that facilitates its cellular uptake (e.g. an uptake (import) peptide sequence domain) and a linker domain. In a further exemplary embodiment, the oligopeptidic compound may also comprise a nuclear localisation signal sequence domain. In still another embodiment the nuclear localization signal sequence domain may function as a linker domain.

Thus, it will be seen that in such embodiments the agent of the invention may take the form of a construct containing (i.e. comprising) an oligopeptidic compound which comprises a PCNA interacting motif as defined herein, together with a domain that facilitates its cellular uptake (e.g. an uptake peptide sequence) and optionally additional domains. In this aspect the invention may accordingly be seen to provide a construct comprising an oligopeptidic compound which is capable of interacting with PCNA.

As noted above the longer or extended PCNA motif of the invention has been determined to mediate the interaction of an oligopeptidic compound (e.g. peptide) or protein containing such a motif with PCNA. However, the inventors have unexpectedly determined that oligopeptidic compounds may containing a PCNA motif also interact with PCNA equivalent proteins, e.g., proteins that are functionally equivalent and/or structurally similar to PCNA, such as the β-clamp protein from bacteria, e.g., E. coli. Thus, it is thought that oligopeptidic compounds containing a PCNA motif (including the longer or extended PCNA motif defined herein) may interact with proteins in bacterial cells that are functionally equivalent to PCNA, but structurally distinct. In some instances, the oligopeptidic compounds may interact with proteins in bacterial cells that are structurally similar to PCNA, but functionally distinct. However, the compounds of the invention may be characterised insofar as they must be capable of interacting with PCNA, i.e. the oligopeptidic compounds of the invention and for use in the methods and uses of the invention must be competent and/or proficient PCNA interacting molecules. The PCNA protein used to determine the capacity and/or affinity of the oligopeptidic compound:PCNA interaction may be from any suitable source, e.g. a PCNA from any animal, particularly a mammal such as a human, rodent (e.g. mouse, rat) or any other non-human animal. In preferred embodiments, the oligopeptidic compound:PCNA interaction is determined, characterised or assessed using human PCNA protein.

The interaction may be direct or indirect, and may involve direct binding of the motif to the PCNA protein, or the motif may bind indirectiy, for example binding may be mediated by another molecule. This reference to "PCNA-interacting" or "PCNA-binding" can thus include any form of interaction, and both direct and indirect binding. Preferably the interaction is direct binding.

Any reference herein to a "motif" should be understood to mean $X_1X_2X_3X_4X_5X_6$ as defined herein.

$X_1$ is preferably selected from lysine (K), arginine (R), histidine (H), ornithine (Om), methyllysine (MeK), diaminobutyric acid (Dbu), citrulline (Cit), acetyllysine (AcK) and any suitable basic amino acid selected from the non-conventional amino acids in Table 2. Whilst the standard or conventional basic amino acids are preferred, e.g. K, R and H, particularly K and R, these may be substituted by any functionally equivalent non-conventional basic amino acid.

$X_2$ is preferably selected from phenylalanine (F), tryptophantyrosine (Y), tert-butylglycine, cyclohexylalanine, tert-butylphenylalanine, biphenylalenine and tri tert-butyltyptophan (in certain embodiments this list may exclude W). Whilst the standard and conventional aromatic amino acids are preferred, e.g. F, W and Y, these may be substituted by any functionally equivalent non-conventional aromatic amino acid, e.g. from Table 2. In some embodiments, $X_2$ may be selected from W and Y, F and Y, or F and W or in specific embodiments $X_2$ may be F or W or Y, or a functionally equivalent non-conventional aromatic amino acid.

The binding of the motif to PCNA may in certain embodiments be improved when $X_2$ is W or Y. Thus, in one embodiment, $X_2$ is not F. However, as indicated above, in other embodiments it may be F.

$X_3$ is preferably selected from phenylalanine (F), tryptophan (W), tyrosine (Y), tert-butylglycine, cyclohexylalanine, tert-butylphenylalanine, biphenylalenine and tri tert-butyltrotophan, leucine (L), isoleocine (I), valine (V), methionine (M), norteucine (Nor) (in certain embodiments this list may exclude W or L).

In some embodiments, is preferably an aromatic amino acid selected from phenylalanine (F), tryptophan (W), tyrosine (Y), tert-butylglycine, cyclohexylalanine, tert-butylphanylalanine, biphenylalenine and tri tert-butyltryptophan (in certain embodiments this list may exclude W). Whilst the standard or conventional aromatic amino acids are preferred, e.g. F, W and Y, these may be substituted by any functionally equivalent non-conventional aromatic amino acid, e.g. from Table 2. In some embodiments, $X_3$ may be selected from W and Y, F and Y, or F and W or in specific embodiments $X_3$ may be F, or W or Y, or functionally equivalent non-conventional aromatic amino acids.

In some embodiments, $X_3$ is preferably a hydrophobic amino acid with an R group containing at least 3 carbon atoms, particularly an aliphatic amino acid with an R group containing at least 3 carbon atoms. Thus, in some embodiments, $X_3$ may be selected from leucine (L), isoleucine (I), valine (V), methionine (M) or any suitable hydrophobic amino acid with an R group containing at least 3 carbon atoms selected from the non-conventional amino acids in Table 2. More particularly, $X_3$ may be selected from L, I, V, M or Nor and any suitable hydrophobic (preferably aliphatic) amino acid with an R group containing at least 3 carbon atoms selected from the non-conventional amino acids in Table 2.

Thus, in some embodiments, $X_3$ may be selected from L, I, V and M and preferably from L, I and V or I, V and M and optionally non-conventional functional equivalents thereof.

$X_4$ is preferably a hydrophobic or polar amino acid, particularly an aliphatic amino acid or polar amino acid. Thus, in some embodiments, $X_4$ may be selected from leucine (L), isoleucine (I), valine (V), alanine (A) methionine (M), nodeucine (Nor), serine (S), threonine (T), glutamine (Q), aspargine (N) or cysteine (C) or any suitable hydrophobic or polar amino acid selected from the non-conventional amino acids in Table 2. More particularly, $X_4$ may be selected from L, I, V, A, M, Nor, S or T and any suitable hydrophobic (preferably aliphatic) or polar (preferably a polar amino acid that does not contain an amine group ($NH_2$) in the R-group) amino acid selected from the non-conventional amino acids in Table 2. Preferably, $X_4$ is not N or Q or a non-conventional functional equivalent thereof and/or in certain embodiments $X_4$ is not M, S and/or T or a non-conventional functional equivalent thereof. $X_4$ may not be glycine (G) or proline (P) and this limitation is also intended to exclude non-conventional functional equivalents thereof.

Thus, in some embodiments, $X_4$ may be selected from L, I, A, V, M, S and T, and preferably from L, I, A, V, S and T and optionally non-conventional functional equivalents thereof.

In some embodiments, $X_4$ may be a hydrophobic, and more preferably an aliphatic amino acid. Thus, in some embodiments, $X_4$ may be selected from L, I, A, V, M, and preferably from L, I, V and A and optionally non-conventional functional equivalents thereof.

$X_5$ is preferably a hydrophobic, polar, basic or thiol-containing amino acid or proline. Thus, in some embodiments $X_5$ an aliphatic amino acid or a polar amino acid. In some preferred embodiments, the polar amino acid does not contain an amine group ($NH_2$) in the R-group. Thus, $X_5$ preferably may be selected from L, I, V, A, M, Nor, S, T, Q, N, H, K, R, G, C or P and any suitable hydrophobic (preferably aliphatic) or polar (preferably a polar amino acid that does not contain an amine group ($NH_2$) in the R-group), basic or thiol-containing amino acid selected from the non-conventional amino acids in Table 2. In some embodiments, $X_5$ is an uncharged amino acid other than an aromatic amino acid, as defined in $X_4$. Thus, in some embodiments, the basic amino acid may be selected from the amino acids as defined in $X_1$ although in some embodiments, e.g. where $X_3$ is not an aromatic amino acid, e.g. when $X_3$ is L, $X_5$ is not K. In certain embodiments $X_5$ is not C or a non-conventional functional equivalent thereof and/or N or Q or a non-conventional functional equivalent thereof. In certain embodiments $X_5$ is not H and preferably $X_5$ is not R, K or H or a non-conventional functional equivalent thereof. In still further embodiments $X_5$ is not S or T or a non-conventional functional equivalent thereof. In some embodiments, $X_5$ is not P, $X_5$ may not be an aromatic amino acid (as defined in $X_2$) or acidic amino acid, e.g. aspartic acid (D) or glutamic acid (E), and this limitation is also intended to exclude non-conventional functional equivalents thereof.

Thus, in some embodiments, $X_5$ may be selected from L, V, I, A, M, S, T and G, and preferably from L, V, A, I, S and T and optionally non-conventional functional equivalents thereof.

In other embodiments, $X_5$ may be a hydrophobic amino acid, and more preferably an aliphatic amino acid or G. Thus, in some embodiments, $X_5$ may be selected from L, I, A, V, M, and G and preferably from L, V, I and A and optionally non-conventional functional equivalents thereof.

$X_6$ may be a hydrophobic, polar, basic or thiol-containing amino acid or proline as defined above with respect to $X_5$. However, as noted above, $X_5$ may not be a hydrophobic, polar or thiol-containing amino acid when $X_3$ is not an aromatic amino acid. Alternatively viewed, $X_5$ may be a hydrophobic, polar thiol-containing amino acid only when $X_3$ is an aromatic amino acid. Thus, in some embodiments, $X_6$ is preferably a basic amino acid or proline and may be selected from K, R, H, Om, MeK, Dbu, Cit, AcK, P and any functionally equivalent amino acid selected from the non-conventional amino acids in Table 2. Whilst the standard or conventional amino acids are preferred, e.g. K, R, H and P, particularly K, R and H, e.g. K and R, these may be substituted by any functionally equivalent non-conventional basic amino acids.

Thus, in some embodiments $X_6$ is a basic amino acid, preferably selected from K, R and H and optionally non-conventional functional equivalents thereof.

Thus, in some embodiments $X_4$ and/or $X_5$ is a polar amino acid. Accordingly, in certain embodiments only one of $X_4$ and $X_5$ is a polar amino acid.

In some embodiments $X_5$ and/or $X_6$ is a basic amino acid. Accordingly in certain embodiments $X_6$ is a basic amino acid.

In some embodiments, $X_4$ and $X_5$ are both uncharged amino acid other than an aromatic amino acid.

In still further embodiments, $X_2$ and $X_3$ are both aromatic amino acids, but preferably are not both W, as described further below.

A functionally equivalent amino acid may be defined as an amino acid that may be used as a substitute in a peptide or protein for a conventional, amino acid without affecting significantly the function of the peptide or protein (or an amino acid that would not be expected to affect or alter significantly the function of the peptide or protein), e.g. an amino acid that has similar structural and/or chemical properties to the conventional amino acid. Thus, a functionally equivalent amino acid may be viewed as having the base structure of a standard amino acid, with a non-standard non-conventional R-group that is structurally and/or chemically similar to the standard R-group. Preferably, the R-group is structurally similar to the standard R-group of the amino acid being substituted.

A conventional or standard amino acid is an amino acid that is used in vivo to produce a polypeptide or protein molecule, i.e. a proteinogenic amino acid. In other words, an amino acid with a standard or conventional R-group or an amino acid which possesses a side chain that is coded for by the standard genetic code, i.e. "coded amino acids".

Thus, the invention provide an oligopeptidic compound comprising the motif [R/K/H]-[W/F/Y]-[W/F/Y/L/I/V/M]-[L/I/V/A/M/S/T/N/Q/C]-[L/I/V/A/M/G/S/T/N/Q/R/H/K/C/P]-[K/R/H/P/L/I/V/A/M/G/S/T/N/Q/C] (SEQ ID NO: 2), wherein when the third amino acid ($X_3$) is L (e.g. $X_3$ is not an aromatic amino acid), the fifth amino acid ($X_5$) is not K, wherein when $X_3$ is not an aromatic amino acid, the sixth amino acid ($X_6$) is a K, R, H or P and wherein said oligopeptidic compound is capable of interacting with PCNA.

Accordingly, in some embodiments the motif maybe defined as:

[R/K/H]-[W/F/Y]-[L/I/V/M]-[L/I/V/A/M/S/T/N/Q/C]- (SEQ ID NO: 3)

[L/I/V/A/M/G/S/T/N/Q/R/H/C/P]-[K/R/H/P].

In another embodiment be defined as:

[R/K/H]-[W/F/Y]-[L/I/V/M]-[L/I/V/A/M/S/T]- (SEQ ID NO: 4)

[L/I/V/A/M/G/S/T/N/Q/R/H]-[K/R/H/P].

In another embodiment the motif may be defined as:

[R/K/H]-[W/F/Y]-[L/I/V/M]-[L/I/V/A/M/S/T]- (SEQ ID NO: 5)

[L/I/V/A/M/G/S/T/N/Q/R/H]-[K/R/H].

In another embodiment the motif may be define as:

[R/K/H]-[W/F/Y]-[L/I/V/M]-[L/I/V/A/M/S/T]-[L/I/V/ (SEQ ID NO: 6)

A/M/G/S/T/R]-[K/R/H].

In another embodiment the motif may be defined as:

[R/K/H]-[W/F/Y]-[L/I/V/M]-[L/I/V/A/M/S/T]-[L/I/V/ (SEQ ID NO: 7)

A/M/G/S/T]-[K/R/H].

In another embodiment the motif may be defined as:

[R/K]-[W/F/Y]-[L/I/V/M]-[L/I/V/A/M/S/T]-[L/I/V/ (SEQ ID NO: 8)

A/M/G/S/T]-[K/R].

In another embodiment the motif may be defined as:

[R/K]-[W/F]-[L/I/V/M]-[L/I/V/A/M/S/T]-[L/I/V/A/M/ (SEQ ID NO: 9)

G/S/T]-[K/R].

In another embodiment the motif may be defined as:

[R/K]-[W/F]-[L/I/V/M]-[L/I/V/A/M/T]-[L/I/V/A/M/G/ (SEQ ID NO: 10)

S/T]-[K/R].

In another embodiment the motif may be defined as:

[R/K]-[W/F]-[L/I/V/M]-[L/I/V/A/M/T]-[L/I/V/A/M/S/ (SEQ ID NO: 11)

T]-[K/R].

In another embodiment the motif may be defined as:

[R/K]-[W/F]-[L/I/V/M]-[L/I/V/A/M/S/T]-[L/I/V/A/M/ (SEQ ID NO: 12)

G]-[K/R].

In another embodiment the motif may be defined as:

[R/K]-[W/F]-[L/I/V/M]-[L/I/A/V/M/T]-[L/I/V/A/M/S/ (SEQ ID NO: 13)

T]-[K/R].

In another embodiment the motif may be defined as:

[R/K]-[W/F]-[L/I/V/M]-[L/I/V/A/M/S/T]-[L/V/A/I/S/ (SEQ ID NO: 14)

T]-[K/R].

In another embodiment the motif may be defined as:

[R/K]-[W/F]-[L/I/V/M]-[L/V/I/A/T]-[L/V/A/I/S/T]- (SEQ ID NO: 15)

[K/R].

In another embodiment the motif may be defined as:

[R]-[W/F/Y]-[L/I/V/M]-[L/V/I/A]-[L/V/A/S/T/M]- (SEQ ID NO: 16)

[K/R].

In another embodiment the motif may be defined as:

[R]-[W/F/Y]-[L/I/V/M]-[L/V/I/A/T]-[L/V/A/S/T/M]- (SEQ ID NO: 17)

[K].

In another embodiment the motif may be defined as:

[R/K]-[F/Y]-[L/I/V/M]-[L/V/I/A]-[L/V/A/I/M]-[K/R]. (SEQ ID NO: 18)

In another embodiment the motif may be defined as:

[R/K]-[F/W/Y]-[L/I/V/M]-[L/I/V/A]-[L/I/V/A]-[K/R]. (SEQ ID NO: 19)

In yet another embodiment the motif may be defined as:

[R/K]-[W/Y]-[L/I/V/M]-[L/V/I/A/S/T]-[L/V/A/S/T/M]-[K/R]. (SEQ ID NO: 20)

In yet another embodiment the motif may be defined as:

[K]-[F/Y/W]-[L/I/V/M]-[L/V/I/A/T]-[L/V/A/I/S/T/M]-[K]. (SEQ ID NO: 21)

In another embodiment the motif may be define as:

[R/K]-[W/F]-[L/I/V]-[L/V/I/A/T]-[L/V/A/I/S/T]-[K/R]. (SEQ ID NO: 1221)

In another embodiment the motif may be defined as:

[R]-[W/F/Y]-[L/I/V]-[L/V/I/A]-[L/V/A/S/T/M]-[K/R]. (SEQ ID NO: 1222)

In another embodiment the motif may be defined as:

[R]-[W/F/Y]-[L/I/V]-[L/V/I/A/T]-[L/V/A/S/T/M]-[K]. (SEQ ID NO: 1223)

In another embodiment the motif may be defined as:

[R/K]-[F/Y]-[L/I/V]-[L/V/I/A]-[L/V/A/I/M]-[K/R]. (SEQ ID NO: 1224)

In another embodiment the motif may be defined as:

[R/K]-[F/W/Y]-[L/I/V]-[L/I/V/A]-[L/I/V/A]-[K/R]. (SEQ ID NO: 1225)

In yet another embodiment the motif may be defined as:

[R/K]-[W/Y]-[L/I/V]-[L/V/I/A/S/T]-[L/V/A/S/T/M]-[K/R]. (SEQ ID NO: 1226)

In yet another embodiment the motif may be defined as:

[K]-[F/Y/W]-[L/I/V]-[L/V/I/A/T]-[L/V/A/I/S/T/M]-[K]. (SEQ ID NO: 1227)

In still further embodiments may be defined as:

[R/K/H]-[W/F/Y]-[W/F/Y]-[L/I/V/A/M/S/T/N/Q]-[L/I/V/A/M/G/S/T/N/Q/R/H/K]-[K/R/H/P/L/I/V/A/M/G/S/T/N/Q/C]. (SEQ ID NO: 1228)

In another embodiment the motif may be defined as:

[R/K/H]-[W/F/Y]-[W/F/Y]-[L/I/V/A/M/S/T]-[L/I/V/A/M/G/S/T/N/Q/R/H/K]-[K/R/H/P/L/I/V/A/M/G/S/T/N/Q/C]. (SEQ ID NO: 1229)

In another embodiment the motif may be defined as:

[R/K/H]-[W/F/Y]-[W/F/Y]-[L/I/V/A/M/S/T]-[L/I/V/A/M/G/S/T/N/Q/R/H/K]-[K/R/H/P/L/I/V/A/M/G/S/T]. (SEQ ID NO: 1230)

In another embodiment the motif may be defined as:

[R/K/H]-[W/F/Y]-[W/F/Y]-[L/I/V/A/M/S/T]-[L/I/V/A/M/G/S/T/N/Q/R/H/K]-[K/R/H/P/L/I/V/A/M]. (SEQ ID NO: 1231)

In another embodiment the motif may be define as:

[R/K/H]-[W/F/Y]-[W/F/Y]-[L/I/V/A/M/S/T]-[L/I/V/A/M/G/S/T/N/Q/R/H/K]-[K/R/H/P]. (SEQ ID NO: 1232)

In another embodiment the motif be defined as:

[R/K/H]-[W/F/Y]-[W/F/Y]-[L/I/V/A/M/S/T]-[L/I/V/A/M/G/S/R/K]-[K/R/H]. (SEQ ID NO: 1233)

In another embodiment the motif may be defined as:

[R/K/H]-[W/F/Y]-[W/F/Y/L/I/V/M]-[L/I/V/A/M/S/T]-[L/I/V/A/M/G/S/T]-[K/R/H]. (SEQ ID NO: 1234)

In another embodiment the motif may be define as:

[R/K]-[W/F/Y]-[W/F/Y/L/I/V/M]-[L/I/V/A/M/S/T]-[L/I/V/A/M/G/S/T]-[K/R]. (SEQ ID NO: 1235)

In another embodiment the motif may be defined as:

[R/K]-[W/F]-[W/F/Y/L/I/V/M]-[L/I/V/A/M/S/T]-[L/I/V/A/M/G/S/T]-[K/R]. (SEQ ID NO: 1236)

In another embodiment the motif may be defined as:

(SEQ ID NO: 1237)
[R/K]-[W/F]-[W/F/Y/L/I/V/M]-[L/I/V/A/M/T]-
[L/I/V/A/M/G/S/T]-[K/R].

In another embodiment the motif may be defined as:

(SEQ ID NO: 1238)
[R/K]-[W/F]-[W/F/Y/L/I/V/M]-[L/I/V/A/M/T]-
[L/I/V/A/M/S/T]-[K/R].

In another embodiment the motif may be defined as:

(SEQ ID NO: 1239)
[R/K]-[W/F]-[W/F/Y/L/I/V/M]-[L/I/V/A/M/S/T]-
[L/I/V/A/M/G]-[K/R].

In another embodiment the motif may be defined as:

(SEQ ID NO: 1240)
[R/K]-[W/F]-[W/F/Y/L/I/V/M]-[L/I/A/V/M/T]-
[L/I/V/A/M/S/T]-[K/R].

In another embodiment the motif may be defined as:

(SEQ ID NO: 1241)
[R/K]-[W/F]-[W/F/Y/L/I/V/M]-[L/I/V/A/M/S/T]-
[L/V/A/I/S/T]-[K/R].

In another embodiment the motif may be defined as:

(SEQ ID NO: 1242)
[R/K]-[W/F]-[W/F/Y/L/I/V/M]-[L/V/I/A/T]-
[L/V/A/I/S/T]-[K/R].

In another embodiment the motif may be defined as:

(SEQ ID NO: 1243)
[R]-[W/F/Y]-[W/F/Y/L/I/V/M]-[L/V/I/A]-
[L/V/A/S/T/M]-[K/R].

In another embodiment the motif may be defined as:

(SEQ ID NO: 1244)
[R]-[W/F/Y]-[W/F/Y/L/I/V/M]-[L/V/I/A/T]-
[L/V/A/S/T/M]-[K].

In another embodiment the motif may be defined as:

(SEQ ID NO: 1245)
[R/K]-[F/Y]-[W/F/Y/L/I/V/M]-[L/V/I/A]-
[L/V/A/I/M]-[K/R].

In another embodiment the motif may be defined as:

(SEQ ID NO: 1246)
[R/K]-[F/W/Y]-[W/F/Y/L/I/V/M]-[L/I/V/A]-
[L/I/V/A]-[K/R].

In yet another embodiment the motif may be defined as:

(SEQ ID NO: 1247)
[R/K]-[W/Y]-[W/F/Y/L/I/V/M]-[L/V/I/A/S/T]-
[L/V/A/S/T/M]-[K/R].

In yet another embodiment the motif may be defined as:

(SEQ ID NO: 1248)
[K]-[F/Y/W]-[W/F/Y/L/I/V/M]-[L/V/I/A/T]-
[L/V/A/I/S/T/M]-[K].

In another embodiment the motif may be defined as:

(SEQ ID NO: 1249)
[R/K]-[W/F]-[W/F/Y/L/I/V]-[L/I/V/A/M/S/T]-
[L/V/A/I/S/T]-[K/R].

In another embodiment the motif may be defined as:

(SEQ ID NO: 1250)
[R/K]-[W/F/Y]-[F/Y/L/I/V/M]-[L/I/V/A/M/S/T]-
[L/V/A/I/S/T]-[K/R].

In another embodiment the motif may be defined as:

(SEQ ID NO: 1251)
[R/K]-[W/F]-[W/F/Y/L/I/V]-[L/V/I/A/T]-
[L/V/A/I/S/T]-[K/R].

In another embodiment the motif may be defined as:

(SEQ ID NO: 1252)
[R]-[W/F/Y]-[W/F/Y/L/I/V]-[L/V/I/A]-
[L/V/A/S/T/M]-[K/R].

In another embodiment the motif may be defined as:

(SEQ ID NO: 1253)
[R]-[W/F/Y]-[W/F/Y/L/I/V]-[L/V/I/A/T]-
[L/V/A/S/T/M]-[K].

In another embodiment the motif may be defined as:

(SEQ ID NO: 1254)
[R/K]-[F/Y]-[W/F/Y/L/I/V]-[L/V/I/A]-
[L/V/A/I/M]-[K/R].

In another embodiment the motif may be defined as:

(SEQ ID NO: 1255)
[R/K]-[F/W/Y]-[W/F/Y/L/I/V]-[L/I/V/A]-
[L/I/V/A]-[K/R].

In yet another embodiment the motif may be defined as:

[R/K]-[W/Y]-[W/F/Y/L/I/V]-[L/V/I/A/S/T]- (SEQ ID NO: 1256)
[L/V/A/S/T/M]-[K/R].

In yet another embodiment the motif may be defined as:

[K]-[F/Y/W]-[W/F/Y/L/I/V]-[L/V/I/A/T]- (SEQ ID NO: 1257)
[L/V/A/I/S/T/M]-[K].

In some embodiments $X_1$ and $X_2$ are RW, RF, KF, KW, RY or KY.

In some embodiments $X_2$ and $X_3$ are not both W. Thus, in some embodiments, the second and third amino acids in the sequences above (i.e. $X_2$ and $X_3$) are selected from the group consisting of WF, WY, WL, WI, WV, WM, FW, FF, FY, FL, FI, FV, FM, YW, YF, YY, YL, YI, YV and YM.

In some embodiments $X_4$ and $X_5$ are LL, LA, LV, AL, VL, VI, LI, IL, VV, VA, IV, II, AV, IA, AI, AM, LM, LS, LT, IS, MV, TV, AA, IM, LN, LQ, VM, TL, SL, IT, VT, LG, MA, ML, NL, QL, QI, TI, SI, AS, VS, SV, CA, IG, LR, VR, TK or IR. In some embodiments $X_4$ and $X_5$ are LL, LA, LV, AL, VL, VI, LI, IL, VV, VA, IV, II, AV, IA, AI, AM, LM, LS, LT, IS, MV, TV, AA, IM, LN, LQ or VM. In some embodiments $X_4$ and $X_5$ are LV, IV, SV, LS, AV, LG, LA, IR, LR, VR, AR, IK, LK, VK or AK. In particularly preferred embodiments $X_4$ and $X_5$ are LL, LA, LV, AL, VL, VI, LI, IL, VV, VA, IV, II, AV, IA, AI, AM, LM, LS or LT, preferably LL, LA, LV, AL, VL, VI, LI, IL, VV, VA, IV, II, AV, IA or AI. Thus, in certain embodiments $X_4$ and $X_5$ are not any one or more of AG, AC, CC, NN, QQ, NQ, QN, TS, SS, ST or TT. In yet further embodiments $X_4$ and $X_5$ are SL, LS, SV, LT or AV.

In some embodiments $X_3$ and $X_4$ are not FS, FT, WA or WS. In some embodiments $X_3$ and $X_4$ are FS or FT.

In some embodiments $X_6$ is K. In some embodiments $X_6$ is P.

Thus, in a preferred embodiment, the oligopeptidic compound has or comprises the sequence RWXLVK (SEQ ID NO: 28). In other preferred embodiments, the oligopeptidic compound has or comprises a sequence selected from any one or more of: RWXLLK (SEQ ID NO: 22); RFXLLK (SEQ ID NO: 23); RYXLLK (SEQ ID NO: 24); RWXLLR (SEQ ID NO: 25); RFXLLR (SEQ ID NO: 26); RYXLLR (SEQ ID NO: 27); RWXLVK (SEQ ID NO: 28); RFXLVK (SEQ ID NO: 29); RYXLVK (SEQ ID NO: 30); RWXLVR (SEQ ID NO: 31); RFXLVR (SEQ ID NO: 32); RYXLVR (SEQ ID NO: 33); RWXIVK (SEO ID NO: 34); RFXIVK (SEQ ID NO: 36); RYXIVK (SEQ ID NO: 36); RWXIVR (SEQ ID NO: 37); RFXIVR (SEQ ID NO: 38); RYXIVR (SEQ ID NO: 39); RWXLSK (SEQ ID NO: 40); RFXLSK (SEQ ID NO: 41); RYXLSK (SEQ ID NO: 42); RWXLSR (SEQ ID NO: 43); RFXLSR (SEQ ID NO: 44); RYXLSR (SEQ ID NO: 45); RWXISK (SEQ ID NO: 46); RFXISK (SEQ ID NO: 47); RYXISK (SEQ ID NO: 48); RWXISR (SEQ ID NO: 49); RFXISR (SEQ ID NO: 50); RYXISR (SEQ ID NO: 51); RWXSVK (SEQ ID NO: 52); RFXSVK (SEQ ID NO: 53); RYXSVK (SEQ ID NO: 54); RWXSVR (SEQ ID NO: 55); RFXSVR (SEQ ID NO: 56); RYXSVR (SEQ ID NO: 57); RWXAVK (SEQ ID NO: 58); RFXAVK (SEQ ID NO: 59); RYXAVK (SEQ ID NO: 60); RWXAVR (SEQ ID NO: 61); RFXAVR (SEQ ID NO: 62); RYXAVR (SEQ ID NO: 65); RWXLGR (SEQ ID NO: 64); RFXLGR (SEQ ID NO: 65); RYXLGR (SEQ ID NO: 66); RWXLGK (SEQ ID NO: 67); RFXLGK (SEQ ID NO: 68); RYXLGK (SEQ ID NO: 69); RWXLAR (SEQ ID NO: 70); RFXLAR (SEQ ID NO: 71); RYXLAR (SEQ ID NO: 72); RWXLAK (SEQ ID NO: 73); RFXLAK (SEQ ID NO: 74); RYXLAK (SES ID NO: 75); RWXLTK (SEQ ID NO: 76); RFXLTK (SEQ ID NO: 77); RYXLTK (SEQ ID NO: 78); RWXLTR (SEQ ID NO: 79); RFXLTR (SEQ ID NO: 80); RYXLTR (SEQ ID NO: 81); RWXITK (SEQ ID NO: 82); RFXITK (SEQ ID NO: 83); RYXITK (SEQ ID NO: 84); RWXITR (SEQ ID NO: 85); RFXITR (SEQ ID NO: 86); RYXITR (SEQ ID NO: 87); RWXTVK (SEQ ID NO: 88); RFXTVK (SEQ ID NO: 89); RYXTVK (SEQ ID NO: 90); RWXTVR (SEQ ID NO: 91); RFXTVR (SEQ ID NO: 92); RYXTVR (SEQ ID NO: 93); RWXIRK (SEQ ID NO: 94); RFXIRK (SEQ ID NO: 95); RYXIRK (SEQ ID NO: 96); RWXIRR (SEQ ID NO: 97); RFXIRR (SEQ ID NO: 98); RYXIRR (SEQ ID NO: 99); RWXLRK (SEQ ID NO: 100); RFXLRK (SEQ ID NO: 101); RYXLRK (SEQ ID NO: 102); RWXLRR (SEQ ID NO: 103); RFXLRR (SEQ ID NO: 104); RYXLRR (SEQ ID NO: 105); KWXLLK (SEQ ID NO: 106); KFXLLK (SEQ ID NO: 107); KYXLLK (SEQ ID NO: 108); KWXLLR (SEQ ID NO: 109); KFXLLR (SEQ ID NO: 110); KYXLLR (SEQ ID NO: 111); KWXLVK (SEQ ID NO: 112); KFXLVK (SEQ ID NO: 113); KYXLVK (SEQ ID NO: 114); KWXLVR (SEQ ID NO: 115); KFXLVR (SEQ ID NO: 116); KYXLVR (SEQ ID NO: 117); KWXIVK (SEQ ID NO: 118); KFXIVK (SEQ ID NO: 119); KYXIVK (SEQ ID NO: 120); KWXIVR (SEQ ID NO: 121); KFXIVR (SEQ ID NO: 122); KYXIVR (SEQ ID NO: 123); KWXLSK (SEQ ID NO: 124); KFXLSK (SEQ ID NO: 125); KYXLSK (SEQ ID NO: 126); KWXLSR (SEQ ID NO: 127); KFXLSR (SEQ ID NO: 128); KYXLSR (SEQ ID NO: 129); KWXISK (SEQ ID NO: 130); KFXISK (SEQ ID NO: 131); KYXISK (SEQ ID NO: 132); KWXISR (SEQ ID NO: 133); KFXISR (SEQ ID NO: 134); KYXISR (SEQ ID NO: 135); KWXSVK (SEQ ID NO: 136); KFXSVK (SEQ ID NO: 137); KYXSVK (SEQ ID NO: 138); KWXSVR (SEQ ID NO: 139); KFXSVR (SEQ ID NO: 140); KYXSVR (SEQ ID NO: 141); KWXAVK (SEQ ID NO: 142); KFXAVK (SEQ ID NO: 143); KYXAVK (SEQ ID NO: 144); KWXAVR (SEQ ID NO: 145); KFXAVR (SEQ ID NO: 146); KYXAVR (SEQ ID NO: 147); KWXLGR (SEQ ID NO: 148); KFXLGR (SEQ ID NO: 149); KYXLGR (SEQ ID NO: 150); KWXLGK (SEQ ID NO: 151); KFXLGK (SEQ ID NO: 152); KYXLGK (SEQ ID NO: 153); KWXLAR (SEQ ID NO: 154); KFXLAR (SEQ ID NO: 155); KYXLAR (SEQ ID NO: 156); KWXLAK (SEQ ID NO: 157); KFXLAK (SEQ ID NO: 158); KYXLAK (SEQ ID NO: 159); KWXLTK (SEQ ID NO: 160); KFXLTK (SEQ ID NO: 161); KFXLTK (SEQ ID NO: 162); KWXLTR (SEQ ID NO: 163); KFXLTR (SEQ ID NO: 164); KYXLTR (SEQ ID NO: 165); KWXITK (SEQ ID NO: 166); KFXITK (SEQ ID NO: 167); KYXITK (SEQ ID NO: 168); KWXITR (SEQ ID NO: 169); KFXITR (SEQ ID NO 170); KYXITR (EQ ID NO: 171); KWXTVK (SEQ ID NO: 172); KFXTVK (SEQ ID NO: 173); KYXTVK (SEQ ID NO: 174); KWXTVR (SEQ ID NO: 175); KFXTVR (SEQ ID NO: 176); KYXTVR (SEQ ID NO: 177); KWXLRK (SEQ ID NO: 178); KFXLRK (SEQ ID NO: 179); KYXLRK (SEQ ID NO: 180); KWXLRR (SEQ ID NO: 181); KFXLRR (SEQ ID NO: 182); KYXLRR (SEQ ID NO: 183); KWXIRK (SEQ ID NO: 184); KFXIRK (SEQ ID NO: 185); KYXIRK (SEQ ID NO: 188); KWXIRR (SEQ ID NO: 187); KFXIRR (SEQ ID NO: 188); KYXIRR (SEQ ID NO: 189); RWXVVK (SEQ ID NO: 190); RFXVVK (SEQ ID NO: 191); RYXVVK (SEQ ID NO: 192); RWXVVR (SEQ ID NO: 193); RFXVVR (SEQ ID NO: 194); RYXVVR (SEQ ID NO: 195); KWXVVK (SEQ ID NO: 196); KFXVVK (SEQ ID NO: 197); KYXVVK (SEQ ID NO: 198); KWXVVR (SEQ ID NO: 199); KFXVVR (SEQ ID NO: 200); KYXVVR (SEQ ID NO: 201); RWXALK (SEQ ID NO: 202); RFXALK (SEQ ID NO: 203); RYXALK (SEQ ID NO: 204); RWXALR (SEQ ID NO: 205); RFXALR (SEQ ID NO: 206); RYXALR (SEQ ID NO: 207); MVXALK (SEQ ID NO: 208); KFXALK (SEQ ID NO: 209); KYXALK (SEQ ID NO: 210); KWXALR (SEQ ID NO: 211); KFXALR (SEQ ID NO: 212); KYXALR (SEQ ID NO: 213); RWXVLK (SEQ ID NO: 214); RFXVLK (SEQ ID NO: 215); RYXVLK (SEQ ID NO: 216); RWXVLR (SEQ ID NO: 217); RFXVLR (SEQ ID NO: 218); RYXVLR (SEQ ID NO: 219); KWXVLK (SEQ ID NO: 220); KFXVLK (SEQ ID NO: 221); KYXVLK (SEQ ID NO: 222); KWXVIR (SEQ ID NO: 223); KFXVLR (SEQ ID NO: 224); KYXVLR (SEQ ID NO: 225); RWXILK (SEQ ID NO: 226); RFXILK (SEQ ID NO: 227); RYXILK (SEQ ID NO: 228); RWXILR (SEQ ID NO: 229); RFXILR (SEQ ID NO: 230); RYXILR (SEQ ID NO: 231); KWXILK (SEQ ID NO: 232); KEXILK (SEQ ID NO: 233); KYXILK (SEQ ID NO: 234); KWXILR (SEQ ID NO: 235); KFXILR (SEQ ID NO: 236); KYXILR (SEQ ID NO: 237); RWXVIK (SEQ ID NO: 238); RFXVIK (SEQ ID NO: 239); RYXVIK (SEQ ID NO: 240); RWXVIR (SEQ ID NO: 241); RFXVIR (SEQ ID NO: 242); RYXVIR (SEQ ID NO: 243); KWXVIK (SEQ ID NO: 244); KFXVIK (SEQ ID NO: 245); KYXVIK (SEQ ID NO: 246); KWXVIR (SEQ ID NO: 247) KFXVIR (SEQ ID NO: 248); KYXVIR (SEQ ID NO: 249); RWXIIK (SEQ ID NO: 250); RFXIIK (SEQ ID NO: 251); RYXIIK (SEQ ID NO: 252); RWXIIR (SEQ ID NO: 253); REXIIR (SEQ ID NO: 254); RYXIIR (SEQ ID NO: 255); KWXIIK (SEQ ID NO: 256); KFXIIK (SEQ ID NO: 257); KYXIIK (SEQ ID NO: 258); KWXIIR (SEQ ID NO: 259); KFXIIR (SEQ ID NO: 260); KYXIIR (SEQ ID NO: 261); RWXLIK (SEQ ID NO: 282); RFXLIK (SEQ ID NO: 263); RYXLIR (SEQ ID NO: 264); RWXLIR (SEQ ID NO: 265); RFXLIR (SEQ ID NO: 266); RYXLIR (SEQ ID NO: 267); KWXLIK (SEQ ID NO: 268); KFXLIK (SEQ ID NO: 269); KYXLIK (SEQ ID NO: 270); KWXLIR (SEQ ID NO: 271); KFXLIR (SEQ ID NO: 272); KYXLIR (SEQ ID NO: 273); RWXIAK (SEQ ID NO: 274); RFXIAK (SEQ ID NO: 275); RYXIAK (SEQ ID NO: 276); RWXIAR (SEQ ID NO: 277); RFXIAR (SEQ ID NO: 278); RYXIAR (SEQ ID NO: 279); KWXIAK (SEQ ID NO: 280); KFXIAK (SEQ ID NO: 281); KYXIAK (SEQ ID NO: 282); KWXIAR (SEQ ID NO: 283); KFXIAR (SEQ ID NO: 284); KYXIAR (SEQ ID NO: 285); RWXVAK (SEQ ID NO: 286); RFXVAK (SEQ ID NO: 287); RYXVAK (SEQ ID NO: 288); RWXVAR (SEQ ID NO: 289); RFXVAR (SEQ ID NO. 290); RYXVAR (SEQ ID NO: 291); KWXVAK (SEQ ID NO: 292); KFXVAK (SEQ ID NO: 293); KYXVAK (SEQ ID NO: 294); KWXVAR (SEQ ID NO: 295); KFXVAR (SEQ ID NO: 296); KYXVAR (SEQ ID NO: 297); RFXSLK (SEQ ID NO: 1206); and RWXLVP (SEQ ID NO: 1209); wherein X ($X_3$) is selected from the group consisting of W, F, Y, I, V and M, preferably W, F and Y.

In some embodiments, the sequences do not contain two adjacent tryptophan residues, i.e. the sequences do not contain WW. Alternatively viewed, in the sequences above, when the second amino acid ($X_2$) is W, X ($X_3$) is selected from the group consisting of F, Y, L, I, V and M. Thus, in some embodiments, the second and third amino acids in the sequences above (i.e. $X_2$ and $X_3$) are selected from the group consisting of WF, WY, WL, WI, WV, WM, FW, FF, FY, FL, FI, FV, FM, YW, YF, YY, YL, YI, YV and YM. In some embodiments, $X_2$ and $X_3$ are selected from WF, WY, FF, FY, FW, YF, YY and YW. However, in some embodiments, $X_2$ and $X_3$ may be WW.

In other embodiments, the sequences may contain two adjacent tryotophan residues, i.e. the sequences contain WW. Thus, in some embodiments, the second and third amino acids in the sequences above (i.e. $X_2$ and $X_3$) are selected from the group consisting of WW, WF, WY, WL, WI, WV, WM, FW, FF, FY, FL, FI, FV, FM, YW, YF, YY, YL, YI, YV and YM. In some embodiments, $X_2$ and $X_3$ are selected from WW, WF, WY, FF, FY, FW, YF, YY and YW.

These specific sequences are listed by way of example and they are not intended to be limiting on the scope of the present invention. In some preferred embodiments the oligopeptidic compound has or comprises the sequence RWXLVK (SEQ ID NO: 28) or RFXLVK (SEQ ID NO: 29) or RWXVIK (SEQ ID NO: 238) or RFXVIK (SEQ ID NO: 239). In particularly preferred embodiments the oligopeptidic compound has or comprises the sequence RWFLVK (SEQ ID NO: 1258), RWYLVK (SEQ ID NO: 1259), RWLLVF (SEQ ID NO: 1260), RWILVK (SEQ ID NO: 1261), RWVLVK (SEQ ID NO: 1262), RWMLVK (SEQ ID NO: 1263), RFWLVK (SEQ ID NO: 1264), RFFLVK (SEQ ID NO: 1265), RFYLVK (SEQ ID NO: 1266), RFLLVK (SEQ ID NO: 1267), RFILVK (SEQ ID NO: 1268), RFVLVK (SEQ ID NO: 1269), RFMLVK (SEQ ID NO: 1270), RYWLVK (SEQ ID NO: 1271), RYFLVK (SEQ ID NO: 1272), RYYLVK (SEQ ID NO: 1273), RYLLVK (SEQ ID NO: 1274), RYILVK (SEQ ID NO: 1275), RYVLVK (SEQ ID NO: 1276), RYMLVK (SEQ ID NO: 1277), RWFVIK (SEQ ID NO: 1278), RWYVIK (SEQ ID NO: 1279), RWLVIK (SEQ ID NO: 1280), RWIVIK (SEQ ID NO: 1281), RWVVIK (SEQ ID NO: 1282), RWMVIK (SEQ ID NO: 1283), RFWVIK (SEQ ID NO: 1284), RFFVIK (SEQ ID NO: 1285), RFYVIK (SEQ ID NO: 1286), RFLVIK (SEQ ID NO: 1287), RFIVIK (SEQ ID NO: 1288), RFVVIK (SEQ ID NO: 300), RFMVIK (SEQ ID NO: 301) or RWWLVK (SEQ ID NO: 1310).

In still further embodiments, the oligopeptidic compound has or comprises the sequence RWXLTK (SEQ ID NO: 76), RFXLSK (SEQ ID NO: 41), RFXSLK (SEQ ID NO: 1207), RWXLSK (SEQ ID NO: 40), RWXSVK (SEQ ID NO: 52) RWXAVK (SEQ ID NO: 58) or RWXLVP (SEQ ID NO: 1209), wherein X ($X_3$) is selected from the group consisting of W, F, Y, L, I, V and M, preferably W, F and Y, as defined above.

Whilst the PCNA interacting motifs listed above are preferred motifs of the invention, in some embodiments any one or more of these motifs may be excluded, e.g. any 1, 2, 3, 4, 5, 6, 7, 8, 9, 10, 12, 15, 20 or more motifs may be excluded, such as any 25, 30, 40, 50 or more motifs or any integer in this range. Thus, in some embodiments the oligopeptidic compound does not have or comprise a sequence selected from any one or more of SEQ ID NOs: 22-297, 300, 301, 1207, 1209, 1258-1288 and 1310.

The oligopeptidic compound is preferably an isolated compound, e.g. an isolated peptide and most preferably the oligopeptidic compound is a synthetic compound, e.g. a synthetic peptide. The nucleic acid molecule encoding the oligopeptidic compound is preferably an isolated nucleic acid molecule and most preferably the nucleic acid molecule is a synthetic nucleic acid molecule. In other words, the oligopeptidic compound and its encoding nucleic acid molecule are non-native, i.e. non-naturally occurring, molecules.

The domain that facilitates the uptake of the oligopeptidic compound may be an uptake (import) peptide sequence, which may be a sequence which acts to transport the oligopeptidic compound into a cell, or across a cell membrane (i.e. into the interior of a cell). It may thus be a so-called "cell penetrating" sequence (or more particularly "cell penetrating peptide") also known in the art as a protein transduction domain (PTD) or protein transduction sequence.

Accordingly, as noted above the invention may provide an agent or construct comprising (i) an oligopeptidic compound comprising an APIM motif (i.e. PCNA-interacting motif) as defined herein, and (ii) a cell penetrating sequence (more particularly a cell penetrating peptide).

Cell penetrating peptide (CPP) technology has developed greatly over recent years and a wide variety of cell penetrating peptides are known and described in the art and indeed a range of such peptides are commercially available. Cell penetrating peptides may vary greatly in size, sequence and charge, and indeed in their mechanism of function (which is presently not known for some peptides and not fully elucidated for others), but share the common ability to translocate across the plasma membrane and deliver an attached or associated moiety (the so-called "cargo") into the cytoplasm of a cell. CPPs are thus peptide-based delivery vectors.

Whilst CPPs are not characterized by a single structural or functional motif, tools to identify CPPs are available and the skilled person can readily determine whether a peptide sequence may function to facilitate the uptake of the peptide of which it forms a domain, i.e., whether a peptide sequence may function as an uptake (import) peptide, e.g. a CPP. For example, Hansen et al (Predicting cell-penetrating peptides, Advanced Drug Delivery Reviews, 2008, 60, pp. 572-579), provides a review or methods for CPP prediction based on the use of principal component analysis ("z-predictors") and corresponding algorithms based on original work by Hällbrink et al (Prediction of Cell-Penetrating Peptides, International Journal of Peptide Research and Therapeutics, 2005, 11(4), pp. 249-259). In brief, the methodology works by computing z-scores of a candidate peptide as based on a numerical value and an associate range. If the z-scores fall within the range of known CPP z-scores, the examined peptides are classified as CPPs. The method was shown to have high accuracy (about 95% prediction of known CPPs).

Additional methods for the prediction of CPPs have been developed subsequently (see e.g. Sanders et al., Prediction of Cell Penetrating Peptides by Support Vector Machines, PLOS Computational Biology, 2011, 7(7), pp. 1-12, herein incorporated by reference) and a CPP database is available (Gautam et al., CPPSite: a curated database of cell penetrating peptides, Database, 2012, Article ID bas015 and http://crdd.osdd.net/raghava/cppsite/index.php, both herein incorporated by reference). Accordingly, any suitable CPP may find utility in the invention and, as discussed below, a variety of CPPs have already been identified and tested and could form the basis for determining and identifying new CPPs.

CPPs may be derived from naturally-occurring proteins which are able to translocate across cell membranes such as the *Drosophila* homeobox protein Antennapedia (a transcriptional factor), viral proteins such as the HIV-1 transcriptional factor TAT and the capsid protein VP22 from HSV-1, and/or they may be synthetically-derived, e.g. from chimeric proteins or synthetic polypeptides such as polyarginine. As noted above, there is not a single mechanism responsible for the transduction effect and hence the design of CPPs may be based on different structures and sequences. Cell penetrating peptides are also reviewed in Jarver et al. 2006 (Biochimica et Biophysica Acta 1758, pages 260-263) and Table 1 below lists various representative peptides. U.S. Pat. No. 6,645,501 (herein incorporated by reference) further describes various cell penetrating peptides which might be used.

TABLE 1

| CPP | SEQUENCE | REFERENCE |
|---|---|---|
| Antp Class | | |
| Penetratin | RQIKIWFQNRRMKWKK (SEQ ID NO: 302) | Bolton (2000) Eur. J. Neuro. 12: 287 |
| Penetratin derivatives | RRMKWKK (SEQ ID NO: 303)<br>NRRMKWKK (SEQ ID NO: 304)<br>QNRRMKWKK (SEQ ID NO: 305)<br>FQNRRMKWKK (SEQ ID NO: 306)<br>RREKWKK (SEQ ID NO: 307)<br>RRQKWKK (SEQ ID NO: 308)<br>KRMKWKK (SEQ ID NO: 309)<br>RKMKWKK (SEQ ID NO: 310)<br>RROKWKK (SEQ ID NO: 311)<br>RRMKQKK (SEQ ID NO: 312)<br>RRMKWFK (SEQ ID NO: 313)<br>RORKWKK (SEQ ID NO: 314)<br>RRMWKKK (SEQ ID NO: 315)<br>RRMKKWK (SEQ ID NO: 316)<br>(using standard single amino acid notation, ornithine (O), diaminobutyric acid (B), norleucine (N)) | U.S. Pat. No. 6,472,507<br>EP4855781<br>WO 97/12912 |
| D-Penetratin | rqikiwfqnrrmkwkk (SEQ ID NO: 317) | Rouselle, C. et al. (2000) Mol. Pharm 57: 679 |

TABLE 1-continued

| CPP | SEQUENCE | REFERENCE |
| --- | --- | --- |
| Protegrin Class | | |
| Pegelin (SynB) | RGGRLSYSRRRFSTSTGR (SEQ ID NO: 318) | Rouselle, C. et al. (2000) Mol. Pharm 57: 679 |
| HIV-TAT Class | | |
| HIV-TAT | GRKKRRQRRRPPQ (SEQ ID NO: 319) | Vives E.J Biol, Chem 1997, 272: 16010 Snyder (2004) PLOS 2: 186 |
| 47-57 OF HIV-TAT | YGRKKRRQRRR (SEQ ID NO: 320) | Potocky et al. (2003) JBC |
| VP22 | DAATATRGRSAASRPTERPRAPARSASRPRRVD (SEQ ID NO: 321) | Elliott g. Cell 1997, 88: 223-233 |
| Amphipathic peptides | | |
| MAP | KLALKLALKALKAALKLA (SEQ ID NO: 322) | Morris MC., Nat Biotechnol, 2001, 19: 1173-1176 |
| Tratisportan | GWTLNSAGYLLGKINLKALAALAKKIL (SEQ ID NO: 323) | Pooga M, FASEB J 1998, 12: 67-77 |
| Transportan-10 | AGYLLGKINLKALAALAKKIL (SEQ ID NO: 324) | Soomets U, Biochim Biophys Acta 2000, 1467: 165-176 |
| KALA | WEAKLAKALAKALAKHLAKALAKALKACEA (SEQ ID NO: 325) | Oehike J., Biochim Biophys Acta 1998, 1414: 127-139 |
| Pep-1 | KETWWETWWTEWSQPKKKRKV (SEQ ID NO: 326) | Wyman Biochemistry 1997, 36: 3008-3017 |
| Pep-2 | KETWFETWFTEWSQPKKKRKV (SEQ ID NO: 327) | |
| MPG | GALFLGFLGAAGSTMGAWSQPKSKRKV (SEQ ID NO: 328) | Wagstaff KM Curr Med Chem 2006, 13: 1371-1387 |
| Vectocell peptides | VKRGLKLRHVRPRVTRMDV (SEQ ID NO: 329) SRRARRSPRHLGSG* (SEQ ID NO: 330) LRREROQSRLRRERQSR* (SEQ ID NO: 331) GAYDLRRRERQSRLRRRERQSR (SEQ ID NO: 332) *indicates addition of cys for conjugation to carqo | Coupade (2005) Biochem. J. 407 |
| Wr-T transporter | KETWWETWWTEWWTEWSQ-GPG-rrrrrrrr (SEQ ID NO: 333) r = D-enantiomer arginine | Kondo (2004) Mol. Can. Thera 1623 |

TABLE 1-continued

| CPP | SEQUENCE | REFERENCE |
| --- | --- | --- |
| Other peptides | | |
| R7 | RRRRRRR (SEQ ID NO: 334) | Rothbard et. al., Nat. Med 6 (2000) 1253-1257 |

Antennapedia-derived CPPs (Antp class) represent a class of particular interest, based around the 16 amino acid Penetratin sequence as shown in Table 1, which corresponds to the third loop of antennapedia protein and was shown to be responsible for translocation of the protein. Penetratin has been extensively developed as a delivery vehicle, including particularity for pharmaceutical use, and a wide range of Penetratin derivatives and modified sequences have been proposed and described. Reference may be made in particular to WO 91/1891, WO 00/1417, WO 00/29427, WO 2004/069279 and U.S. Pat. No. 6,080,724 (herein incorporated by reference). Thus, the 16 amino acid sequence of Penetratin may be modified and/or truncated, or the peptide may be chemically-modified or retro-, inverso- or retro-inverso analogues may be made whilst retaining cell-penetrating activity.

Another group of cell penetrating peptides which may advantageously be used are based on the HIV-TAT sequence and HIV-TAT and fragments thereof represent a preferred class of CPPs for use according to the present invention. Various TAT-based CPPs are described in U.S. Pat. No. 5,656,122 (herein incorporated by reference). An exemplary HIV-TAT peptide as used in the Examples below is RKKRRQRRR (SEQ ID NO: 335) but it will readily be appreciated that longer or shorter TAT fragments may be used.

As mentioned above no particular structural features or sequence motifs are common to all PPs. However, various classes of CPPs may be identified by particular features, such as for example peptides which are amphipathic and net positively charged. Other groups of CPPs may have a structure exhibiting high α-helical content. Another group may be peptides characterised by a high content of basic amino acids. CPPs may thus be or may comprise oligomers of basic amino acids such as arginine e.g. 5 to 20, 6 to 15 or 6 to 12 R residues e.g. $R_7$ (SEQ ID NO: 334), $R_6$ (SEQ ID NO: 336) or $R_{11}$ (SEQ ID NO: 337) or $QSR_6$ (SEQ ID NO: 338).

Thus, in some embodiments, the domain that facilitates the uptake of the oligopeptidic compound (e.g. CPP) may be defined as peptide of 4-30 amino acids (e.g. 5-29, 6-28, 7-27, 8-26, 9-25 etc. amino acids), wherein at least 4 amino acids (e.g. at least 5, 6, 7, 8, 9, 10 or 11 amino acids, e.g. 4-20, 5-19, 6-18, 7-17, 8-16, 9-15, 10-14, 11-13 amino acids) are positively charged amino adds, preferably selected from K, R or H.

Proline-rich amphipathic peptides are another class of CPP and such peptides characterised by the presence of pyrrolidine rings from prolines are described in Pujals et al, 2008 Advanced Drug Delivery Reviews 60, pages 473-484 (herein incorporated by reference).

Other successfully developed CPPs include pVEC (Elmquist et al, 2003 Biol. Chem 384, pages 387-393; Holm et al, 2005 Febs Lett 579, pages 5217-5222, all herein incorporated by reference) and calcitonin-derived peptides (Krauss et al. 2004 Bioorg. Med. Chem. Lett., 14, pages 51-54 herein incorporated by reference).

Commercially available CPPs include Chariot, based on the Pep-1 peptide (Active Motif, France), the Syn-B vectors based on the protegrin peptide PG-1 (Syntem, France), and Express-si Delivery based on the MPG peptide from Genospectra, USA.

Other CPPs include the R41, R8, M918 and YTA-4 peptides (SEQ ID NOs: 1210-1213, respectively) disclosed in Eriksson et al, 2013, Antimicrobial Agents and Chemotherapy, vol. 57(8), pp. 3704-3712 (incorporated herein by reference).

In some embodiments the CPPs may be cyclic peptides, such as those disclosed in Oh et at, 2014, Mol. Pharmaceutics, vol. 11, pp. 3528-3536 (incorporated herein by reference). In particular, the CPPs may be amphiphilic cyclic CPPs, particularly containing tryptophan and arginine residues. In some embodiments the CPPs may be cyclic polyarginine peptides and may be modified by the addition of a fatty acyl moiety, e.g. octanoyl, dodecanoyl, hexaderahoyl, N-acetyl-L-tryptophanyl-12-aminododecanoyl etc. Suitable cyclic CPPs for use in the invention are presented in SEQ ID NOs: 1214-1220.

In addition to publically available and reported CPPs, novel or derivative CPP peptides may be designed and synthesized based on known or reported criteria (e.g. known CPP sequences or features such as basic amino acid content, α-helical content etc. as discussed above). Additionally, randomly-designed or other peptides may be screened for CPP activity, for example by coupling or attaching such a peptide containing a reporter molecule, e.g. a detectable label or tag such as fluorescent tag to the desired cargo (e.g., an oligopeptidic compound as described herein) and testing to see if the construct is translocated across the cell membrane, for example by adding these peptides to live cells followed by examination of cellular import e.g. using confocal microscopy.

Indeed, whilst it is generally the case that a CPP will penetrate or enter virtually any animal cell type, it has been surprising found that CPPS may also facilitate the uptake of peptides into prokaryotic cells. It is thought that the capacity of CPPs to function in prokaryotic cells is a result of their structural similarity to anti-bacterial peptides, e.g. short, cationic peptides with amphipathic properties. Nevertheless, it is evident from the data in the Examples that the primary anti-bacterial activity of the peptides of the invention arises from the APIM motif rather than the presence of a CPP sequence. It may in some cases be observed that successful or efficient delivery may be dependent, or may vary depending, on the precise nature of the cargo (e.g. cargo peptide sequence) and/or the CPP used. It would be well within the routine skill of the person skilled in the art to determine optimum peptide sequences and combinations etc., and to test and/or modify cargo and/or CPP sequence or structure etc.

Thus, by way of summary, the skilled person will be aware of suitable cell penetrating peptide sequences that, based on the findings of the inventors, may facilitate the uptake of the oligopeptidic compound, but by way of example the sequences may include Penetratin™ a 16-amino acid peptide corresponding to the third helix of the homeodomain of Antennapedia protein, R rich tags such as R6-Penetratin (in which arginine-residues were added to the N-terminus of Penetratin) and derivatives of the HIV Tat protein such as GRKKRRQRRRPPQQ (SEQ ID NO: 339).

Thus, in some embodiments the domain that facilitates the cellular uptake of the oligopeptidic compound is a CPP and may be selected from any one of:
  (i) an antennapedia class peptide;
  (ii) a protegrin class peptide;
  (iii) a HIV-TAT class peptide;
  (iv) an amphipathic class peptide selected from an amphipathic and net positively charged peptide, a proline-rich amphipathic peptide, a peptide based on the Pep-1 peptide and a peptide based on the MPG peptide;
  v) a peptide exhibiting high α-helical content;
  (vi) a peptide comprising oligomers of basic amino acids;
  (vii) pVEC;
  (viii) a calcitonin-derived peptide and
  (ix) an amphiphilic cyclic CPP.

In some embodiments the domain that facilitates the cellular uptake of the oligopeptidic compound is a CPP and may be selected from a sequence selected from any one of SEQ ID NOs: 302-1162 or a fragment and/or derivative thereof. The details and properties of the CPPs identified in SEQ ID NOs: 340-1162 can be found at http://crdd.osdd.net/raghava/cppsite/index.php, CPPSite: A database of cell penetrating peptides (herein incorporated by reference).

In some embodiments the domain that facilitates the cellular uptake of the oligopeptidic compound is SEQ ID NO: 337.

In some embodiments, the oligopeptidic compound also comprise more domains that provide a signal (target or transit) sequence. In some embodiments, the signal sequence may target the oligopeptidic compound to a specific cell type. Additionally or alternatively, in some embodiments the oligopeptidic compound may comprise a signal peptide that is capable of localising the compound to a specific intracellular compartment, e.g. the nucleus. In some embodiments, the uptake (import) peptide, e.g. CPP, may be sufficient to direct or localise the oligopeptidic compound to the appropriate cellular location.

The signal sequence or signal sequence domain may thus be viewed as any sequence which acts to localise (or is capable of localising), or alternatively put, to direct, translocate or transport (or is capable of directing, translocating or transporting), the oligopeptidic compound to any desired location a desired cell type, e.g., prokaryotic, or subcellular location, e.g. nucleus.

As mentioned above, in some embodiments the oligopeptidic compound (or constructs) of the invention and for use in the use and methods of the invention may comprise one or more signal sequences (i.e. one or more domains that function as signal sequences or are capable of functioning as signal sequences in some cell types), e.g. a signal peptide which directs the compound (or construct) into a particular sub-cellular compartment, such as the nucleus. Nuclear localisations signals (NLSs) are again well known in the art and widely described in the literature. For instance, a searchable database of known and predicted NLSs is available, see e.g. Cokol et al (Finding nuclear localization signals, EMBO Reports, 2000, 1(5), pp. 411-415, herein incorporated by reference). The PSORT II database, http://psort.hgc.jp/ (herein incorporated by reference) can be used for the prediction of nuclear localization of proteins based on NLSs. Accordingly, any known or functional NLS may find utility in the invention.

An NLS may vary in length and/or sequence and a wide range of specific NLS sequences have been described. In general, however, it has been found that peptides comprising positively charged amino acids (notably lysine (K), arginine (R) and/or histidine (H)) may function as an NLS. An exemplary NLS may thus be a peptide of e.g. 4-20, more particularly 4-15, 4-12, 4-10 or 4-8 amino acids, wherein at least 4 amino more particularly at least 60, 70, 75, 80, 85, or 90% of the amino acid residues in the NLS peptide) are positively charged amino acids, preferably selected from K, R or H. Such an exemplary NLS may for example have or comprise the sequence RKRH (SEQ ID NO: 1163).

Nuclear localisation signals, including both actual experimentally-determined and predicted or proposed NLS sequences, and strategies for identifying NLSs are also described in Lange et al., J. Biol. Chem, 2007, 282(8), 5101-5105; Makkerh et al., Current Biology 1996, 6(8), 1025-1027; Leslie et al., Methods 2006, 39, 291-308; and Lusk et al. Nature Reviews MCB 2007, 8, 414-420 (all herein incorporated by reference).

A classical NLS consists of either one (monopartite) or two (bipartite) stretches of basic amino acids. A monopartite NLS may be exemplified by the SV40 large T antigen NLS ($^{126}$PKKKRKV$^{132}$[SEQ ID NO: 1164]) and a bipartite NLS by the nucleoplasmin NLS ($^{155}$KRPAATKKAGQAK-KKK$^{170}$[SEQ ID NO: 1165]). The monopartite NLS consensus sequence K-[K/R]-X-[K/R] (SEQ ID NO: 1166) has been proposed and accordingly an NLS according to the present invention may in one embodiment comprise or consist of such a consensus sequence (where X is any amino acid).

A representative bipartite NLS according to the invention may have the sequence KR-[X]$_{5-20}$-KKKK (SEQ ID NO: 1167), e.g. KR-X$_{10}$-KKKK (SEQ ID NO: 1168) (where X is any amino acid).

An alternative exemplary bipartite NLS may take the forum RKRH-[X]$_{2-10}$-KK (SEQ ID NO: 1169), e.g. RKRH-X$_2$-KK (SEQ ID NO: 1170), for example RKRH-II-KK (SEQ ID NO: 1171).

The oncoprotein c-myc NLS differs from classical NLS in that only 3 of 9 amino acid residues are basic (PAAKRVKLD [SEQ ID NO: 1172]), indicating that an NLS need not necessarily conform to the consensus or classical sequences given above. Makkerh et al (supra) describe NLS sequences in which a cluster of basic amino acids (e.g. KKKK [SEQ ID NO: 1173]) is flanked by neutral and acidic residues, for example PAAKKKKLD (SEQ ID NO: 1174).

Other possible NLS sequences which may be given by way of example include: PKKKRKVL (SEQ ID NO: 1175), KKKRK (SEQ ID NO: 1176), KKKRVK (SEQ ID NO: 1177), KKKRKVL (SEQ ID NO: 1178) and RKKRKVL (SEQ ID NO: 1179). Any NLS which is a derivative of a known NLS e.g. the SV40, nucleoplasmin, UNG2 or c-myc NLS may be used.

A putative, proposed or predicted NLS sequence can be tested for NLS activity using principles and assays known and described in the art. For example a candidate NLS sequence may be attached to the desired cargo (in this case an oligopeptidic compound as defined herein) and the construct may be provided with a detectable reporter molecule (e.g. a tag or label which may be visualised, for example a fluorescent label) and contacted with a test cell. Distribution of the construct in the cell may then be determined.

Thus, by way of summary, the skilled person will be aware of suitable signal sequences, but by way of example the following are mentioned herein. Examples of nuclear localisation sequences include the SV40 protein derivative KKKRK (SEQ ID NO: 1176).

Thus, in embodiments the oligopeptidic compound comprises a signal sequence (i.e., a domain comprising a signal peptide) that localizes or directs the oligopeptidic compound to a sub-cellular location (or is capable of localizing or directing the oligopeptidic compound to a sub-cellular location in some cell types), such as a NLS and may be selected from any one of:

(i) a peptide of 4-20 amino acids, wherein at least 4 amino acids are positively charged amino acids, preferably selected from K, R or H; and/or (ii) a sequence selected from any one of SEQ ID NOs; 1163-1179 or a fragment and/or derivative thereof.

In some embodiments the nuclear localisation signal sequence comprises a sequence selected from any one of SEQ ID NOs: 1163-1179 or a fragment and/or derivative thereof, preferably wherein said fragment and/or derivative comprises at least 4 positively charged amino acids, preferably selected from any of K, R or H.

In some embodiments an oligopeptidic compound or construct according to the present invention may comprise at least three domains, including (i) an APIM motif domain as defined herein, (ii) a linker domain, which may in some embodiments comprise a nuclear localisation signal sequence, and (iii) a peptide sequence domain that facilitates the cellular uptake of said compound or construct (i.e. an uptake/import peptide sequence domain, e.g. cell penetrating signal sequence domain).

The separate elements or components (domains) of a construct according to the present invention may be contained or presented in any order, but preferably in the orders indicated above (e.g. APIM oligopeptidic compound-CPP or APIM oligopeptidic compound-linker-CPP).

In some embodiments, the APIM motif located at or towards the N-terminus of the peptide. For instance, the APIM motif may be described as being N-terminal to the peptide sequence domain that facilitates the cellular uptake of said compound (e.g. the CPP) and optionally N-terminal to the linker sequence, if present.

In a preferred embodiment, the oligopeptidic compound comprises a PCNA interacting motif as set forth in SEQ ID NOs: 28-30 (particularly SEQ ID NOs: 28 or 29), a nuclear localisation signal sequence/linker sequence as set forth in SEQ ID NO: 1176 and a cell penetrating signal sequence as set forth in SEQ ID NO: 337.

In a particularly preferred embodiment, the oligopeptidic compound comprises a PCNA interacting motif as set forth in any one of SEQ ID NOs: 1258, 1259, 1265-1269 or 1280, a nuclear localisation signal sequence as set forth in SEQ ID NO: 1176 and a cell penetrating signal sequence as set forth in SEQ ID NO: 337.

In a further preferred embodiment, the oligopeptidic compound comprises a PCNA interacting motif as set forth in any one of SEQ ID NOs: 76, 41, 1207, 40, 52, 58 or 1209, a nuclear localisation signal sequence as set forth in SEQ ID NO: 1176 and a cell penetrating signal sequence as set forth in SEQ ID NO: 337.

Furthermore, in some embodiments an oligopeptidic compound or construct according to the invention may contain more than one PCNA-interacting motif. Thus, alternatively put, an agent for use in the uses and methods of the present invention may contain or encode an oligopeptidic compound comprising more the one PCNA-interacting motif, preferably more than one longer or extended PCNA-interacting motif (APIM) as defined herein. A construct or oligopeptidic compound may for example contain 1-10, e.g. 1-6, or 1-4 or 1-3 or one or two motifs. Within a construct also containing a signal sequence, such motifs may be spaced or located according to choice, e.g. they may be grouped together, or they may be separated by signal sequence elements e.g. motif-motif-CPP, motif-linker-motif-CPP or motif-linker-motif-motif-CPP; or motif-motif-linker-CPP etc.

As referred to herein a "fragment" may comprise at least 30, 40, 50, 60, 70, 80, 85, 90, 95, 96, 97, 98 or 99% of the amino acids of the sequence from which it is derived. Said fragment may be obtained from a central or N-terminal or C-terminal portions of the sequence. Whilst the size of the fragment will depend the size of the original sequence, in some embodiments the fragments may be 1, 2, 3, 4, 5, 6, 9, 10, 11, 12, 13, 14, 15 or more amino acid residues shorter than the sequence from which it is derived, e.g. 1-10, 2-9, 3-8, 4-7 amino acid residues shorter than the sequence from which it is derived.

As referred to herein a "derivative" of a sequence is at least 55, 60, 65, 70, 75, 80, 85, 90, 95, 96, 97, 98 or 99% identical to the sequence to which it is compared.

Sequence identity may be determined by, e.g., using the SWISS-PROT protein sequence databank using FASTA pep-cmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 200, 100, 50, 20 or 10 contiguous amino acids.

Preferably such sequence identity related polypeptides, i.e. derivatives, are functionally equivalent to the peptides which are set forth in the recited SEQ ID NOs. Similarly, the peptides with sequences as set forth in the SEQ ID NOs. may be modified without affecting the sequence of the polypeptide as described below.

Furthermore, "fragments" as described herein may be functional equivalents. Preferably these fragments satisfy the identity (relative to a comparable region) conditions mentioned herein.

As referred to herein, to achieve "functional equivalence" the peptide may show some reduced efficacy in performing the function relative to the parent molecule (i.e. the molecule from which it was derived, e.g. by amino acid substitution), but preferably is as efficient or is more efficient. Thus, functional equivalence may relate to a peptide which is effective in localizing or directing the oligopeptidic compound to the cell type or cellular location, e.g. to facilitate to the uptake of the peptide as described above. This may be tested by comparison of the effects of the derivative peptide relative to the peptide from which it is derived in a qualitative or quantitative manner, e.g. by performing the in vitro analyses described above. Where quantitative results are possible, the derivative is at least 30, 50, 70 or 90% as effective as the parent peptide.

Functionally-equivalent peptides which are related to or derived from the parent peptide, may be obtained by modifying the parent amino acid sequence by single or multiple amino acid substitution, addition and/or deletion (providing they satisfy the above-mentioned sequence identity requirements), but without destroying the molecule's function. Preferably the parent sequence has less than 20 substitutions; additions or deletions, e.g. less than 10, 5, 4, 3, 2, or 1 such modifications. Such peptides may be encoded by "functionally-equivalent nucleic acid molecules" which may be generated by appropriate substitution, addition and/or deletion of one or more bases.

The domains (which may be viewed as components, elements or separate parts) of an oligopeptidic compound or construct of the invention as described herein may be attached or linked to one another in any desired or convenient way according to techniques well known in the art. Thus, the domains may be linked or conjugated chemically, e.g. using known chemical coupling technologies or the compound or constructs may be formed as a single whole using genetic engineering techniques e.g. techniques for forming fusion proteins, or they may simply be synthesized as a whole, e.g., using peptide synthesis techniques.

The domains may be linked directly to each other or they may be linked indirectly by means of one or more linker (or spacer) sequences. Thus, a linker sequence may interspace or separate two or more individual domains (i.e. parts, e.g. or separate motif elements) in an oligopeptidic construct or compound. The precise nature of the linker sequence is not critical and it may be of variable length and/or sequence, for example it may have 0-40, more particularly 0-20, 0-15, 0-12, 0-10, 0-8, or 0-6, 0-4 or 0-3 residues e.g. 1, 2 or 3 or more residues. By way of representative example the linker sequence, if present, may have 1-15, 1-12, 1-10, 1-8, 1-6 or 1-4 residues etc. The nature of the residues is not critical and they may for example be any amino acid, e.g. a neutral amino acid, or an aliphatic amino acid, or alternatively they may be hydrophobic, or polar or charged structure-forming e.g. proline. A range of different linker sequences have been shown to be of use, including short (e.g. 1-6) sequences of neutral and/or aliphatic amino acids.

Exemplary linker sequences thus include any single amino acid residue, e.g. A, I, L, V, G, R, Q, T, or W, or a di-, tri- tetra- penta- or hexa-peptide composed of such residues.

As representative linkers may be mentioned I, II, IL, R, W, WW, WWW, RIL, RIW, GAQ, GAW, VAT, IILVI (SEQ ID NO: 1180), IILVIII (SEQ ID NO: 1181) etc.

The linkers between different domains (components, elements or parts) may be the same or different.

As mentioned above, in some embodiments the linker may comprise or consist of an NLS. Alternatively viewed, in some embodiments an NLS, when present, may function both as a signal peptide and a linker. Thus, the oligopeptidic compound may comprise a signal peptide (e.g. an NLS) and a linker.

Representative compounds (or more particularly constructs) for use in the methods and uses of the invention include:

Representative compounds (or more particularly constructs) of the invention and for use in the methods and uses of the invention include:

```
                                         (SEQ ID NO: 1182)
MDRFFLVKWKKKRKIRRRRRRRRRRR, (SEQ ID NO: 1183)
MDRFYLVKWKKKRKIRRRRRRRRRRR, (SEQ ID NO: 1184)
MDRWYLVKWKKKRKIRRRRRRRRRRR, (SEQ ID NO: 1185)
MDRFVLVKWKKKRKIRRRRRRRRRRR, (SEQ ID NO: 1186)
MDRFILVKWKKKRKIRRRRRRRRRRR,
```

```
-continued
                                         (SEQ ID NO: 1187)
MDRFLLVKWKKKRKIRRRRRRRRRRR, (SEQ ID NO: 1188)
MDRWFLVKWKKKRKIRRRRRRRRRRR, (SEQ ID NO: 1189)
MDRFWLVKWKKKRKIRRRRRRRRRRR, (SEQ ID NO: 1190)
MDRFMLVKWKKKRKIRRRRRRRRRRR, (SEQ ID NO: 1191)
MDRWILVKWKKKRKSRRRRRRRRRRR, (SEQ ID NO: 1192)
MDRWLLVKWKKKRKIRRRRRRRRRRR, (SEQ ID NO: 1193)
MDRWVLVKWKKKRKIRRRRRRRRRRR, (SEQ ID NO: 1194)
MDRWMLVKWKKKRKIRRRRRRRRRRR, (SEQ ID NO: 1195)
MDRYFLVKWKKKRKIRRRRRRRRRRR, (SEQ ID NO: 1196)
MDRYILVKWKKKRKSRRRRRRRRRRR, (SEQ ID NO: 1197)
MDRYLLVKWKKKRKIRRRRRRRRRRR, (SEQ ID NO: 1198)
MDRYVLVKWKKKRKIRRRRRRRRRRR, (SEQ ID NO: 1199)
MDRYMLVKWKKKRKIRRRRRRRRRRR, (SEQ ID NO: 1200)
MDRYYLVKWKKKRKIRRRRRRRRRRR, (SEQ ID NO: 1201)
MDRYWLVKWKKKRKIRRRRRRRRRRR, (SEQ ID NO: 1202)
MDRWLVIKWKKKRKIRRRRRRRRRRR, (SEQ ID NO: 1203)
MDRWFVIKWKKKRKIRRRRRRRRRRR, (SEQ ID NO: 1204)
MDRWYVIKWKKKRKIRRRRRRRRRRR, (SEQ ID NO: 1208)
MDRWIVIKWKKKRKIRRRRRRRRRRR, (SEQ ID NO: 1311)
MDRWWLVKWKKKRKIRRRRRRRRRRR, (SEQ ID NO: 1316)
MDRFFLVKWKKKRKIRQIKIWFQNRRMKWKK;
or (SEQ ID NO. 1315)
MDRWWLVKWKKKRKIRQIKIWFQNRRMKWKK.
```

In a particularly preferred embodiment, the oligopeptidic compound comprises a sequence as set forth in SEQ ID NOs: 1182, 1183, 1184, 1185, 1186 or 1311. The oligopeptidic compounds shown above comprise N-terminal amino acids that do not form part of the domains that are essential for the compounds to have activity in the methods and uses of the invention, i.e. an "MD" sequence. Some of the peptides may also comprise N-terminal modification, e.g., acetyl groups. These additional amino acids and modifications may facilitate the production of the oligopeptidic compounds, e.g. in vitro or in vivo, and/or help to protect the compounds from degradation in vivo. It will be evident that the oligopeptidic compounds do not require these additional amino acids or modifications for their activity. Accordingly, further representative sequences according to the invention include any of SEQ ID NOs: 1182 to 1204, 1208, 1311, 1315 or 1316, omitting the N-terminal "MD". Furthermore, the presence of additional amino acids or modifications at either terminus would not be expected to disruptor inhibit the function of the oligopeptidic compounds described herein. Thus, in some embodiments, the oligopeptidic compound may comprise an N-terminal sequence, e.g. a sequence at the N-terminus that does not comprise a domain defined above, e.g. a so-called N-terminal flanking sequence. In some embodiments, the oligopeptidic compound may comprise a C-terminal sequence, e.g. a sequence at the C-terminus that does not comprise a domain defined above, e.g. a so-called C-terminal flanking sequence. In some embodiments, the oligopeptidic compound may comprise an N-terminal and C-terminal flanking sequence.

In some embodiments, the oligopeptidic compound of the invention may be in the form of a salt. For instance, the oligopeptidic compound may be in the form of an acidic or basic salt. In some embodiments, the oligopeptidic compound is in a neutral salt form. In some embodiments, the oligopeptidic compound may be in the form of an acetate salt or derivative thereof, e.g. trichloroacetate (TCA), trifluoroacetate (TFA) etc. In some embodiments, the oligopeptidic compound may be stabilized by preparing it in the form of a salt, e.g. an acetate salt.

A flanking sequence may comprise from about 1-150 amino acids, such as 1-120, 1-100, 1-90, 1-80, 1-70, 1-60, 1-50, 1-40, 1-35, 1-30 etc. Thus, a flanking sequence may comprise 1, 2, 3, 4, 5, 6, 7, 8, 9, 10, 11, 12, 13, 14, 15, 16, 17, 18, 19, 20, 21, 22, 23, 24 or 25 amino acids, e.g. 1-40, 2-39, 3-38, 4-37, 5-36, 6-35, 7-34, 8-33, 9-32, 10-31, 11-30, 12-29, 13-28, 14-27, 15-26 amino acids or any combination thereof.

Oligopeptidic compounds having sequences as set out in SEQ ID NOs. 1182-1204, 1208 and 1311 comprise separate domains (i.e. components) making up the constructs (i.e., motif-containing sequence, linker/NLS, CPP, etc.) Thus, it will be seen that SEQ ID NOs, 1182-1204, 1208 and 1311 represent constructs comprising at least one motif-containing sequence, a linker/NLS and a CPP. Linker sequences based on the NLS sequence from SV40 are used, and the CPP, sequences are based on an R-rich peptide.

The standard amino acid one letter code is used herein, so K stands for lysine (Lys), I stands for isoleucine (Ile) and so on.

As mentioned above, the oligopeptidic compound, and more particularly, the APIM motif, may comprise non-conventional or non-standard amino acids. Other domains in the oligopeptidic compound may also incorporate non-standard amino acids. In some embodiments, the oligopeptidic compound may comprise one or more, e.g. at least 1, 2, 3, 4 or 5 non-conventional amino acids, i.e. amino acids which possess a side chain that is not coded for by the standard genetic code, termed herein "non-coded amino acids" (see e.g. Table 2). These may be selected from amino adds which are formed through metabolic processes such as ornithine or taurine, and/or artificially modified amino acids such as 9H-fluoren-9-ylmethoxycarbonyl (Fmoc), (tert)-(B)utyl (o)xy (c)arbonyl (Boc), 2,2,5,7,8-pentamethylchroman-6-sulphonyl (Pmc) protected amino acids, or amino acids having the benzyloxy-carbonyl (Z) group. Preferably, where such non-coded amino acids are present, they are not located within the motif, but in some embodiments one or more non-coded amino acids are present within the motif. In some embodiments, non-coded amino acids are present in more than one domain of the oligopeptidic compound.

In vitro and/or in vivo stability of the oligopeptidic compound may be improved or enhanced through the use of stabilising or protecting means known in the art, for example the addition of protecting or stabilising groups, incorporation of amino acid derivatives or analogues or chemical modification of amino acids. Such protecting or stabilising groups may for example be added at the N and/or C-terminus. An example of such a group is an acetyl group and other protecting groups or groups which might stabilise a peptide are known in the art.

The oligopeptidic compounds of the invention will typically comprise only amino acids having the L-configuration, but one or more amino acids having the D configuration may be present. In some embodiments the oligopeptidic compound contains at least 1, 2, 3, 4 or 5 D-amino acids and they are preferably found in the motif, but in another embodiment, D-amino acids are present only outside of the motif. In a still further embodiment, D-amino acids may be found in more than one, domain of the oligopeptidic compound. The oligopeptidic compound may be linear or cyclic, preferably linear.

Thus, included particularly are retro-inverso oligopeptidic compounds of the oligopeptidic compounds of the invention (and more particularly retro-inverso peptides). Retro-inverso oligopeptidic compounds comprise D-amino acids in reverse (opposite) order to the parental or reference compound sequence. A retro-inverso analogue thus has reversed termini and reversed order of e.g. peptide bonds, while approximately maintaining the topology of the side chains as in the parental or reference sequence.

The oligopeptidic compound may include retro-inverso sequences. i.e. a domain or part of a domain may comprise a retro-inverso sequence.

By "oligopeptidic compound" is meant a compound which is composed of amino acids or equivalent subunits, which are linked together by peptide or equivalent bonds. Thus, the term "oligopeptidic compound" includes peptides and peptidomimetics.

By "equivalent subunit" is meant a subunit which is structurally and functionally similar to an amino acid. The backbone moiety of the subunit may differ from a standard amino acid, e.g. it may incorporate one or more nitrogen atoms instead of one or more carbon atoms. In preferred embodiments, the subunit comprises a standard amino acid backbone, i.e. the backbone of a standard or coded amino acid. In other words, preferably the subunit is an amino acid. However, the amino acid subunit may comprise a non-standard (non-coded) R-group.

By "peptidomimetic" is meant a compound which is functionally equivalent or similar to a peptide and which can adopt a three-dimensional structure similar to its peptide counterparts, but which is not solely composed of amino acids linked by peptide bonds. A preferred class of peptidomimetics are peptoids, i.e. N-substituted glycines. Peptoids are closely related to their natural peptide counterparts, but they differ chemically in that their side chains are appended to nitrogen atoms along the molecule's backbone, rather than to the α-carbons as they are in amino acids.

Peptidomimetics, particularly non-peptidic molecules may be generated through various processes, including conformational-based drug design, screening, focused library design and classical medicinal chemistry. Not only may oligomers of unnatural amino acids or other organic building blocks be used, but also carbohydrates, heterocyclic or macrocyclic compounds or any organic molecule that comprises structural elements and conformation that provides a molecular electrostatic surface that mimics the same properties of the 3-dimensional conformation of the peptide may be used by methods known in the art.

Thus the peptidomimetics may bear little or no resemblance to a peptide backbone. Peptidomimetics may comprise an entirely synthetic non-peptide form (e.g. based on a carbohydrate backbone with appropriate substituents) or may retain one or more elements of the peptide on which it is based, e.g. by derivatizing one or more amino acids or replacing one or more amino acids with alternative non-peptide components. Peptide-like templates include pseudopepticles and cyclic peptides. Structural elements considered redundant for the function of the peptide may be minimized to retain a scaffold function only or removed where appropriate.

In preferred embodiments, peptidomimetics retain one or more peptide elements, i.e. more than one amino acid, although such amino adds may be replaced with a non-standard or structural analogue thereof. Amino acids retained in the sequences may also be derivatised or modified (e.g. labelled, glycosylated or methylated) as long as the functional properties of the oligopeptidic compound are retained. The peptidomimetics are referred to as being "derivable from" a certain polypeptide sequence. By this it is meant that the peptidomimetic is designed with reference to the peptide sequence defined above, such that it retains the structural features of the peptide which are essential for its function. This may be the particular side chains of the peptide, or hydrogen bonding potential of the structure. Such features may be provided by non-peptide components or one or more of the amino acid residues or the bonds linking said amino acid residues of the polypeptide may be modified so as to improve certain functions of the peptide such as stability or protease resistance, while retaining the structural features of the peptide which are essential for its function.

Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-conventional, i.e. non-coded, amino acids are listed in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methynorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpencillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |

TABLE 2-continued

| Non-conventional amino acid | Code | Non-conventional amino acid | Code |
|---|---|---|---|
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | L-O-methyl serine | Omser |
| | | L-O-methyl homoserine | Omhser |

In preferred embodiments, the oligopeptidic compound is a peptide. In particularly preferred embodiments, the oligopeptidic compound is a peptide consisting of L-amino acids. In yet a further preferred embodiment, the oligopeptidic compound is a peptide consisting of standard or coded L-amino acids.

As mentioned above, the oligopeptidic compound may comprise non-standard amino acids. Thus, in some embodiments the oligopeptidic compound may incorporate di-amino acids and/or β-amino acids. However, in preferred embodiments, at least the APIM motif domain, consists of α-amino acids. Most preferably, the oligopeptidic compound, i.e. all domains and optionally all flanking sequences, consists of α-amino acids.

As mentioned above, the oligopeptidic compound defined herein comprises more than 6 subunits, but the length of the construct will depend on the size of the uptake peptide sequence and on the number and size of other domains, e.g. linker domains, flanking sequences etc., if present. Thus, the prefix "oligo" is used to designate a relatively small number of subunits such as amino acids, i.e. less than 200, preferably less than 150, 100, 90, 80, 70, 60 or 50 subunits. The oligopeptidic compound of the invention may thus comprise more than 5 but no more than 200 subunits. Preferably, it comprises at least 12, 13, 14, 15, 16, 17, 18, 19, 20, 21, 22, 23, 24 or 25 subunits. Alternatively defined it comprises no more than 50, 45, 40, 35, 34, 33, 32, 31 or 30 subunits. Representative subunit ranges thus include 12-50, 12-45, 12-40, 12-35, 12-30, 12-25, 12-22, 12-20, 12-18 etc. 12-30 and 12-40 being preferred. Further representative subunit ranges include 20-50, 21-45, 22-40, 23-35, 24-30, e.g. 25, 26, 27, 28, 29 or 30.

The nature of the subunits of the oligopeptidic compound outside of the APIM motif domain and the uptake peptide sequence is not critical, so the subunits outside of the motif may for example be alanine residues or any other suitable residues.

Peptidomimetics typically have longer half life within a patient's body, so they may be preferred in embodiments where a longer lasting effect is desired. This can help reduce the frequency at which the composition has to be re-administered. Furthermore, peptidommetics may be particularly useful in the in vitro methods described herein. However, for bio-safety reasons a shorter half life may be preferred in other embodiments; in those embodiments peptides are preferred.

The oligopeptidic compound may form part of a larger unit, e.g. it may be fused to a polypeptide to form a recombinant fusion protein or attached to a scaffold to form a peptide aptamer. Thus, fusion proteins or aptamers incorporating the oligopeptidic compound may also find utility in the uses and methods of the invention, i.e. in some embodiments the agent may be a fusion protein or aptamer comprising the oligopeptidic compound defined above.

Yet further embodiments of the invention include pharmaceutical positions comprising the agent defined herein, e.g. comprising the oligopeptidic compound, fusion protein or aptamer, together with at least one pharmacologically acceptable carrier or excipient. Said composition may be provided for use in the uses and methods of the invention defined below.

In a further aspect, a nucleic acid molecule encoding a peptide having or comprising (e.g. of) SEQ ID NO: 1, as defined above, is provided for use in the methods and uses of the invention. Alternatively viewed, the agent or composition for use in the uses and methods of the invention may be a nucleic acid molecule encoding a peptide having or comprising (e.g. of) SEQ ID NO: 1, as defined above. In this respect, the nucleic acid molecule may not need to encode all of the domains of the oligopeptidic compound described above, e.g. the domain that facilitates the cellular uptake of the peptide. For instance, the nucleic acid molecule may be delivered into the cell by another mechanism, e.g. via a liposome. However, in a preferred embodiment, the invention provides a nucleic acid molecule encoding an oligopeptidic compound or construct (e.g. a peptide) as defined above, comprising a PCNA interacting motif (APIM motif) domain and a peptide sequence (domain) that facilitates the uptake of said peptide. Also provided is the complement of such, a nucleic acid molecule for use in the uses and methods of the invention. Thus, in some embodiments the nucleic acid molecule may also encode one or more linker and/or signal sequences, as defined above.

The nucleic acid molecule of the invention comprises at least 18 nucleotides, preferably at least 36 nucleotides, and preferably no more than 800 nucleotides, more preferably no more than 700, 650, 600, 550, 500, 450, 400, 350, 300, 260, 200, 160, 100, 75 or 50 nucleotides. The nucleic acid molecule is preferably an isolated or synthetic molecule.

A further aspect of the invention relates to a vector comprising a nucleic acid molecule as defined herein for use in the uses and methods defined below. Preferably, the vector comprises a promoter sequence operably linked to the sequence encoding a peptide as defined above. The vector may also contain further elements typically found in a vector such as an origin of replication, a selectable marker such as antibiotic resistance, and/or a multiple cloning site. The vector may further be an expression vector, and may comprise further elements, e.g. transcriptional and/or translational control or regulatory elements for expression of the nucleic acid molecules. Such control elements, e.g. promoters, ribosome binding sites, enhancers, terminators etc., are well known and widely described in the art.

The vector may for example be a plasmid or a viral genome (or part thereof), preferably the viral genome is from a virus selected from a retrovirus, an adenovirus and an adenovirus-associated virus. In some embodiments, e.g. where the vector comprises a nucleic acid molecule encoding a bactericidal peptide, the vector may be a viral genome (or part thereof) from a virus capable of infecting a bacterium such as a bacteriophage. Thus, in some embodiments, the vector may be administered in the form of a virus comprising a vector containing a nucleic acid molecule encoding an oligopeptidic compound described above. Alternatively viewed, in some embodiments the vector may be a virus.

As mentioned above, the invention provides a composition (e.g. a pharmaceutical composition) comprising an agent as defined herein and its use in the methods and uses of the invention. Accordingly, said composition (e.g. a pharmaceutical composition) may comprise an oligopeptidic compound (including a fusion protein or aptamer) and/or nucleic acid molecule as defined herein and/or a vector as defined herein, together with at least one pharmacologically (or pharmaceutically) acceptable carrier or excipient.

The excipient may include any excipients known in the art, for example any carrier or diluent or any other ingredient or agent such as buffer, antioxidant, chelator, binder, coating, disintegrant, filler, flavour, colour, glidant, lubricant, preservative, sorbent and/or sweetener etc.

The excipient may be selected from, for example, lactic acid, dextrose, sodium metabisulfate, benzyl alcohol, polyethylene glycol, propylene glycol, microcrystalline cellulose, lactose, starch, chitosan, pregelatinized starch, calcium carbonate, calcium sulfate, dextrates, dextrin, dextrose, dibasic calcium phosphate dihydrate, tribasic calcium phosphate, magnesium carbonate, magnesium oxide, maltodextrin, mannitol, powdered cellulose, sodium chloride, sorbitol and/or talc.

The pharmaceutical composition may be provided in any form known in the art, for example as a tablet, capsule, coated tablet, liquid, suspension, tab, sachet, implant, inhalant, powder, pellet, emulsion, lyophilisate, effervescent, spray, salve, emulsion, balm, plaster or any mixtures thereof. It may be provided e.g. as a gastric fluid-resistant preparation and/or in sustained action form. It may be a form suitable for oral, parenteral, topical, rectal, genital, subcutaneous, transurethral, transdermal, intranasal, intraperitoneal, intramuscular and/or intravenous administration and/or for administration by inhalation. In embodiments where the composition is used in combination with UV radiotherapy, the composition preferably may be formulated for topical administration, e.g. for the treatment or prevention of a bacterial infection in a wound, including a surgical wound.

In a representative embodiment, the pharmaceutical composition may be in a form suitable for liposomal administration, so preferably liposomes containing the pharmaceutical composition are provided. When liposomes are used, it may not be necessary to include a further excipient, so in a further embodiment the invention also provides liposomes containing an agent, e.g. oligopeptidic compound, as defined herein, and their use in the methods and uses of the invention.

The term "treatment" as used herein refers broadly to any effect or step (or intervention) beneficial in the management of a clinical condition or disorder and thus includes both therapeutic and prophylactic treatments. Treatment may include reducing, alleviating, ameliorating, slowing the development of, or eliminating the condition or one or more symptoms thereof, which is being treated, relative to the condition or symptom prior to the treatment, or in any way improving the clinical status of the subject. A treatment may include any clinical step or intervention which contributes to, or is a part of, a treatment programme or regimen. A prophylactic treatment may include delaying, limiting, reducing or preventing the condition or the onset of the condition, or one or more symptoms thereof, for example relative to the condition or symptom prior to the prophylactic treatment. Prophylaxis thus explicitly includes both absolute prevention of occurrence or development of the condition, or symptom thereof, and any delay in the onset or development of the condition or symptom, or reduction or limitation on the development or progression of the condition or symptom.

Thus, treatment includes killing, inhibiting or slowing the growth of bacterial cells, or the increase in size of a body or population of bacterial cells, reducing bacterial cell number or preventing the spread of bacterial cells (e.g. to another anatomic site), reducing the size of a bacterial cell colony or infection site etc. The term "treatment" does not necessarily imply the cure or complete abolition or elimination of bacterial cell growth, or growth of bacterial cells.

The term "inhibit" is used broadly to include any reduction or decrease in bacterial cell growth as well as the prevention or abolition of bacterial cell growth. "Inhibition" thus includes the reduction or prevention of bacterial cell growth, e.g. including reducing the rate of cell growth. This may be determined by any appropriate or convenient means, such as determining or assessing cell number, cell viability and/or cell death etc., as may be determined by techniques well known in the art.

"Growth" of bacterial cell as referred to herein is also used broadly to include any aspect of bacterial cell growth, including in particular the proliferation (i.e. increase in number) of bacterial cells.

The agents as defined herein may thus be used in the treatment or prevention of any bacterial infection, which may be a disease or condition (used broadly herein to include any disorder or any clinical situation) which is responsive to reduction of bacterial cell growth (particularly bacterial cell proliferation). The agents accordingly find utility in any therapy (or treatment) which targets bacterial cell growth (or proliferation). In other words, the agents may be used in any therapeutic application in which it desirable or advantageous to inhibit bacterial cell proliferation.

A "bacterial infection" may be defined as any atypical, unwanted, undesirable, excessive and/or harmful infection and includes a "bacterial infectious disease" and may be defined as a disease, condition or disorder caused by the invasion of a subject, e.g. one or more organs or tissues of said subject, by one or more disease-causing bacteria and their subsequent multiplication. In some instances, an infection or infectious disease may be characterised by the reaction of the subject (e.g. organ or tissues of said subject) to said organisms and, in some cases, to the toxins produced by said organisms. A bacterial infection or bacterial infectious disease may be local or systemic. A bacterial infection may be any bacterial infection caused by a bacterium.

Since the therapeutic applications and utilities of the present invention may generally involve inhibiting bacterial cell proliferation, any proliferating bacterial cell may be targeted in the therapies and utilities disclosed and encompassed herein.

In some aspects of the invention the bacteria may be a gram positive or gram negative, or gram test non-responsive. They may be aerobic or anaerobic bacteria. For instance, the bacteria may be from any of the genus *Acinetobacter, Bacillus, Burkholderia, Chlamydia, Clostridium, Helicobacter, Staphylococcus, Streptococcus, Pseudomonas, Legionella, Listeria, Mycobacterium, Proteus, Klebstalla, Fusobacterium* or other enteric or conform bacteria.

Thus, for instance, the bacterial infection or bacterial infectious disease may be caused by a gram-positive bacterium such as, *M. tuberculosis, M. bovis, M. typhimurium, M. bovis* strain BCG, BCG substrains, *M. avium, M. intracellulare, M. africanum, M. kansasil, M. marinum. M. ulcerans, M. avium* subspecies *paratuberculosis, Staphylococcus aureus, Staphylococcus epidermidis, Staphytococcus equi, Streptococcus pyogenes, Streptococcus agalactiae, Listeria monocytogenes, Listeria ivanovii, Bacillus anthracis, B. subtilis, Nocardia asteroides, Actinomyces israelii, Propionibacterium acnes,* and *Enterococcus* species.

In other embodiments, the bacterial infection or bacterial infectious disease may be caused by a gram-negative bacterium such as *Clostridium tetani, Clostridium perfringens, Clostridium botulinum, Pseudomonas aeruginosa, Vibrio cholerae, Actinobacillus pleuropneumoniae, Pasteurella haemolytica, Pasteurella multocida, Legionella pneumophila, Salmonella typhi, Brucella abortus, Chlamydi trachomatis, Chlamydia psitteci, Coxiella bumetti, Escherichia coli, Neiserria meningitidis, Neiserria gonorrhea, Haemophilus influenzae, Haemophilus ducreyi, Yersinia pestis, Yersinia enterolitica, Escherichia coli, E. hiree, Burkholderia cepecia, Burkholderia pseudomallei, Francisella tularensis, Bacteroides fragillis, Fusobascterium nucleatum,* and *Cowdria ruminantium.*

In some embodiments, the bacterial infection or bacterial infectious disease may be caused by a bacterium is selected from the following genera: *Achromobacter, Acinetobacter, Actinobacilius, Aeromonas, Agrobacterium, Alcaligenes, Alteromonas, Bacteroides, Bartonella, Borrellia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas Corynebactenum, Coxiella, Cryptobacterium, Edwardsiella, Eikenella, Enterobacter, Enterococcus, Erwinia, Helicobacfer, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocerdiopsis, Pantoea, Parachlamydia, Pasteurella, Peptococcus, Peptostreptococcus, Prevotella, Propionibacterium, Proteus, Providencia, Pseudomonas, Raistonia, Rickettsia, Salmonella, Shewenella, Shigella, Sphingobacterium, Sphingomonas, Staphylococcus* (e.g. *Staphylococcus aureus* NCTC 6571 also called Oxford Staph.), *Stenotrophomonas, Streptobacillus, Streptococcus, Streptomyces, Treponem* and *Yersinia.* In some embodiments, the bacterium is a MDR bacterium.

In some embodiments, the MDR bacterium is a Methicillin-resistant *Staphylococcus aureus* (MRSA) bacterium. Alternatively viewed, the MDR bacterial infection is an MRSA infection.

MRSA infections are caused by strains of *Staphylococcus aureus* that have become resistant to the antibiotics commonly used to treat ordinary *Staphylococcus aureus* infections.

Most MRSA infections occur in people who have been in hospitals or other health care settings, such as nursing homes and dialysis centres, where it is known as health care-associated MRSA (HA-MRSA). HA-MRSA infections typically are associated with invasive procedures such as surgery or the use of devices, such as intravenous tubing or artificial joints.

MRSA infections may also occur in the wider community i.e. among healthy people; this form of MRSA infection, community-associated MRSA (CA-MRSA), often begins as a painful skin boil. It is spread by skin-to-skin contact and at-risk populations include groups that frequently are in contact with other people, such as high school wrestlers, child care worker and people who live in crowded conditions.

Many strains of MRSA have been identified and any strain of MRSA may be treated using the agents, compositions and methods of the invention. Particular strains are described below and identified in WO 2010/139957 (incorporated herein by reference) and may be viewed as preferred strains to be treated according to the present invention.

MRSA 1021b is resistant is penicillin, clindamycin, gentamycin, fusidic acid, erythromycin, trimethoprin, sulphamethoxazole, cefoxitin, ciprofioxacin, and fosphomycin glucose 6 phosphate.

MRSA 1141b is resistant to penicillin, clindamycin, fusidic acid, erythromycin, trimethoprin, cefoxitin, ciprofloxacin and mupirocin.

MRSA 1108 is resistant to penicillin, fusidic acid, trimethoprin, cefoxitin, rifampicin and ciprofloxacin.

MRSA 1047 is resistant to penicillin, fusidic acid, erythromycin, trimethoprin, cefoxitin, ciprofloxacin, mupirocin, chloramphenicol, and fosphamycin glucose 6 phosphate.

MRSA 1040 is resistant to penicillin, gentamycin, fusidic acid, erythromycin, trimethoprin, sulphamethoxazole, tetracycline, cefoxitin, ciprofloxacin and mupirocin.

MRSA 1096 is resistant to penicillin, gentamycin, erythromycin, trimethoprin, sulphamethoxazole, cefoxitin and ciprofioxacin.

*Staphylococcus aureus* ATC-43300 is resistant to methicillin and oxacillin.

Particularly preferred strains to be treated according to the present invention are MRSA 1040 and/or MRSA 1096.

In some embodiments, an MRSA infection may be treated using an agent or composition of the invention in combination with an antibiotic. In some embodiments, the antibiotic is a macrolide antibiotic, such as Azithromycin, Erythromycin, Clarithromycin, Telithromycin, Carbomycin A, Josamycin, Kitasamycin, Midecamycinim/decamycin acetate, Oleandomycin, Solithromycin, Spiramycin, Troleandomycin, Tylosin/tylocine or Roxithromycin. In some embodiments, the macrolide antibiotic is Azithromycin or Erythromycin.

In some embodiments the MDR bacterium is an *Enterococous faecium* bacterium. Alternatively viewed, the MDR bacterial infection is an *Enterococcus faecium* infection.

An example of an MDR strain of *Enterococcus faecium* CCUG 37832 (TO-3).

*Enterococcus faecium* is commonly associated with endocarditis, urinary tract infections and infections in wounds. *Enterococcus faecium* may also cause meningitis, e.g. neonatal meningitis. Thus, in some embodiments, the subject to be treated according to the methods and uses of the invention has endocarditis, a urinary tract infection, an infected wound or meningitis, e.g. neonatal meningitis, some embodiments, an *Enterococcus faecium* infection may be treated using an agent or composition of the invention in combination with an antibiotic. In some embodiments, the antibiotic is a DNA gyrase inhibitor, such as an aminocoumarin (e, g, novobiocin) or a quinolone (e.g. nalidixic acid or ciprofloxacin). In some embodiments, the antibiotic is 2,4-Diamin S. methizol, S. methoxa, S. dimetho, Sulfaceta, Trimethoprim, Flumeq, Levoflox, Pruliflox, Metronid or Nitrofur.

A bacterial infection to be treated or prevented by the agent or composition of the invention may be in any tissue or organ of the subject to be treated, such as the lungs (including the respiratory tract), stomach, gastrointestinal tract (GIT), blood, skin (including wounds, such as surgical wounds), bladder (including the urinary tract), kidney, ear, eye, meninges etc. Hence, the bacterial infection may be a respiratory infection, stomach infection, GIT infection, blood infection, skin infection, bladder infection, kidney infection, ear infection, eye infection, meningial infection etc. A skin infection may include an infection of a mucosal membrane, such as the oral cavity, oesophagus or eye, e.g. cornea.

Thus, in some embodiments of the invention the infectious disease or a disease or condition exacerbated or caused by a bacterial infection may include any one of bacterial pneumonia, cystic fibrosis, gastric ulcers, bacterial meningitis, Legionellosis (Legionnaires' disease), Legionellosis (Pontiac fever) Pertussis (Whooping cough), Salmonellosis, Tuberculosis, sepsis etc.

As noted above, in some embodiments the agent or composition as defined herein is used in combination with one or more additional active agents, e.g. a cytotoxic or cytostatic compound, in order to enhance or complement the effect of agent or composition defined herein. In some embodiments, the additional active agent may be used to treat symptoms of the bacterial infection or infectious disease, e.g. secondary symptoms, such agents may be, e.g. an anti-inflammatory compound, steroid (e.g. a corticosteroid) etc. and will be dependent on the nature of the disease, including the severity of the symptoms etc. However, in some embodiments, the agent as defined herein may be used alone, i.e. as the only active agent in a composition and/or medicament.

In some embodiments the additional active agent, is a cytostatic or cytotoxic agent. In particularly preferred embodiments, the cytotoxic or cytostatic agent is an intracelluarly-active agent, i.e. it targets an intracellular process. In other words, in some embodiments, the cytotoxic or cytostatic agent does not act at or on the cell wall or cell membrane, i.e. it does not exert its cytotoxic or cytostatic effect by affecting the cell wall or cell membrane, e.g. by inhibiting cell wall synthesis or by permabilzing the cell.

By "cytostatic agent" is meant an agent which is capable of inhibiting or suppressing the growth and/or multiplication (replication/proliferation) of bacterial cells, e.g. an antibacterial agent, such as an antibiotic agent.

Included as cytostatic agents are cytotoxic agents and any agent which may be indicated for an anti-bacterial application. Thus, included are agents used in anti-bacterial treatment protocols. However, cytostatic agents that are not typically used for suppressing or inhibiting bacterial growth may find utility in combination with the agents defined herein, e.g. agents that generally have an effect do cell growth, such as chemotherapeutic agents, particularly DNA damaging agents.

In some embodiments, the cytostatic or cytotoxic agent is an antibiotic agent.

Suitable antibiotic agents include but are not limited to any one or more of Aminocoumarins (such as Novobiocin, Albamycin, Coumermycin and Clorobiocin), Aminoglycosides (such as Amikacin, Apramycin, Gentamicin, Kanamycin, Neomycin, Netilmicin, Tobramycin, Paromomycin and Spectinomycin), Ansamycins (such as Geldanamycin, Herbimycin, Rifaximin and Streptomycin), Carbapenems (such as Ertapenem, Daripenem, Cilastatin ('Imipenem') and Meropenem), Cephalosporins (such as Cefadroxil, Cefazolin, Cefalothin ('Cefalotin'), Cefalexin, Cefaclor, Cefamandole, Cefoxitin, Cefprozil, Cefuroxime, Cefixime, Cefdinir, Cefoperazone, Cefotaxime, Cefpodoxime, Ceftazidime, Ceftibuten, Ceftizoxime, Ceftriaxone, Cefepime, Ceftaroline fosamil and Ceftobiprole) Glycopeptides (such as Teicoplanin, Vancomycin and Telavancin), Lincosamides (such as Clindamycin and Lincomycin), Lipopeptides (such as Daptomycin), Macrolides (such as Azithromycin, Clarithromycin, Dirithromycin, Erythromycin, Roxithromycin, Troleandomycin, Telithromycin and Spiramycin), Monobactams (such as Aztreonam), Nitrofurans (such as Furazolidone and Nitrofurantoin), Oxazolidonones (such as Linezolid, Posizolid, Radezolid and Torezolid), Penicillins (such as Amoxicillin. Ampicillin, Aziocillin, Carbeniallin, Cloxacillin, Didoxacillin, Flucloxacillin, Mezlocillin, Methicillin, Nafcillin, Oxacillin, Pencillin G, Penicillin V, Piperacillin, Temocillin and Ticarcillin), Penicillin combinations (such as Amoxicillin/clavulanate, Ampicillin/sulbactam, Piperacillin/tazobactam and Ticarcillin/davulanate), Polyethers (such as Monensin), Polypeptides (such as Sacitracin, Colistin and Polymyxin B), Quinolones (such as Ciprofloxacin, Enoxacin, Gatifloxacin, Levofloxacin, Lomefloxacin, Moxifloxacin, Nalidixic acid, Norfloxacin, Ofloxacin, Trovalioxacin, Grepafloxacin, Sparfloxacin and Temafloxacin); Sulfonamides (such as Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Sulfamethoxazole (Co-trimexazole, TMP-SMX, 'Trimethoprim') and Sulfonamidochrysoidine), Tetracyclines (such as Demeclocycline, Doxycycline, Minocycline, Oxytetracycline and Tetracycline) and Others (such as Clofazimine, Dapsone, Capreomycin, Cycloserine, Ethambutol, Ethionamide, Isoniazid, Pyrazinamide, Rifampicin ('Rifampin'), Rifabutin, Rifapentine, Streptomycin, Arsphenamine, Chloramphenicol, Fosfomycin, Fusidic acid, Metronidazole, Mupirocin, Platensimycin, Ouinupristin (Dalfopristin), Thiamphenicol, Tigecycline, Tinidazole and Trimethoprim).

Other cytostatic agents that may find utility in the invention may be grouped into different classes according to their mechanism of action and all of these classes are contemplated herein. Thus, the cytostatic agent may be an alkylating agent, a cross-linking agent, an intercalating agent, a nucleotide analogue, an inhibitor of spindle formation, and/or an inhibitor of topoisomerase I and/or II. Other types or classes of agent include anti-metabolites, plant alkaloids and terpenoids, or an anti-tumour antibiotic. Preferably, it is an alkylating agent.

Alkylating agents modify DNA by alkylating nucleosides, which leads to the prevention of correct DNA replication. Nucleotide analogues become incorporated into DNA during replication and inhibit DNA synthesis. Inhibitors of spindle formation disturb spindle formation, leading to the arrest of mitosis during metaphase. Intercalating agents intercalate between DNA bases, thereby inhibiting DNA synthesis. Inhibitors of topoisomerase I or II affect the torsion of DNA, thereby interfering with DNA replication.

Suitable cytostatic agents are known in the art, but by way of example MMS (Methyl methanesulphonate), actinomycin D, BCNU (carmustine), carboplatin, CCNU, Campothecin (CPT), cantharidin, Cisplatin, cyciophosphamide, cytarabine, dacarbazine, daunorubicin, docetaxel, Doxorubicin, DTIC, epirubicin, Etoposide, gefinitib, gemcitabine, ifosfamide and/or irinotecan, ionomycin, Melphalan, Methotrexate, Mitomycin C (MMC), mitozantronemercaptopurine, Oxaliplatin, Paclitaxel (taxol), PARP-1 inhibitor, taxotere, ternozolomide (TZM), teniposide, topotecane, treosulfane vinorelbine, vincristine, vinbiestine, 5-Azacytidine, 5,6-Dihydro-5-azacytidine and 5-fluorodracil are named herein.

The skilled person will be aware of suitable dosage ranges for any given cytostatic agent and, in one embodiment, the cytostatic agent is present in the pharmaceutical composition, or administered to the subject, in its typical dose range. In an advantageous embodiment, a lower dose of the cytostatic agent may be used because the agent defined herein sensitises the bacterial cells to the cytostatic agents and so when used in combination with the agent of the invention, a lower dose of the cytostatic agent will have the same or comparable therapeutic effect as a higher dose of the cytostatic agent on its own.

As discussed above, a suitable dose for the agent or composition as defined herein may be defined as a dose that is sufficient, either alone or in combination with an additional active agent, to inhibit bacterial cell growth (e.g. in vivo or in vitro). In some embodiments, a suitable dose may be defined as a dose that is sufficient, either alone or in combination with an additional active agent to kill the majority of the bacterial cells causing, or associated with, the infection or infectious disease. In some embodiments, a suitable dose for the agent or composition defined herein may be defined as a dose that is sufficient to sensitize a bacterium to a cytotoxic or cytostatic agent, wherein contacting the bacterium with (e.g. treatment with or administration of) an agent and a cytotoxic or cytostatic agent is sufficient to inhibit bacterial cell growth (e.g. in vivo or in vitro) and/or sufficient to kill the majority of the bacterial cells causing, or associated with, the infection or infectious disease.

In some embodiments, dose may be defined as a dose that does not induce apoptosis in animal cells significantly, i.e. an apoptosis non-inducing dose for animal cells, particularly human cells. Thus, a suitable dose may be defined as a "low dose" or "low amount" of the agent (e.g. oligopeptidic compound), which may be seen as a dose or amount that is not sufficient to cause or induce apoptosis animal cells either directly or indirectly. However, as noted above and in the Examples below, the oligopeptidic compounds of the invention do not readily induce apoptosis in healthy animal cells, i.e. the oligopeptidic compounds of the invention are not cytotoxic to animal cells and accordingly, a wide variety of doses may be suitable in the methods and uses of the present invention.

The "majority of cells" may be defined as at least 50% of the bacterial cells, e.g. at least 60, 70, 80, 85, 90, 91, 92, 93, 94, 95, 96, 97, 98, 99 or 100% of the cells causing, or associated with, the infection or infectious disease.

Thus a dose that does not induce apoptosis in animal cells significantly may be viewed as a dose that causes or induces apoptosis of less than 20% of the animal cells in the target area, e.g. less than 15, 10 9, 8, 7, 6, 5, 4, 3, 2 or 1% of the animal cells in the target area. The target area may be the area to which the agent or composition is administered, e.g. an organ or a portion thereof.

The effective dose or amount of agent may depend on the characteristics of the peptide, e.g. the strength of the interaction between the PCNA interacting motif and the binding domain of the target protein(s). Furthermore, effective dose or amount of the agent may depend upon the nature of the compound used (i.e. peptide, nucleic acid molecule etc.), the mode of administration, the course of treatment, the age and weight of the patient, the medical indication, the body or body area to be treated, or the in vitro use, and may be varied or adjusted according to choice. Generally however, a low dose or amount may result in an active concentration range of about 0.01, 0.05, 0.1, 0.25, 0.5, 0.75, 1.0, 1.25, 1.50, 1.75, 2.0, 3.0, 4.0, 5.0 to 10 µM, e.g. 0.01 to 10 µM, e.g. 0.05 to 7.5 µM, such 0.1 to 7.5 µM, e.g. 0.5 to 5 µM. A high dose or amount, may result in an active concentration range of about 1.0, 2.0, 3.0, 4.0, 5,0, 7.5, 10, 15, 20, 25, 30, 40 to 50 µM, e.g. 1.0 to 50 µM, e.g. 2.0 to 40 µM, such as 3.0 to 30 µM, e.g. 5.0 to 25 µM. Said concentrations are determined by reference to the amount of the compound itself and thus appropriate allowances should be made to take into account the purity of the composition.

The subject is an animal (i.e. any human or non-human animal), preferably a mammal, most preferably a human.

As noted above, the agent or composition of the invention as defined herein may be provided or administered via a product, device, implant or material to which the agent or composition has been applied, impregnated or chemically bonded. Hence, the invention also provides a product, material, device or implant which is coated, impregnated or chemically bonded with an agent or composition as described herein. The invention also extends to the use of such products, materials, devices or implants in the methods and uses as described herein. In particular, the products, materials, devices or implants may be coated, impregnated or chemically bonded with an agent or composition as described herein to prevent or inhibit the formation of a bacterial biofilm.

Thus, the present invention also provides a method of preventing or inhibiting the formation of a bacterial biofilm on a product, material, device or implant, said method comprising:

(i) providing a product, material, device or plant; and (ii) coating or impregnating said device with an agent or composition defined herein, or chemically bonding are agent or composition as defined herein to said product, material, device or implant.

To this end, bandages, plasters (e.g. adhesive patches), gauze, surgical tape, cotton swabs or other absorbent materials, e.g. a puff, fleece, or sponge, supportive matrices or wound dressings may be coated, impregnated or chemically bonded with an agent or composition as described herein. For example, many positions can be applied to the skin using dermal patches that are well described in the art, e.g. US 2008/0038300, US 2009/0043236, WO 2005/067499 and WO 2009/085302, which are incorporated herein by reference. In some embodiments, the material comprising the agent or composition as described herein may be in the form of a device that can be, e.g. worn by the subject to be treated. For instance, the agent or composition as described herein may be applied, impregnated or chemically bonded onto a material or supportive matrix that forms all or part of a diaper, glove, sock etc.

In some embodiments, the product or material a bandage, plaster (e.g. adhesive patch), gauze, surgical tape, cotton swab, puff, fleece, sponge, supportive matrix, wound dressing, diaper, glove or sock.

In still further embodiments, the device or implant may be a medical or surgical device or implant. For instance, the device or implant may be selected from, but is not limited to, a stent (e.g. coronary stent), ear tube (tympanostomy tube), artificial eye lens (i.e. a pseudophakos or intra-ocular lens), an orthopedic implant (e.g. screw, pin, plate or rod, such as for traumatic fracture repair or spinal fusion), an artificial bone (e.g. a spinal disc, hip, knee etc.), a dental implant (e.g. an artificial tooth or part thereof), a cardiac device (e.g. an implantable cardioverter defibrillator, pacemaker etc.), a cosmetic implant (e.g. breast implant), intra-uterine device (IUD), a catheter (e.g. central venous or urinary catheter) or a prosthetic device.

In some embodiments, the product or deice may be a contact lens or contact lens storage case.

The agent, composition, product, material, device or implant can be included in a container, pack, or dispenser together with instructions for administration and/or use.

The invention will now be further described with reference to the following non-limiting Examples and Figures in which:

FIG. 1 shows a graph that demonstrates that the growth of gram-negative bacteria, *Pseudomonas aeruginosa* ATCC 15692, *Acinetobacter baumenni* ATCC 19606, *Escherichla coli* ATCC 25922 and *Pseudomonas aeruginosa* TO-5A (clinical isolate) is inhibited by varying concentrations of APIM peptide, ATX-101 (SEQ ID NO: 1289). Growth of the strains is given relative to growth in cultures without ATX-101.

Figure 7:
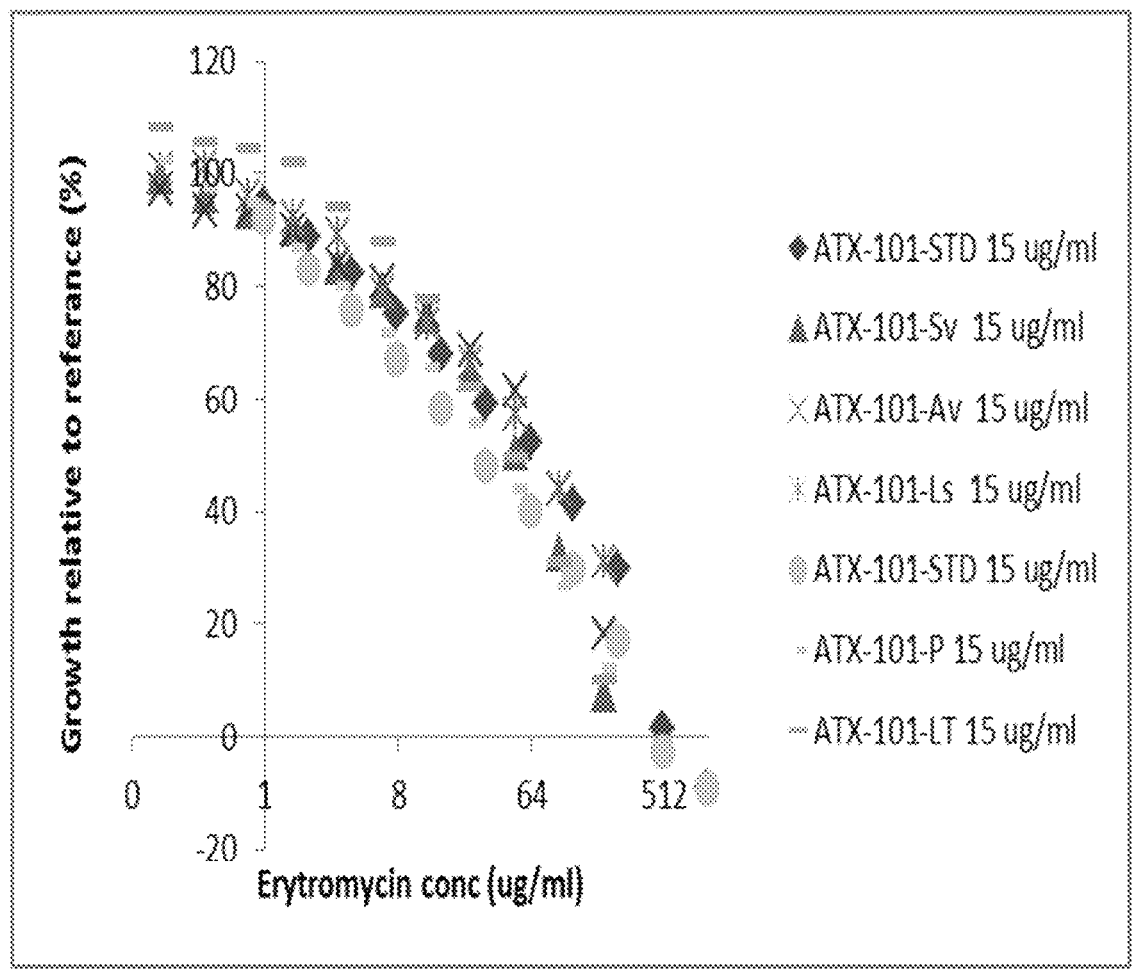

FIG. 7 shows a graph that demonstrates that various APIM peptide variants are capable of reducing the MIC of erythromycin required to inhibit the growth of the MDR bacterium Methicillin-resistant *Staphylococcus aureus* (MRSA 1040), wherein: ATX-101-STD is SEQ ID NO: 1298; ATX-101-Sv is SEQ ID NO: 1298; ATX-101-Av is SEQ ID NO: 1299; ATX-101-Ls is SEQ ID NO: 1302; ATX-101-P is SEQ ID NO: 1303; and ATX-101-LT is SEQ ID NO: 1300.

Figure 8:
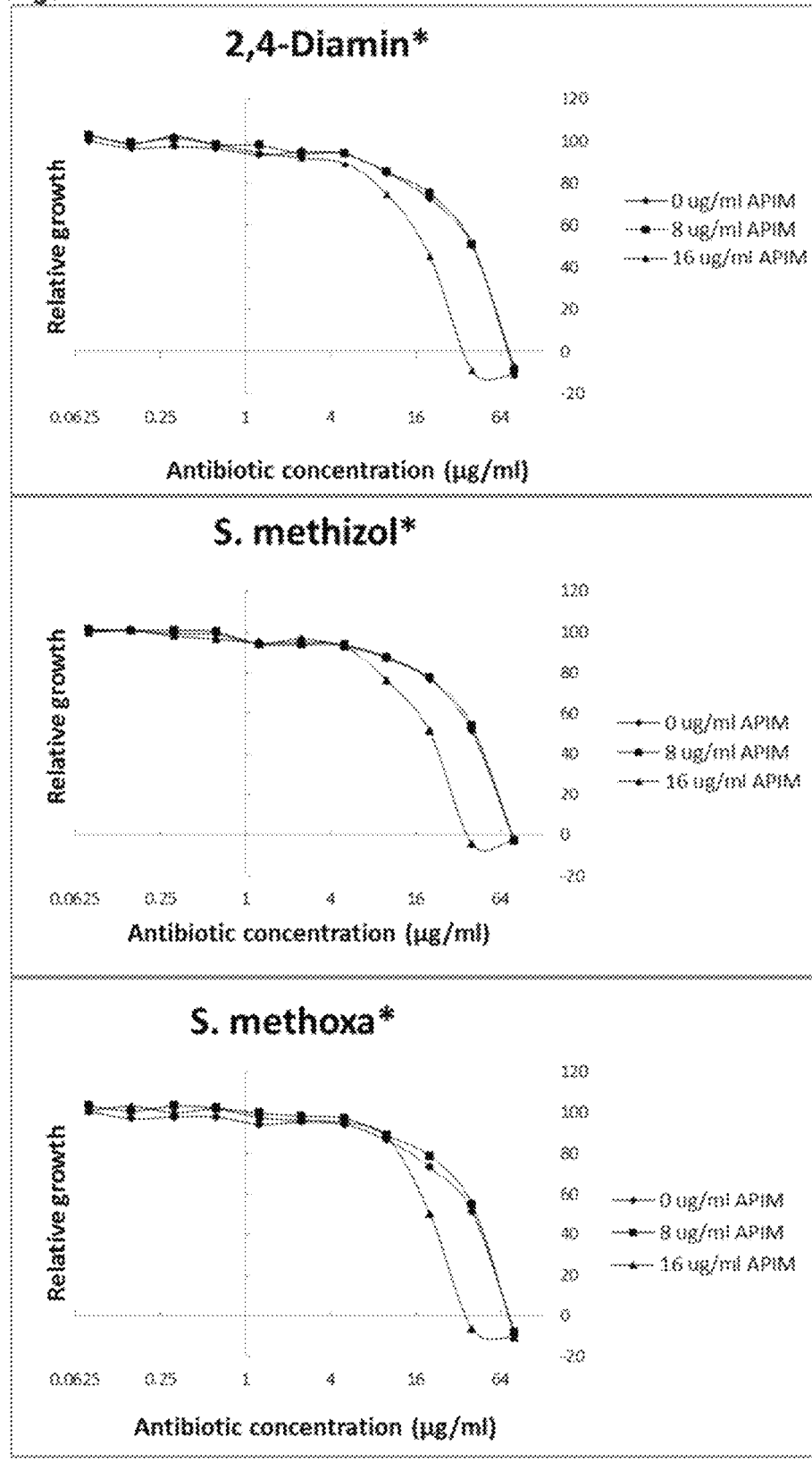
Figure 8:
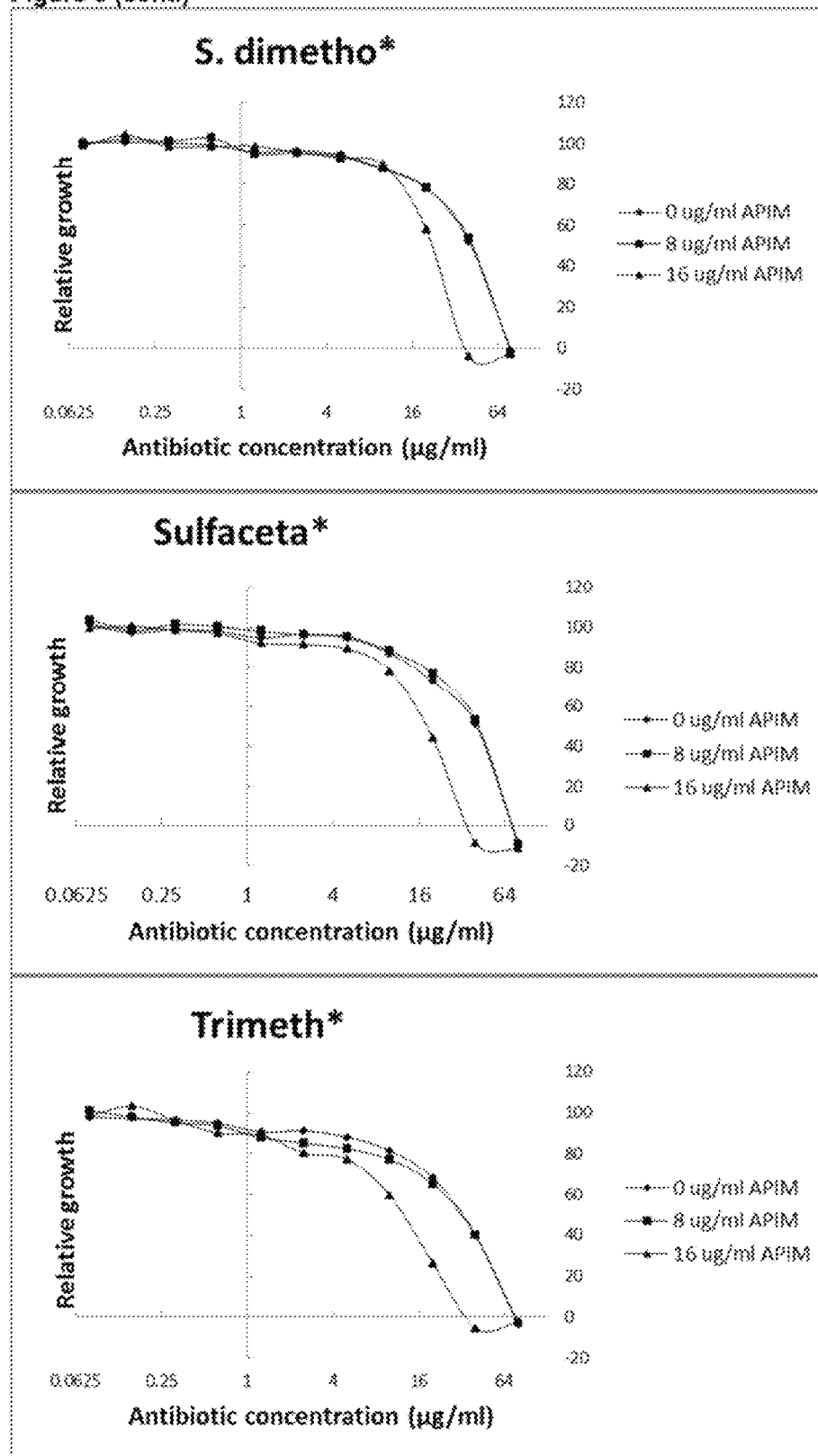
Figure 8:
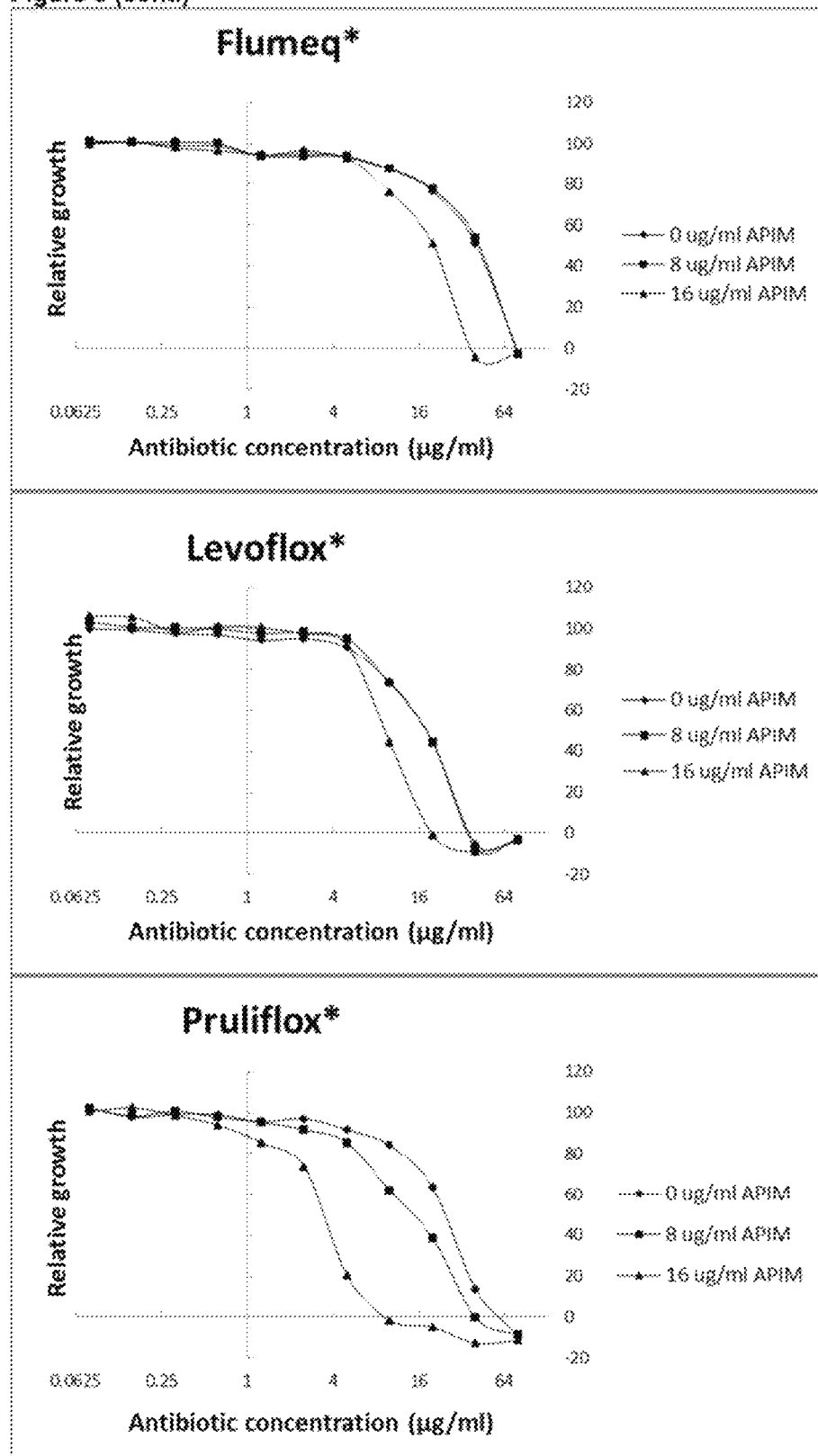

FIG. 8 shows graphs that demonstrate that the growth of the MDR bacterium *E. faecium* CCUG 37832 (TO-3) is more sensitive to various DNA gyrase inhibitors, when grown in the presence of ATX-101.

Figure 9:
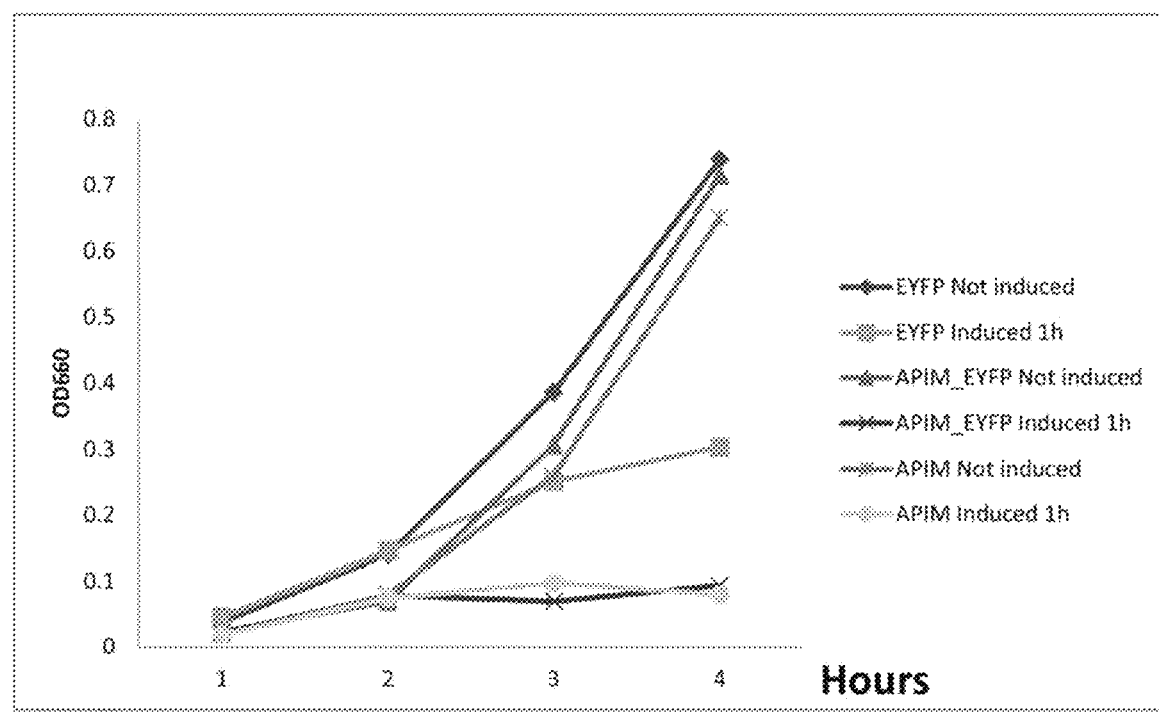
Figure 9:
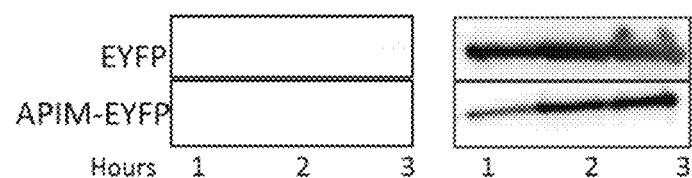

FIG. 9 show (A) a graph showing the growth of *E. coli* in which the overexpression of various proteins or peptides is induced or not induced and demonstrates that the induction of an APIM peptide (SEQ ID NO: 1290), alone or as part of a fusion protein with EYFP, inhibits bacterial growth. (B) shows a Western blot showing levels of EYFP-proteins in un-induced (left) versus induced (right) cell cultures.

Figure 10:
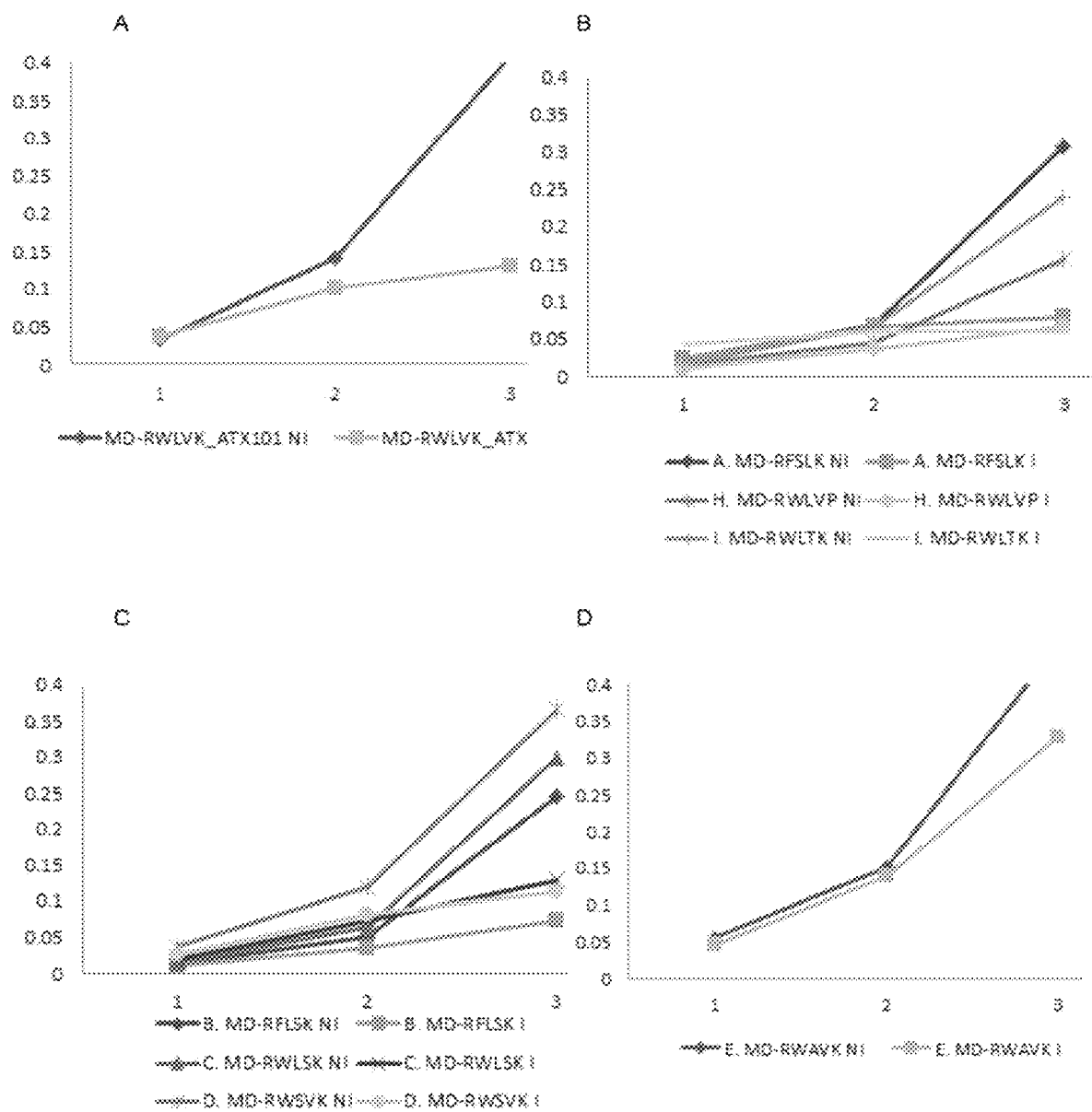

FIG. 10 shows graphs showing the growth of *E. coli* in which the overexpression of various APIM peptides is induced (I) or not induced (NI). The APIM sequences are: (A) SEQ ID NO: 1290; (B) SEQ ID NOs: 1291, 1292 and 1293; (C) SEQ ID NOs: 1294, 1295 and 1296; (D) SEQ ID NO: 1297.

Figure 11:
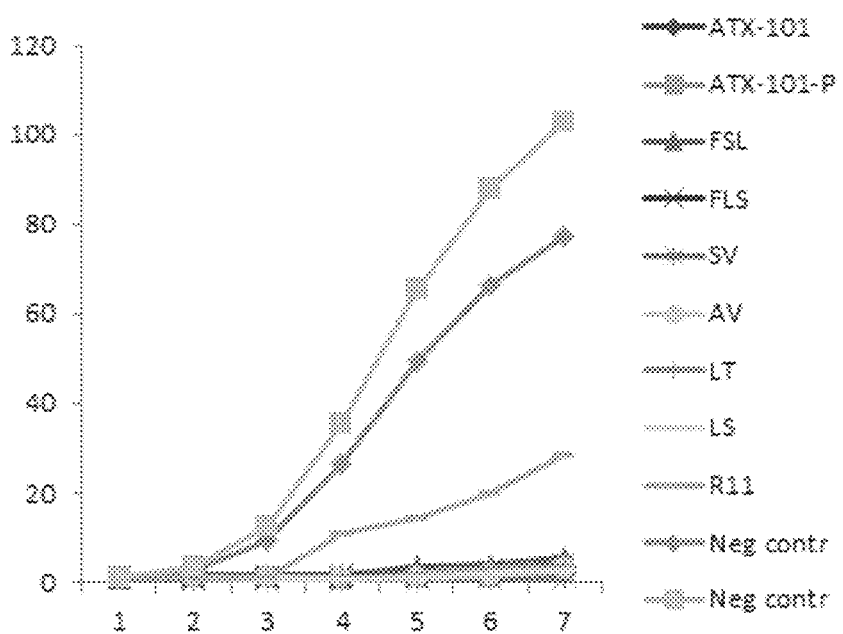
Figure 11:
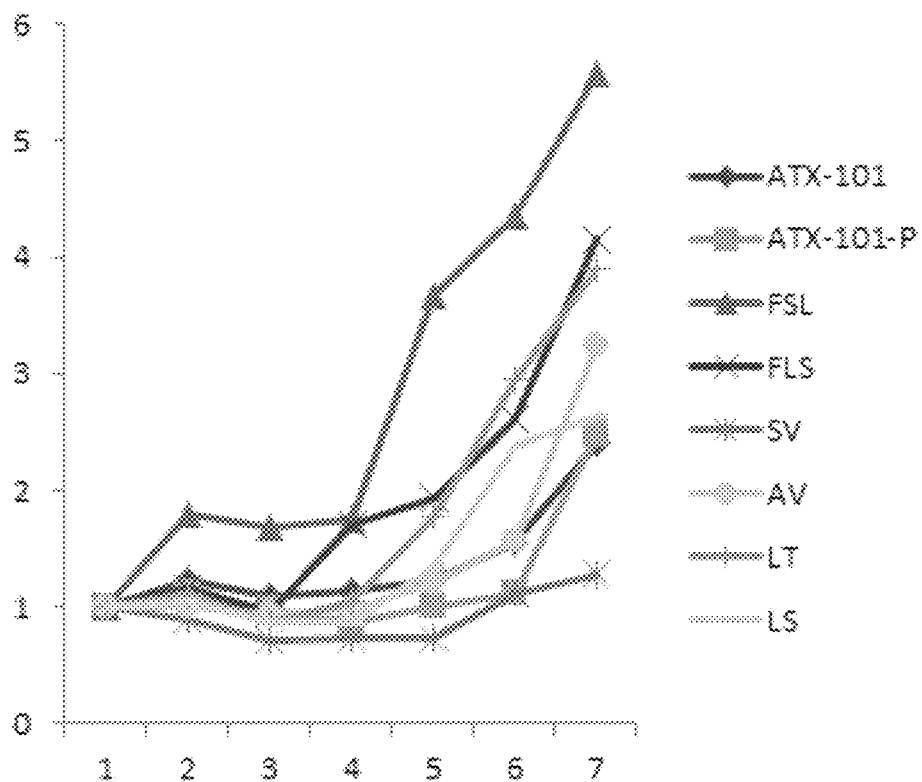

FIG. 11 shows graphs showing the growth of *E. coli* in the presence of 30 µM of various APIM peptides. The same data is presented in (A) and (B), however the control growth curves are not shown in (B). ATX-101 is SEQ ID NO: 1289; ATX-101-P is SEQ ID NO: 1303; FSL, is SEQ ID NO: 1304; FLS is SEQ ID NO: 1301; SV is SEQ ID NO: 1298; AV is SEQ ID NO: 1299; LT is SEQ ID NO: 1300; LS is SEQ ID NO: 1302; R11 is SEQ ID NO: 337; Neg contr is no peptide added.

Figure 12:
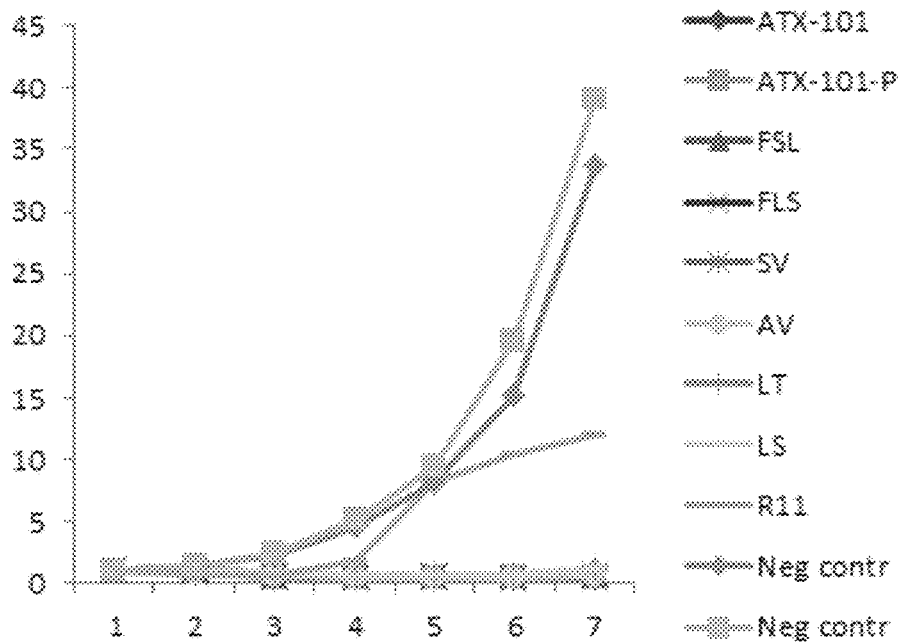
Figure 12:
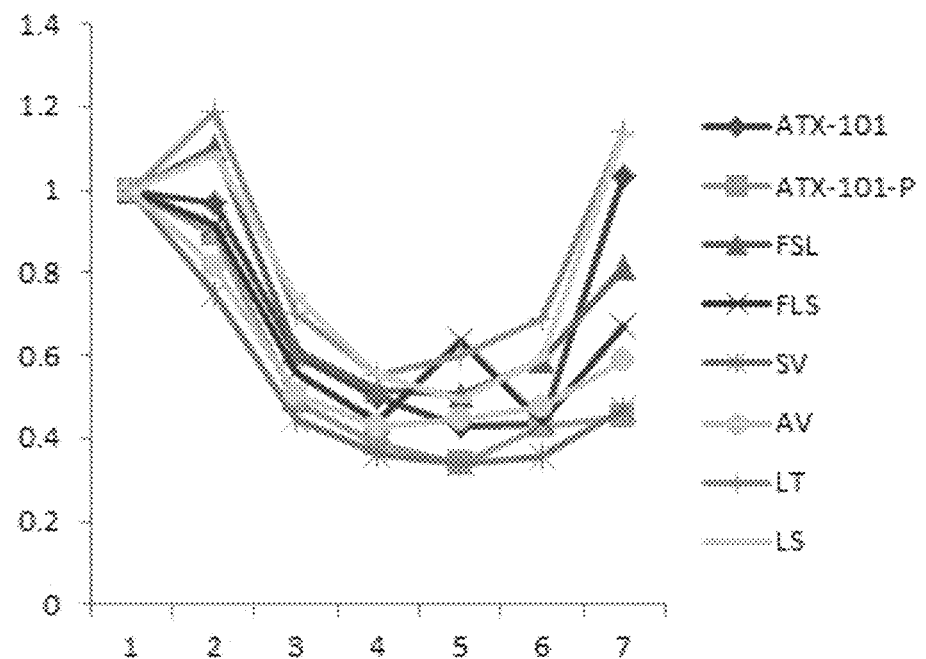

FIG. 12 shows graphs showing the growth of *E. coli* in the presence of 30 µM of various APIM peptides after the bacteria have been irradiated with UVC. The same data is presented in (A) and (B), however the control growth curves are not shown in (B). ATX-101 is SEQ ID NO: 1289; ATX-101-P is SEQ ID NO: 1303; FSL is SEQ ID NO: 1304; FLS is SEQ ID NO: 1301; SV is SEQ ID NO: 1298; AV is SEQ ID NO: 1299; LT is SEQ ID NO: 1300; LS is SEQ ID NO: 1301; R11 is SEQ ID NO: 337; Neg contr is no peptide added.

Figure 13:
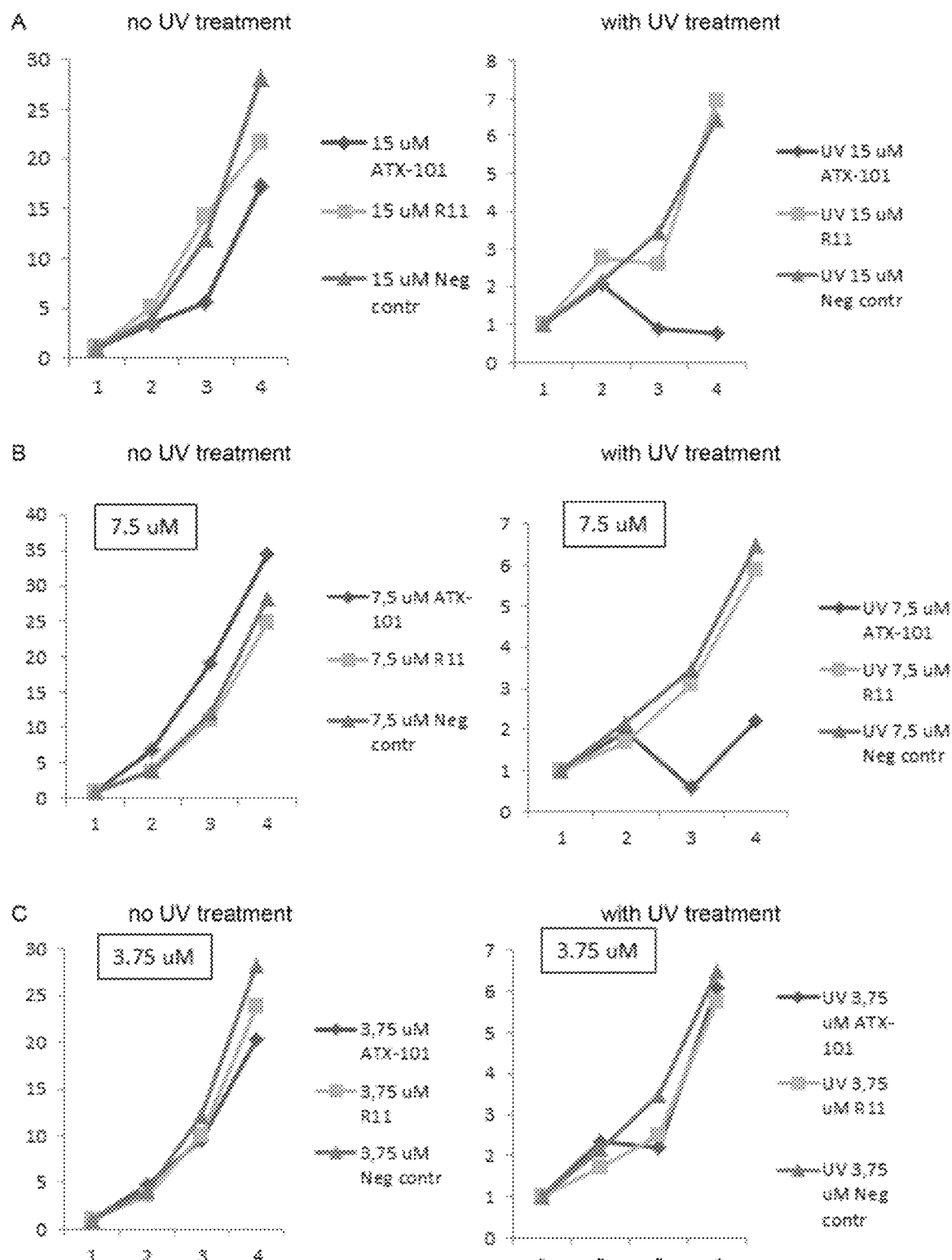

FIG. 13 shows graphs showing the growth of *E. coli* in the presence of ATX-101 (SEQ ID NO: 1289) at various concentrations, without UVC irradiation (left panels) or with UVC irradiation (right panels). R11 is SEQ ID NO: 337 and Neg contr is no peptide added. (A) 15 µM, (B) 7.5 µM and (C) 3.75 µM.

Figure 14:
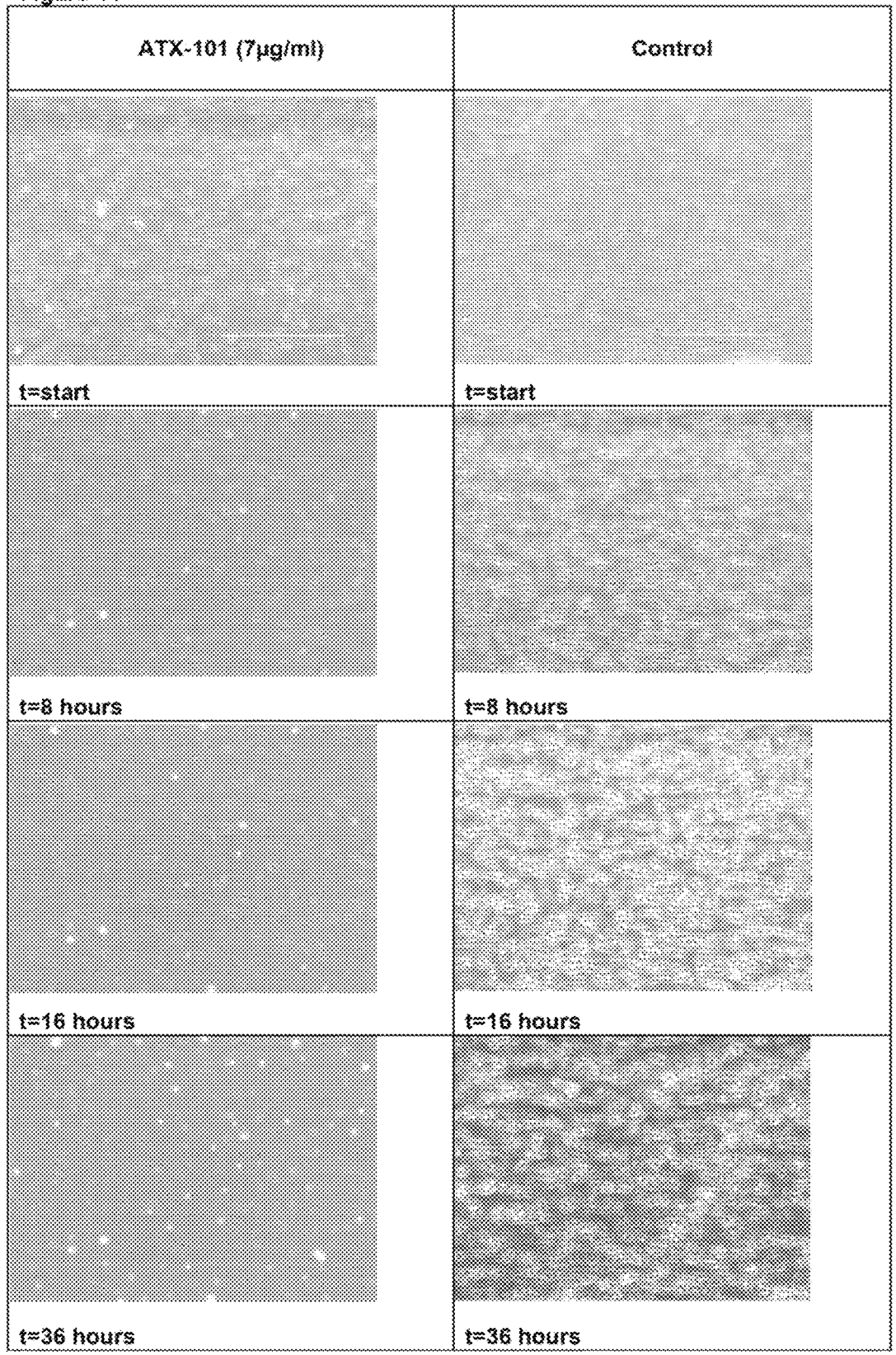

FIG. 14 shows micrographs of biofilm formation of the MDR bacterium Methicillin-resistant *Staphylococcus aureus* (MRSA 1040) in the presence of 7 µg/ml ATX-101 (SEQ ID NO: 1289) (left panels) or no peptide (right panels) over a period of 36 hours and demonstrates that biofilm formation is inhibited by ATX-101.

Figure 15:
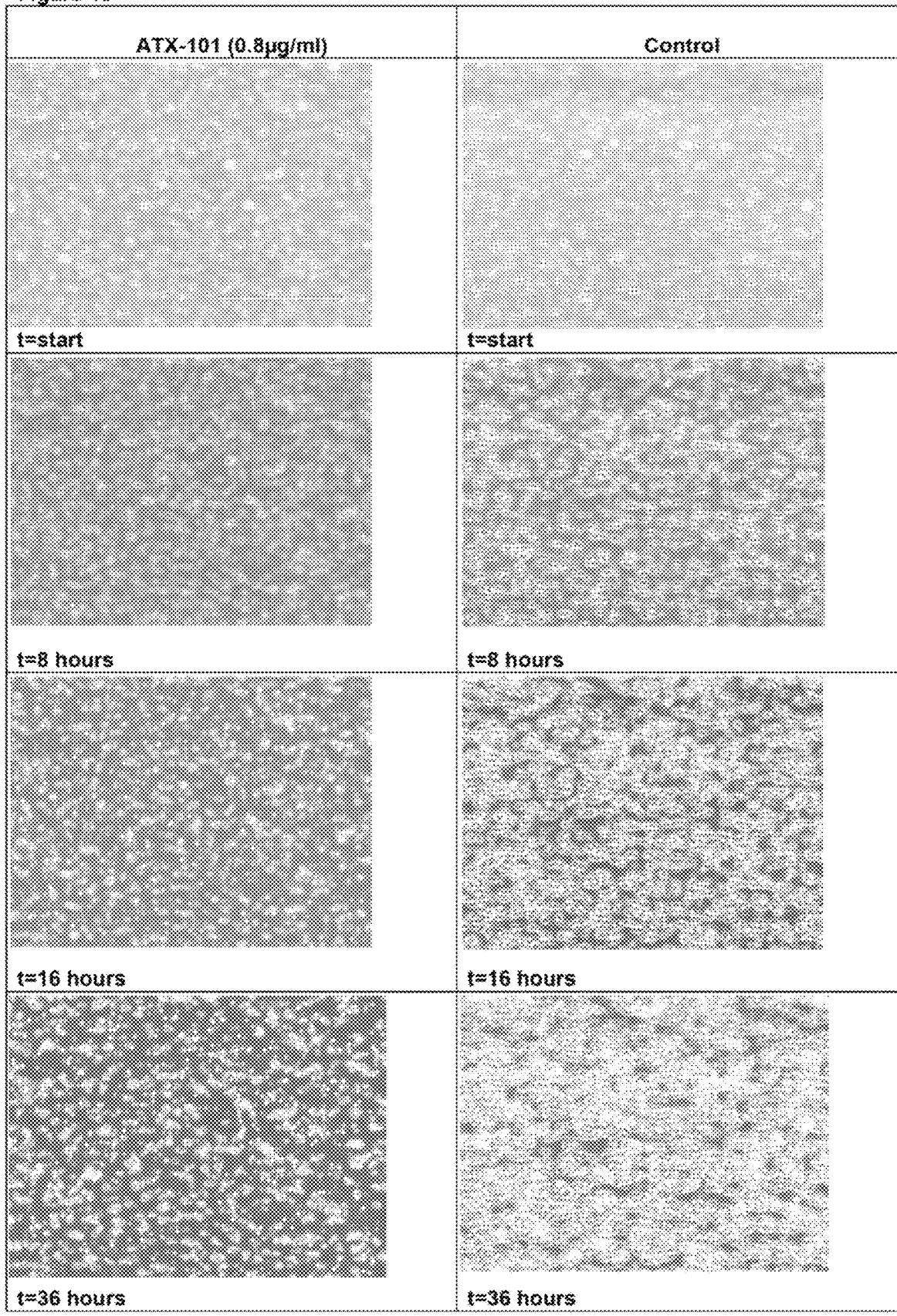

FIG. 15 shows micrographs of biofilm formation of the MDR bacterium Methicillin-resistant *Staphylococcus auraus* (MRSA 1040) in the presence of 0.8 µg/ml ATX-101 (SEQ ID NO: 1289) (left panels) or no peptide (right panels) over a period of 36 hours and demonstrates that biofilm formation is inhibited by ATX-101

Figure 16:
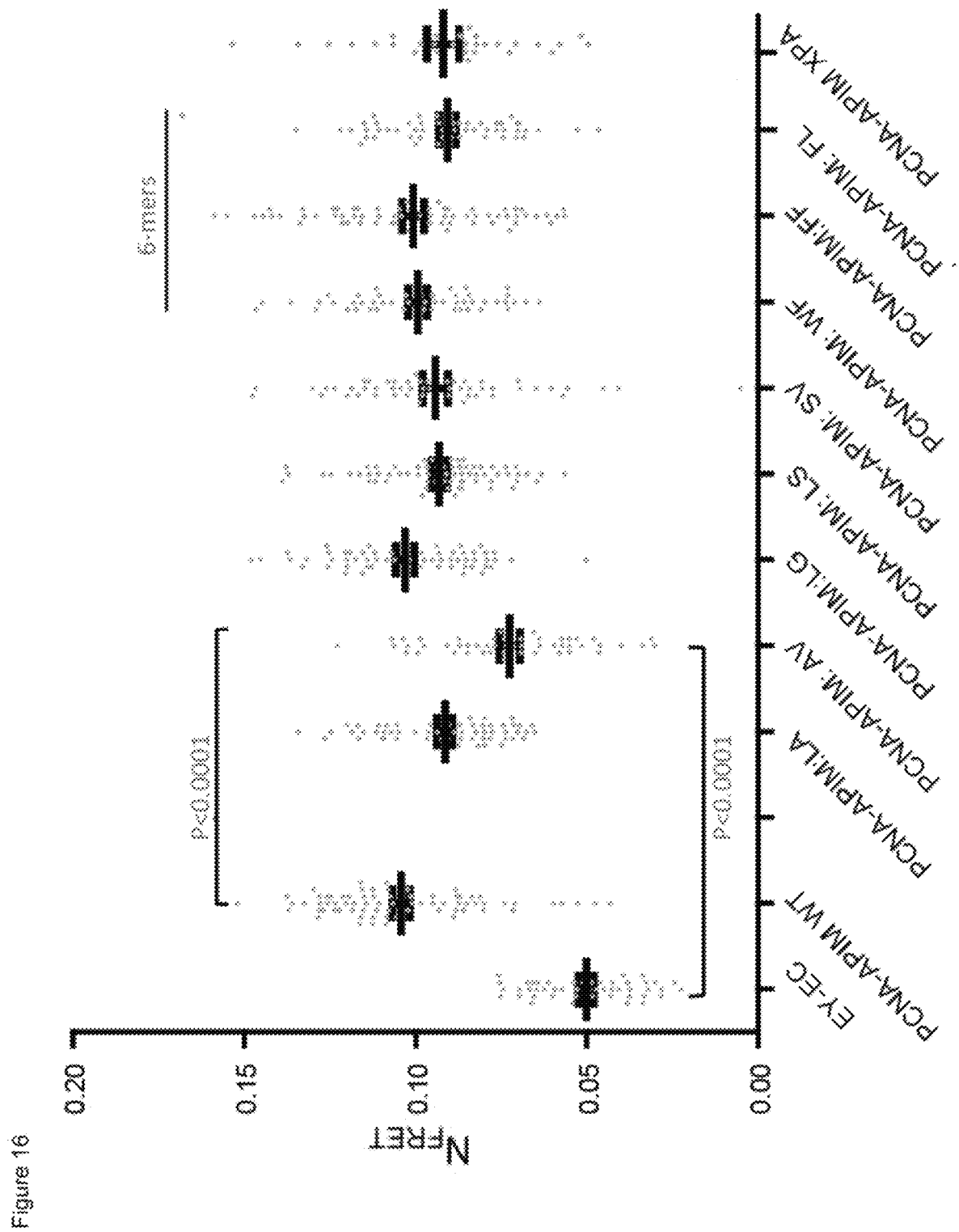

FIG. 16 shows a graph showing the results of FRET analysis. Normalised FRET ($N_{FRET}$) measurements are shown between EYFP (yellow fluorescent protein)/ECFP (cyan fluorescent protein) (Lane 1 (EY-EC), background due to dimerisation of the tags). EYFP-APIM motif/ECFP-PCNA for various motifs are shown in the other lanes, wherein the annotations on the X-axis refer to the following APIM sequences: WT (RWLVK, SEQ ID NO: 1290); LA (RWLAK, SEQ ID NO: 1305); AV (RWAVK, SEQ ID NO: 1297); LG (RWLGK, SEQ ID NO: 1306); LS (RWLSK, SEQ ID NO: 1294); SV (RWSVK, SEQ ID NO: 1296); WF (RWFLVK, SEQ ID NO: 1258); FF (RFFLW, SEQ ID NO: 1265); FL (RFLLVK, SEQ ID NO: 1267); and XPA (KFIVK, SEQ ID NO: 1307).

Figure 17:
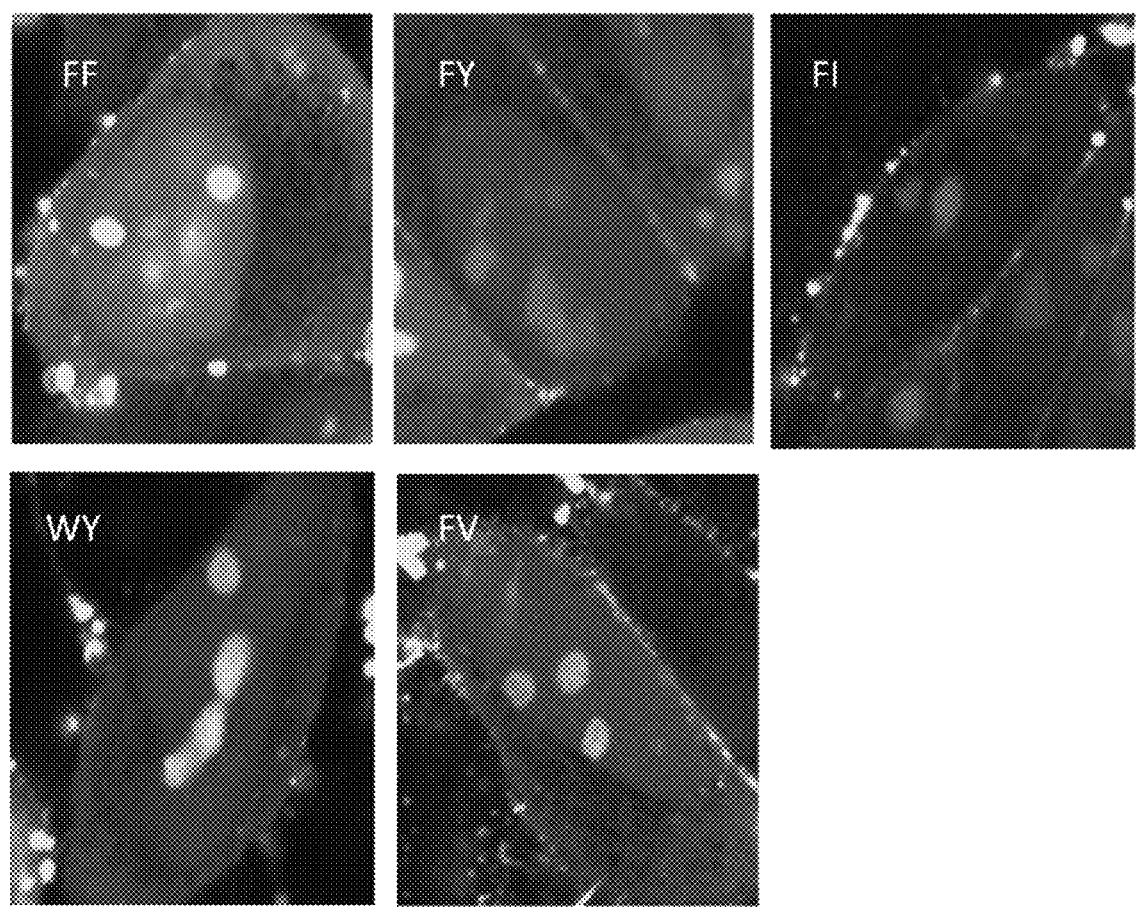

FIG. 17 shows confocal microscope images which show that fluorescently-labelled peptides (FAM-tagged peptides) containing "extended" APIM sequences are taken up by mammalian cells (see Example 13). The two letter annotations refer to peptides containing the following APIM sequences: WY (RWYLVK, SEQ ID NO: 1259); FF (RFFLVK, SEQ ID NO: 1265); FY (RFYLVK, SEQ ID NO: 1266), FV (RFVLVK, SEQ ID NO: 1269); and FI (RFILVK, SEQ ID NO: 1268)

Figure 18:
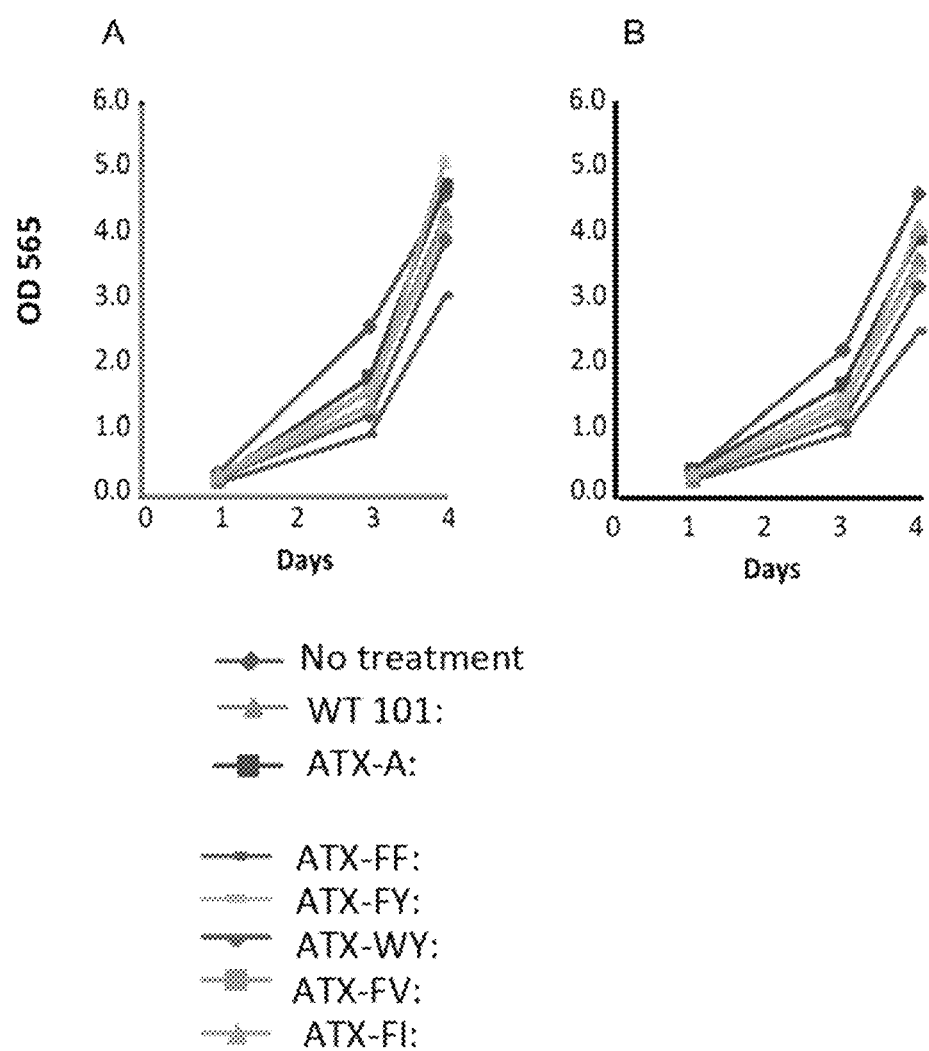

FIG. 18 shows graphs showing the results of cytotoxicity assays with various APIM peptides, as described in Example 14. The annotations in the legend refer to the following APIM sequences; WT-101, MDRWLVKWKKKRKIR-RRRRRRRRRR (SEQ ID NO: 1289); ATX-A, MDRALVK-WKKKRKIRRRRRRRRRR (SEQ ID NO: 1206) (negative control); ATX-FF, MDRFFLVKWKKKRKIR-RRRRRRRRRR (SEQ ID NO: 1182); ATX-FL MDRFLL-VKWKKKRKIRRRRRRRRRR (SEQ ID NO: 1187); ATX-WY, MDRWYLVKWKKKRKIRRRRRRRRRR (SEQ ID NO: 1184); ATX-FV, MDRFVLVKWKKKRKIR-RRRRRRRRRR (SEQ ID NO: 1185); and ATX-FI MDRFILVKWKKKRKIRRRRRRRRRR (SEQ ID NO: 1186).

Figure 19:
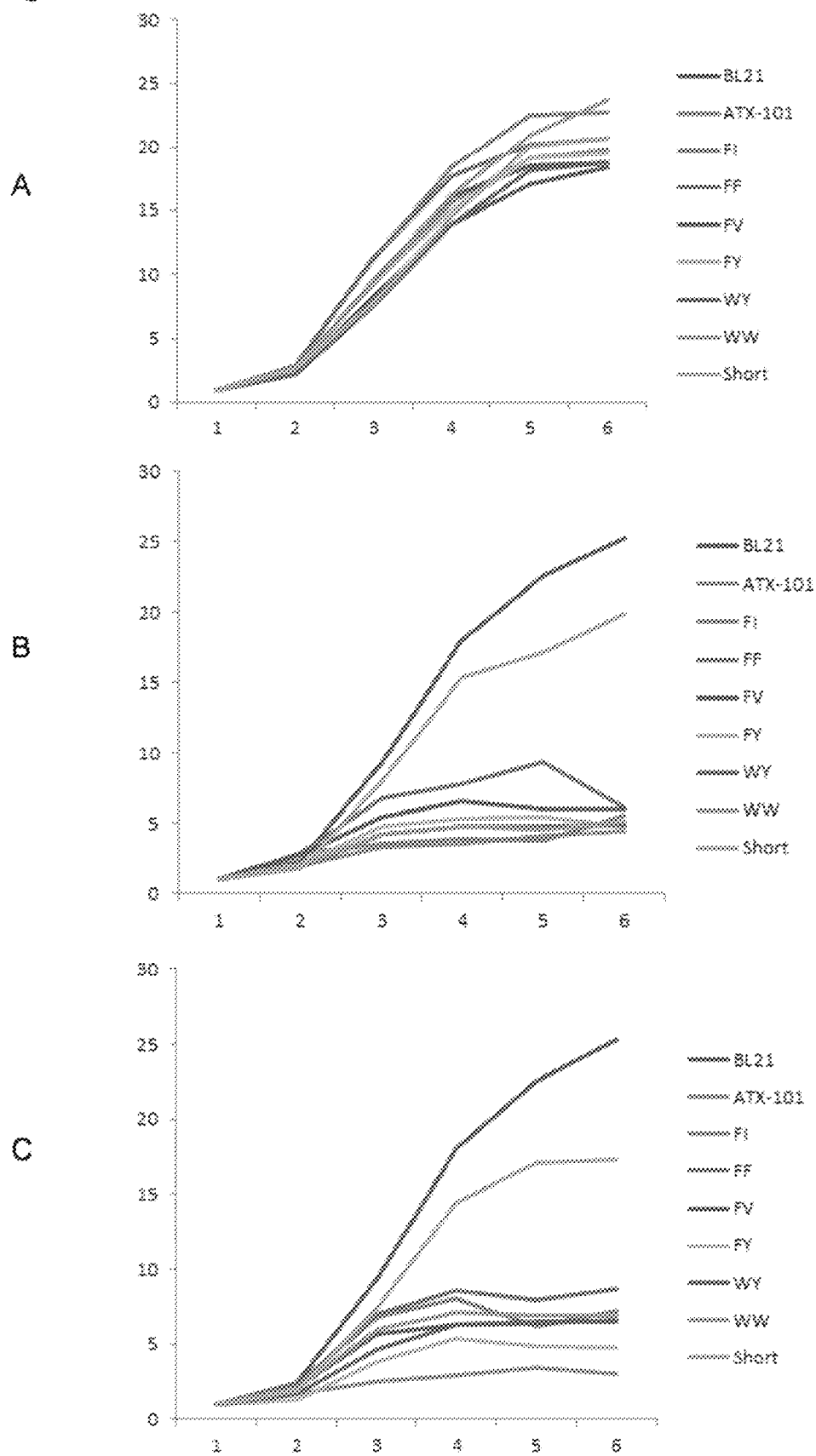

FIG. 19 shows graphs showing the growth of *E. coli* in which the overexpression of various APIM peptides is (A) not induced: (B) induced after 1 hour of growth: and (C) induced after 2 hours of growth. The annotations in the legend refer to the following: BL21, no plasmid (negative control); ATX-101 is SEQ ID NO: 1290; ATX-FI is SEQ ID NO: 1268; ATX-FF is SEQ ID NO: 1265; ATX-FV is SEQ ID NO: 1269; ATX-FY is SEQ ID NO. 1266; ATX-WY is SEQ ID NO: 1259; ATX-WW is SEQ ID NO: 1310; and Short is SEQ ID NO: 1312 (negative control).

Figure 20:
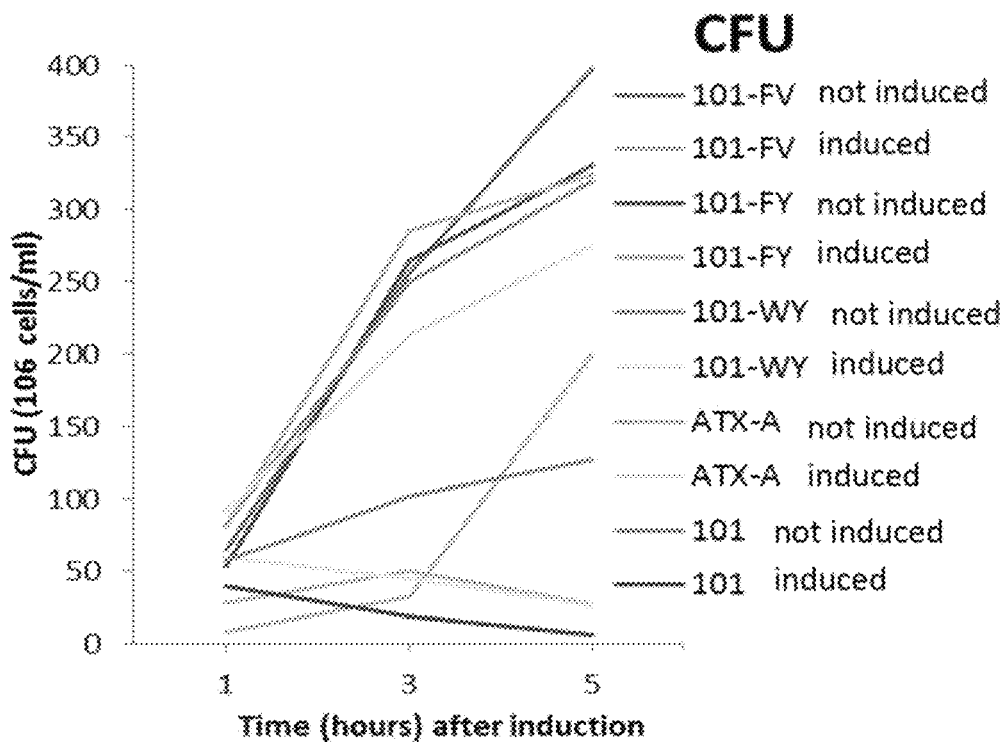
Figure 20:
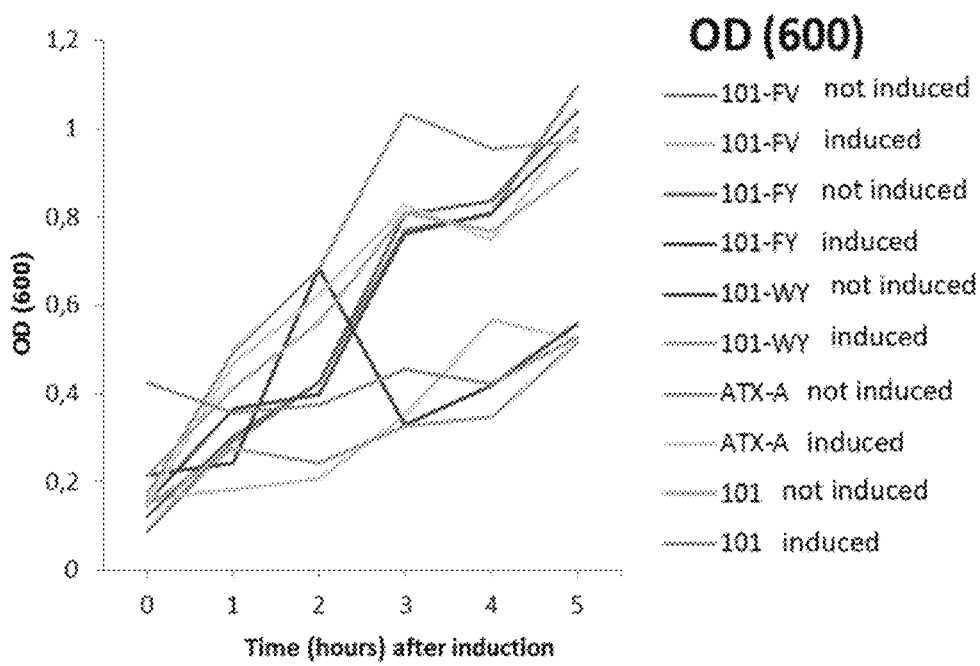
Figure 20:
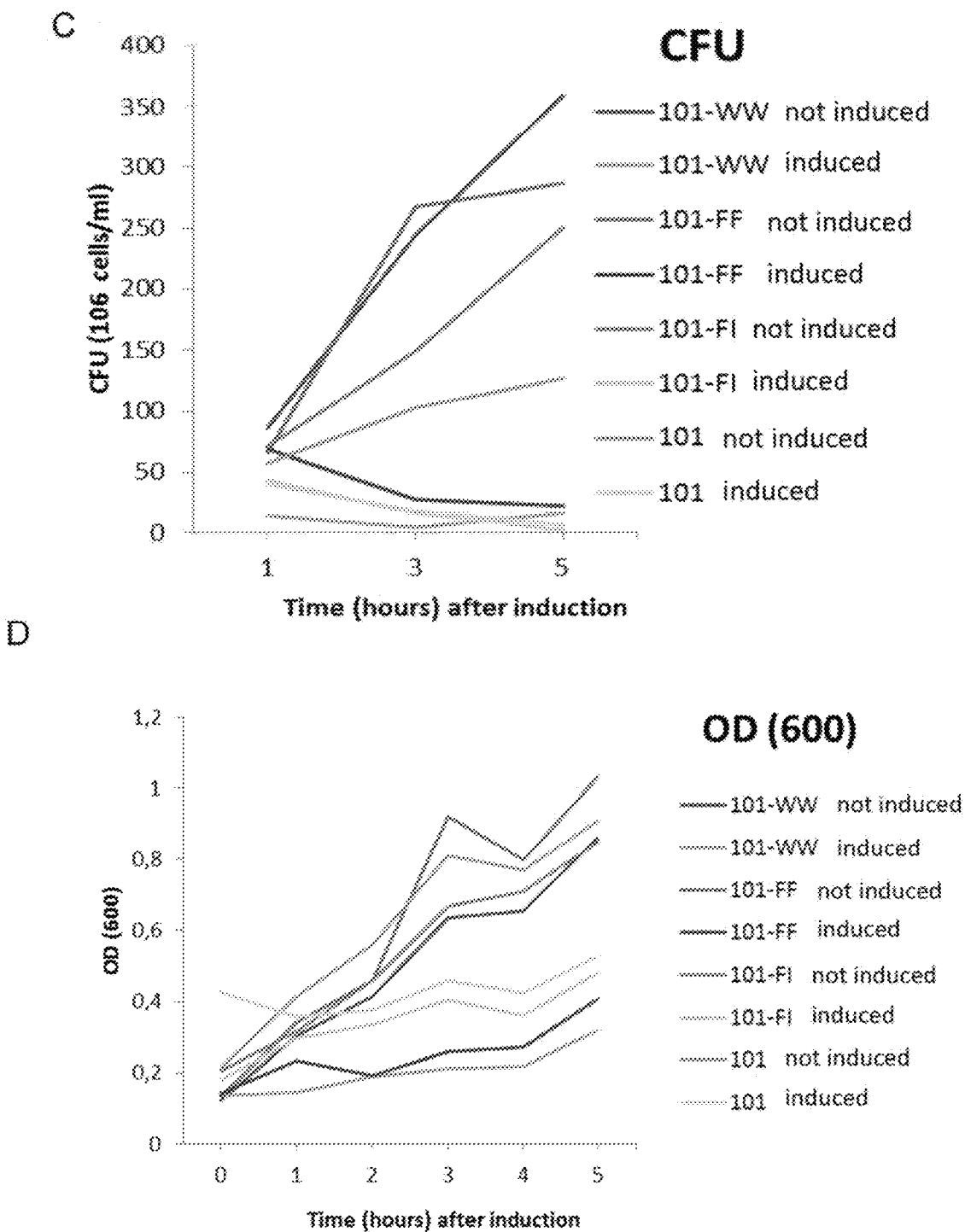

FIG. 20 shows graphs depicting the growth curves of cultures of *E. coli* BL21 overexpressing variants of several APIM peptides (101, 101-FV, 101-FY, 101-WY, 101-WW, 101-FF, 101-FI) and a negative control (ATX-A) measured by CFU (A and C) and $OD_{600}$ (B and D). Both induced and not induced cultures are included in the figures. The annotations in the legend (mentioned above) refer to the following sequences: 101, MDRWLVKWKKKRKIR-RRRRRRRRRR (SEQ ID NO: 1289); 101-FV, MDFRFVLVKWKKKRKIRRRRRRRRRRR (SEQ ID NO: 1155); 101-FY, MDRFYLVKWKKKRKIRRRIR-RRRRRRR (SEQ ID NO: 1183); 101-WY, MDRWYLVK-WKKKRKIRRRRRRRRRR (SEQ ID NO: 1184); 101-WW, MDRWWLVKWKKKRKIRRRRRRRRRR (SEQ ID NO: 1311); 101-FF, MDRFFLVKVVKKKRKIR-RRRRRRRRRR (SEQ ID NO: 1182); 101-FI, MDRFIL-VKWKKKRKIRRRRRRRRRR (SEQ ID NO: 1186); and ATX-A, MDRALVKWKKKRKIRRRRRRRRRR (SEQ ID NO: 1206).

Figure 21:
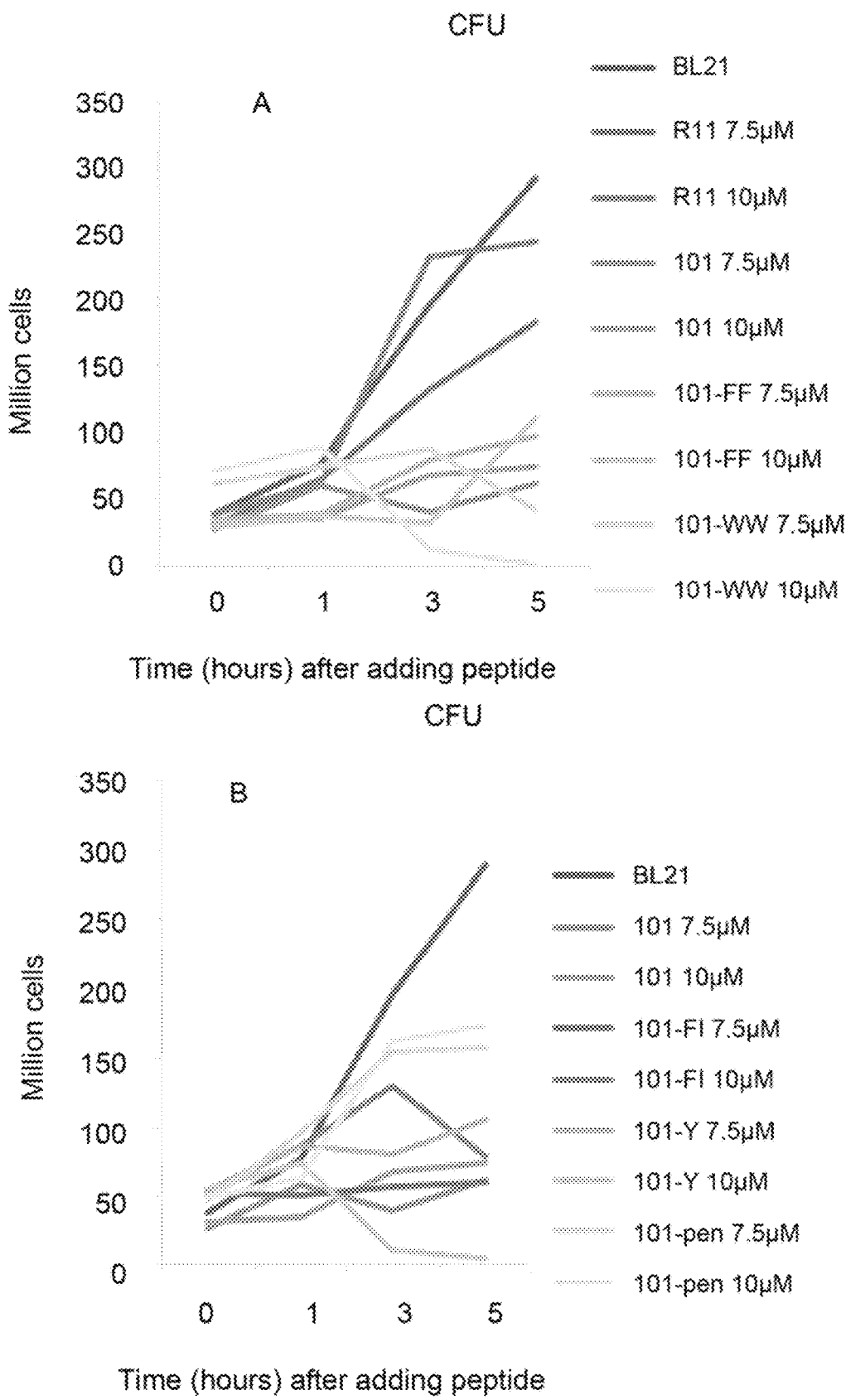
Figure 21:
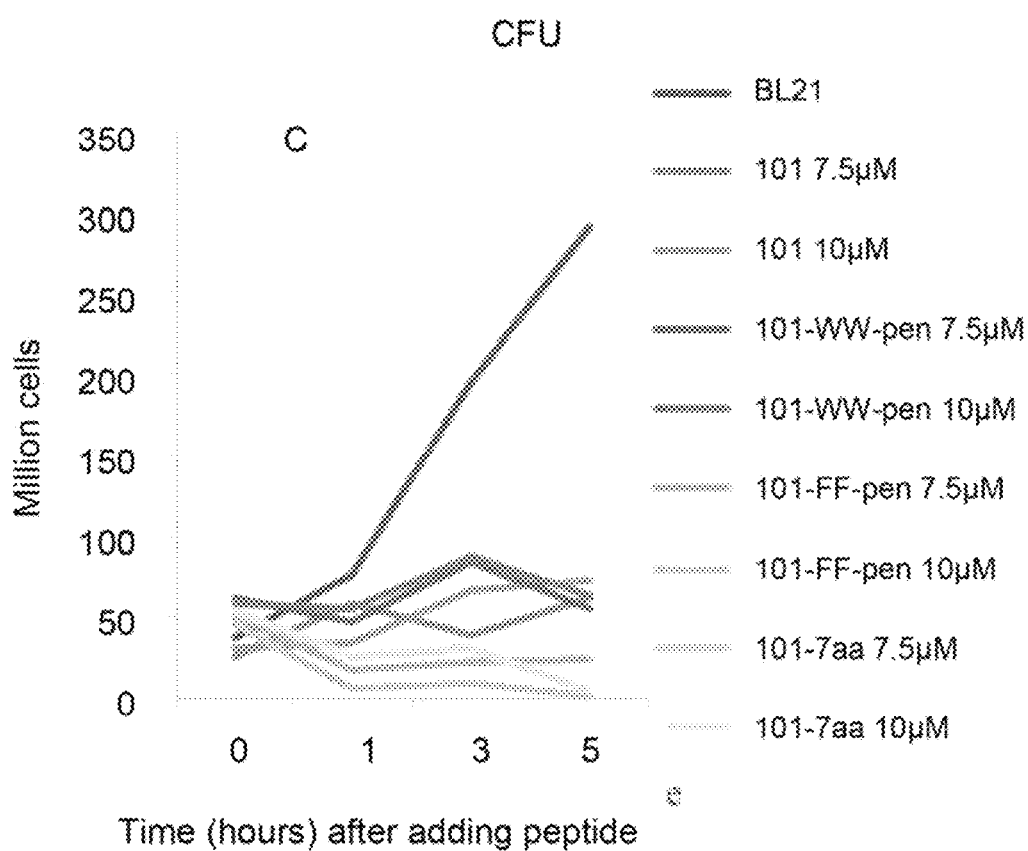
Figure 22:
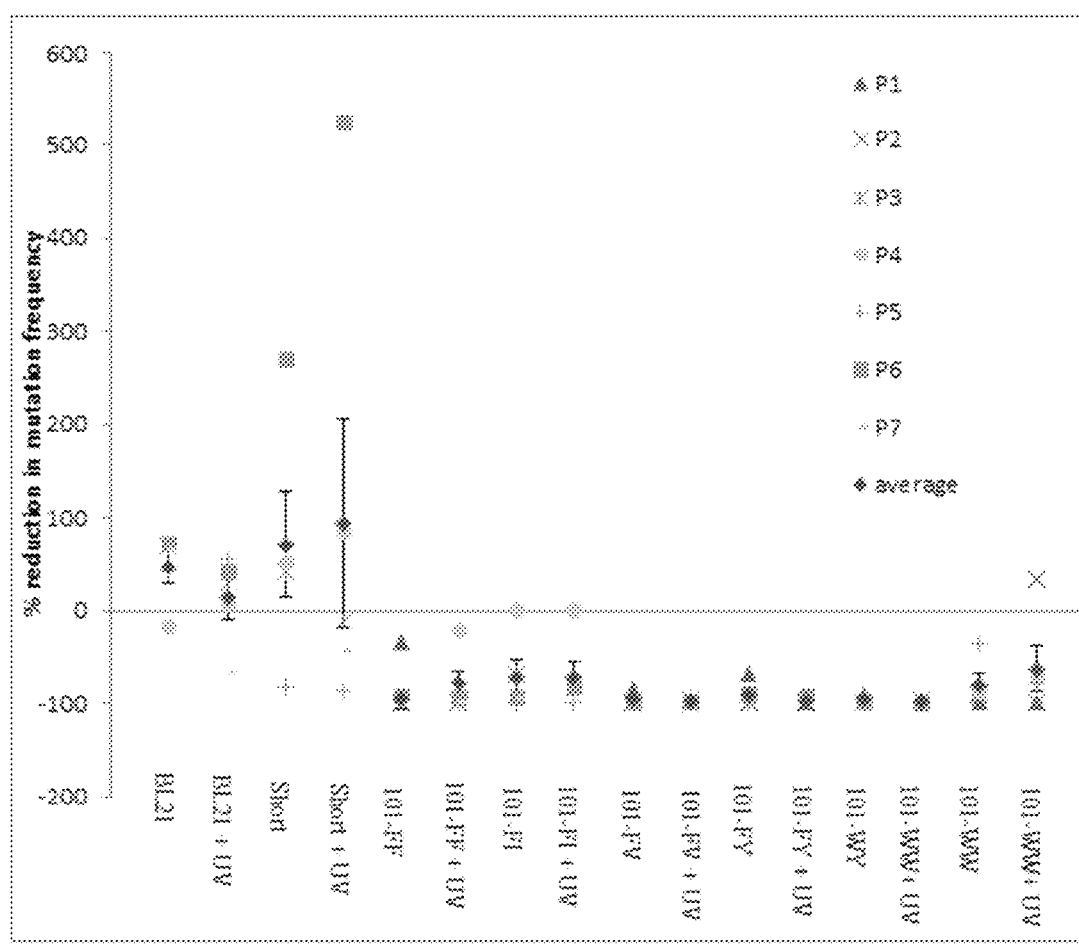

FIG. 21 shows graphs depicting the growth curves of cultures of *E. coli* BL21 measured by CFU and data 1, 3 and 5 hours after adding variants of severe APIM peptides (101, 101-FF, 101-WW, 101-Y, 101-pen, 101-WW-pen, 101-FF-pen and 101-7aa) and a negative control (R11). BL21 represents the growth with the addition of a peptide. The annotations in the legend (mentioned above) refer to the following sequences: 101, MDRWLVKWKKKRKIR-RRRRRRRRRR (SEQ ID NO: 1289); 101-WW, MDRW-WLVKWKKKRKIRRRRRRRRRR (SEQ ID NO: 1311); 101-FI, MDRFILVKWKKKRKIRRRRRRRRRR (SEQ ID NO: 1186); 101-Y, MDRYLVKWKKKRKIR-RRRRRRRRRR (SEQ ID NO: 1313); 101-pen MDRWLVKWKKKRKIRQIKIWFQNRRMKWKK (SEQ ID NO: 1314); 101-WW-pen, MDRWWLVKWKK-KRKIRQIKIWFQNRRMKWKK (SEQ ID NO: 1315); 101-FF-pen, MDRFFLVKWKKKRKIRQIKIWFQNRRMK-WKK (SEQ ID NO: 1316); and 101-7aa, MDRWLVKGAQPKVLRRRRRRRRRRR (SEQ ID NO: 1317), FIG. 22 shows a graph depicting the percentage reduction in mutation frequency for *E. coli* BL21 and *E. coli* BL21 with overexpression of different variants of several APIM peptides (101-FF, 101-FI, 101-FV, 101-FY. 101-WY and 101-WW) and a negative control peptide (short). Data are shown for parallel (P) 1 to 7 and presented as means+/–SEM. The annotations in the legend (mentioned above) refer to the following sequences: 101-FF, MDRFFLVKWKK-KRKIRRRRRRRRRRR (SEQ ID NO: 1182); 101-FI MDRFILVKWKKKRKIRRRRRRRRRR (SEQ ID NO: 1186); 101-FV, MDRFVLVKWXKKKRKIRRRRRRRRRR (SEQ ID NO: 1185); 101-FY, MDRFYLVKWKKKRKIR-RRRRRRRRRR (SEQ ID NO: 1183); 101-WY, MDRWYL-VKWKKKRKIRRRRRRRRRR (SEQ ID NO: 1184); 101-WW, MDRWWLVKWKKKRKIRRRRRRRRRR (SEQ ID NO: 1311); and short, MDRWIXWKKKRKIR-RRRRIRRRRRR (SEQ ID NO: 1318).

Figure 23:
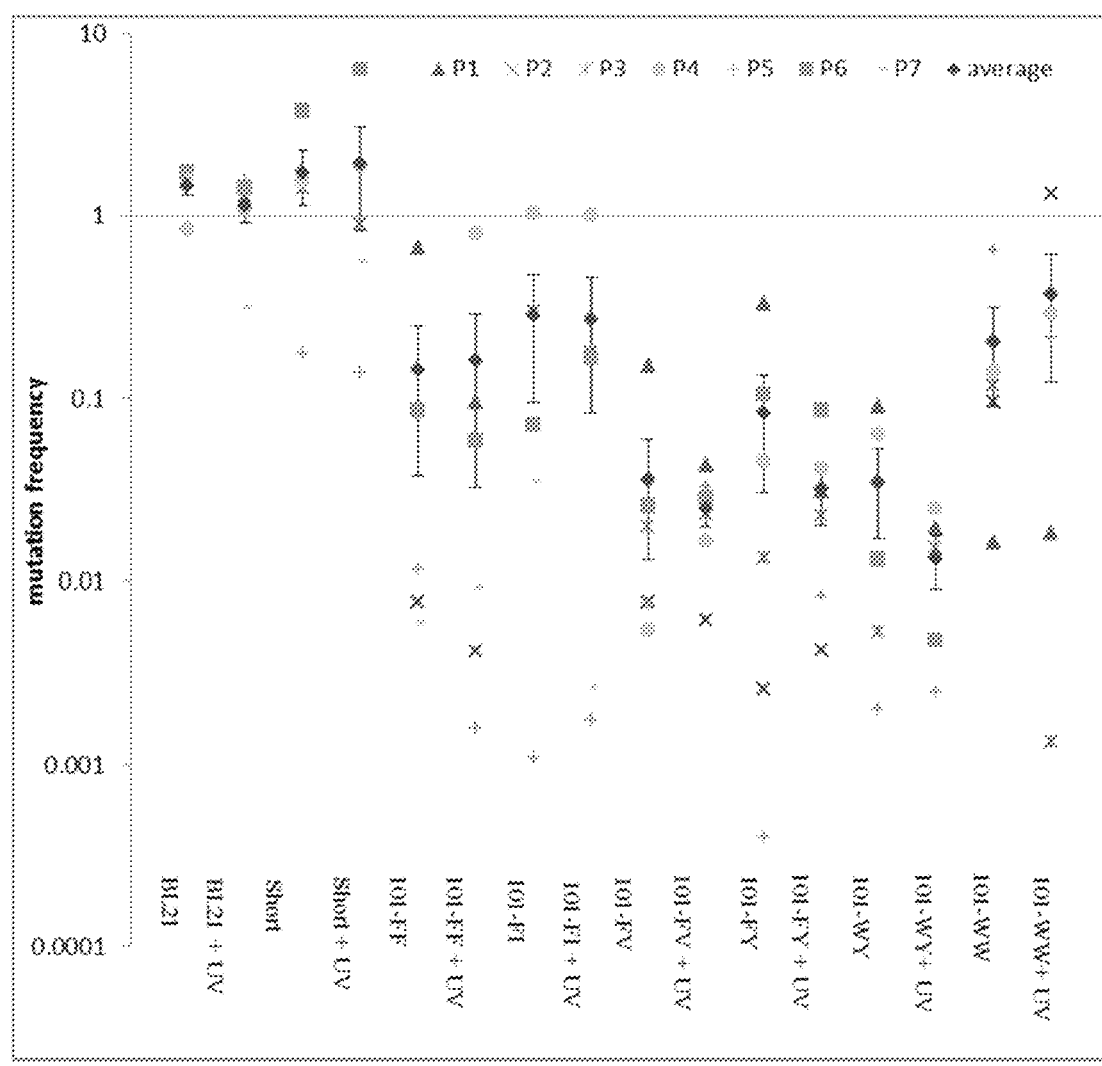

FIG. 23 shows a graph depicting the mutation frequency for *E. coli* BL21 and *E. coli* BL21 with overexpression of different variants of several APIM peptides (101-FF, 101-FI, 101-FV, 101-FY, 101-WY and 101-WW) and a negative control peptide (short). Data are shown for parallel (P) 1 to 7 and presented as means+/–SEM. The annotations in the legend (mentioned above) refer to the following sequences: 101-FF, MDRFFLVKWKKKRKIRRRRRIRRRRRR (SEQ ID NO: 1182); 101-FI, MDRFILVKWKKKRKIR-RRRRRRRRRR (SEQ ID NO: 1186); 101-FV, MDRFV-LVKWKKKRKIRRRRRRRRRR (SEQ ID NO: 1185); 101-FY, MDRFYLVKWKKKRKIRRRRRRRRRR (SEQ ID NO: 1183); 101-WY, MDRWYLVKWKKKRKIR-RRRRRRRRRR (SEQ ID NO: 1184); 101-WW, MDRW- WLVKWKKKRKIRRRRRRRRRR (SEQ ID NO: 1311); and short, MDRWLKWKKKRKIRRRRRRRRRR (SEQ ID NO: 1318).

Figure 24:
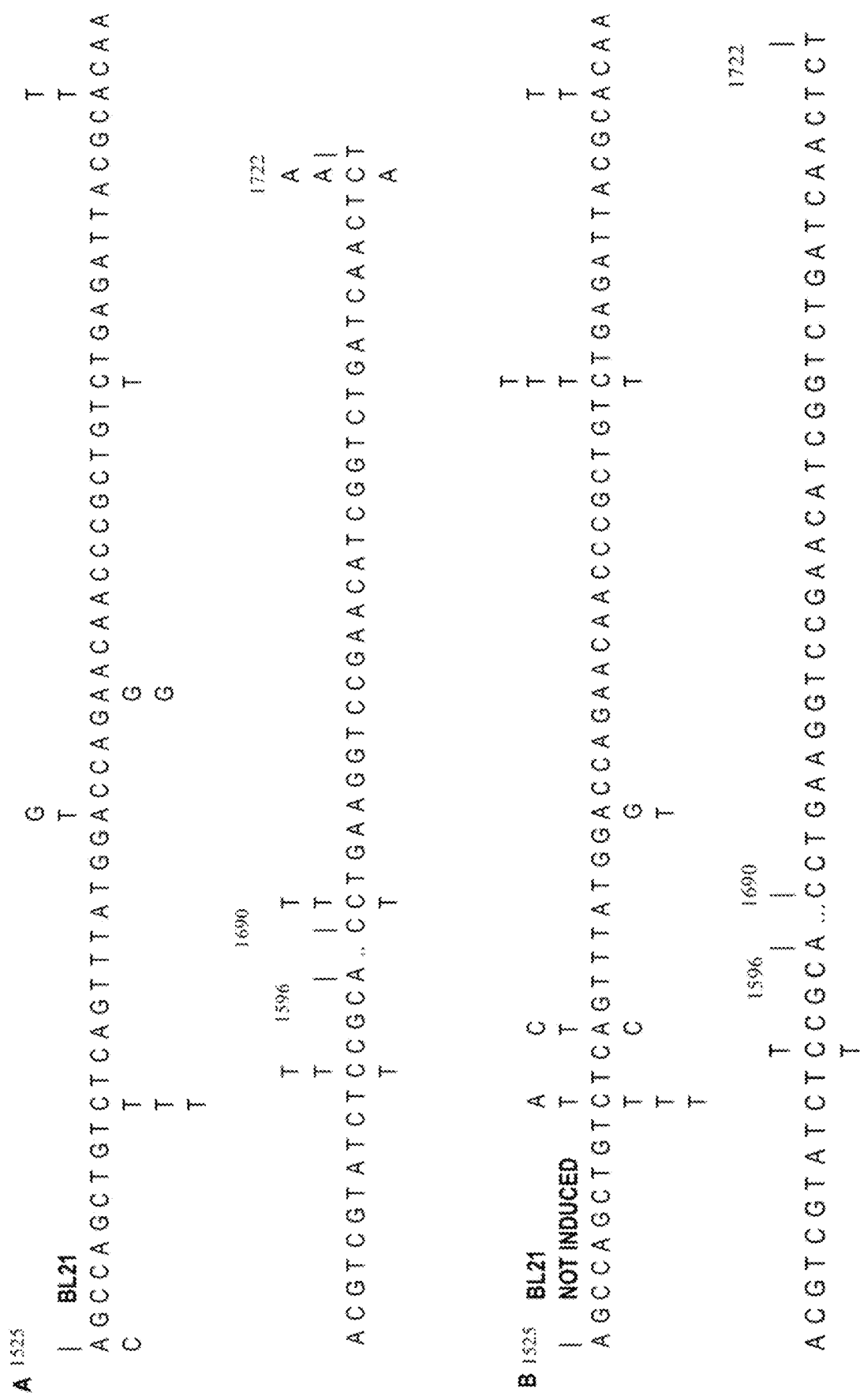

FIG. 24 shows the mutation spectra of rpoB (1525-1722 SEQ ID NOs: 1319 (1525-1596 bp) and 1320 (1690-1722 bp)) from rifampicin resistant colonies (A) *E. coli* BL21 induced, (B) *E. coli* BL21 not induced, and overexpression of variants of the APIM-peptide (C) 101-WY, (D) 101-WW, (E) 101-FI and (F) 101-FF. Data represent mutant colonies from different parallels. Spontaneous mutations are shown above sequence line and mutations found after LN exposure below line. Number of colonies varies due to low mutation frequency in BL21 with overexpression of variants of the APIM peptides. Number of colonies, n=not UV/UV, BL21 n=10/10, BL21 not induced n=10/10, 101-WY n=10/10, 101-WW n=10/8, 101-FI n5/9, 101-FF n=3/12.

Figure 25:
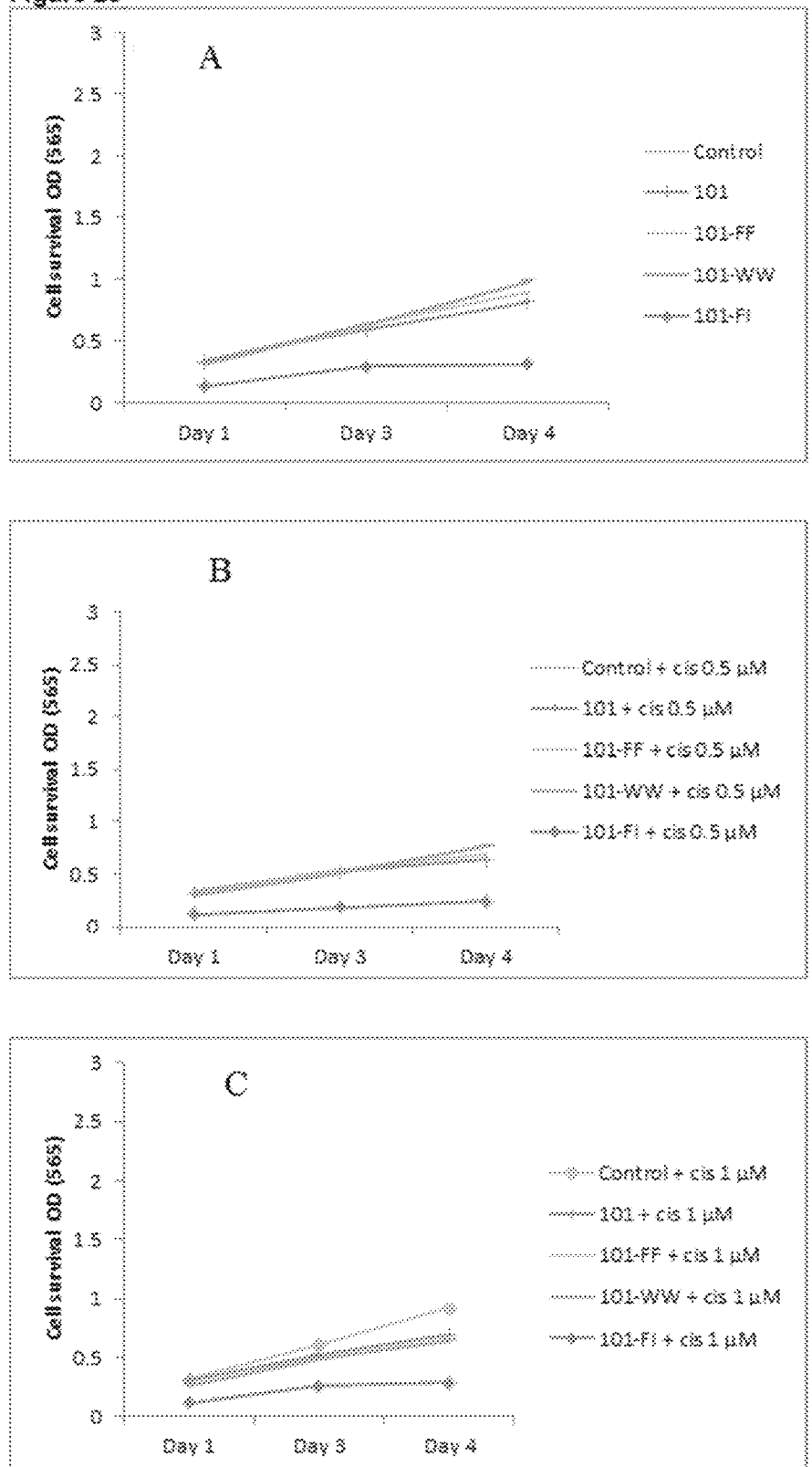
Figure 25:
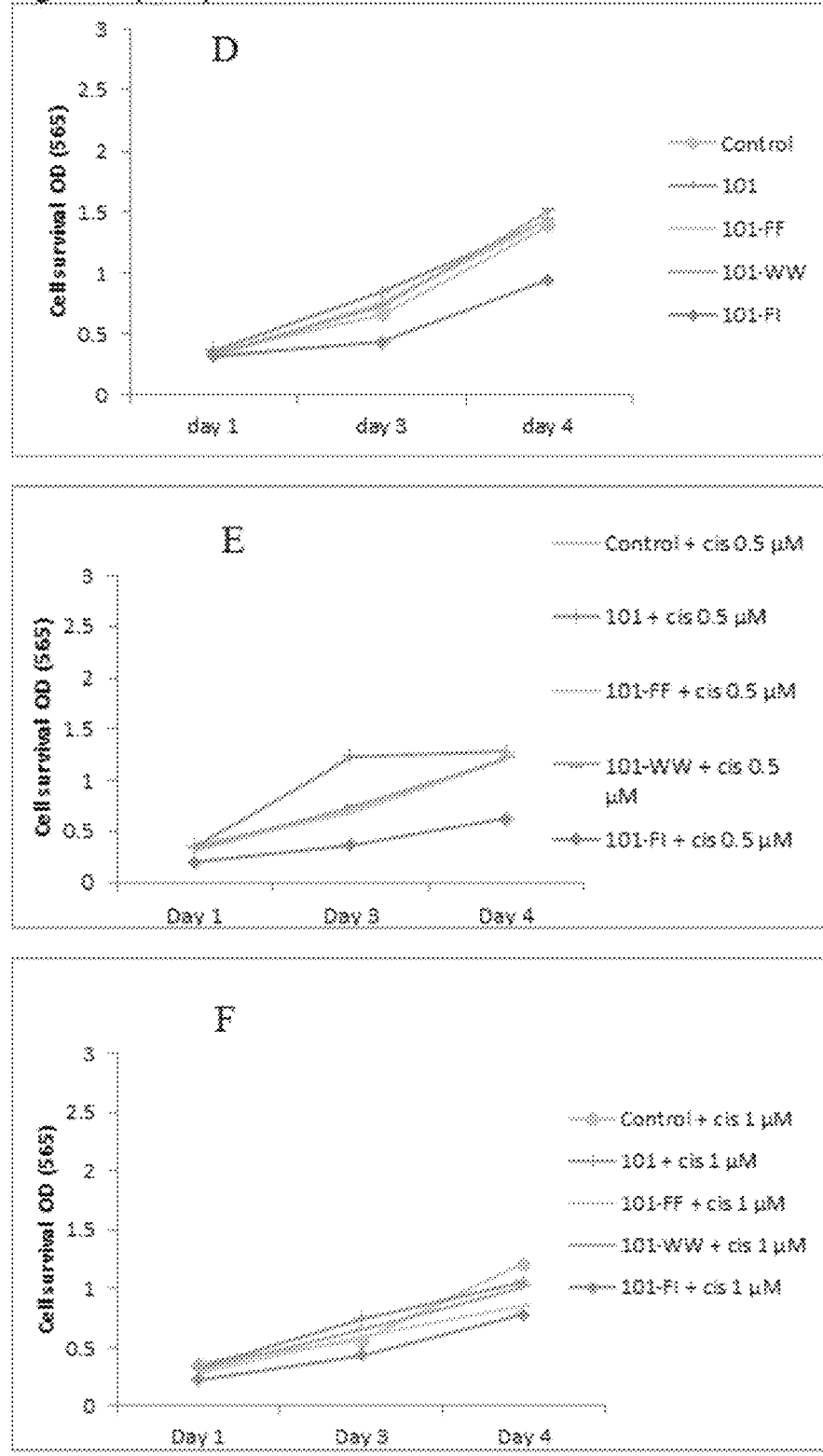
Figure 25:
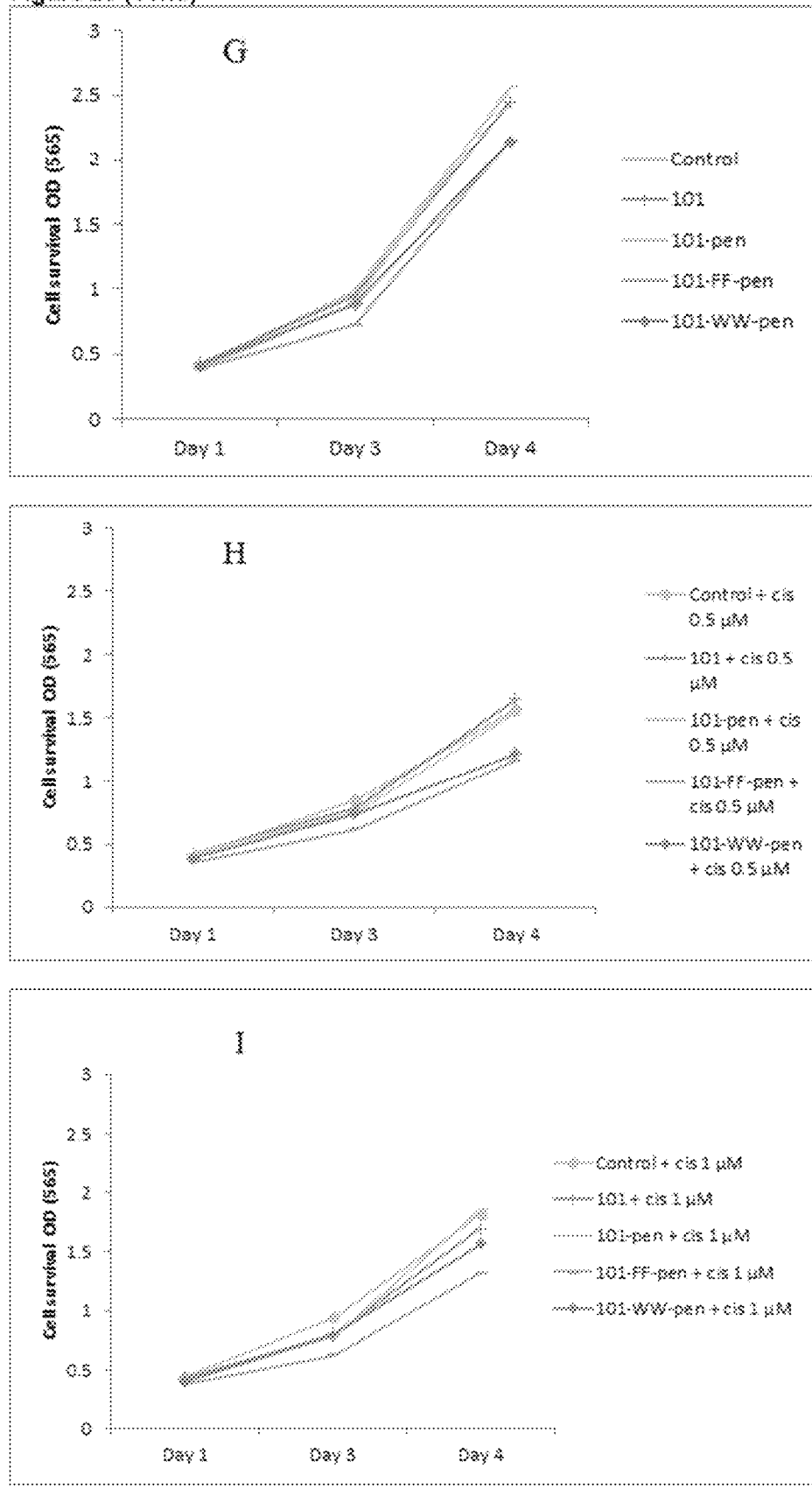

FIG. 25 shows graphs showing the results of cytotoxicity assays with various "standard" and "extended" APIM peptides. (A)-(C) show the levels cell survival of HEK 293 cells treated with 6 µM of peptides alone (A), with 0.5 µM cisplatin (b) or with 1 µM cisplatin (C) as described in Example 18, (D)-(I) show the levels of cell survival of HEK 293 cells treated with 12 µM of peptides alone (D) and (G), with 0.5 µM cisplatin (E) and (H) or with 1 µM cisplatin (F) and (I) as described in Example 18. The annotations in the legend refer to APIM sequences as described above.

Figure 26:
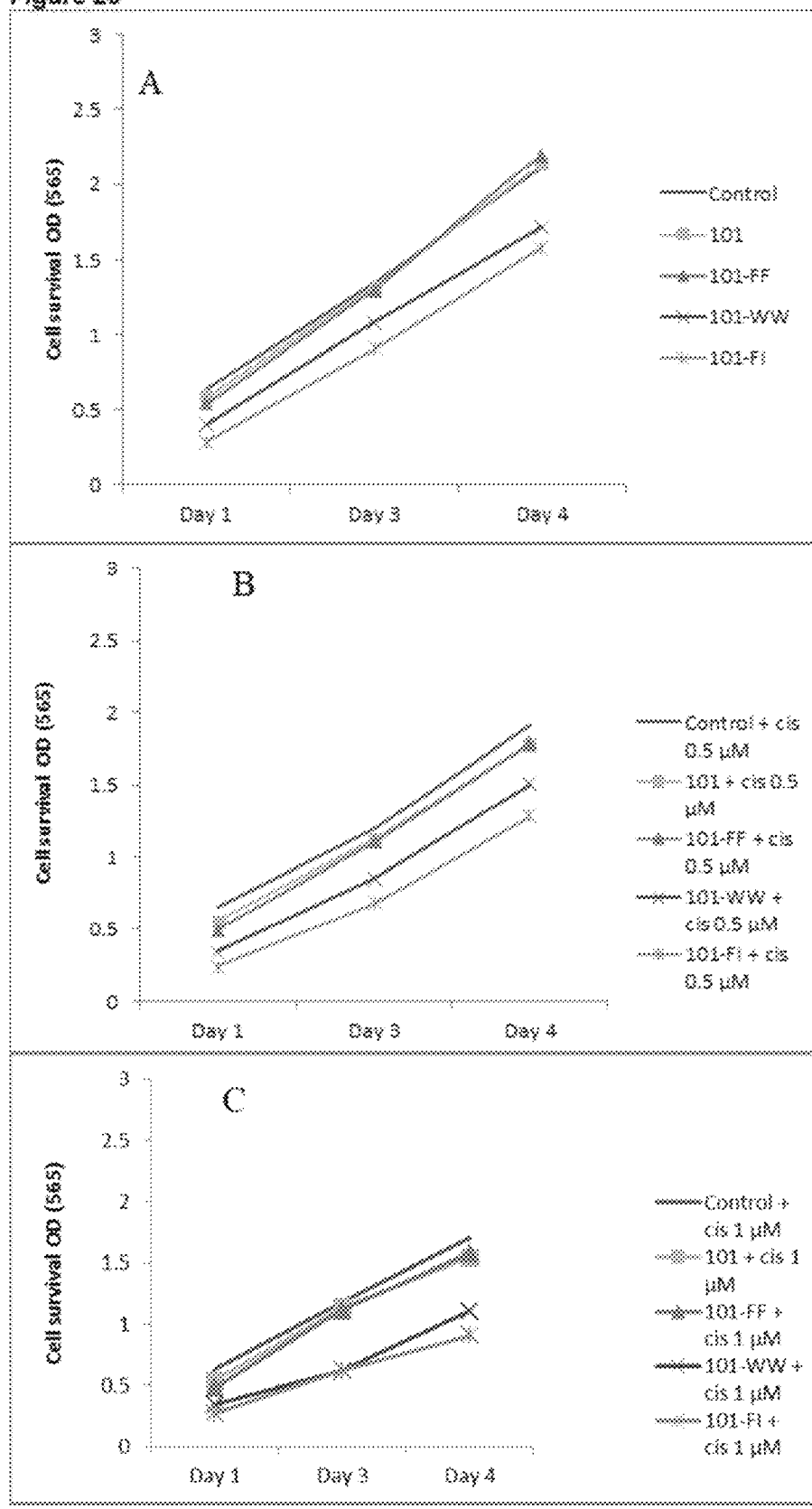
Figure 26:
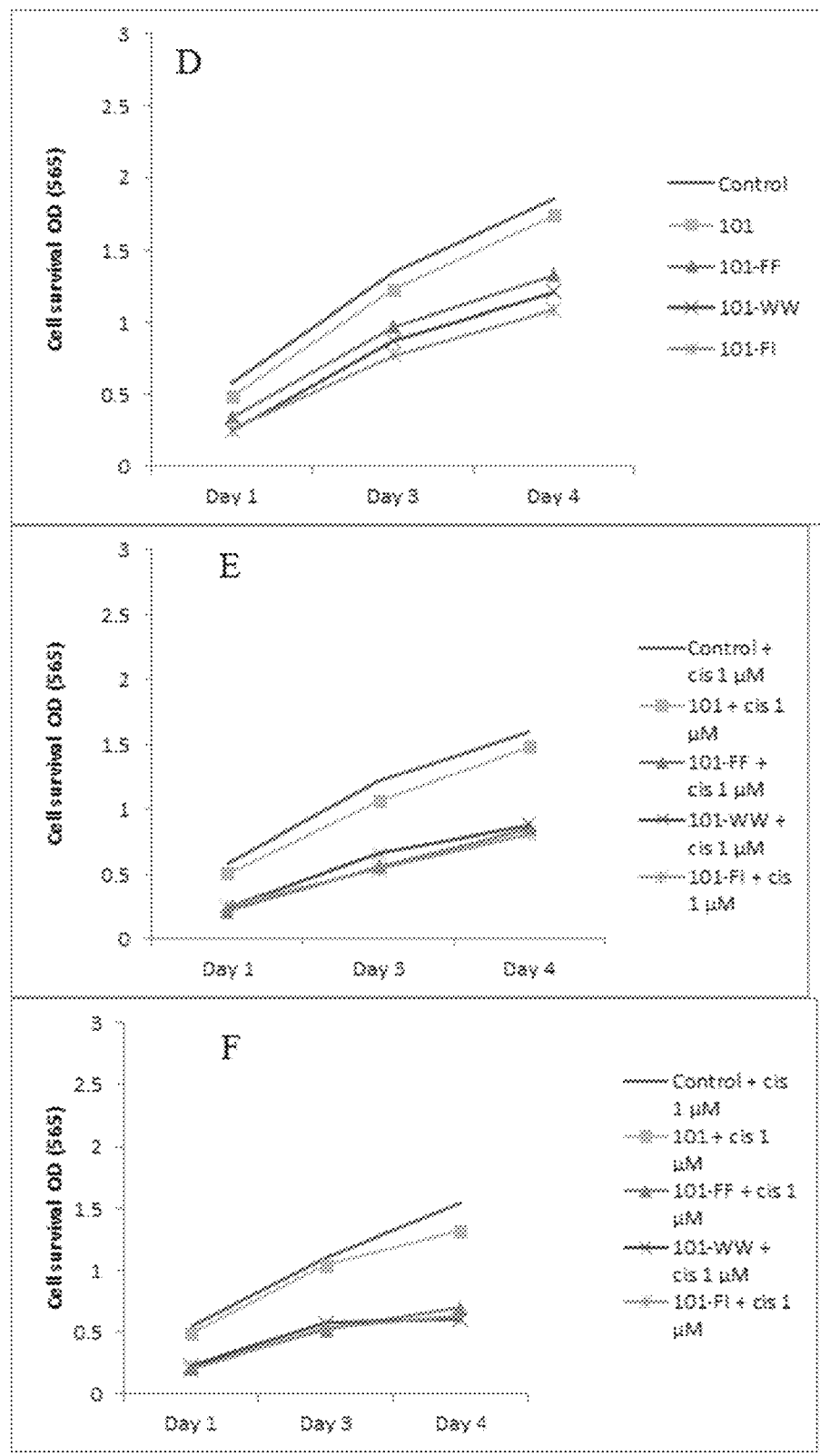
Figure 26:
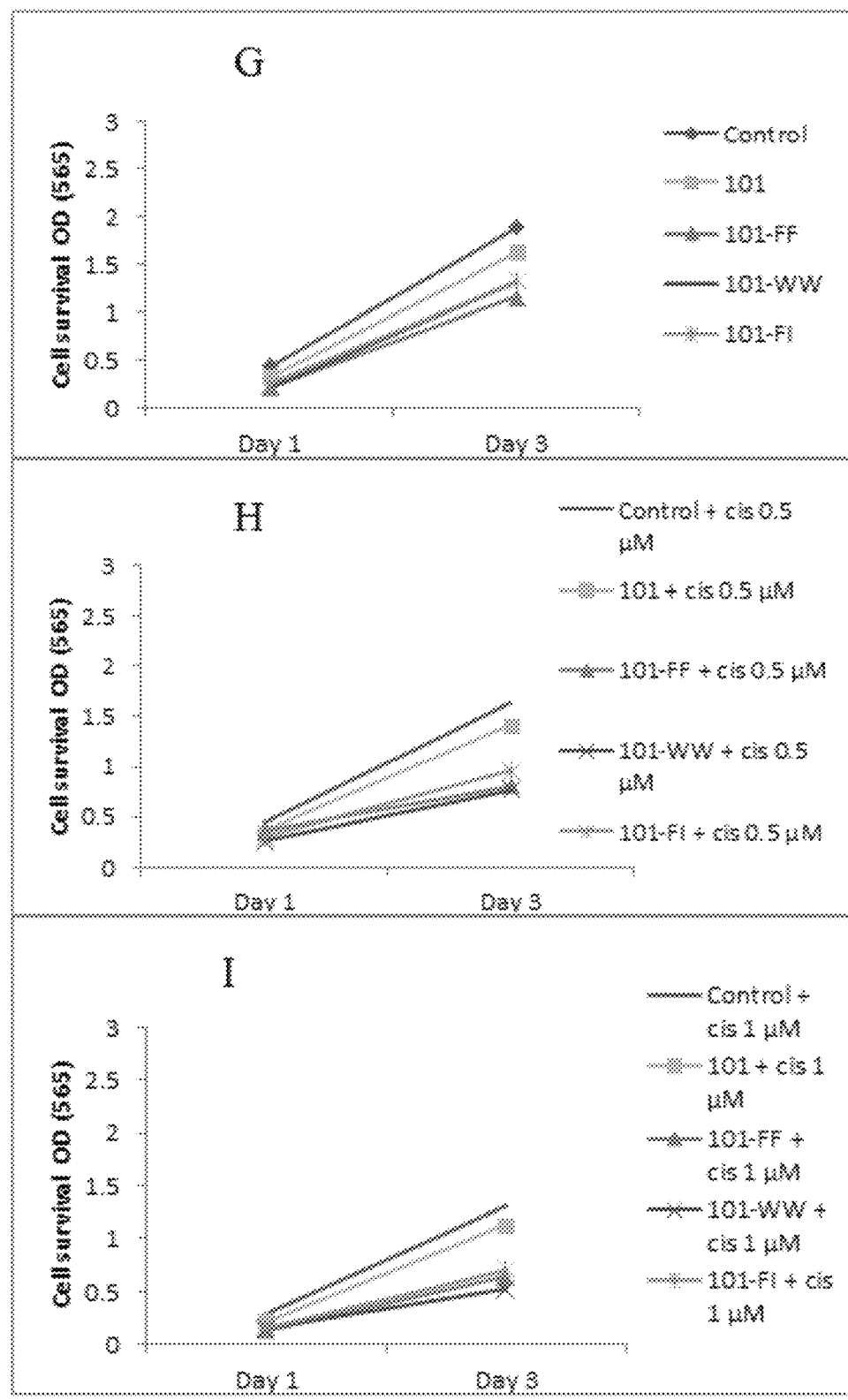

FIG. 26 snows graphs showing the results of cytotoxicity assays with various "standard" and "extended" APIM peptides. (A)-(C) show the levels cell survival of U2OS delis treated with 4 µM of peptides alone (A), with 0.5 µM cisptatin (B) or with 1 µM cisplatin (C) as described in Example 18. (D)-(F) show the levels of cell survival of U2OS cells treated with 6 µM of peptides alone (D), with 0.5 µM cisplatin (E) or with 1 µM cisplatin (F) as described in Example 18. (G)-(I) show the levels of cell survival of U2OS cells treated with 12 µM of peptides alone (G), with 0.5 µM cisplatin (H) or with 1 µM cisplatin (I) as described in Example 18. The annotations in the legend refer to APIM sequences as described above.

Figure 27:
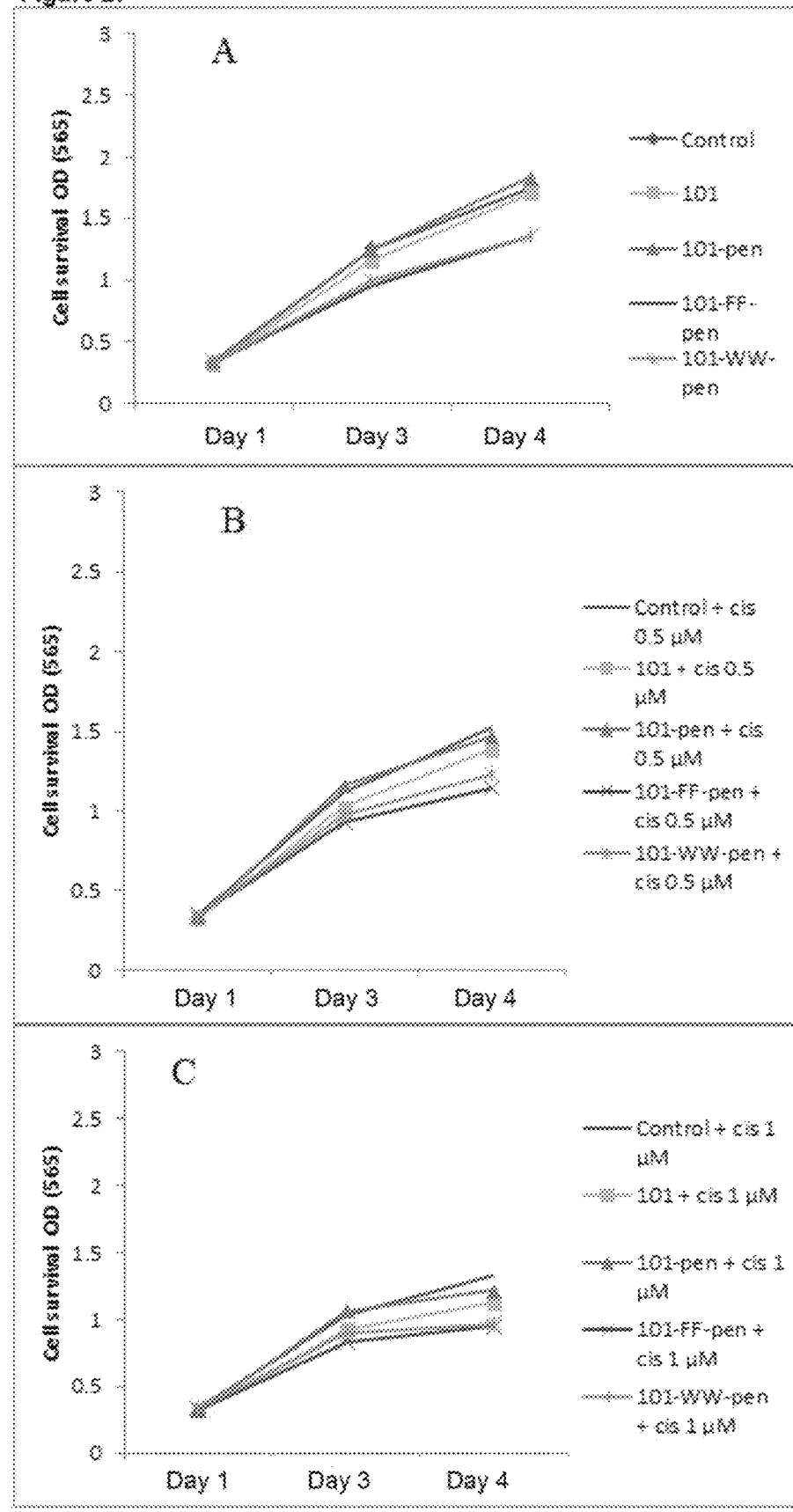

FIG. 27 shows graphs showing the results of cytotoxicity assays with various "standard" and "extended" APIM peptides. (A)-(C) show the levels cell survival of U2OS cells treated with 12 µM of peptides alone (A), with 0.5 µM cisplatin (B) or with 1 µM displatin (C) as described in Example 14. The annotations in the legend refer to APIM sequences as described above.

EXAMPLES

The inventors have surprisingly found that an oligopeptidic compound comprising a "conventional" APIM motif and a cell-penetrating peptide is imported into bacterial cells and is capable of inhibiting the growth of said cells. It is thought that oligopeptidic compounds comprising an APIM motif may compete with PCNA-like proteins in bacteria for proteins that interact with said PCNA-like proteins, thereby inhibiting various cellular processes, e.g. DNA synthesis, signal transduction etc. The effects of oligopeptidic compounds comprising an APIM motif on bacterial cells have been established in both gram positive and gram negative bacteria using an exemplary cell-penetrating APIM-containing peptide ATX-101 (SEQ ID NO:1289, which contains the APIM motif, RWLVK (SEQ ID NO: 1290)).

The data presented below suggest that oligopeptidic compounds comprising an APIM motif, including an extended or longer APIM motif as defined herein, are useful as antibacterial agents, e.g. antibiotics, either alone or in combination with other cytostatic or cytotoxic agents. Accordingly, the data supports the use of oligopeptidic compounds comprising an APIM motif, including an extended or longer APIM motif as defined herein, in the treatment or prevention of bacterial infections or bacterial infectious diseases.

The inventors have also unexpectedly found that "conventional" APIM sequence may be substantially modified as described herein to produce extended or longer APIM peptides that are capable of interacting with PCNA. As shown by the experimental results discussed below (Examples 12-14), the extended or longer APIM peptides interact with PCNA with a similar or improved affinity relative to the conventional APIM peptides, but are not cytotoxic to normal, healthy animal cells. Accordingly, it can be inferred from the data, provided herein that peptides containing the extended or longer APIM sequence as defined herein would also find utility in the treatment or prevention of bacterial infections or bacterial infectious diseases.

Example 1

Determining the Effect of ATX-101 on Bacteria

The minimum inhibitory concentration (MIC) of ATX-101 (SEQ ID NO: 1289) was determined for various gram negative and gram positive bacteria. The bacteria, *Pseudomonas aeruginosa* ATCC 15692, *Acinetobacter baumenni* ATCC 19600, *Escherichia coli* ATCC 25922, *Pseudomonas aeruginosa* TO-5A (clinical isolate), *Enterococous faecium* CCUG 37832, *Enterococcus faecium* CTC 492, *Micrococcus luteus* ATCC 9341 and *Escherichie coli* NCIMB 12210 were grown in the presence of various concentrations of ATX-101 and/or antibiotic.

Robotic MIC Assay:

ATX-101 was dissolved in Mueller-Hinton broth to 1.25 times of the desired assay concentration. Antibiotics were dissolved in Mueller-Hinton broth and Mueller-Hinton broth with ATX-101 at a concentration of 1.25 times the highest desired assay concentrations. Antibiotics were pharmaceutical grade purchased from Sigma-Aldrich.

Two-fold serial dilutions of antibiotics were made in Mueller-Hinton with different concentrations of ATX-101, and the solutions were placed in four parallel wells is Nunc 384-well micro plates (30 µl per well in Nunc 242757 microplates). A group of 8 wells with no addition of antibiotics for each ATX-101 concentration was included on each micro plate as a growth reference.

At the day of analysis, overnight TSB cultures inoculated from freeze stocks (6 ml in 50 ml tube tilted to 45-degrees angle, 200 rpm, 2.5 cm amplitude, 37° C.) were diluted in TSB until the OD800 was 0.10, and further diluted 1:40 in Mueller-Hinton broth. Each well in the 384-well assay plates was inoculated with 7.5 µl of the diluted culture, giving the same dilution of the culture in the assay cultures. The microplates were placed in plastic bags and incubated without shaking at 37° C. The optical density at 600 nm in the microwells was measured after approximately 19 hours of incubation, and the relative growth yield was calculated based on the growth in the reference groups. The MIC value was set to the highest concentration giving less than 30% growth in all 4 parallel wells within the sample groups. The microplates were further incubated for 6 hours, and optical density in the cultures was measured once more for confirmation of the estimated MIC-values.

Figure 1:
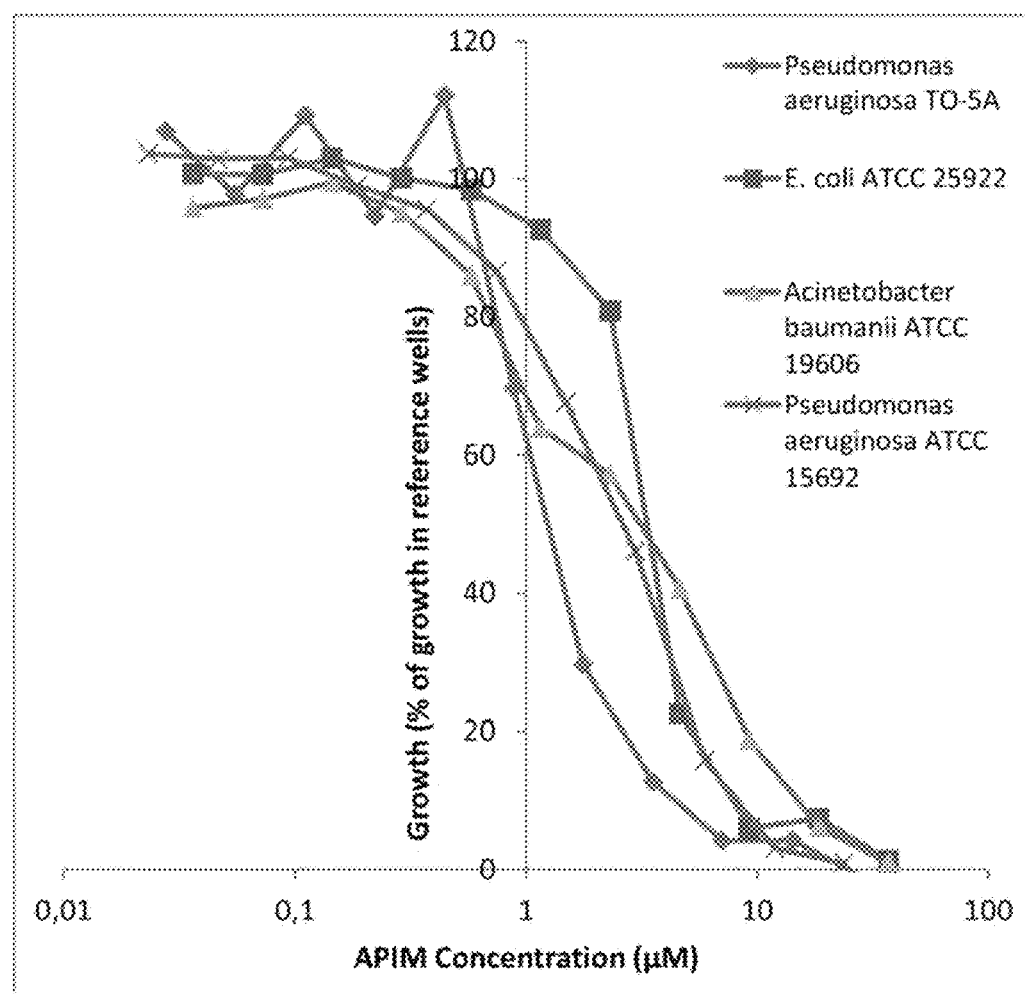
Figure 2:
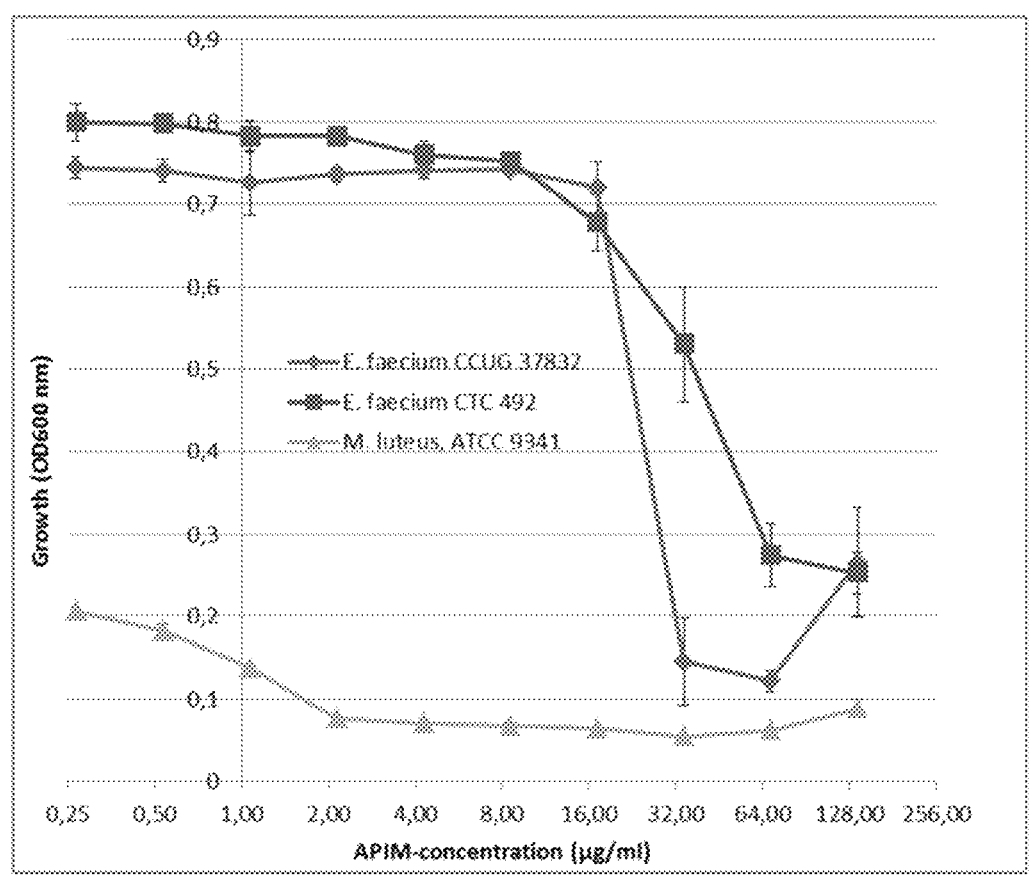
FIG. 2 shows graph that demonstrates that the growth of gram-positive bacteria, *Enterococcus faecium* CCUG 37832, *Enterococcus faecium* CTC 492 and *Micrococcus luteus* ATCC 9341, is inhibited by varying concentrations of APIM peptide, ATX-101.

FIG. 1 shows that the growth of various gram negative bacteria is inhibited by ATX-101 from about 1 µM. FIG. 2 shows that the growth of various gram positive bacteria is inhibited by ATX-101 from about 1 µM. The MIC for the gram negative bacteria tested to date was determined to be in the range of 5-10 µg/ml. The MIC for gram positive bacteria tested to date was determined to be in the range of 1 µg/ml. These data suggest that, in general, gram positive bacteria are more sensitive to APIM peptides than gram negative bacteria. However, based on these results, APIM peptides are expected to be useful as antibiotic agents for all bacteria.

Figure 3:
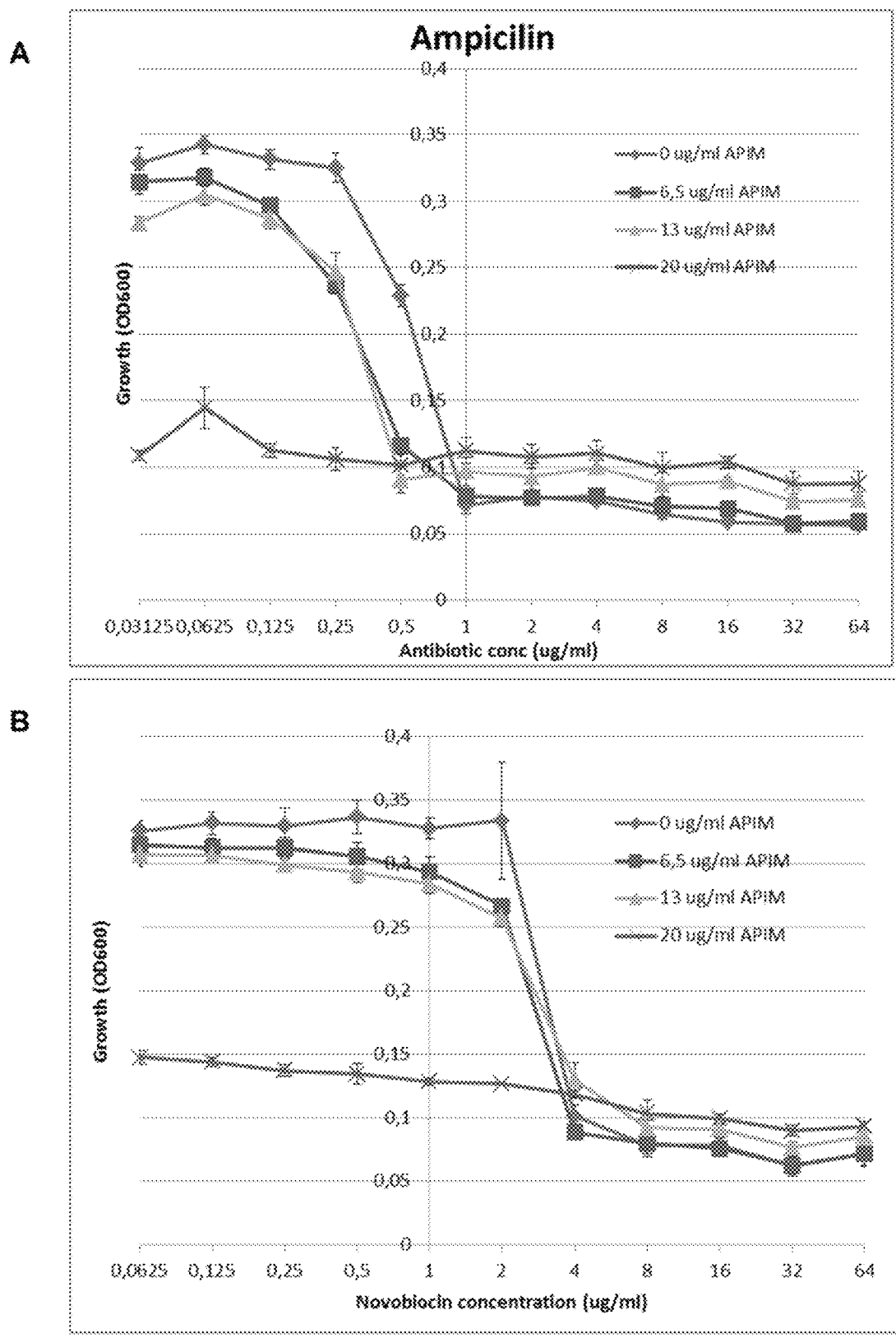
FIG. 3 shows a graph that demonstrates that the growth of the gram-positive bacterium *Enterococcus faecium* CTC 492 is more sensitive to: (A) Ampicillin; and (B) Novobiocin, (both cytotoxic agents i.e. antibiotics) when grown in the presence of ATX-101.
Figure 4:
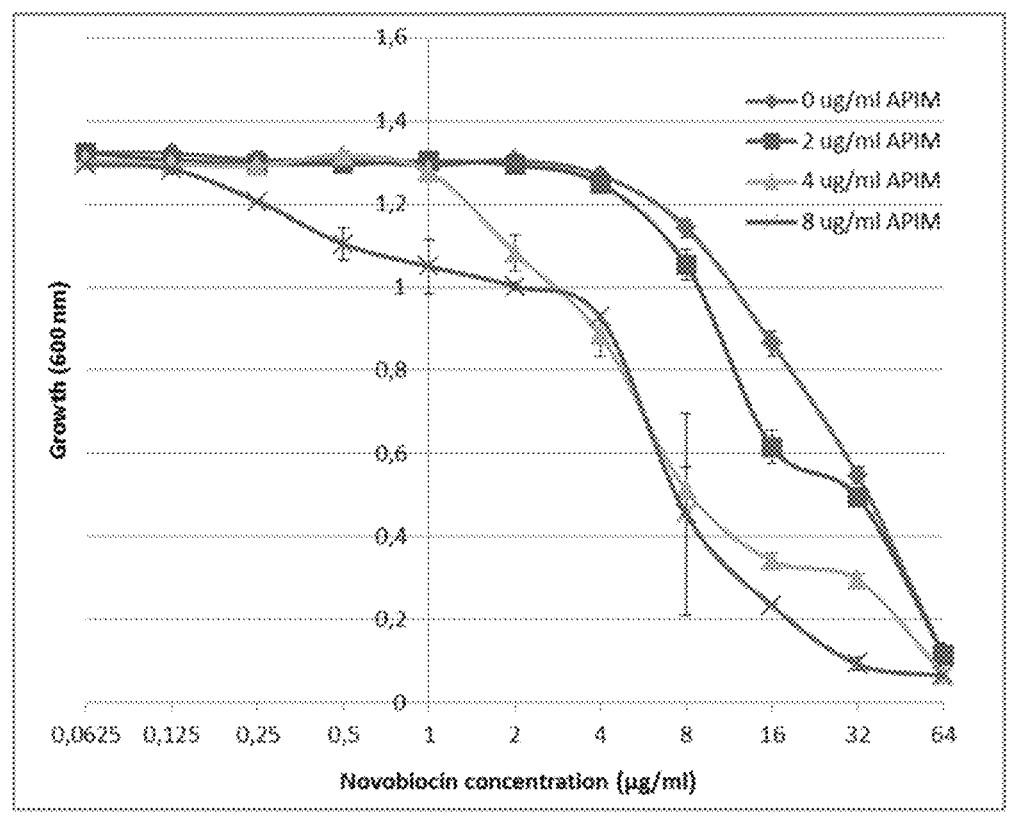
FIG. 4 shows a graph that demonstrates that the growth of the gram-negative bacterium *Escherichia coli* NCIMB 12210 is more sensitive to Novobiocin (a cytotoxic agent, i.e. an antibiotic) when grown in the presence of ATX-101.

FIG. 3 shows that *Enterococcus faecium* CTC 492 shows increased sensitivity to ampicillin and novobiocin combination with ATX-101. A combination of 6.5 µg/ml or 13 µg/ml ATX-101 is sufficient to inhibit bacterial growth at a concentration of about 0.5 µg/ml ampicillin, whereas a concentration of 1 µg/ml ampicillin without ATX 101 was required to achieve the same level of inhibition. Similarly, 6.5 µg/ml or 13 µg/ml ATX-101 enhances the inhibition of bacterial growth at a concentration of about 0.5-2 µg/ml novobiocin. FIG. 4 shows that that ATX-101 is capable of reducing the MIC for novobiocin by 16-fold. Thus, these data suggest that ATX-101 has an additive or synergistic inhibitory effect on bacterial growth in combination with an antibiotic. FIG. 3 also demonstrates that higher concentrations of ATX-101, e.g. 20 µg/ml, are sufficient to kill bacteria, as no growth was observed at this concentration, with or without ampicillin or novobiocin.

Based on these results, APIM peptides are expected to be useful in combination with other antibiotic agents, i.e. may enable known antibiotics to be used effectively at lower concentrations.

Example 2

Determining the Effect of Other APIM Peptides on Bacteria

The inventors have shown that other APIM peptides, i.e. comprising PCNA binding motifs that are different to the motif in ATX-101, are also effective antibiotics. In this respect, peptides comprising the sequences: MDRWSVK-WKKKRKIRRRRRRRRRRR (SEQ ID NO: 1298) and MDRWAVKWKKKRKIRRRRRRRRRRR (SEQ ID NO: 1299) are particularly effective and show lower MICs than ATX-101. These data indicate that the antimicrobial effect arises from the PCNA interacting motif, because the other domains in these peptides are identical.

Example 3

In Silica Characterisation of APIM Consensus Motif

The inventors have performed sequence analyses to determine how much variation within the APIM motif occurs naturally, i.e. in native sequences across a number of species. As PCNA is highly conserved across eukaryotic organisms, it is expected that sequence variation of the APIM motif in orthologues of polypeptides that are thought to interact with PCNA is representative of the variation that may be used in the oligopeptidic compounds of the invention, i.e. variation of amino acids within the APIM motif at some positions may be permitted without losing affinity to PCNA.

The inventors used identified 657 human polypeptide sequences that comprise the motif [K/R]-[F/W/Y]-[A/L/V/I]-[A/L/V/I]-[K/R] (SEQ ID NO: 1308) from a possible 21,673 polypeptide sequences. Of the 657 sequences identified, 291 were excluded because insignificant information about the function of the polypeptides was available. The remaining 366 were considered to be polypeptides that are likely to interact with PCNA and these sequences were used to identify orthologues in: *Bos taurus* (288 orthologues); *Rattus norvegicus* (286 orthologues); *Mus musculus* (312 orthologues); *Gallus gellus* (236 orthologues) *Xenopus tropicalis* (200 orthologues); *Dania rerio* (189 orthologues): *Caenrhabditis elegans* (102 orthologues): *Drosophila melanogaster* (136 orthologues); and *Saccharomyces cerevisiae* (65 orthologues). Alignment of the domains of the orthologues that comprise the APIM motif suggested that the motif may defined as:

(SEQ ID NO: 1309)
[R/K/H]-[W/F/Y]-[L/I/V/A/M/S/T/N/Q/C]-
[L/I/V/A/M/G/S/T/N/Q/R/H/K/C]-[K/R/H/P], wherein specific combinations of amino acids at positions 3 and 4 that were identified in the orthologues include:
LL, LA, LV, AL, VL, VI, LI, IL, VV, VA, IV, II, AV, IA, AI, AM, LM, LS, LT, IS, MV, TV, AA, IM, LN, LQ, VM, TL, SL, IT, VT, LG, MA, ML, NL, QL, QI, TI, SI, AS, VS, SV, CA, IG, LR, VR, TK and IR. Particularly or common combinations are LL, LA, LV, AL, VL, VI, LI, IL, VV, VA, IV, II, AV, IA, AI, AM, LM, LS and LT, the most being LL, LA, LV, AL, VL, VI, LI, VV, VA, IV, II, AV, IA and AI.

Thus, the broadest definition of the APIM motif was derived from this analysis, and all polypeptides comprising an APIM motif according to this definition could reasonably be expected to interact with, i.e. bind to, PCNA.

Example 4

In Vivo Characterisation of APIM Consensus Motif

This work described in this Example investigates interaction between APIM peptides and PCNA.

In living S-phase cells, PCNA tagged with green fluorescent protein (EGFP) forms distinct foci representing sites of replication and thus can be used as a S-phase marker.

PCNA tagged with cyan fluorescent protein (ECFP) was co-expressed with various APIM peptide constructs fused with yellow fluorescent protein (EYFP). To examine the degree of proximity of APIM peptides and PCNA, fluorescence resonance energy transfer (FRET) was measured.

Live HeLa cells were examined 16-24 hours after transient transfection (by Fugene 6 (Roche Inc.) according to the manufacturer's recommendations) of ECFP and EYFP fusion constructs. Fluorescent images were acquired using a Zeiss LSM 510 Meta laser scanning microscope equipped with a Plan-Apochromate 63×/1.4 oil immersion objective. Enhanced cyan fluorescent protein (ECFP) was excited at $\lambda=458$ nm and detected at $\lambda=470-500$ nm and enhanced yellow fluorescent protein (EYFP) was excited at $\lambda=514$ nm and detected at $\lambda=530-600$ nm, using consecutive scans. The thickness of the slice was 1 µm.

Fluorescent resonance energy transfer (FRET) occurs if the tags (EYFP and ECFP) are less than 100 Å (10 nm)apart. We detected FRET using the sensitised emission method, measuring acceptor (EYFP) emission upon donor (ECFP) excitation. We had FRET when the intensity of emitted light from EYFP after excitation of the ECFP fluorochrome was stronger than the light emitted by ECFP or EYFP-tagged proteins alone, after excitation with the EYFP and ECFP lasers respectively (bleed through), given by the equation: $FRET=I_2-I_1(I_{D2}/I_{D1})-I_3(I_{42}/I_{43})$ is >0. FRET was normalised for expression levels using the equation: $N_{FRET}=FRET/(I_1 \times I_3)^{1/2}$. $N_{FRET}$ was calculated from mean intensities (I) within a region of interest (ROI) containing more than 25 pixels where all pixels had intensities below 250 and the average intensities were between 100 and 200 for both the donor and the acceptor constructs. Channel 1 (ECFP) and 3 (EYFP) were measured as described above for imaging, and channel 2 (FRET) was excited with $\lambda$=458 nm and detected at $\lambda$=530-600 nm. $I_{D1,D2,D3}$ and $I_{A1,A2,A3}$ were determined for cells transfected with ECFP and EYFP constructs only, with same settings and same fluorescence intensities as co-transfected cells ($I_1$ and $I_3$). ECFP-PCNA and EYFP-PCNA were included as positive controls, and due to dimerisation of co-expressed tags, ECFP and EYFP proteins expressed from empty vectors were included as negative controls in all experiments.

Figure 5:
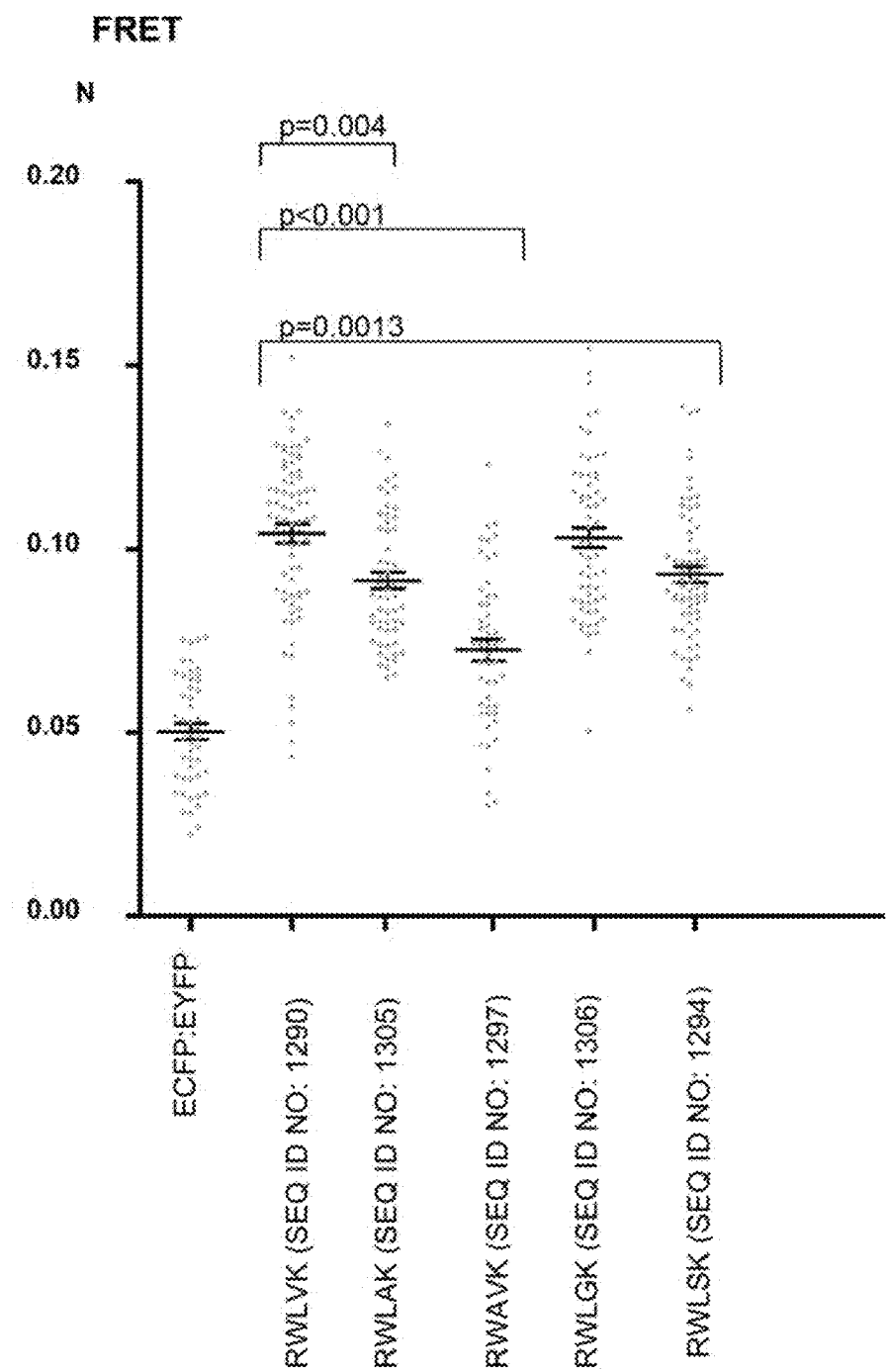
FIG. 5 shows a graph showing the results of FRET analysis, Normalised FRET ($N_{FRET}$) measurements are shown between EYFP (yellow fluorescent protein)/ECFP (cyan fluorescent protein) (Lane 1, background due to dimerisation of the tags). EYFP-APIM motif/ECFP-PCNA for various motifs are shown in the other lanes.

FIG. 5 shows that a significant FRET signal could be detected for all of the variants tested, which verifies that a variety of peptides within the APIM motif definition described herein (and that occur in polypeptides that are expected to interact with PCNA) are capable of interacting with PCNA and would therefore be expected to find utility in the method and uses described herein, i.e. as antimicrobial peptides.

Example 5

Determining the Effect of APIM Peptides on the Minimum Inhibitory Concentration of Various Antibiotics on Bacteria The APIM peptide ATX-101 was used to determine the effect of APIM peptides on the MIC for various antibiotics on a range of bacteria.

The APIM peptide was dissolved in Mueller-Hinton broth to 1.25 times of the desired assay concentration. Antibiotics were dissolved in Mueller-Hinton broth and Mueller-Hinton broth with APIM at a concentration of 1.25 times the highest desired assay concentrations. Antibiotics were pharmaceutical grade purchased from Sigma-Aldrich.

Two-fold serial dilutions of antibiotics were made in Mueller-Hinton with different concentrations of APIM, and the solutions were placed in four parallel wells in Nunc 384-well micro plates (30 μl per well in Nunc 242757 microplates). A group of 8 wells with no addition of antibiotics for each APIM concentration was included on each micro plate as growth reference.

At the day of analysis, overnight TSB cultures inoculated freeze stocks (6 ml in 50 ml tube tilted to 45-degrees angle, 200 rpm, 2.5 cm amplitude, 37° C.) were diluted in TSB until the $OD_{600}$ was 0.10, and further diluted 1:40 in Mueller-Hinton broth. Each well in the 384-well assay plates was inoculated with 7.5 μl of the diluted culture. The microplates were placed in plastic bags and incubated without shaking at 37° C. The optical density at 600 nm in the microwells was measured after approximately 19 hours of incubation, and the relative growth yield in each well was calculated based on the growth in the reference groups. The MIC value was set to the highest concentration giving less than 30% growth in all 4 parallel wells within the sample groups. The microplates were further incubated for 6 hours, and optical density in the cultures was measured once more for confirmation of the estimated MIC-values.

Table 3 shows that APIM peptides are capable of reducing the MIC for numerous antibiotics by at least 50% in various bacteria.

TABLE 3

| Strain | Antibiotic | APIM conc. μg/ml | Est MIC (μg/ml) |
|---|---|---|---|
| E. faecium CTC 492 | Ampicillin | 0 | 1 |
| E. faecium CTC 492 | Ampicillin | 6.5 | 0.5 |
| E. faecium CTC 492 | Ampicillin | 13 | 0.5 |
| E. faecium CTC 492 | Apramycin | 0 | 64 |
| E. faecium CTC 492 | Apramycin | 6.5 | 64 |
| E. faecium CTC 492 | Apramycin | 13 | 32 |
| E. faecium CTC 492 | Rifampicin | 0 | 16 |
| E. faecium CTC 492 | Rifampicin | 6.5 | 32 |
| E. faecium CTC 492 | Rifampicin | 13 | 4 |
| E. faecium CTC 492 | Rifampicin | 20 | 8 |
| E. faecium CTC 492 | Erythromycin | 0 | 4 |
| E. faecium CTC 492 | Erythromycin | 6.5 | 4 |
| E. faecium CTC 492 | Erythromycin | 13 | 1 |
| E. faecium CTC 492 | Chloramphenicol | 0 | 2 |
| E. faecium CTC 492 | Chloramphenicol | 6.5 | 2 |
| E. faecium CTC 492 | Chloramphenicol | 13 | 1 |
| E. faecium CTC 492 | Imipenem | 0 | 4 |
| E. faecium CTC 492 | Imipenem | 6.5 | 2 |
| E. faecium CTC 492 | Imipenem | 13 | 2 |
| E. faecium CTC 492 | Tobramycin | 0 | 64 |
| E. faecium CTC 492 | Tobramycin | 6.5 | 64 |
| E. faecium CTC 492 | Tobramycin | 13 | 32 |
| E. faecium CTC 492 | Monensin | 0 | 1 |
| E. faecium CTC 492 | Monensin | 6.5 | 0.5 |
| E. faecium CTC 492 | Monensin | 13 | 0.5 |
| E. coli NCIMB 12210 | Chloramphenicol | 0 | 2 |
| E. coli NCIMB 12210 | Chloramphenicol | 2 | 2 |
| E. coli NCIMB 12210 | Chloramphenicol | 4 | 2 |
| E. coli NCIMB 12210 | Chloramphenicol | 8 | 1 |
| E. coli NCIMB 12210 | Novobiocin | 0 | 64 |
| E. coli NCIMB 12210 | Novobiocin | 2 | 32 |
| E. coli NCIMB 12210 | Novobiocin | 4 | 8 |
| E. coli NCIMB 12210 | Novobiocin | 8 | 4 |
| A. baumanii ATCC 19606 | Rifampicin | 0 | 2 |
| A. baumanii ATCC 19606 | Rifampicin | 2 | 2 |
| A. baumanii ATCC 19606 | Rifampicin | 4 | 1 |
| A. baumanii ATCC 19606 | Rifampicin | 8 | 1 |
| A. baumanii ATCC 19606 | Imipenem | 0 | 0.25 |
| A. baumanii ATCC 19606 | Imipenem | 2 | 0.125 |
| A. baumanii ATCC 19606 | Imipenem | 4 | 0.125 |
| A. baumanii ATCC 19606 | Gentamicin | 0 | 16 |
| A. baumanii ATCC 19606 | Gentamicin | 2 | 16 |
| A. baumanii ATCC 19606 | Gentamicin | 4 | 8 |
| A. baumanii ATCC 19606 | Monensin | 0 | 64 |
| A. baumanii ATCC 19606 | Monensin | 2 | 64 |
| A. baumanii ATCC 19606 | Monensin | 4 | 64 |
| A. baumanii ATCC 19606 | Monensin | 8 | 32 |
| A. baumanii ATCC 19606 | Vancomycin | 0 | 32 |
| A. baumanii ATCC 19606 | Vancomycin | 2 | 32 |
| A. baumanii ATCC 19606 | Vancomycin | 4 | 16 |
| A. baumanii ATCC 19606 | Novobiocin | 0 | 8 |
| A. baumanii ATCC 19606 | Novobiocin | 2 | 8 |
| A. baumanii ATCC 19606 | Novobiocin | 4 | 8 |
| A. baumanii ATCC 19606 | Novobiocin | 8 | 2 |

Example 6

The Effect of APIM Peptides on MDR Bacteria

The efficacy of APIM peptides as antibiotics against MDR bacteria was tested using strains at MRSA and MDR E faecium.

Table 4 demonstrates that APIM peptides, exemplified using ATX-101, are particularly effective against MRSA, as the MIC of APIM peptide needed to inhibit growth of two strains of MRSA was greatly reduced in comparison to a control strain of S. aureus.

TABLE 4

| Strain | Starting concentration of ATX-101 (µg/ml) | Factor of inhibition | MIC of ATX-101 (µg/ml) |
|---|---|---|---|
| *Staphylococcus aureus* NCTC 6571 | 150 | 1 | 150 |
| *Staphylococcus aureus* MRSA 1040s | 150 | 0.25 | 37.5 |
| *Staphylococcus aureus* MRSA 1096 | 150 | 0.0625 | 9.375 |

In view of the anti-bacterial effect of ATX-101 on strains of MRSA, the MIC for a variety of APIM variants was determined using *Staphylococcus aureus* MRSA 1040s. The results in Table 5 show that all APIM peptides have similar antibacterial activity, i.e. variation of the APIM sequence within the parameters defined in Example 3, does not reduce activity. A cell penetrating peptide (SEQ ID NO: 337) present in all of the APIM peptides, was used as a negative control. Whilst the CPP alone demonstrates some antibacterial activity, its combination with the APIM sequence greatly improves its activity, thereby indicating that the APIM sequence is responsible for the antibacterial effect.

TABLE 5

| Peptide sequence | APIM sequence | MIC (µg/ml) |
|---|---|---|
| MDRWSVKWKKKRKIRRRRRRRRRR (SEQ ID NO: 1298) | RWSVK (SEQ ID NO: 1296) | 32 |
| MDRWAVKWKKKRKIRRRRRRRRRR (SEQ ID NO: 1299) | RWAVK (SEQ ID NO: 1297) | 32 |
| MDRWLSKWKKKRKIRRRRRRRRRR (SEQ ID NO: 1302) | RWLSK (SEQ ID NO: 1294) | 32 |
| MDRWLTKWKKKRKIRRRRRRRRRR (SEQ ID NO: 1300) | RWLTK (SEQ ID NO: 1293) | 32 |
| MDRWLVPWKKKRKIRRRRRRRRRR (SEQ ID NO: 1303) | RWLVP (SEQ ID NO: 1292) | 32 |
| MDRWLVKWKKKRKIRRRRRRRRRR (SEQ ID NO: 1289) | RWLVK (SEQ ID NO: 1290) | 32 |
| RRRRRRRRRR (SEQ ID NO: 337) | — | 118 |

Figure 6:
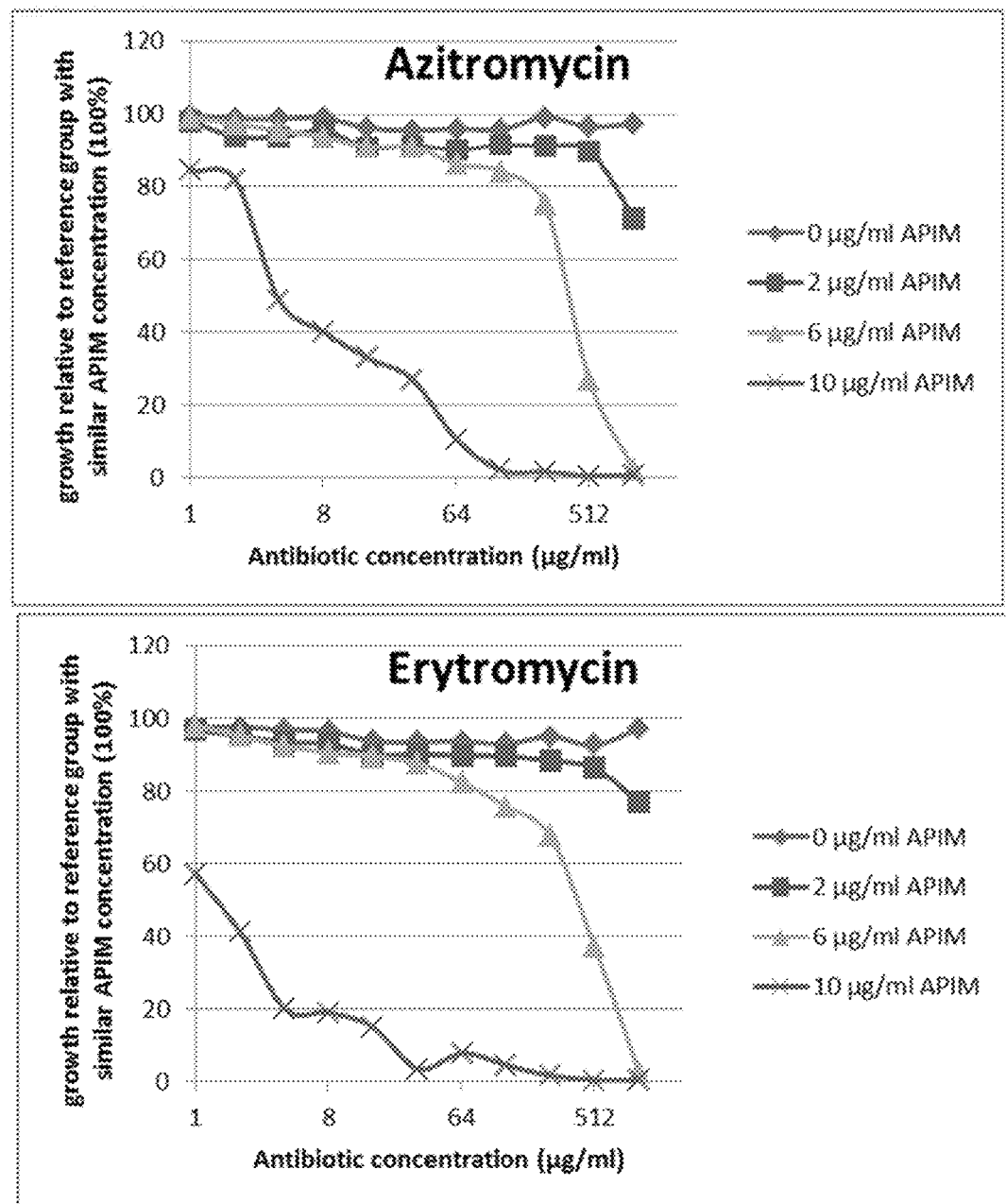
FIG. 6 shows graph that demonstrates that the growth of the MDR bacterium Methicillin-resistant *Staphylococcus aureus* (MRSA 1040) is more sensitive to macrolide antibiotics, azitmomycin and erythromycin, when grown in the presence of ATX-101.

Next, the effect of APIM peptides on the MIC of antibiotics was determined using *Staphylococcus aureus* MRSA 1040s. Table 6 and FIG. 6 show that ATX-101 reduces the MIC for erythromycin and azithromycin significantly. Table 7 and FIG. 7 demonstrate that similar effects are observed for other APIM variants. These data indicate that APIM peptides may be particularly effective in treating MRSA infections, either alone or in combination with antibiotics, particularly macrolide antibiotics.

TABLE 6

| | MIC µg/ml | MIC (µg/ml) when combined with 10 µg/ml of ATX-101 |
|---|---|---|
| ATX-101 | 16 | — |
| Erythromycin | >1034 | 2 |
| Azithromycin | >1034 | 8 |

TABLE 7

| Peptide sequence | APIM sequence | Concentration of APIM peptide (µg/ml) | MIC of Erythromycin (Relative values) |
|---|---|---|---|
| MDRWLVKWKKKRKIRRRRRRRRRR (SEQ ID NO: 1289) | RWLVK (SEQ ID NO: 1290) | 7.5 | 1000 |
| MDRWLVKWKKKRKIRRRRRRRRRR (SEQ ID NO: 1289) | RWLVK (SEQ ID NO: 1290) | 15 | 125 |

TABLE 7-continued

| Peptide sequence | APIM sequence | Concentration of APIM peptide (μg/ml) | MIC of Erythromycin (Relative values) |
|---|---|---|---|
| MDRWSVKWKKKRKIRRRRRRRRRR (SEQ ID NO: 1298) | RWSVK (SEQ ID NO: 1296) | 15 | 100 |
| MDRWAVKWKKKRKIRRRRRRRRRR (SEQ ID NO: 1299) | RWAVK (SEQ ID NO: 1297) | 15 | 200 |
| MDRWLSKWKKKRKSRRRRRRRRRR (SEQ ID NO: 1302) | RWLSK (SEQ ID NO: 1294) | 15 | 200 |
| MDRWLTKWKKKRKIRRRRRRRRRR (SEQ ID NO: 1300) | RWLTK (SEQ ID NO: 1293) | 15 | 100 |
| MDRWLVPWKKKRKIRRRRRRRRRR (SEQ ID NO: 1303) | RWLVP (SEQ ID NO: 1292) | 15 | 100 |

Additive effects were also observed when APIM peptides were combined with various antibiotics to treat a MDR strain of *E. faecium* (*E. faecium* CCUG 37832 (TO-3)), which is commonly associated with endocarditis, urinary tract infections and infections in wounds.

The MIC for APIM peptide ATX-101 on *E. faecium* CCUG 37832 (TO-3) was determined to be 7.5 μg/ml. Accordingly, concentrations of 8 μg/ml and 16 μg/ml of ATX-101 were combined with various antibiotics selected from; 2,4-Diamin, S. methizol, S. methoxa, S. dimetho, Surfaceta, Trimeth, Flumeq, Levoflox, Pruliflox, Metronid and Nitrofur. FIG. 8 shows that the MIC of each antibiotic could be reduced by combining it with an APIM peptide. Thus, these data indicate that APIM peptides may be particularly effective in treating *E. faecium* infections (particularly MDR *E. faecium* infections), either alone or in combination with antibiotics, particularly DNA gyrase inhibitors.

Example 7

Overexpression of APIM Peptides in *E. coli*

In order to verify further that the anti-microbial effect of the APIM peptides arise from the APIM sequence, peptides containing only the APIM sequence (i.e. without a cell-penetrating peptide) were over-expressed in *E. coli* using the expression vector pET28. The APIM peptide was expressed alone or as part of a fusion protein with EYFP. Expression of EYFP alone was used as a control.

The expression vectors containing the respective peptides were transfected into the bacterial strain *E. coli* BL21 (ripl). Single colonies, 4-6 of each strain, were inoculated in 150 ml LB media (+Km/Clm) in 96 wells plates, and incubated at 37° C. Overnight cultures were diluted 1:100 and grown for 1 h before induction with 1 mM IPTG (initiating peptide expression). OD was measured every hour.

FIG. 9A shows that expression of the APIM peptide, either alone or as part of a fusion protein with EYFP, inhibits bacterial growth. This result demonstrates that the APIM sequence RWLVK (SEQ ID NO: 1290) has antibacterial properties even in the absence of a cell-penetrating peptide.

FIG. 10 shows that APIM variant sequences are similarly effective at inhibiting bacterial growth when overexpressed in *E. coli*. FIG. 13B indicates that the APIM variants RWLTK (SEQ ID NO: 1293), RFSLK (SEQ ID NO: 1291) and RWLVP (SEQ ID NO: 1292) are particularly effective. However, all of the variants tested show a significant inhibitory effect on bacterial growth.

Example 8

Determination of APIM Peptide Interaction with the β-clamp Protein from *E. coli*

Microscale thermophoresis (MST) was used to determine the dissociation constant for various APIM containing peptides.

The β-clamp protein from *E. coli* was labeled with a fluorescent molecule. Concentration of PCNA was kept constant, whereas dilutions of each APIM containing peptide were prepared (1:1). In a mix of protein and peptide, the signal was recorded in all capillaries with varying concentrations of the unlabeled peptide, and any change of thermophoretic properties was observed as a change in fluorescence intensity.

Table 8 shows that various APIM peptides show specific interactions with the β-clamp protein (a low Kd value indicates a strong interaction, whereas a high Kd value indicates a weak interaction). The R11 peptide (SEQ ID NO: 337) was used as a control and no data could be obtained by MST for this peptide, indicating that this peptide does not interact with the β-clamp protein. This data further verifies that the APIM sequence contributes to the antibacterial effects of the APIM peptides.

TABLE 8

| Peptide sequence | APIM sequence | Kd |
|---|---|---|
| MDRWLVKWKKKRKIRRRRRRRRRR (SEQ ID NO: 1289) | RWLVK (SEQ ID NO: 1290) | 101 |
| MDRWSVKWKKKRKIRRRRRRRRRR (SEQ ID NO: 1298) | RWSVK (SEQ ID NO: 1296) | 408 |

TABLE 8-continued

| Peptide sequence | APIM sequence | Kd |
|---|---|---|
| MDRWAVKWKKKRKIRRRRRRRRRR (SEQ ID NO: 1299) | RWAVK (SEQ ID NO: 1297) | 57 |
| MDRWLSKWKKKRKIRRRRRRRRRR (SEQ ID NO: 1302) | RWLSK (SEQ ID NO: 1294) | 115 |
| MDRWLTKWKKKRKIRRRRRRRRRR (SEQ ID NO: 1300) | RWLTK (SEQ ID NO: 1293) | 22 |
| MDRWLVPWKKKRKIRRRRRRRRRR (SEQ ID NO: 1303) | RWLVP (SEQ ID NO: 1292) | 366 |
| MDRFLSKWKKKRKIRRRRRRRRRR (SEQ ID NO: 1301) | RFLSK (SEQ ID NO: 1295) | 511 |
| MDRFSLKWKKKRKIRRRRRRRRRR (SEQ ID NO: 1304) | RFSLK (SEQ ID NO: 1291) | 20 |
| R11 (SEQ ID NO: 337) | — | Nd |

Example 9

Determination of the Effect of UV Radiation on the Anti-microbial Properties of APIM Peptides Pre-cultures of *E. coli* BL21 (ripl) were grown over-night in LB at 37° C. The cultures were then diluted 1:100 and 150 ml/well was added/well in 96 wells plates. The cultures were further incubated for 1 h and each plate was exposed to UVC, 2 J/cm², with a Stratalinker The plates were incubated for 30 minutes following UV treatment and various APIM peptides, 15 µM or 30 µM of each peptide, were added to 6 parallel wells. $OD_{550}$ was measured every hour. Values were normalised and average was plotted.

FIGS. 11A and B show the effect of various APIM peptides (30 µM) on bacteria that have not been exposed to UV radiation. The graph in FIG. 11B shows the same growth curves as FIG. 14A without the controls (no peptide was added), which are the two highest grow curves in FIG. 11A. Thus, FIG. 11B shows that there is some re-growth 5 hours after the APIM peptides were added. However, this assay shows that all of the APIM peptides tested have a significant inhibitory effect on bacterial growth.

FIGS. 15A and B are equivalent to FIGS. 11A and B when the bacteria have been exposed to UV radiation. These Figures demonstrate that there is no re-growth when the APIM peptides are combined with UV radiation. Furthermore, no re-growth was observed in samples even when they were incubated over-night (data not shown). This suggests that UV radiation sensitizes the cells to APIM peptides or vice versa. Thus, these data demonstrate that a combination of APIM peptides and UV radiation, particularly UVC radiation, may be useful in treating bacterial infections.

The treatments using APIM peptides at 15 µM (data not shown) showed effects to the 30 µM treatment, which is shown in FIGS. 11 and 12.

FIG. 13 shows that treatment with UV radiation is effective even when using lower concentrations of APIM peptides. APIM peptide concentrations of 15 µM (FIG. 13A), 7.5 µM (FIG. 13B) and 3.75 µM (FIG. 13C) were all effective at inhibiting bacterial growth following treatment with UV radiation. Overall, these data show that bacteria are more 2-5 fold more sensitive to APIM peptides after UV-irradiation.

Example 10

Effect of ATX-101 n Methicillin Resistant *Staphyllococcus aureus* (MRSA) Biofilm Under Flow APIM peptides were tested to determine whether they have an effect on biofilm formation.

The IBIDI flow-system coupled with EVOS Auto Imaging system was optimized and used for testing the effect of ATX-101 on MRSA biofilm under flow. MRSA 1040 (u50) was used as model organism; it normally produces a dense biofilm in the growth channel during 36 hours of flow. The effect of 3 different concentrations of ATX-101 was tested (7 µg/ml, 3.5 µg/ml and 0.8 µg/ml). The flow system was programmed with share stress similar to those found in capillary networks (3.49 dyne/cm²), 2% Luria Bertani (LB) was used for dilution and flow medium. Good effect of ATX-101 was observed for all tested concentrations, the highest and lowest concentrations are presented in FIGS. 14 and 15, respectively.

Example 11

Determining the Minimum Inhibitory Concentration (MIC) of Various APIM Peptides on Bacteria The MICS for various APIM peptides were determined for various bacteria, as described above. The results are shown in Table 9 and show that all of the tested variants have anti-bacterial properties, when used alone, across a variety of bacteria. The results also demonstrate that the APIM peptides are particularly effective against MDR bacteria, e.g. *E. faecium* TO-3 and MRSA 1040.

TABLE 9

| | MIC (µM) | | | | | | |
|---|---|---|---|---|---|---|---|
| Peptide sequence | P. aeruginosa | E. coli | A. baumanii | E. faecium TO-3 | E. faecium TO-12 | MRSA 1040 | S. aureus NCTC6571 |
| MDRWLVKWKKKRKIRRRRRRRRRR (SEQ ID NO: 1289) | 37.9 | nd | nd | 7.5 | 16.8 | 7.5 | 37.9 |
| MDRWSVKWKKKRKIRRRRRRRRRR (SEQ ID NO: 1298) | nd | 37.9 | nd | 7.5 | 37.9 | 7.5 | 37.9 |
| MDRWAVKWKKKRKIRRRRRRRRRR (SEQ ID NO: 1299) | nd | nd | nd | 7.5 | 25.3 | 7.5 | 37.9 |

TABLE 9-continued

| | MIC (µM) | | | | | | |
|---|---|---|---|---|---|---|---|
| Peptide sequence | P. aeruginosa | E. coli | A. baumanii | E. faecium TO-3 | E. faecium TO-12 | MRSA 1040 | S. aureus NCTC6571 |
| MDRWLSKWKKKRKIRRRRRRRRRRR (SEQ ID NO: 1302) | nd | 37.9 | nd | 7.5 | 16.8 | 7.5 | 37.9 |
| MDRWLTKWKKKRKIRRRRRRRRRRR (SEQ ID NO: 1300) | nd | nd | nd | 7.5 | 25.3 | 7.5 | 37.9 |
| MDRWLVPWKKKRKIRRRRRRRRRRR (SEQ ID NO: 1303) | nd | 37.9 | 25.3 | 7.5 | 25.3 | 7.5 | 37.9 |
| MDRFLSKWKKKRKIRRRRRRRRRRR (SEQ ID NO: 1301) | nd | 37.9 | nd | 7.5 | 25.3 | 7.5 | 37.9 |
| MDRFSLKWKKKRKIRRRRRRRRRRR (SEQ ID NO: 1304) | nd | nd | nd | 7.5 | 25.3 | 7.5 | 37.9 |

Example 12

In Vivo Characterisation of an "Extended" APIM Consensus Motif

The work described in this Example investigates the interaction between "extended" APIM peptides and PCNA.

The inventors have determined unexpectedly that the "conventional" APIM sequence may be substantially modified without reducing the affinity interaction of the peptide with PCNA. In particular, the inventors have determined that an aromatic or hydrophobic amino acid may be inserted into the APIM sequence to generate a new consensus sequence, as defined by SEQ ID NO: 1. The inventors have also determined that the insertion of an aromatic or hydrophobic amino acid, particularly an aromatic amino acid, allows an increase in flexibility at the C-terminal end of the APIM sequence. Whilst not wishing to be bound by theory, it is thought that the insertion of an aromatic or hydrophobic amino acid, particularly an aromatic amino acid, within the APIM sequence improves the affinity of the peptide, such that it is not essential to include a basic amino acid at the C-terminal end of the APIM sequence to maintain the capacity of the peptide to bind to PCNA.

FRET assays were used to determine the capacity of the extended APIM peptides (peptides containing an extended or longer APIM sequence) to bind to PCNA, as described in Example 4.

FIG. 16 shows the FRET signal for a variety of APIM peptides containing a pentamer motif and three peptides containing an "extended" hexamer APIM sequence. A significant FRET signal could be detected for all of the "extended" APIM variants tested. Furthermore, all of the "extended" APIM peptides generate a signal that is equivalent to, or higher than, the APIM peptides containing a pentamer motif. These results verify that a variety of peptides within the APIM motif definition described herein are capable of interacting with PCNA. Accordingly, peptides containing the "extended" APIM sequence would therefore be expected to find utility in the method and uses described herein akin to peptides containing the pentamer APIM sequence, i.e., as anti-bacterial peptides, e.g. for treating or preventing a bacterial infection or a bacterial infectious disease as evidenced by the data in the Examples above.

It is particularly surprising that the "extended" APIM sequence is capable of facilitating the interaction between peptides containing the sequence and PCNA because the extended sequence does not typically occur in proteins that are known to interact with PCNA. Moreover, it was completely unexpected that this "extended" sequence would facilitate the interaction with PCNA with a similar or improved affinity relative to various pentamer sequences.

Example 13

Import of "Extended" APIM-containing Peptides

Fluorescently-labelled (FAM-tagged) extended APIM peptide constructs (oligopeptidic compounds as defined herein) were incubated with HeLa cells.

It was found that all of the "extended" APIM peptides were imported into said cells, showing that the cell penetrating peptide coupled to the extended APIM sequence as defined herein is sufficient to mediate the cellular uptake of the peptides (FIG. 17). This demonstrates that the oligopeptidic compounds of the invention are readily imported into cells and are available to interact with PCNA.

Example 14

Peptides Containing the "Extended" APIM Sequence are not Cytotoxic to Animal Cells Cytotoxicity of the peptides containing the "extended" APIM sequence was investigated by an MTT assay as described below. The ATX-101 peptide, which contains a "standard" pentamer APIM sequence was used as a control.

HEK293 cells (Human embryonic kidney cells) were seeded into 96 well plates (6000 cells/well) and incubated for 3 hours. After 24 hours peptides were added to the cells in serum free media and incubated for 1 h. Fresh media was added and the cells were harvested after additional 24, 72 and 96 hours. MTT was added to the cells (3-(4,5-Dimethylthiazol-2-yl)-2,5-diphenyltetrazolium bromide) and OD was measured at 565 nm, and the average from at least 6 wells was used to calculate cell survival. Data is presented in FIG. 18 as growth from one representative experiment and has been reproduced at least 2 times.

The results show that the peptides containing the "extended" APIM sequence do not affect the growth of normal animal cells, i.e., the peptides are not cytotoxic to animal cells, even though they may bind to PCNA with a greater affinity than some peptides containing the "standard"

pentamer APIM sequence. The absence of cytotoxic activity in normal animal cells also indicates that peptides containing the "extended" APIM motif would be useful in the methods and uses defined herein as the peptides have similar functional activity to peptides containing the "standard" pentamer sequence, which have been shown to function as anti-bacterial peptides, as discussed in the Examples above.

Example 16

Overexpression of "extended" APIM Peptides in *E. coli*

In order to verify that the extended APIM peptides have an anti-bacterial effect, peptides containing only the "extended" APIM sequence (i.e. without a cell-penetrating peptide) were over-expressed in *E. coli* using the expression vector pET28, using the method described in Example 7. Expression of a short version of the APIM sequence, which does not fall within the consensus sequence, was used as a control. The bacterial strain without a plasmid was used as a further control.

FIG. 19 shows that expression of various peptides containing an extended APIM peptide inhibits bacterial growth (measured by OD). This result demonstrates that the extended APIM sequences have anti-bacterial properties even in the absence of a cell-penetrating peptide. FIG. 20 shows the number of colony forming units (CFU) or bacterial growth as measured by $OD_{600}$ of *E. coli* BL21 over-expressing various "standard" and "extended" APIM peptides. The results demonstrate that the "extended" APIM peptides are antibacterial.

Example 16

Antibacterial Activity of API Peptides by Addition to *E. coli* BL21

To verify that peptides containing an "extended" APIM sequence are capable of inhibiting bacterial growth, several APIM peptides (without a FAM-tag) were added to cultures of *E. coli* BL21 at various concentrations. The growth of the bacteria was assessed by counting the number of CFUs.

FIG. 21 shows that all tested APIM peptides were effective at reducing bacterial growth in comparison to control peptides, e.g. R11 (a cell penetrating peptide) or no peptide. Furthermore, the peptides were effective irrespective of the cell-penetrating peptide attached to the APIM sequence.

Example 17

Effect of APIM Peptides on Mutation Frequency in *E. coli* BL21

The frequency of rifR (mutations in the rpoB gene) was determined by calculating number of rifR per CFU. Cultures of *E. coli* BL21(ripl) expressing various "extended" APIM peptides were grown on LB and the cultures were induced with (IPTG) (1 mM) at $OD_{600}$=0.3-0.4 inducing protein expression. Diluted aliquots from the culture were mixed with 3 ml soft agar (LB agar plates with 0.5% agar) and plated on LB agar plates (37° C., 16 h) and LB agar plates with rifampicin (100 µg/ml) (37° C., 48 h). Some cultures were treated with UV (1.5 $J/cm^3$). Controls included untransfected *E. coli* BL21 cells and cells transfected with a vector encoding a "short" sequence that does not fall within the APIM consensus. FIG. 22 shows the percentage reduction in mutation frequency and demonstrates that expression of APIM peptides significantly reduces mutation frequency. Whilst not wishing to be bound by theory, it is thought that the APIM peptides may impair the interaction between the β-clamp and translesion (TLS) polymerases, thereby inhibiting the activity of the TLS polymerases and their effects on mutation frequency.

FIG. 23 shows the mutation frequency in the *E. coli* cultures and again confirms that expression of APIM peptides significantly reduces mutation frequency.

FIG. 24 shows the mutation spectra of rpoB (1525-1722 bp) from rifampicin resistant colonies in various *E. coli* cultures. The figure demonstrates that the expression of APIM peptides results in a change in mutation hotspots, which further supports the hypothesis that the APIM peptides may impair the interaction between the β-clamp and translesion (TLS) polymerases.

Example 18

Cytotoxicity of "Extended" APIM-containing Peptides

Cytotoxicity of the peptides containing the "extended" APIM sequence (without a FAM-tag) was investigated by an MTT assay as described in Example 14, using both HEK 293 and U2OS cells. The ATX-101 peptide ("101"), which contains a "standard" pentamer APIM sequence was used as a control. Furthermore, the peptides were tested in combination with various concentrations of a cytostatic agent, cisplatin.

FIGS. 25-27 show that the peptides containing "extended" APIM sequence do not affect considerably the growth of normal healthy cells, i.e. the peptides are not cytotoxic to healthy cells, and do not significantly potentiate the effects of cytostatic agents.

The data in FIGS. 25 and 27 also demonstrates that APIM peptides may be coupled to various cell penetrating peptides without affecting the toxicity of the peptides.

The invention claimed is:

1. A method of treating a bacterial infection, said method comprising administering an agent, or a composition containing an agent, to a subject in need thereof, wherein said agent comprises:
an oligopeptidic compound comprising a PCNA interacting motif and a domain that facilitates the cellular uptake of said compound,
wherein the PCNA interacting motif is $X_1X_2X_3X_4X_5X_6$ (SEQ ID NO: 1) and
wherein:
$X_1$ is a basic amino acid;
$X_2$ is an aromatic amino acid;
$X_3$ is an aromatic amino acid or a hydrophobic amino acid that has an R group comprising at least three carbon atoms;
$X_4$ is an uncharged amino acid other than an aromatic amino acid, glycine (G) and proline (P);
$X_5$ is a hydrophobic amino acid, a basic amino acid, a polar amino acid, a thiol-containing amino acid or proline wherein $X_5$ is not asparagine (N), an aromatic amino acid, or an acidic amino acid; and
$X_6$ is any amino acid other than an acidic amino acid or an aromatic amino acid, wherein when $X_3$ is not an aromatic amino acid, $X_5$ is not lysine (K) and $X_6$ is a basic amino acid or proline (P).

2. The method of claim 1, wherein said agent or composition is provided as a combined preparation with one or more additional active agents for separate, simultaneous or sequential use or administration.

3. The method of claim 1, wherein said method further comprises a step of UV radiotherapy, which may be administered simultaneously, sequentially or separately to said agent or composition.

4. The method of claim 1, wherein said bacterial infection is caused by a biofilm.

5. The method of claim 1, wherein the bacterial infection is caused by a bacterium selected from any of the genera *Achromobacter, Acinetobacter, Actinobacillus, Aeromonas, Agrobacterium, Alcaligenes, Alteromonas, Bacteroides, Bartonella, Borrelia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas, Corynebacterium, Coxiella, Cryptobacterium, Edwardsiella, Eikenella, Enterobacter, Enterococcus, Erwinia, Helicobacter, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces, Treponem* and *Yersinia*.

6. The method of claim 1, wherein the bacterium is a MDR bacterium.

7. The method of claim 6, wherein the MDR bacterium is a Methicillin-resistant *Staphylococcus aureus* (MRSA) bacterium or an *Enterococcus faecium* bacterium.

8. The method of claim 2, wherein said one or more additional active agents is an antibiotic.

9. The method of claim 8, wherein said antibiotic agent is selected from one or more of a Macrolide, an Aminocoumarin, an Aminoglycosid, an Ansamycin, a Carbapenem, a Cephalosporin, a Glycopeptide, a Lincosamide, a Lipopeptide, a Monobactam, a Nitrofuran, an Oxazolidonone, a Penicillin, a Penicillin combination, a Polyether antibiotic, a Polypeptide antibiotic, a Quinolone, a sulfonamide, or a Tetracycline.

10. The method of claim 1, wherein (i) $X_5$ is a hydrophobic amino acid, a basic amino acid, a polar amino acid, or proline and not an aromatic amino acid, an acidic amino acid, or asparagine; and /or (ii) $X_3$ is an aromatic amino acid; and/or (iii) $X_4$ is a hydrophobic or polar amino acid.

11. The method of claim 1, wherein:
(i) the basic amino acid selected from any one of arginine (R), lysine (K), histidine (H), ornithine (Orn), methyllysine (MeK), diaminobutyric acid (Dbu), citrulline (Cit), acetyllysine (AcK), and any basic amino acid selected from the non-conventional amino acids in Table 2; and/or
(ii) $X_4$ is selected from any one of leucine (L), isoleucine (I), valine (V), alanine (A) methionine (M), norleucine (Nor), serine (S) or threonine (T), glutamine (Q), asparagine (N) or cysteine (C) or any hydrophobic or polar amino acid selected from the non-conventional amino acids in Table 2; and/or
(iii) $X_5$ is selected from any one of from V, L, I, A, M, Nor, S, T, Q, H, K, R, G, P or C or any hydrophobic, polar, basic or thiol-containing amino acid selected from the non-conventional amino acids in Table 2; and/or
(iv) the aromatic amino acid is selected from any one of tryptophan (W), tyrosine (Y), phenylalanine (F), tert.-butylglycine, cyclohexylalanine, tert.-butylphenylalanine, biphenylalanine or tri tert.-butyltryptophan or any aromatic amino acid selected from the non-conventional amino acids in Table 2.

12. The method of claim 1, wherein the PCNA interacting motif comprises a sequence selected from SEQ ID NOs: 6-21, 1221-1227, 1233-1257 or 22 to 297, 300, 301, 1207, 1209, 1258 to 1288 and 1310.

13. The method of claim 1, wherein the domain that facilitates the cellular uptake of the oligopeptidic compound is a cell penetrating peptide (CPP).

14. The method of claim 13, wherein the CPP is selected from any one of:
(i) an antennapedia class peptide;
(ii) a protegrin class peptide;
(iii) a HIV-TAT class peptide;
(iv) an amphipathic class peptide selected from an amphipathic and net positively charged peptide, a proline-rich amphipathic peptide, a peptide of SEQ ID NO:326 and a peptide of SEQ ID NO:328;
(v) a peptide exhibiting high a-helical content;
(vi) a peptide comprising oligomers of basic amino acids;
(vii) pVEC;
(viii) a calcitonin-derived peptide; and
(ix) an amphiphilic cyclic CPP.

15. The method of claim 13, wherein the CPP is selected from any one of SEQ ID NOs: 302 to 1162, or 1210 to 1220 or a fragment and/or derivative thereof.

16. The method of claim 1, wherein the agent further comprises a linker domain.

17. The method of claim 1, wherein the agent comprises a PCNA interacting motif as set forth in any one of SEQ ID NOs: 28-30, a linker sequence as set forth in SEQ ID NO: 1176 and a cell penetrating signal sequence as set forth in SEQ ID NO: 337.

18. The method of claim 1, wherein the agent comprises a sequence as set forth in any one of SEQ ID NOs: 1182 to 1204, 1208 or 1311.

19. The method of claim 1, wherein the bacterial infection is caused by a bacterium of a genus selected from the group consisting of *Acinetobacter, Enterococcus, Escherichia, Micrococcus, Pseudomonas* and *Staphylococcus*.

20. The method of claim 1, wherein $X_6$ is a basic amino acid or proline (P).

21. A product, material, device or implant which is coated, impregnated or chemically bonded with an agent or composition comprising the agent,
wherein the agent comprises:
an oligopeptidic compound comprising a PCNA interacting motif and a domain that facilitates the cellular uptake of said compound,
wherein the PCNA interacting motif is $X_1X_2X_3X_4X_5X_6$ (SEQ ID NO: 1) and
wherein:
$X_1$ is a basic amino acid;
$X_2$ is an aromatic amino acid;
$X_3$ is an aromatic amino acid or a hydrophobic amino acid that has an R group comprising at least three carbon atoms;
$X_4$ is an uncharged amino acid other than an aromatic amino acid, glycine (G) and proline (P);
$X_5$ is a hydrophobic amino acid, a basic amino acid, a polar amino acid, a thiol-containing amino acid or proline wherein $X_5$ is not asparagine (N), an aromatic amino acid, or an acidic amino acid; and
$X_6$ is any amino acid other than an acidic amino acid or an aromatic amino acid,
wherein when $X_3$ is not an aromatic amino acid, $X_5$ is not lysine (K) and $X_6$ is a basic amino acid or proline (P).

22. The product, material, device or implant of claim 21, wherein when the product, material, device or implant is impregnated:
(i) said product or material is a bandage, gauze, surgical tape, cotton swab, puff, fleece, sponge or supportive matrix, diaper, glove, sock, contact lens or contact lens storage case; or
(ii) said device or implant is a stent, an ear tube, an artificial eye lens, an orthopedic implant, an artificial bone, a dental implant, a cardiac device, a cosmetic implant, an intra-uterine device, a catheter or a prosthetic device.

23. The product, material, device or implant of claim 21, wherein $X_6$ is a basic amino acid or proline (P).

24. An oligopeptidic compound comprising a PCNA interacting motif and a domain that facilitates the cellular uptake of said compound,
wherein the PCNA interacting motif is $X_1X_2X_3X_4X_5X_6$ (SEQ ID NO: 1) and
wherein:
$X_1$ is a basic amino acid;
$X_2$ is an aromatic amino acid;
$X_3$ is an aromatic amino acid or a hydrophobic amino acid that has an R group comprising at least three carbon atoms;
$X_4$ is an uncharged amino acid other than an aromatic amino acid, glycine (G) and proline (P);
$X_5$ is a hydrophobic amino acid, a basic amino acid, a polar amino acid, a thiol-containing amino acid or proline wherein $X_5$ is not asparagine (N), an aromatic amino acid, or an acidic amino acid; and
$X_6$ is any amino acid other than an acidic amino acid or an aromatic amino acid,
wherein when $X_3$ is not an aromatic amino acid, $X_5$ is not lysine (K) and $X_6$ is a basic amino acid or proline (P).

25. A pharmaceutical composition comprising an oligopeptidic compound as defined in claim 24, a nucleic acid molecule encoding said oligopeptidic compound or a vector comprising said nucleic acid molecule, together with at least one pharmacologically acceptable carrier or excipient.

26. The oligopeptidic compound of claim 24, wherein $X_6$ is a basic amino acid or proline (P).

\* \* \* \* \*